(12) United States Patent
Horowitz et al.

(10) Patent No.: US 12,114,877 B2
(45) Date of Patent: Oct. 15, 2024

(54) CLOT REMOVAL METHODS AND DEVICES WITH MULTIPLE INDEPENDENTLY CONTROLLABLE ELEMENTS

(71) Applicant: Retriever Medical, Inc., Las Vegas, NV (US)

(72) Inventors: Michael Bruce Horowitz, Naples, FL (US); Benjamin William Bobo, Las Vegas, NV (US); Brandon Matthew Repko, Mars, PA (US)

(73) Assignee: Retriever Medical, Inc., Las Vegas, NV (US)

( * ) Notice: Subject to any disclaimer, the term of this patent is extended or adjusted under 35 U.S.C. 154(b) by 596 days.

(21) Appl. No.: 17/450,978

(22) Filed: Oct. 14, 2021

(65) Prior Publication Data

US 2022/0104840 A1 Apr. 7, 2022

Related U.S. Application Data

(60) Continuation-in-part of application No. 17/127,521, filed on Dec. 18, 2020, now Pat. No. 11,583,301,
(Continued)

(51) Int. Cl.
*A61B 17/22* (2006.01)
*A61B 17/221* (2006.01)
(Continued)

(52) U.S. Cl.
CPC ...... *A61B 17/22032* (2013.01); *A61B 17/221* (2013.01); *A61B 2017/00867* (2013.01);
(Continued)

(58) Field of Classification Search
CPC ............ A61B 17/22032; A61B 17/221; A61B 2017/00867; A61B 2017/22038;
(Continued)

(56) References Cited

U.S. PATENT DOCUMENTS

2011/0202088 A1 8/2011 Eckhouse et al.
2017/0119408 A1 5/2017 Ma

*Primary Examiner* — Richard G Louis
(74) *Attorney, Agent, or Firm* — Francis Law Group

(57) ABSTRACT

A clot removal device for removal of an occlusion from a lumen in a patient's body is provided. The clot removal device has a lumen, an elongated member positioned within the lumen and extending axially from a proximal end to a distal end of the lumen, a handle attached to the proximal end of the lumen, a first expandable member positioned along a length of the elongated member, a second expandable member positioned along the length of the elongated member, wherein the second expandable member is distal to the first expandable member relative to the handle. The handle has at least one actuation mechanism and at least one of the following applies: a) the first expandable member is coupled to the at least one actuation mechanism and is configured to be moveable relative to the second expandable member upon manipulation of the at least one actuation mechanism; b) the first expandable member is configured to mechanically expand or contract by manipulating the at least one actuation mechanism; c) the second expandable member is coupled to the at least one actuation mechanism and is configured to be moveable relative to the first expandable member upon manipulation of the at least one actuation mechanism; or d) the second expandable member is configured to mechanically expand or contract by manipulating the at least one actuation mechanism.

5 Claims, 58 Drawing Sheets

Related U.S. Application Data which is a continuation of application No. 16/205,632, filed on Nov. 30, 2018, now Pat. No. 10,898,215, which is a division of application No. 15/953,151, filed on Apr. 13, 2018, now Pat. No. 10,172,634.

(60) Provisional application No. 63/260,406, filed on Aug. 19, 2021, provisional application No. 63/215,579, filed on Jun. 28, 2021, provisional application No. 63/215,565, filed on Jun. 28, 2021, provisional application No. 63/215,583, filed on Jun. 28, 2021, provisional application No. 63/215,724, filed on Jun. 28, 2021, provisional application No. 63/215,573, filed on Jun. 28, 2021, provisional application No. 63/215,587, filed on Jun. 28, 2021, provisional application No. 63/092,428, filed on Oct. 15, 2020, provisional application No. 62/653,247, filed on Apr. 5, 2018, provisional application No. 62/589,613, filed on Nov. 22, 2017, provisional application No. 62/606,993, filed on Oct. 16, 2017, provisional application No. 62/573,006, filed on Oct. 16, 2017.

(51) Int. Cl.
*A61B 17/00* (2006.01)
*A61M 25/10* (2013.01)

(52) U.S. Cl.
CPC ............... *A61B 2017/22038* (2013.01); *A61B 2017/22051* (2013.01); *A61B 2017/22054* (2013.01); *A61B 2017/22072* (2013.01); *A61B 2017/22079* (2013.01); *A61B 2017/22094* (2013.01); *A61M 2025/1013* (2013.01); *A61M 2025/1015* (2013.01)

(58) Field of Classification Search
CPC ........... A61B 2017/22051; A61B 2017/22054; A61B 2017/22072; A61B 2017/22079; A61B 2017/22094; A61B 17/32075; A61B 2017/00367; A61B 2017/22039; A61B 2017/22044; A61B 17/22012; A61B 2017/22034; A61B 2017/22067; A61B 2017/2212; A61M 2025/1013; A61M 2025/1015; A61M 2025/0042; G09B 23/30
See application file for complete search history.

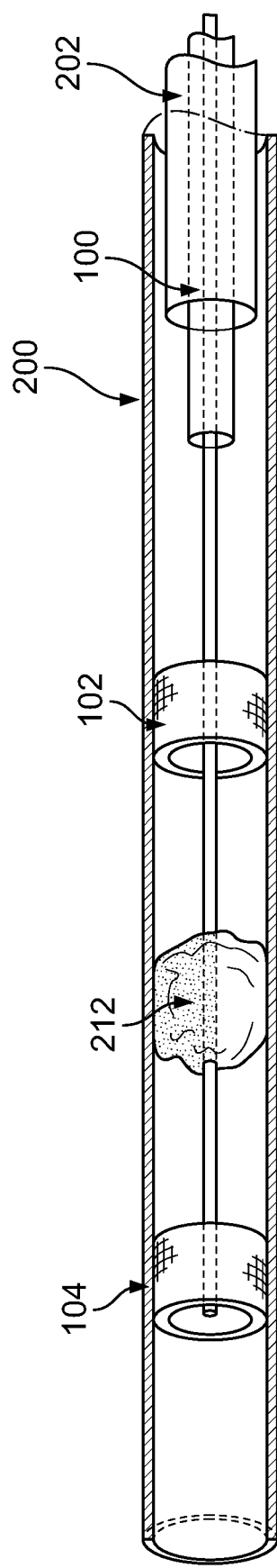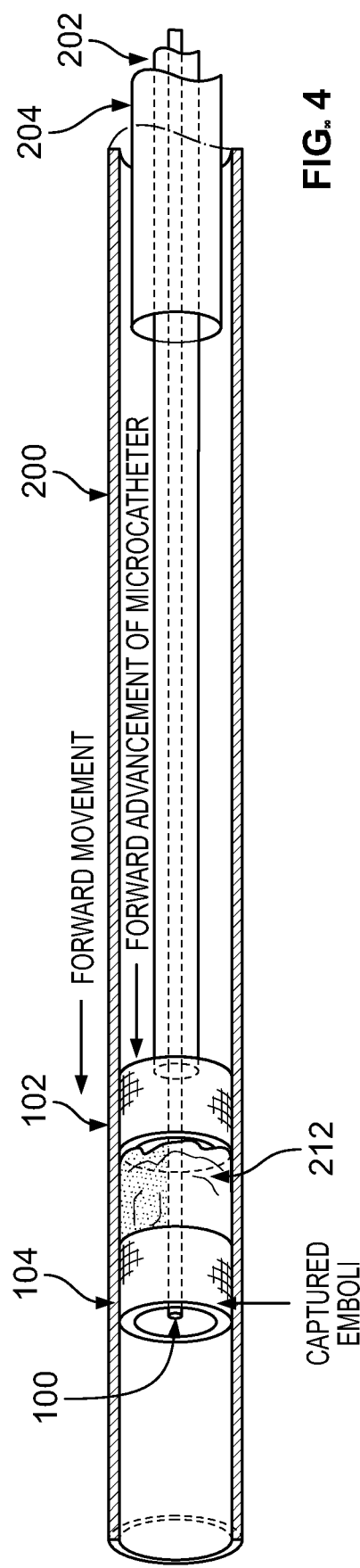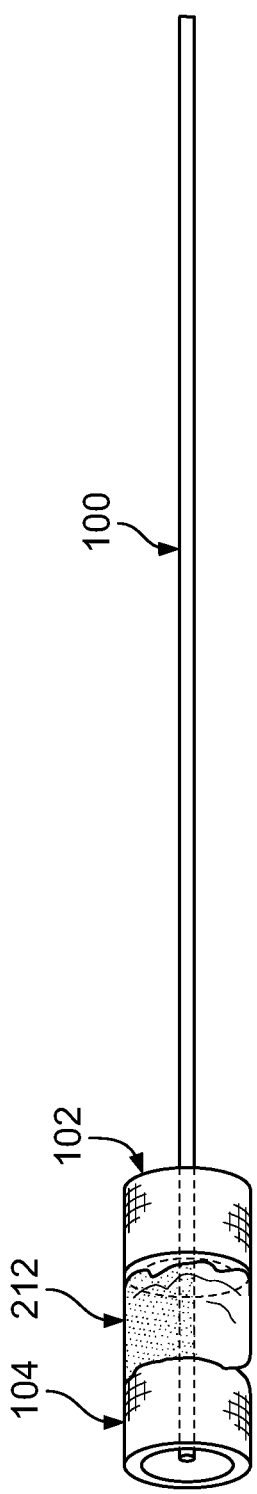

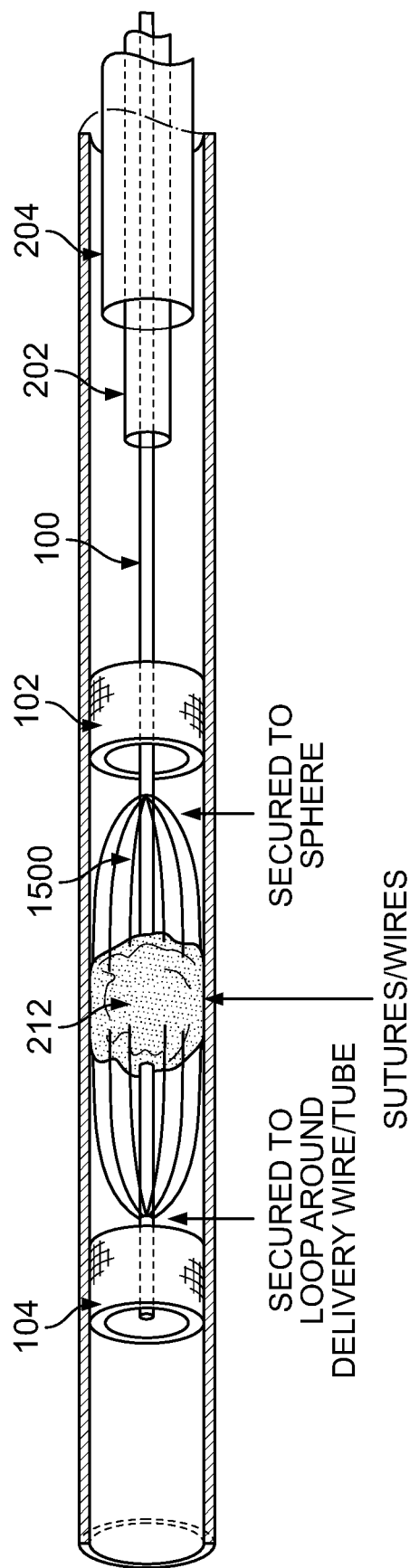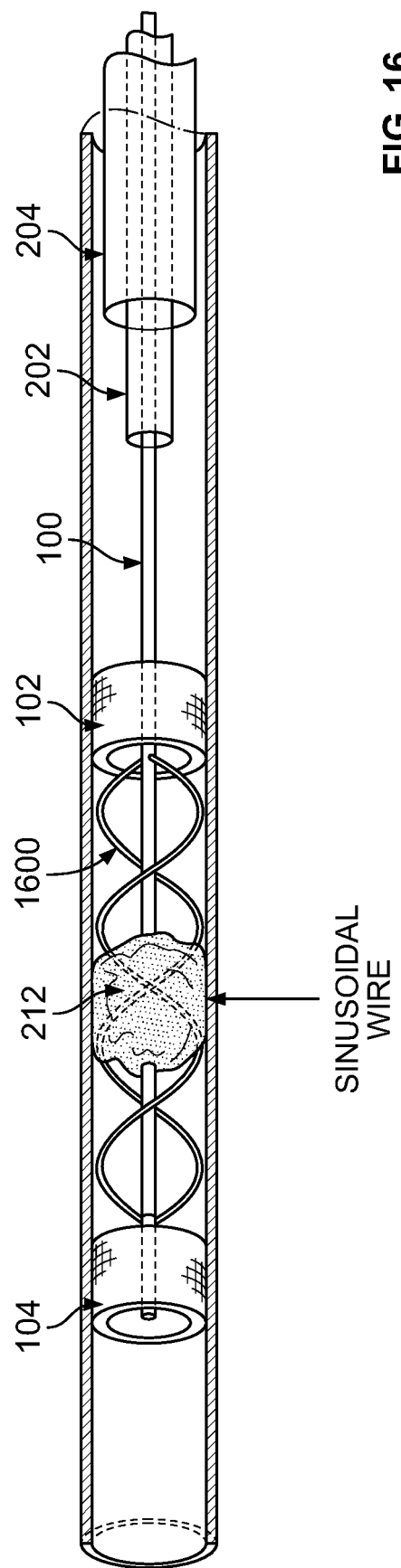

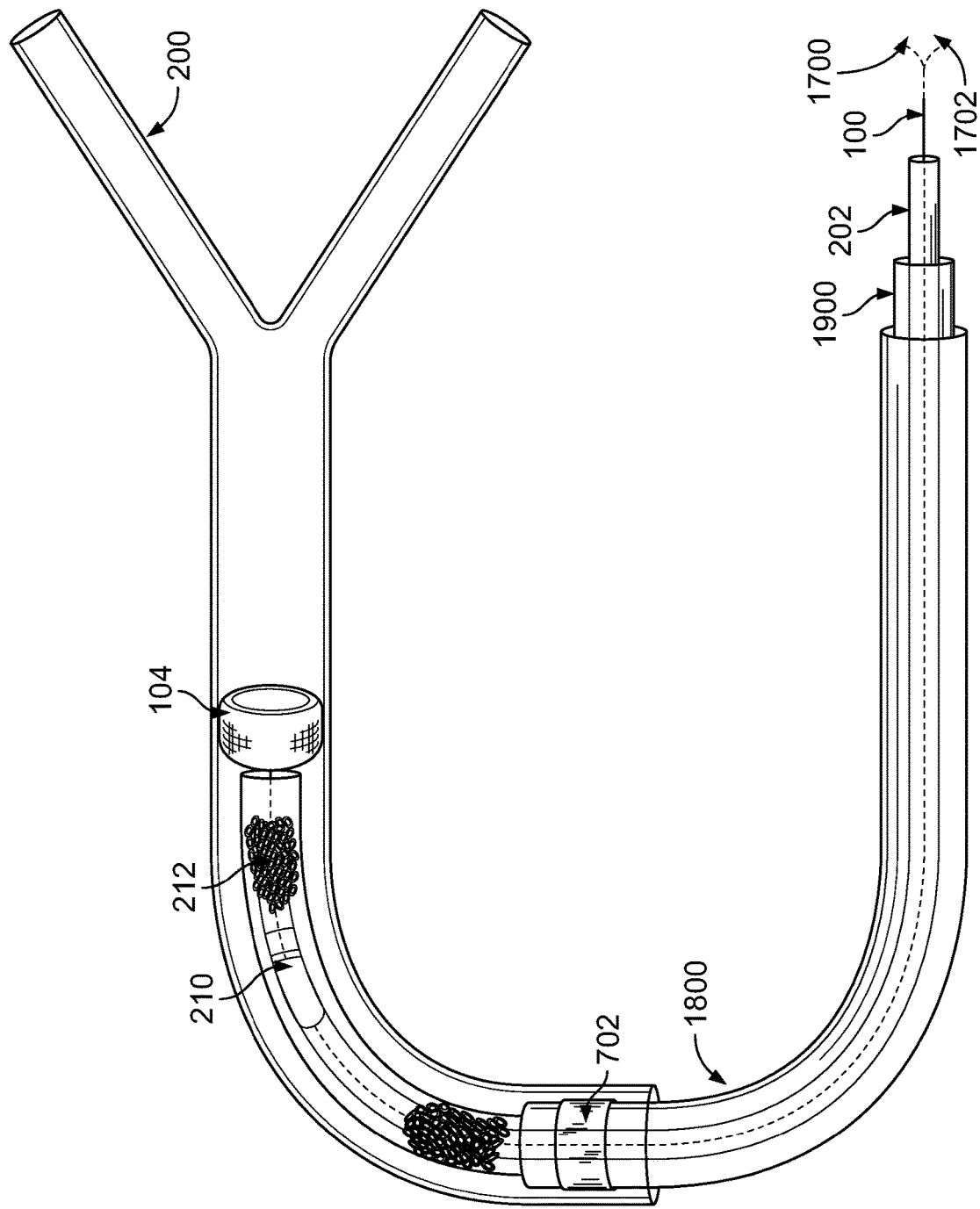

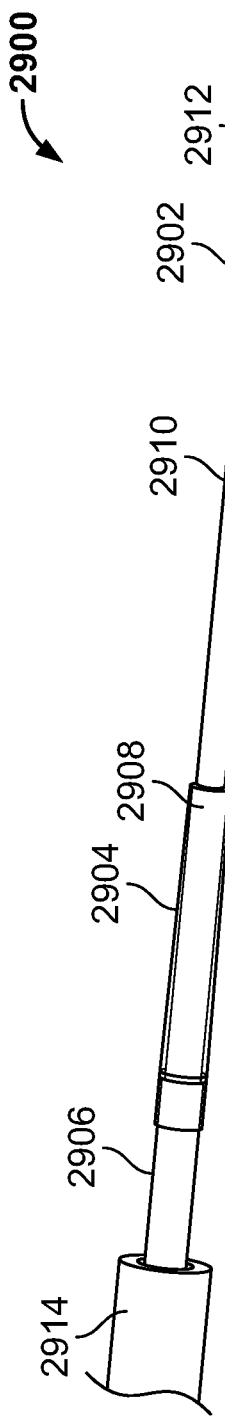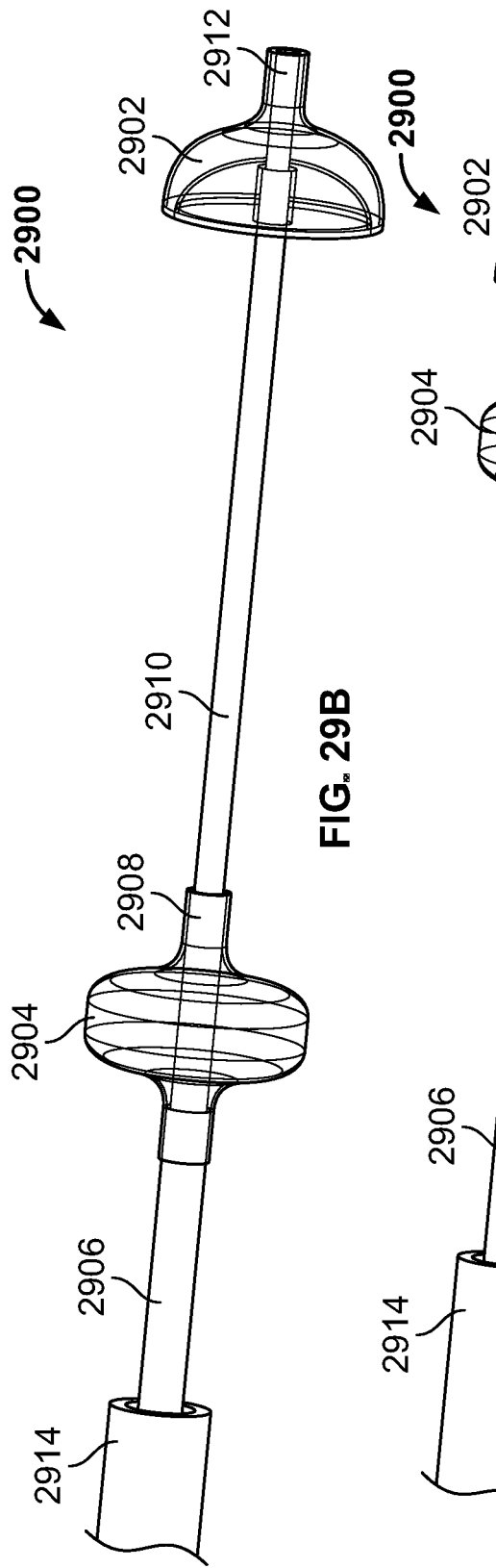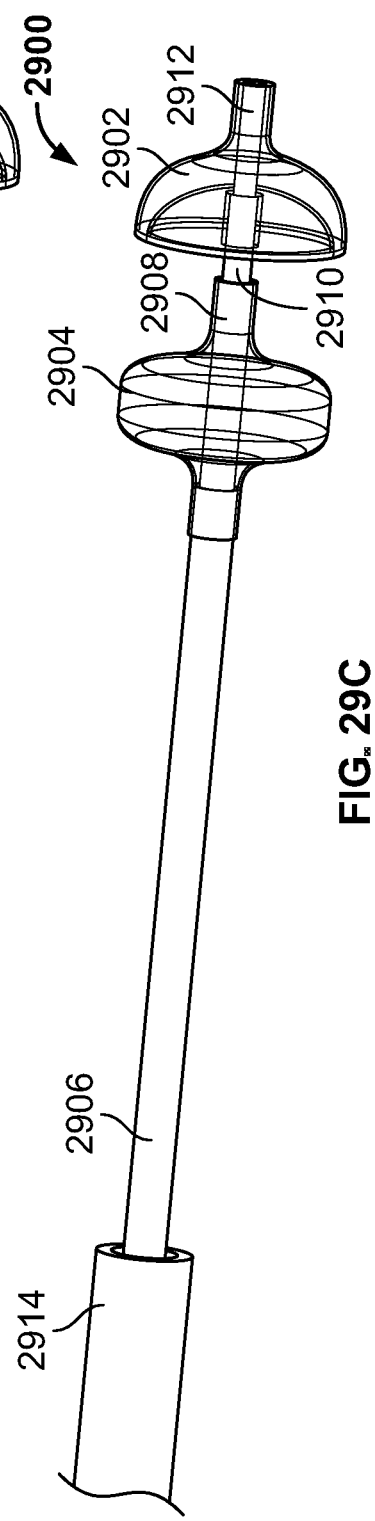
FIG. 29A
FIG. 29B
FIG. 29C

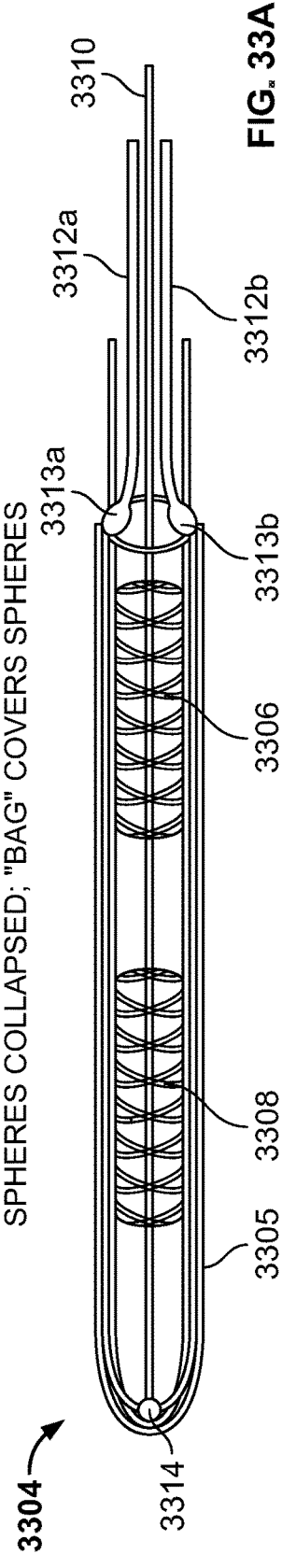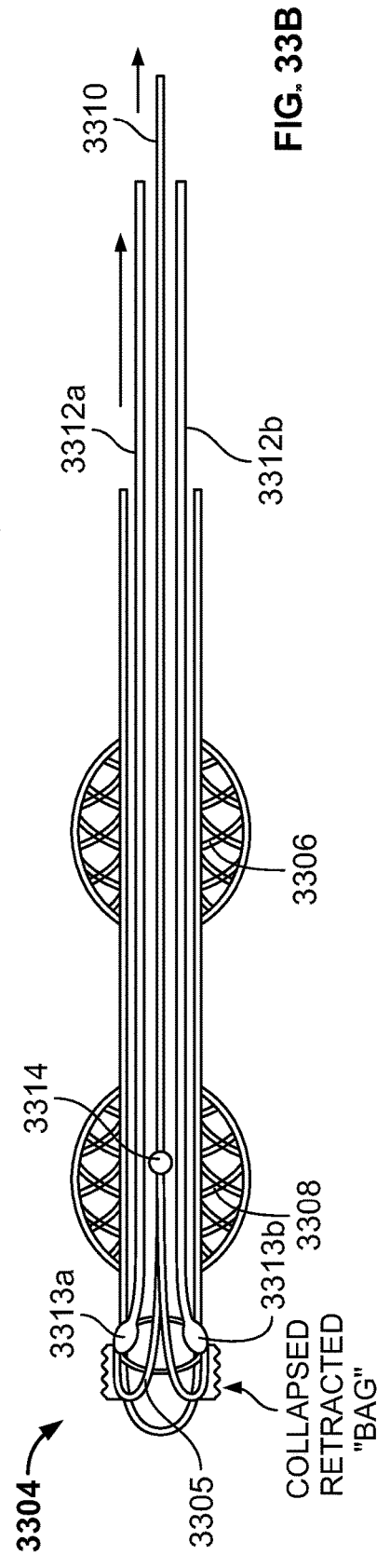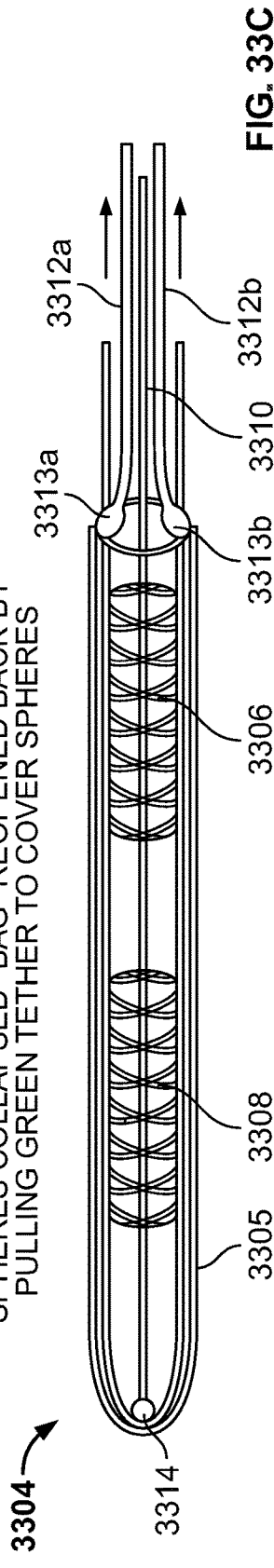

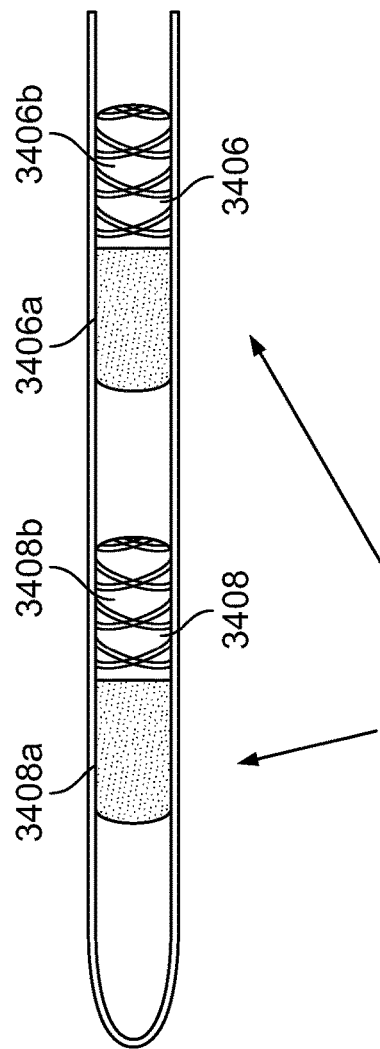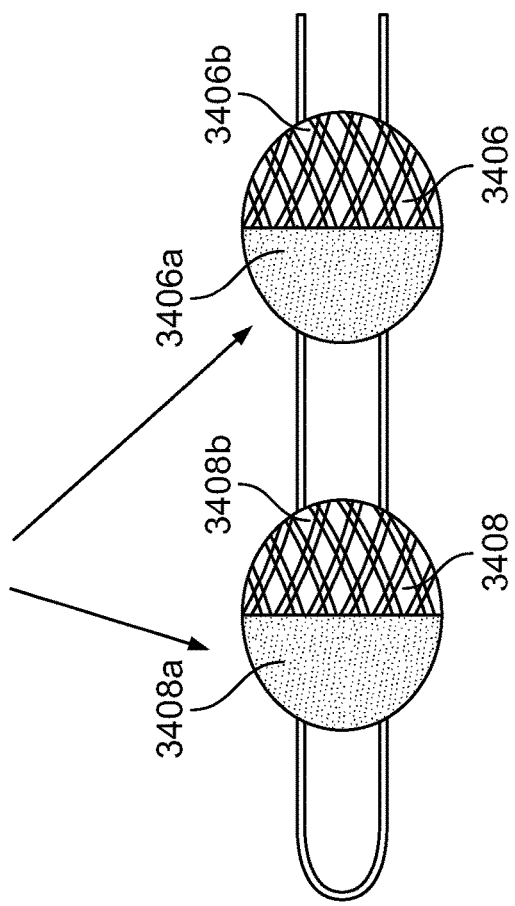
FIG. 34A
FIG. 34B

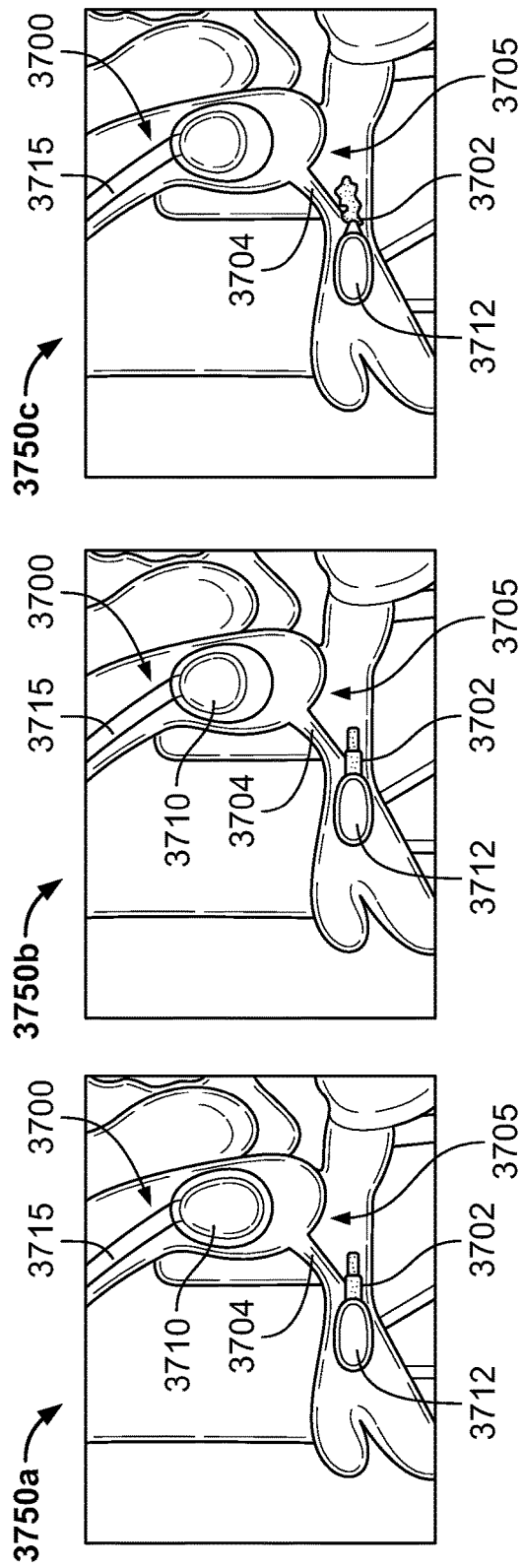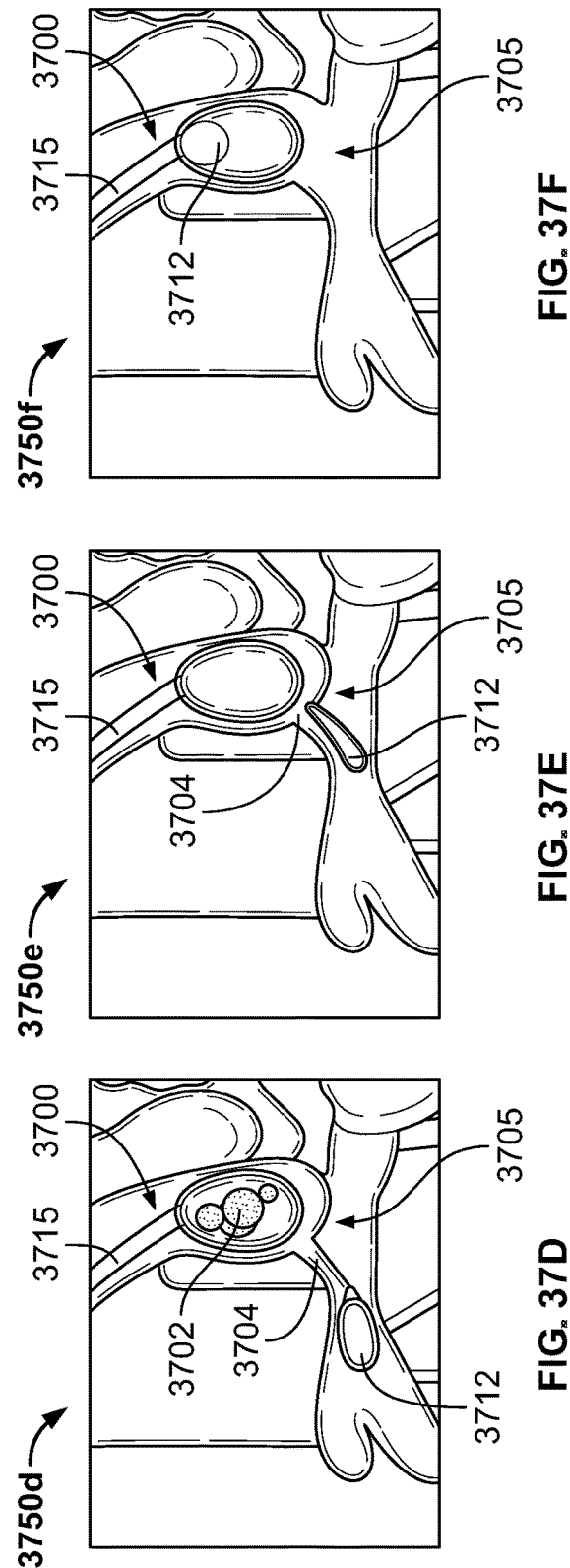

3802

An aspiration catheter (or delivery catheter or sheath) of a retrieval device is positioned near the occlusion (in a lumen of a patient) with a distal end of a trip portion of the retrieval device being positioned within or all the way through the occlusion

3804

A distal element (fixedly attached to the distal end of the tip portion) and a proximal element (slidably coupled to a proximal end of the tip portion) self-expand

3806

The proximal element is moved axially along the tip portion to dislodge the occlusion in a manner that captures the occlusion between the proximal and distal elements

3808

The occlusion is captured between the proximal element and the distal element and is removed by retracting the proximal element, aspirating the occlusion and thereafter retracting the distal element into the aspiration catheter

FIG. 38

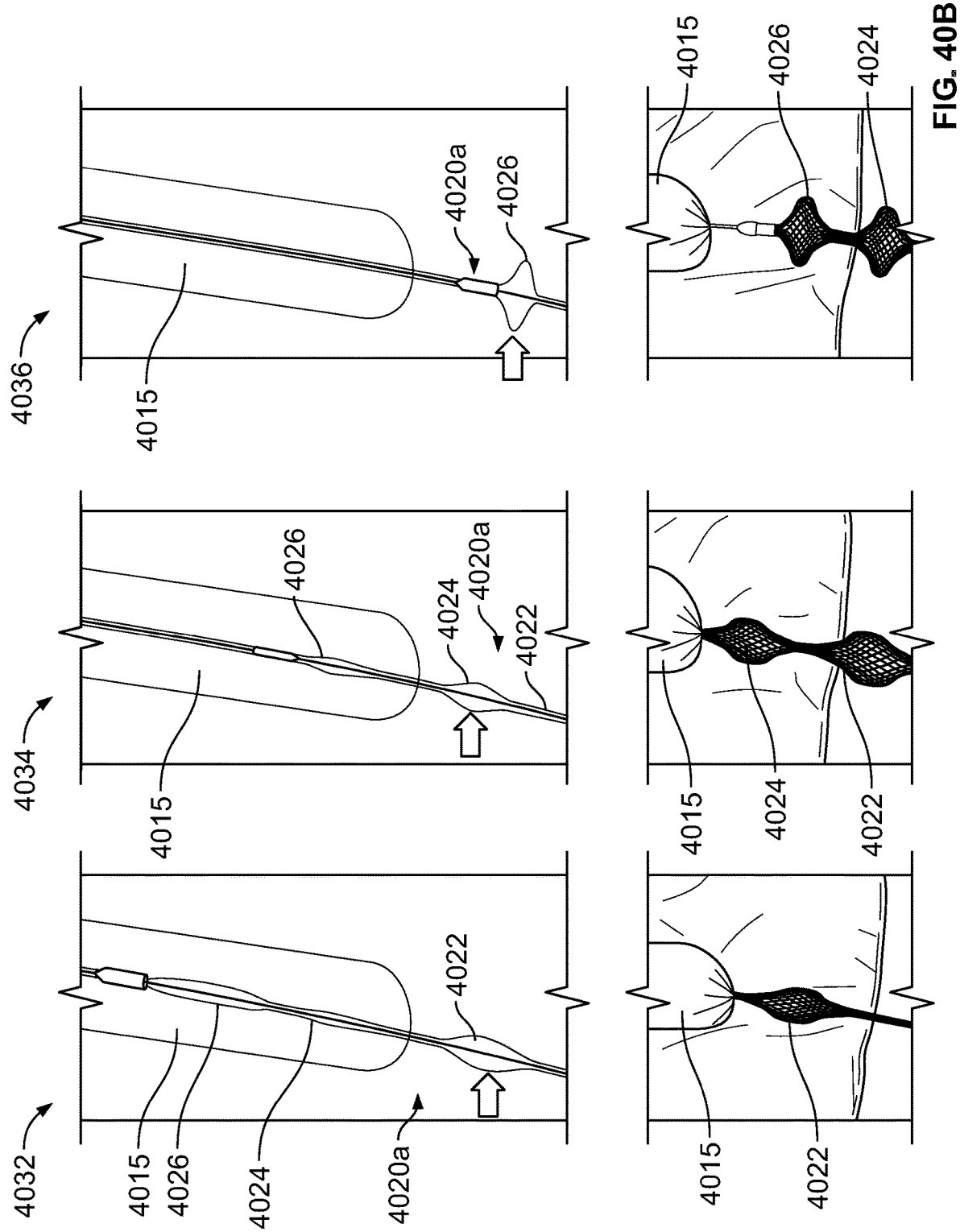

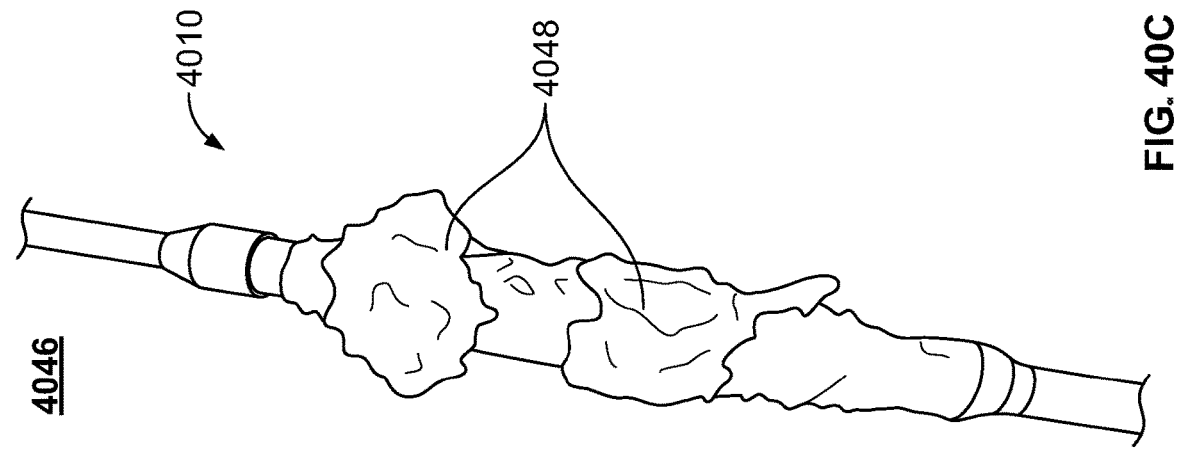
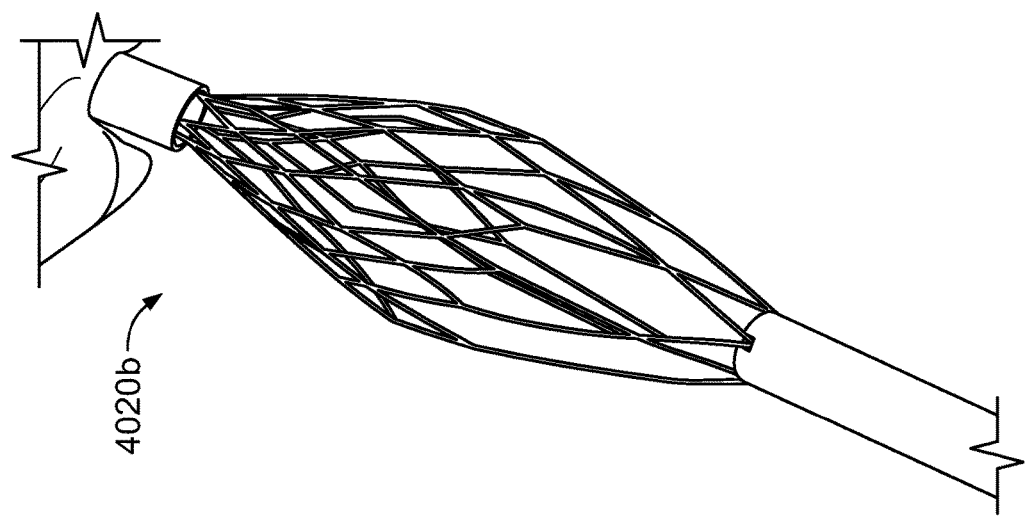
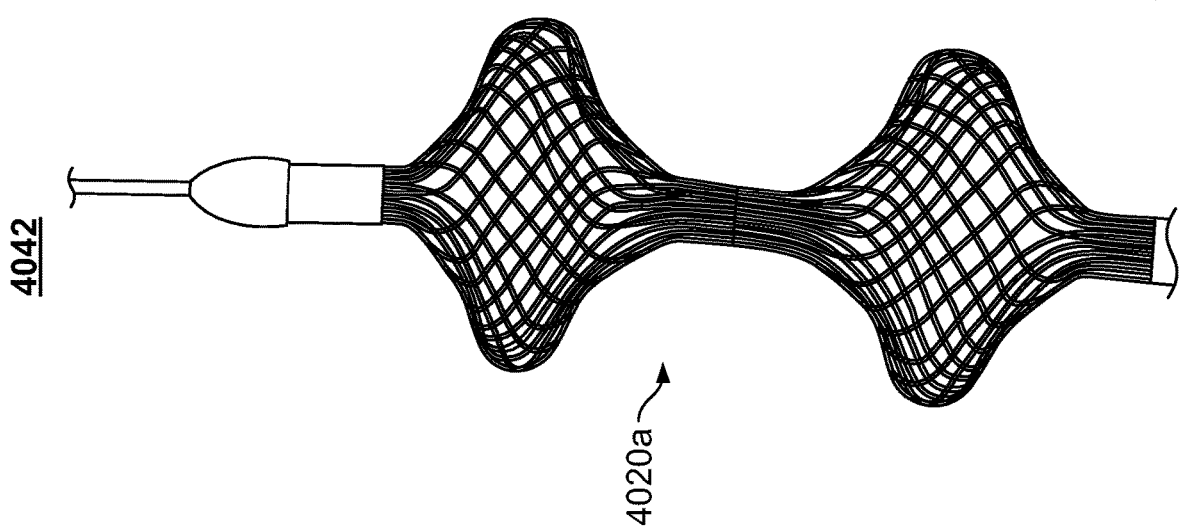
FIG. 40C

CLOT REMOVAL METHODS AND DEVICES WITH MULTIPLE INDEPENDENTLY CONTROLLABLE ELEMENTS

CROSS-REFERENCE

The present application relies on, for priority, the following provisional applications:

U.S. Patent Provisional Application No. 63/260,406, titled "Catheter Based Retrieval Device" and filed on Aug. 19, 2021;

U.S. Patent Provisional Application No. 63/215,724, titled "Device and Method of Using the Device for Repairing A Pathological Connection Between Two Anatomical Structures" and filed on Jun. 28, 2021;

U.S. Patent Provisional Application No. 63/215,579, titled "Hub and Valve Systems for an Aspiration Catheter" and filed on Jun. 28, 2021;

U.S. Patent Provisional Application No. 63/215,573, titled "Aspiration Catheters and Methods of Use Thereof" and filed on Jun. 28, 2021;

U.S. Patent Provisional Application No. 63/215,587, titled "Vascular Closure Devices and Methods of Using Thereof" and filed on Jun. 28, 2021;

U.S. Patent Provisional Application No. 63/215,583, titled "Catheters with Expandable and Collapsible Lumens" and filed on Jun. 28, 2021;

U.S. Patent Provisional Application No. 63/215,565, titled "Catheter Based Retrieval Device" and filed on Jun. 28, 2021; and U.S. Patent Provisional Application No. 63/092,428, titled "Catheter Based Retrieval Device with Proximal Body Having Axial Freedom of Movement" and filed on Oct. 15, 2020.

The present application is also a continuation-in-part application of U.S. patent application Ser. No. 17/127,521, titled "Catheter Based Retrieval Device with Proximal Body Having Axial Freedom of Movement" and filed on Dec. 18, 2020, which is a continuation application of U.S. patent application Ser. No. 16/205,632, titled "Method to Remove a Thrombus", filed on Nov. 30, 2018, and issued as U.S. Pat. No. 10,898,215 on Jan. 26, 2021, which is a divisional application of U.S. patent application Ser. No. 15/953,151, titled "Catheter Based Retrieval Device with Proximal Body Having Axial Freedom of Movement", filed on Apr. 13, 2018, and issued as U.S. Pat. No. 10,172,634 on Jan. 8, 2019, which, in turn, relies on for priority: U.S. Patent Provisional Application No. 62/653,247 filed on Apr. 5, 2018; U.S. Patent Provisional Application No. 62/589,613, filed on Nov. 22, 2017; U.S. Patent Provisional Application No. 62/606,993, filed on Oct. 16, 2017; and, U.S. Patent Provisional Application No. 62/573,006, filed on Oct. 16, 2017.

The present application also relates to U.S. patent application Ser. No. 15/953,173, titled "Catheter Based Retrieval Device with Proximal Body Having Axial Freedom of Movement", filed on Apr. 13, 2018 and issued as U.S. Pat. No. 10,258,357 on Apr. 16, 2019, and U.S. patent application Ser. No. 15/953,186, titled "Catheter Based Retrieval Device with Proximal Body Having Axial Freedom of Movement" and filed on Apr. 13, 2018, both of which rely on, for priority, the following United States Patent Provisional Applications: U.S. Patent Provisional Application No. 62/653,247 filed on Apr. 5, 2018; U.S. Patent Provisional Application No. 62/589,613, filed on Nov. 22, 2017; U.S. Patent Provisional Application No. 62/606,993, filed on Oct. 16, 2017; and, U.S. Patent Provisional Application No. 62/573,006, filed on Oct. 16, 2017.

The present application also relates to PCT Application Number PCT/US18/55606, titled "Catheter Based Retrieval Device with Proximal Body Having Axial Freedom of Movement" and filed on Oct. 12, 2018, which claims the benefit of U.S. patent application Ser. Nos. 15/953,151; 15/953,173; 15/953,186, which in turn, claim priority from U.S. Patent Provisional Application No. 62/653,247 filed on Apr. 5, 2018, U.S. Patent Provisional Application No. 62/589,613, filed on Nov. 22, 2017, U.S. Patent Provisional Application No. 62/606,993, filed on Oct. 16, 2017, and U.S. Patent Provisional Application No. 62/573,006, filed on Oct. 16, 2017.

All of the above-mentioned patents and applications are hereby incorporated by reference in their entirety.

FIELD

The disclosure generally relates to methods and systems for the catheter-based removal of occlusions and unwanted matter from vessels, ducts and other cavities or lumens of an organism.

BACKGROUND

Current medical devices that are used for the removal of occlusions, such as thrombi from the vessels (such as those in the brain), have limitations that reduce their effectiveness, reliability, and ease of use. For example, current devices are designed exclusively for the vascular system, and may not be used for extraction of material from ducts, ureters, urethra, or other anatomical features. Current devices are not appropriate for use in large vascular structures such as aorta, vena cava and many peripheral vascular applications, and often do not work well with calcified, organized material due to inability of the wire structures often used to compress into the embolic material prior to an attempted extraction. Current devices often have a wire structure that must incorporate into a thrombus to remove a clot and provide poor distal protection from secondary emboli during thrombus extraction due to open ended stent retriever or partial grasping of thrombus. This may result in an intended thrombectomy procedure causing distal clot embolization and occlusion of previously patent arterial branches and collaterals. Current devices may be less effective when used with associated arterial stenoses due to device collapse and tendency for a stenosis to strip and debride thrombus from device as it is retracted through the stenotic vessel segment. Current devices often require operators to choose a predetermined device length at time of device insertion, but the chosen device length might not match the size of the target thrombus once the operator is in the vessel and provided a closer view of the target thrombus.

Current catheter-based methods and systems for the removal of foreign bodies from an artery, duct, ureter or other interior physical space, often require multiple co-axial (or concentric) sleeves or delivery catheters, some of which are intended for placement on the proximal side of an occlusion, some for direction through the occlusion for placement on the distal side of the occlusion, and still others for holding inflatable balloons, thrombus removal devices and the like. The presence of multiple catheters increases manufacturing complexity and cost, in addition to increasing complexity of usage during an intervention, with greater moving parts and the required ordering of operation aligned with the function of the multiple catheters. Current catheter-based methods and systems are also manufactured and deployed in the clinical setting with a specific catheter, meaning that if during an intervention a clinician wants to deploy ("load"), for example, a retrieval device having a different size than that first deployed in a vessel, the entire catheter-based tool must be withdrawn and a new catheter-based device with the preferred diameter loaded inserted. Additional limitations of the current catheter-based systems include, but are not limited to, a reliance on fixed-diameter instrumentation and/or inflatable bodies (e.g., balloons) for encapsulation of a foreign body or occlusion. As an example, catheters using an inflatable balloon for a distal body and/or proximal body may require that an interventionist pre-select a balloon model and size prior to entering a vessel or cavity because inflatable balloons have a manufactured minimum and maximum inflation diameter. Thus, if the incorrect balloon size is selected, or the clinical setting requires flexibility in the expansion or contraction diameter of the distal or proximal bodies, the intervention may be interrupted to allow for size adaptation of equipment. Incorrect sizing may also increase the likelihood for negative clinical sequelae, such as embolization and release of occlusive matter if, for example, distal protection is lost.

Additionally, current occlusion removal systems fail to catch or prevent small portions of a dislodged occlusion from passing through a patient's vessels and possibly causing a thrombosis. Existing devices and treatment methods permit portions of the occlusion, albeit smaller sized portions, to pass through the vessel and are not effective at capturing and extracting those portions.

Therefore, there is a need for methods and systems of thrombus, or other matter, removal in which an object targeted for removal may be dynamically surrounded by a retrieval device, rather than incorporated into the target object, wherein the retrieval device can surround the target and may be physically adjusted to match the size of the target object while within the vessel or other cavity. Further, there is a need for methods and systems of thrombus, or other matter, removal in which a larger percentage of such matter is captured while not creating an unduly difficult to use or navigate device.

SUMMARY

The following embodiments and aspects thereof are described and illustrated in conjunction with systems, tools and methods, which are meant to be exemplary and illustrative, and not limiting in scope. The present application discloses numerous embodiments.

The present specification discloses a device adapted to remove unwanted material from a vessel of a patient, wherein the device comprises: an elongated member having a first proximal end and a first distal end; a proximal expandable element having a first proximal end point and a first distal end point, wherein the first proximal end point is attached to a first portion of the elongated member and wherein the first distal end point is attached to a second portion of the elongated member; a distal expandable element having a second proximal end point and a second distal end point, wherein the second proximal end point is attached to a third portion of the elongated member, wherein the second distal end point is attached to a fourth portion of the elongated member, and wherein the first portion, second portion, third portion, and fourth portion represent different locations along the elongated member; a handle in physical communication with the elongated member, wherein the handle comprises a first physically manipulable interface and a second physically manipulable interface, wherein, when moved, the first physically manipulable interface is adapted to mechanically expand or contract the proximal expandable element independent of the distal expandable element, and wherein, when moved, the second physically manipulable interface is adapted to mechanically expand or contract the distal expandable element independent of the proximal expandable element.

Optionally, the handle further comprises a third physically manipulable interface and wherein, when moved, the third physically manipulable interface is adapted to move the proximal expandable element while the distal expandable element remains stationary. Optionally, the third physically manipulable interface is a slider configured to be moved axially along a length of the handle wherein, upon moving the slider axially along the length, the proximal expandable element moves while the distal expandable element remains stationary.

Optionally, the handle further comprises a third physically manipulable interface wherein, when moved, the third physically manipulable interface is adapted to move the distal expandable element while the proximal expandable element remains stationary. Optionally, the third physically manipulable interface is a slider configured to be moved axially along a length of the handle wherein, upon moving the slider axially along the length, the distal expandable element moves while the proximal expandable element remains stationary.

Optionally, the first physically manipulable interface is a slider configured to be moved axially along a length of the handle wherein, upon moving the slider axially along the length, the proximal expandable element expands or contracts.

Optionally, the second physically manipulable interface is a slider configured to be moved axially along a length of the handle wherein, upon moving the slider axially along the length, the distal expandable element expands or contracts.

Optionally, the proximal expandable element comprises a braid having a proximal portion and a distal portion, wherein the braid of the proximal portion is denser or stiffer relative to the braid of the distal portion. Optionally, the proximal portion represents 30-70% of the surface area of the proximal expandable element and the distal portion represents 70-30% of the surface area of the proximal expandable element.

Optionally, the distal expandable element comprises a braid having a proximal portion and a distal portion, wherein the braid of the distal portion is denser or stiffer relative to the braid of the proximal portion. Optionally, the distal portion represents 30-70% of the surface area of the distal expandable element and the proximal portion represents 70-30% of the surface area of the distal expandable element.

Optionally, the proximal expandable element is defined by a first braid structure and the distal expandable element is defined by a second braid structure, wherein the second braid structure is equivalent to the first braid structure.

Optionally, the proximal expandable element is defined by a first braid structure and the distal expandable element is defined by a second braid structure, wherein the second braid structure is equivalent to the first braid structure rotated 180 degrees.

Optionally, the device further comprises a hub valve and a sheath, wherein the hub valve is defined by an enclosure, a first opening in a first end of the enclosure, a second opening in a second end of the enclosure, and an actuator extending upward out of the enclosure wherein the sheath is coupled to the second opening. Optionally, when the actuator is depressed, the hub valve is configured to receive the elongated member through the first opening and allow the elongated member to pass through the second opening and through the sheath. Optionally, when the actuator is not depressed, the hub valve is configured to create a seal around a surface of the elongated member. Optionally, the device further comprises a suction source coupled to a portion of the hub and in pressure communication with the sheath. Optionally, the suction source is a syringe.

Optionally, the handle further comprises a pin positioned to block a movement of the first physically manipulable interface and the second physically manipulable interface, a keyhole accessible from a side of the handle, and a key configured to pass into the keyhole and make physical contact with the pin.

Optionally, the elongated member comprises a first shaft, a second shaft, a third shaft, and a fourth shaft wherein the first shaft is concentrically positioned around the second shaft, the second shaft is concentrically positioned around the third shaft, and the third shaft is concentrically positioned around the fourth shaft. Optionally, the first proximal end point is physically attached to the first shaft, the first distal end point is physically attached to the second shaft, the second proximal end point is physically attached to the third shaft, and the second distal end point is physically attached to the fourth shaft. Optionally, the first physically manipulable interface is configured to axially move the first shaft while the second shaft, third shaft, and fourth shaft remain stationary. Optionally, the first physically manipulable interface is a slider configured to move axially up and down the handle. Optionally, the second physically manipulable interface is configured to axially move the fourth shaft while the first shaft, second shaft, and third shaft remain stationary. Optionally, the second physically manipulable interface is a slider configured to move axially up and down the handle. Optionally, the device further comprises a third physically manipulable interface, wherein the third physically manipulable interface is configured to axially move the first shaft and second shaft together while the third shaft and fourth shaft remain stationary. Optionally, the third physically manipulable interface is a slider configured to move axially up and down the handle.

Optionally, the first physically manipulable interface is configured to axially move the first portion to one of a first plurality of predefined incremented positions while the second portion, third portion, and fourth portion remain stationary, wherein each of the first plurality of predefined incremented positions corresponds to causing the proximal expandable element to adopt one of a plurality of different geometric shapes, and wherein the plurality of different geometric shapes includes at least two of linear, ellipsoid, spheroid, spherical or disk-shaped. Optionally, the second physically manipulable interface is configured to axially move the fourth portion to one of a second plurality of predefined incremented positions while the first portion, second portion, and third portion remain stationary and each of the second plurality of predefined incremented positions corresponds to causing the distal expandable element to adopt one of the plurality of different geometric shapes. Optionally, upon adopting one of the plurality of different geometric shapes other than the linear shape, the proximal expandable element or distal expandable element is adapted to not collapse upon an application of up to 25 Newtons of force.

The present specification also discloses a device adapted to remove unwanted material from a vessel of a patient, wherein the device comprises: an elongated member having a first proximal end and a first distal end; a proximal expandable element having a first proximal end point and a first distal end point, wherein the first proximal end point is attached to a first portion of the elongated member and wherein the first distal end point is attached to a second portion of the elongated member; a distal expandable element having a second proximal end point and a second distal end point, wherein the second proximal end point is attached to a third portion of the elongated member, wherein the second distal end point is attached to a fourth portion of the elongated member, and wherein the first portion, second portion, third portion, and fourth portion represent different locations along the elongated member; a handle in physical communication with the elongated member, wherein the handle comprises a first physically manipulable interface and a second physically manipulable interface, wherein, when moved, the first physically manipulable interface is adapted to mechanically expand or contract at least one of the proximal expandable element or the distal expandable element and wherein, when moved, the second physically manipulable interface is adapted to move the proximal expandable element without moving the distal expandable element or move the distal expandable element without moving the proximal expandable element.

Optionally, when moved, the first physically manipulable interface is adapted to mechanically expand or contract the proximal expandable element. Optionally, the device further comprises a third physically manipulable interface, wherein, when moved, the third physically manipulable interface is adapted to mechanically expand or contract the distal expandable element.

Optionally, the second physically manipulable interface is a slider configured to be moved axially along a length of the handle wherein, upon moving the slider axially along the length, the proximal expandable element moves while the distal expandable element remains stationary.

Optionally, the second physically manipulable interface is a slider configured to be moved axially along a length of the handle wherein, upon moving the slider axially along the length, the distal expandable element moves while the proximal expandable element remains stationary.

Optionally, the first physically manipulable interface is a slider configured to be moved axially along a length of the handle wherein, upon moving the slider axially along the length, the proximal expandable element expands or contracts while a size of the distal expandable element does not change.

Optionally, the first physically manipulable interface is a slider configured to be moved axially along a length of the handle wherein, upon moving the slider axially along the length, the distal expandable element expands or contracts while a size of the proximal expandable element does not change.

Optionally, the proximal expandable element comprises a braid having a proximal portion and a distal portion, wherein the braid of the proximal portion is denser or stiffer relative to the braid of the distal portion. Optionally, the proximal portion represents 30-70% of the surface area of the proximal expandable element and the distal portion represents 70-30% of the surface area of the proximal expandable element.

Optionally, the distal expandable element comprises a braid having a proximal portion and a distal portion, wherein the braid of the distal portion is denser or stiffer relative to the braid of the proximal portion. Optionally, the distal portion represents 30-70% of the surface area of the distal expandable element and the proximal portion represents 70-30% of the surface area of the distal expandable element.

Optionally, the proximal expandable element is defined by a first braid structure and the distal expandable element is defined by a second braid structure, wherein the second braid structure is equivalent to the first braid structure.

Optionally, the proximal expandable element is defined by a first braid structure and the distal expandable element is defined by a second braid structure, wherein the second braid structure is equivalent to the first braid structure rotated 180 degrees.

Optionally, the device further comprises a hub valve and a sheath, wherein the hub valve is defined by an enclosure, a first opening in a first end of the enclosure, a second opening in a second end of the enclosure, and an actuator extending upward out of the enclosure wherein the sheath is coupled to the second opening. Optionally, when the actuator is depressed, the hub valve is configured to receive the elongated member through the first opening and allow the elongated member to pass through the second opening and through the sheath. Optionally, when the actuator is not depressed, the hub valve is configured to create a seal around a surface of the elongated member. Optionally, the device further comprises a suction source coupled to a portion of the hub and in pressure communication with the sheath. Optionally, the suction source is a syringe.

Optionally, the handle further comprises a pin positioned to block a movement of the first physically manipulable interface and the second physically manipulable interface, a keyhole accessible from a side of the handle, and a key configured to pass into the keyhole and make physical contact with the pin.

Optionally, the elongated member comprises a first shaft, a second shaft, a third shaft, and a fourth shaft wherein the first shaft is concentrically positioned around the second shaft, the second shaft is concentrically positioned around the third shaft, and the third shaft is concentrically positioned around the fourth shaft. Optionally, the first proximal end point is physically attached to the first shaft, the first distal end point is physically attached to the second shaft, the second proximal end point is physically attached to the third shaft, and the second distal end point is physically attached to the fourth shaft. Optionally, the first physically manipulable interface is configured to axially move the first shaft while the second shaft, third shaft, and fourth shaft remain stationary. Optionally, the first physically manipulable interface is a slider configured to move axially up and down the handle. Optionally, the first physically manipulable interface is configured to axially move the fourth shaft while the first shaft, second shaft, and third shaft remain stationary. Optionally, the first physically manipulable interface is a slider configured to move axially up and down the handle. Optionally, the second physically manipulable interface is configured to axially move the first shaft and second shaft together while the third shaft and fourth shaft remain stationary. Optionally, the second physically manipulable interface is a slider configured to move axially up and down the handle.

Optionally, the first physically manipulable interface is configured to axially move the first portion to one of a first plurality of predefined incremented positions while the second portion, third portion, and fourth portion remain stationary, wherein each of the first plurality of predefined incremented positions corresponds to causing the proximal expandable element to adopt one of a plurality of different geometric shapes, and wherein the plurality of different geometric shapes includes at least two of linear, ellipsoid, spheroid, spherical or disk-shaped.

Optionally, the first physically manipulable interface is configured to axially move the fourth portion to one of a second plurality of predefined incremented positions while the first portion, second portion, and third portion remain stationary, wherein each of the second plurality of predefined incremented positions corresponds to causing the distal expandable element to adopt one of the plurality of different geometric shapes. Optionally, upon adopting one of the plurality of different geometric shapes other than the linear shape, the distal expandable element is adapted to not collapse upon an application of up to 25 Newtons of force.

In some embodiments, the present specification also discloses a device for removing an occlusion from a lumen within a patient's body, comprising: a handle having a distal end, wherein the distal end is coupled to a proximal end of a tip portion through one or more telescoping tubes, wherein the handle includes at least one actuation mechanism; and an element mounted at the tip portion, wherein the element is in a first state, wherein the handle is configured to steer the tip portion through the lumen so that the element is positioned within the occlusion, wherein the at least one actuation mechanism is manipulated in a first direction to transition the element from the first state to a second state within the occlusion, and wherein the element in the second state is imparted one or more fore and aft motions to dislodge and scrape the occlusion.

Optionally, the first state corresponds to the element being in a contracted configuration and the second state corresponds to the element being in an expanded configuration.

Optionally, the at least one actuation mechanism includes first and second knobs, wherein the first knob is manipulated to transition the element from the first state to the second state, and wherein the second knob is manipulated to impart the one or more fore and aft motions to the element relative to the tip portion.

Optionally, the handle is moved fore and aft to cause the tip portion and therefore the element to be moved fore and aft.

Optionally, the at least one actuation mechanism includes a knob that is manipulated to transition the element from the first state to the second state.

Optionally, the device further includes a delivery catheter and an aspiration catheter, wherein the tip portion is positioned within the delivery catheter and the delivery catheter is positioned within the aspiration catheter, and wherein a negative pressure is applied at a proximal end of the aspiration catheter to aspirate the dislodged and scraped occlusion.

Optionally, the at least one actuation mechanism is manipulated in a second direction opposite to the first direction to transition the element from the second state to the first state, and wherein the handle is used to retract the element in the first state from the lumen.

Optionally, the element has proximal, distal and center portions, wherein the proximal portion is shaped as a first funnel having a first neck directed proximally along a longitudinal axis of the tip portion and the distal portion is shaped as a second funnel having a second neck directed distally along the longitudinal axis, wherein respective cup edges of the first and second funnels are attached across a central axis to form the center portion, said central axis lying approximately orthogonal to the longitudinal axis.

Optionally, the element has a three-dimensional geometric shape in the second state, and wherein the three dimensional geometric shape is one or a combination of spherical, elliptical, conical, polygonal, cylindrical, stent, chalice cup, umbrella, concave, convex, half-sphere, sphere, windsock, dumbbell, star, polygon, or lever shapes.

In some embodiments, the present specification discloses a method of using a device to remove an occlusion from a lumen within a patient's body, wherein the device comprises a handle coupled to a proximal end of a tip portion through one or more telescoping tubes, and an element mounted on the tip portion, and wherein the element is in a first state, the method comprising: positioning the tip portion through a delivery catheter; positioning the delivery catheter through an aspiration catheter; steering, using the handle, the tip portion through the lumen so that the element is positioned within the occlusion; transitioning, by manipulating at least one actuation mechanism on the handle in a first direction, the element from the first state to a second state; and imparting one or more fore and aft motions to the element in order to dislodge and scrape the occlusion.

Optionally, the first state corresponds to the element being in a contracted configuration and the second state corresponds to the element being in an expanded configuration.

Optionally, the at least one actuation mechanism includes first and second knobs, wherein the first knob is manipulated to transition the element from the first state to the second state, and wherein the second knob is manipulated to impart the one or more fore and aft motions to the element relative to the tip portion.

Optionally, the handle is moved fore and aft to cause the tip portion and therefore the element to be moved fore and aft.

Optionally, the at least one actuation mechanism includes a knob that is manipulated to transition the element from the first state to the second state.

Optionally, the method further comprises applying a negative pressure at a proximal end of the aspiration catheter to aspirate the dislodged and scraped occlusion.

Optionally, the method further comprises transitioning, by manipulating the at least one actuation mechanism on the handle in a second direction opposite to the first direction, the element from the second state to the first state; and retracting, using the handle, the element in the first state from the lumen.

Optionally, the element has proximal, distal and center portions, wherein the proximal portion is shaped as a first funnel having a first neck directed proximally along a longitudinal axis of the tip portion and the distal portion is shaped as a second funnel having a second neck directed distally along the longitudinal axis, wherein respective cup edges of the first and second funnels are attached across a central axis to form the center portion, said central axis lying approximately orthogonal to the longitudinal axis.

Optionally, the element has a three-dimensional geometric shape in the second state, and wherein the three-dimensional geometric shape is one or a combination of spherical, elliptical, conical, polygonal, cylindrical, stent, chalice cup, umbrella, concave, convex, half-sphere, sphere, windsock, dumbbell, star, polygon, or lever shapes.

In some embodiments, the present specification discloses a device for removing clot from a lumen within a patient's body, comprising: a handle having a distal end, wherein the distal end is coupled to a proximal end of a tip portion through one or more telescoping tubes, wherein the handle includes at least one actuation mechanism; and an element mounted at the tip portion, wherein the element is in a first state, wherein the handle is configured to steer the tip portion through the lumen so that the element is positioned within the clot, wherein the at least one actuation mechanism is manipulated in a first direction to transition the element from the first state to a second state and from the second state to a third state within the clot, and wherein the element in the second state and/or the third state is imparted one or more fore and aft motions to dislodge and scrape the clot.

Optionally, the second state corresponds to a first radial force that a first size of the element applies to the clot and the third state corresponds to a second radial force that a second size of the element applies to the clot, and wherein the second radial force is different from the first radial force.

Optionally, each of the first and second radial force is in a range of 2 Newtons to 20 Newtons.

In some embodiments, the present specification discloses a clot removal device comprising: a lumen having a proximal end, a distal end, and a length extending between the proximal end and the distal end; an elongated member positioned within the lumen and extending axially from the proximal end to the distal end; a handle attached to the proximal end of the lumen, wherein the handle comprises at least one actuation mechanism; a first expandable member positioned along a length of the elongated member; and a second expandable member positioned along the length of the elongated member, wherein the second expandable member is distal to the first expandable member relative to the handle and wherein at least one of: i) the first expandable member is coupled to the at least one actuation mechanism and is configured to be moveable relative to the second expandable member upon manipulation of the at least one actuation mechanism; ii) the first expandable member is configured to mechanically expand or contract by manipulating the at least one actuation mechanism; iii) the second expandable member is coupled to the at least one actuation mechanism and is configured to be moveable relative to the first expandable member upon manipulation of the at least one actuation mechanism; or iii) the second expandable member is configured to mechanically expand or contract by manipulating the at least one actuation mechanism.

Optionally, the handle comprises at least two actuation mechanisms, wherein the first expandable member is coupled to a first of the at least two actuation mechanisms and is configured to be moveable relative to the second expandable member upon manipulation of the first of the at least two actuation mechanisms and wherein the first expandable member is further configured to mechanically expand or contract by manipulating a second of the at least two actuation mechanisms.

Optionally, a first of the at least two actuation mechanisms comprises a first sliding member accessible on an external surface of the handle, wherein the first sliding member is coupled to a first internal member positioned in the lumen and configured to move axially along a length of the handle, and wherein, upon moving the first sliding member, the first internal member moves axially to cause the first expandable member to move relative to the second expandable member.

Optionally, the first internal member is at least one of a wire, tube, or cylinder coupled to a portion of the first expandable member.

Optionally, a second of the at least two actuation mechanisms comprises a second sliding member accessible on an external surface of the handle, wherein the second sliding member is coupled to a second internal member positioned in the lumen and configured to move axially along a length of the handle, and wherein, upon moving the second sliding member, the second internal member moves axially to cause the first expandable member to mechanically expand or contract.

Optionally, the second internal member is at least one of a wire, tube, or cylinder coupled to a portion of the first expandable member.

Optionally, the first sliding member and the second sliding member are positioned adjacent each other and distributed circumferentially around the external surface of the handle.

Optionally, the handle comprises at least three actuation mechanisms, wherein the first expandable member is coupled to a first of the at least two actuation mechanisms and is configured to be moveable relative to the second expandable member upon manipulation of the first of the at least two actuation mechanisms, wherein the first expandable member is further configured to mechanically expand or contract by manipulating a second of the at least two actuation mechanisms, and wherein the second expandable member is further configured to mechanically expand or contract by manipulating a third of the at least two actuation mechanisms.

Optionally, a first of the at least two actuation mechanisms comprises a first sliding member accessible on an external surface of the handle, wherein the first sliding member is coupled to a first internal member positioned in the lumen and configured to move axially along a length of the handle, and wherein, upon moving the first sliding member, the first internal member moves axially to cause the first expandable member to move relative to the second expandable member.

Optionally, the first internal member is at least one of a wire, tube, or cylinder coupled to a portion of the first expandable member.

Optionally, a second of the at least two actuation mechanisms comprises a second sliding member accessible on an external surface of the handle, wherein the second sliding member is coupled to a second internal member positioned in the lumen and configured to move axially along the length of the handle, and wherein, upon moving the second sliding member, the second internal member moves axially to cause the first expandable member to mechanically expand or contract.

Optionally, the second internal member is at least one of a wire, tube, or cylinder coupled to a portion of the first expandable member.

Optionally, a third of the at least two actuation mechanisms comprises a third sliding member accessible on an external surface of the handle, wherein the third sliding member is coupled to a third internal member positioned in the lumen and configured to move axially along the length of the handle, and wherein, upon moving the third sliding member, the third internal member moves axially to cause the second expandable member to mechanically expand or contract. Optionally, the third internal member is at least one of a wire, tube, or cylinder coupled to a portion of the second expandable member. Optionally, the first sliding member, the second sliding member, and the third sliding member are positioned adjacent each other and distributed circumferentially around the external surface of the handle.

Optionally, the first expandable member is coupled to the at least one actuation mechanism and is configured to be moveable relative to the second expandable member upon manipulation of the at least one actuation mechanism while a position of the second expandable member is not affected by the manipulation of the at least one actuation mechanism.

Optionally, the first expandable member is configured to mechanically expand or contract by manipulating the at least one actuation mechanism while a size of the second expandable member is not affected by the manipulation of the at least one actuation mechanism.

Optionally, the second expandable member is coupled to the at least one actuation mechanism and is configured to be moveable relative to the first expandable member upon manipulation of the at least one actuation mechanism while a position of the first expandable member is not affected by the manipulation of the at least one actuation mechanism.

Optionally, the second expandable member is configured to mechanically expand or contract by manipulating the at least one actuation mechanism while a size of the first expandable member is not affected by the manipulation of the at least one actuation mechanism.

Optionally, at least one of the first expandable member or the second expandable member expands upon moving the at least one actuation mechanism distally and wherein said expansion causes at least one of the first expandable member and the second expandable member to transform from a substantially linear configuration to a first shape, second shape or third shape depending on how far the at least one actuation mechanism has been moved distally.

Optionally, the first shape, second shape or third shape is at least one of a spherical shape, an elliptical shape, a conical shape, a polygonal shape, a cylindrical shape, a shape of a stent, a shape of a chalice cup, a shape of an umbrella, a concave shape, a convex shape, a half-sphere shape, a windsock shape, a dumbbell shape, a star shape, or any combination of said shapes.

Optionally, the first shape has a first outer surface and wherein a furthest distance from the first outer surface to the elongated member is defined by a first distance, wherein the second shape has a second outer surface and wherein a furthest distance from the second outer surface to the elongated member is defined by a second distance, wherein the third shape has a third outer surface, wherein a furthest distance from the third outer surface to the elongated member is defined by a third distance, wherein the third distance is greater than the second distance and wherein the second distance is greater than the first distance.

Optionally, the first shape is configured to maintain said first distance even upon an application of a first external force to the first outer surface in a range of 9 newtons to 15 newtons, wherein the second shape is configured to maintain said second distance even upon an application of a second external force to the second outer surface in a range of 9 newtons to 15 newtons, and wherein the third shape is configured to maintain said third distance even upon an application of a third external force to the third outer surface in a range of 9 newtons to 15 newtons.

Optionally, the first shape is configured to collapse upon application of a force that is greater than the first external force, wherein the second shape is configured to collapse upon application of a force that is greater than the second external force, wherein the third shape is configured to collapse upon application of a force that is greater than the third external force, wherein the first external force is less than the second external force which is less than the third external force.

Optionally, upon expansion, at least one of the first expandable member or the second expandable member has an amount of open surface area relative to an amount of total surface area in a range of 1% to 99%.

Optionally, upon expansion, the first expandable member has a greater amount of the open surface area relative to the amount of the total surface area than the second expandable member.

Optionally, the at least one actuation mechanism is a slider, a knob, a lever, a dial or a push button.

Optionally, at least one of the first expandable member or the second expandable member is a braided structure that transforms from a first configuration that is an elongated braided structure positioned circumferentially around and parallel to the elongated member into a second configuration.

Optionally, the second configuration comprises a first braided structure that is defined by a cone having a first curved face that revolves around the periphery of the base at a first end and narrows into a first plurality of points on the elongated member at an opposing end and a second braided structure integrally formed with the first braided structure and defined by a cone having a second curved face that revolves around the periphery of the base at one end and narrows into a second plurality of points on the elongated member at an opposing end, wherein the first plurality of points and second plurality of points are separated along the length of the elongated member.

Optionally, the second configuration is a sphere shape, elliptical shape, a diamond shape, a polygonal shape, or a bicone.

Optionally, at least one of the first expandable member or the second expandable member is configured to expand using the at least one actuation member using no more than one moving member.

In some embodiments, the present specification discloses a clot removal method using a clot removal device, wherein the clot removal device comprises a catheter having a lumen, a proximal end, a distal end, and a length extending between the proximal end and the distal end, an elongated member positioned within the lumen and extending axially from the proximal end to the distal end, a handle attached to the proximal end of the lumen, a first expandable member positioned along a length of the elongated member, and a second expandable member positioned along the length of the elongated member, wherein the handle comprises a first actuation mechanism, a second actuation mechanism, a third actuation mechanism and wherein the second expandable member is distal to the first expandable member relative to the handle, and wherein the method comprises: introducing a wire through a patient and positioning the wire proximate a clot; positioning the catheter into the patient, over the wire, and proximate the clot; extending the second expandable member out of the lumen and into the clot or distal to the clot by manipulating the elongated member; extending the first expandable member out of the lumen and into the clot or proximal to the clot by manipulating the elongated member; using at least one of the first actuation mechanism or the second actuation mechanism, expanding the second expandable member; using at least one of the first actuation mechanism or the second actuation mechanism, expanding the first expandable member; using the third actuation mechanism, axially moving the first expandable member toward an opening in the lumen; using at least one of the first actuation mechanism or the second actuation mechanism, compressing the first expandable member; using at least one of the first actuation mechanism or the second actuation mechanism, compressing the second expandable member; pulling the first expandable member and the second expandable member into the lumen; and removing the catheter from the patient.

Optionally, the method includes axially moving the first expandable member back and forth along said length using the third actuation mechanism.

Optionally, the method includes axially moving the first expandable member toward an opening in the lumen and subsequently applying suction to said lumen using the third actuation mechanism.

Optionally, the method further comprises applying suction to the lumen.

Optionally, the first expandable member is configured to be moveable relative to the second expandable member while the second expandable member remains stationary.

Optionally, the second expandable member is configured to be moveable relative to the first expandable member while the first expandable member remains stationary.

Optionally, the first expandable member is configured to mechanically expand or contract without affecting a size, dimension or shape of the second expandable member.

Optionally, the second expandable member is configured to mechanically expand or contract without affecting a size, dimension or shape of the first expandable member.

In some embodiments, the present specification discloses a medical retrieval device for removal of an occlusion from a lumen in a patient's body comprising: a handle comprising a groove running longitudinally through a length of the handle; a delivery catheter comprising a tip portion coupled to the handle, wherein the handle is configured to steer the tip portion in proximity to the occlusion; an expandable distal element fixedly attached to a distal end of the tip portion, wherein the distal element is configured as a cup; and, a pusher slidably mounted near a proximal end of the tip portion, wherein the pusher is movable relative to the distal element and adapted to remove the occlusion by placement of the occlusion in the cup.

Optionally, the device further comprises a distal element expander coupled with a distal element anchor tube, wherein the distal element expander is slidably fitted into the groove, and wherein sliding the expander in the groove towards the distal element causes the distal element to expand. Optionally, the expander locks in a position in the groove when the distal element has expanded to a maximum diameter.

Optionally, a shape of the pusher ball when expanded is spherical having a maximum diameter of 20 mm.

Optionally, the distal element anchor tube is a Nitinol tube connected to the distal element for aiding in the expansion of the distal element.

Optionally, the device further comprises a pusher ball expander and a pusher ball slider slidably fitted into the groove, wherein the pusher ball expander when moved in the groove towards the pusher causes the pusher to expand; and wherein the pusher ball slider moves synchronously with the pusher ball expander towards the distal element and in an opposing direction towards the handle one or more times for dislodging the occlusion and placing the occlusion in the distal element.

Optionally, a shape of the pusher when expanded is spherical having a maximum diameter of 18 mm.

Optionally, the pusher ball expander locks in a position in the groove when the pusher ball has expanded to a maximum diameter.

Optionally, the tip portion comprises a plurality of flexible elements aiding in the expansion of the distal element and the pusher.

Optionally, the flexible elements comprise four co-axial telescopic tubes movable relative to each other by using the handle, the relative movement causing expansion and compression of the distal element and the pusher.

Optionally, the distal element is rigid and holds a predefined shape after expansion.

Optionally, the handle comprises an aspiration line to aspirate the occlusion after said occlusion is placed in the distal element.

In some embodiments, the present specification discloses a method of removal of an occlusion from a lumen in a patient's body by using a medical retrieval device comprising at least a handle comprising a groove running longitudinally through a length of the handle; a delivery catheter comprising a tip portion coupled to the handle; an expandable rigid anchor fixedly attached to a distal end of the tip; and a pusher ball slidably mounted near a proximal end of the tip, the method comprising: steering the tip in proximity to the occlusion by using the handle; expanding the pusher ball and the rigid anchor; moving the pusher ball longitudinally along the wire one or more times to dislodge the occlusion and capture the occlusion between the pusher ball and the rigid anchor; and removing the captured occlusion by pulling out the pusher ball, occlusion and rigid anchor together from the lumen of the patient.

Optionally, the rigid anchor is a wire mesh structure, and is mechanically expanded.

Optionally, the rigid anchor is anchored at a distal end of the tip and a pusher on the handle of the retriever is used to cause the wire mesh structure to expand out from the delivery catheter running through a center of the rigid anchor.

Optionally, the rigid anchor is fixed in a predefined position allowing for the pusher ball to move back and forth longitudinally on the wire with respect to the rigid anchor to dislodge the occlusion.

Optionally, the rigid anchor is expanded within the occlusion.

Optionally, the rigid anchor is expanded after driving the tip through the occlusion and positioning the rigid anchor distal to the occlusion.

Optionally, the pusher ball is expanded within the occlusion, such that the pusher ball moves all the way into the rigid anchor for capturing the occlusion within the rigid anchor.

Optionally, removing the captured occlusion comprises moving the pusher ball relative to the rigid anchor.

In some embodiments, the present specification discloses a clot removal device comprising: a lumen having a proximal end, a distal end, and a length extending between the proximal end and the distal end; an elongated member positioned within the lumen and extending axially from the proximal end to the distal end; a handle attached to the proximal end of the lumen, wherein the handle comprises at least one actuation mechanism; a first expandable member positioned along a length of the elongated member; and a second expandable member positioned along the length of the elongated member, wherein the second expandable member is distal to the first expandable member relative to the handle and wherein at least one of: the first expandable member is coupled to the at least one actuation mechanism and is configured to be moveable relative to the second expandable member upon manipulation of the at least one actuation mechanism; the first expandable member is configured to mechanically expand or contract by manipulating the at least one actuation mechanism; the second expandable member is coupled to the at least one actuation mechanism and is configured to be moveable relative to the first expandable member upon manipulation of the at least one actuation mechanism; or the second expandable member is configured to mechanically expand or contract by manipulating the at least one actuation mechanism.

Optionally, the handle comprises at least two actuation mechanisms, wherein the first expandable member is coupled to a first of the at least two actuation mechanisms and is configured to be moveable relative to the second expandable member upon manipulation of the first of the at least two actuation mechanisms and wherein the first expandable member is further configured to mechanically expand or contract by manipulating a second of the at least two actuation mechanisms.

Optionally, a first of the at least two actuation mechanisms comprises a first sliding member accessible on an external surface of the handle, wherein the first sliding member is coupled to a first internal member positioned in the lumen and configured to move axially along a length of the handle, and wherein, upon moving the first sliding member, the first internal member moves axially to cause the first expandable member to move relative to the second expandable member.

Optionally, the first internal member is at least one of a wire, tube, or cylinder coupled to a portion of the first expandable member.

Optionally, a second of the at least two actuation mechanisms comprises a second sliding member accessible on an external surface of the handle, wherein the second sliding member is coupled to a second internal member positioned in the lumen and configured to move axially along a length of the handle, and wherein, upon moving the second sliding member, the second internal member moves axially to cause the first expandable member to mechanically expand or contract.

Optionally, the second internal member is at least one of a wire, tube, or cylinder coupled to a portion of the first expandable member.

Optionally, the first sliding member and the second sliding member are positioned adjacent each other and distributed circumferentially around the external surface of the handle.

Optionally, the handle comprises at least three actuation mechanisms, wherein the first expandable member is coupled to a first of the at least two actuation mechanisms and is configured to be moveable relative to the second expandable member upon manipulation of the first of the at least two actuation mechanisms, wherein the first expandable member is further configured to mechanically expand or contract by manipulating a second of the at least two actuation mechanisms, and wherein the second expandable member is further configured to mechanically expand or contract by manipulating a third of the at least two actuation mechanisms.

Optionally, a first of the at least two actuation mechanisms comprises a first sliding member accessible on an external surface of the handle, wherein the first sliding member is coupled to a first internal member positioned in the lumen and configured to move axially along a length of the handle, and wherein, upon moving the first sliding member, the first internal member moves axially to cause the first expandable member to move relative to the second expandable member.

Optionally, the first internal member is at least one of a wire, tube, or cylinder coupled to a portion of the first expandable member.

Optionally, a second of the at least two actuation mechanisms comprises a second sliding member accessible on an external surface of the handle, wherein the second sliding member is coupled to a second internal member positioned in the lumen and configured to move axially along the length of the handle, and wherein, upon moving the second sliding member, the second internal member moves axially to cause the first expandable member to mechanically expand or contract.

Optionally, the second internal member is at least one of a wire, tube, or cylinder coupled to a portion of the first expandable member.

Optionally, a third of the at least two actuation mechanisms comprises a third sliding member accessible on an external surface of the handle, wherein the third sliding member is coupled to a third internal member positioned in the lumen and configured to move axially along the length of the handle, and wherein, upon moving the third sliding member, the third internal member moves axially to cause the second expandable member to mechanically expand or contract.

Optionally, the third internal member is at least one of a wire, tube, or cylinder coupled to a portion of the second expandable member.

Optionally, the first sliding member, the second sliding member, and the third sliding member are positioned adjacent each other and distributed circumferentially around the external surface of the handle.

Optionally, the first expandable member is coupled to the at least one actuation mechanism and is configured to be moveable relative to the second expandable member upon manipulation of the at least one actuation mechanism while a position of the second expandable member is not affected by the manipulation of the at least one actuation mechanism.

Optionally, the first expandable member is configured to mechanically expand or contract by manipulating the at least one actuation mechanism while a size of the second expandable member is not affected by the manipulation of the at least one actuation mechanism.

Optionally, the second expandable member is coupled to the at least one actuation mechanism and is configured to be moveable relative to the first expandable member upon manipulation of the at least one actuation mechanism while a position of the first expandable member is not affected by the manipulation of the at least one actuation mechanism.

Optionally, the second expandable member is configured to mechanically expand or contract by manipulating the at least one actuation mechanism while a size of the first expandable member is not affected by the manipulation of the at least one actuation mechanism.

Optionally, at least one of the first expandable member or the second expandable member expands upon moving the at least one actuation mechanism distally and wherein said expansion causes at least one of the first expandable member and the second expandable member to transform from a substantially linear configuration to a first shape, second shape or third shape depending on how far the at least one actuation mechanism has been moved distally.

Optionally, the first shape, second shape or third shape is at least one of a spherical shape, an elliptical shape, a conical shape, a polygonal shape, a cylindrical shape, a shape of a stent, a shape of a chalice cup, a shape of an umbrella, a concave shape, a convex shape, a half-sphere shape, a windsock shape, a dumbbell shape, a star shape, or any combination of said shapes.

Optionally, the first shape has a first outer surface and wherein a furthest distance from the first outer surface to the elongated member is defined by a first distance, wherein the second shape has a second outer surface and wherein a furthest distance from the second outer surface to the elongated member is defined by a second distance, wherein the third shape has a third outer surface, wherein a furthest distance from the third outer surface to the elongated member is defined by a third distance, wherein the third distance is greater than the second distance and wherein the second distance is greater than the first distance.

Optionally, the first shape is configured to maintain said first distance even upon an application of a first external force to the first outer surface in a range of 9 newtons to 15 newtons, wherein the second shape is configured to maintain said second distance even upon an application of a second external force to the second outer surface in a range of 9 newtons to 15 newtons, and wherein the third shape is configured to maintain said third distance even upon an application of a third external force to the third outer surface in a range of 9 newtons to 15 newtons.

Optionally, the first shape is configured to collapse upon application of a force that is greater than the first external force, wherein the second shape is configured to collapse upon application of a force that is greater than the second external force, wherein the third shape is configured to collapse upon application of a force that is greater than the third external force, wherein the first external force is less than the second external force which is less than the third external force.

Optionally, upon expansion, at least one of the first expandable member or the second expandable member has an amount of open surface area relative to an amount of total surface area in a range of 1% to 99%.

Optionally, upon expansion, the first expandable member has a greater amount of the open surface area relative to the amount of the total surface area than the second expandable member.

Optionally, the at least one actuation mechanism is a slider, a knob, a lever, a dial or a push button.

Optionally, at least one of the first expandable member or the second expandable member is a braided structure that transforms from a first configuration that is an elongated braided structure positioned circumferentially around and parallel to the elongated member into a second configuration.

Optionally, the second configuration comprises a first braided structure that is defined by a cone having a first curved face that revolves around the periphery of the base at a first end and narrows into a first plurality of points on the elongated member at an opposing end and a second braided structure integrally formed with the first braided structure and defined by a cone having a second curved face that revolves around the periphery of the base at one end and narrows into a second plurality of points on the elongated member at an opposing end, wherein the first plurality of points and second plurality of points are separated along the length of the elongated member.

Optionally, the second configuration is a sphere shape, elliptical shape, a diamond shape, a polygonal shape, or a bi-cone.

Optionally, at least one of the first expandable member or the second expandable member is configured to expand using the at least one actuation member using no more than one moving member.

In some embodiments, the present specification discloses a clot removal method using a clot removal device, wherein the clot removal device comprises a catheter having a lumen, a proximal end, a distal end, and a length extending between the proximal end and the distal end, an elongated member positioned within the lumen and extending axially from the proximal end to the distal end, a handle attached to the proximal end of the lumen, a first expandable member positioned along a length of the elongated member, and a second expandable member positioned along the length of the elongated member, wherein the handle comprises a first actuation mechanism, a second actuation mechanism, a third actuation mechanism and wherein the second expandable member is distal to the first expandable member relative to the handle, and wherein the method comprises: introducing a wire through a patient and positioning the wire proximate a clot; positioning the catheter into the patient, over the wire, and proximate the clot; extending the second expandable member out of the lumen and into the clot or distal to the clot by manipulating the elongated member; extending the first expandable member out of the lumen and into the clot or proximal to the clot by manipulating the elongated member; using at least one of the first actuation mechanism or the second actuation mechanism, expanding the second expandable member; using at least one of the first actuation mechanism or the second actuation mechanism, expanding the first expandable member; using the third actuation mechanism, axially moving the first expandable member toward an opening in the lumen; using at least one of the first actuation mechanism or the second actuation mechanism, compressing the first expandable member; using at least one of the first actuation mechanism or the second actuation mechanism, compressing the second expandable member; pulling the first expandable member and the second expandable member into the lumen; and removing the catheter from the patient.

Optionally, the third actuation mechanism is used to axially move the first expandable member back and forth along said length.

Optionally, the third actuation mechanism is used to axially move the first expandable member toward an opening in the lumen and subsequently applying suction to said lumen.

Optionally, the clot removal method further comprises applying suction to the lumen.

Optionally, the first expandable member is configured to be moveable relative to the second expandable member while the second expandable member remains stationary.

Optionally, the second expandable member is configured to be moveable relative to the first expandable member while the first expandable member remains stationary.

Optionally, the first expandable member is configured to mechanically expand or contract without affecting a size, dimension or shape of the second expandable member.

Optionally, the second expandable member is configured to mechanically expand or contract without affecting a size, dimension or shape of the first expandable member.

In some embodiments, the present specification discloses a device for removing an occlusion from a lumen within a patient's body, comprising: a handle having a distal end, wherein the distal end is coupled to a proximal end of a tip portion through one or more telescoping tubes, wherein the handle includes at least one actuation mechanism; and an element mounted at the tip portion, wherein the element is in a first state, wherein the handle is configured to steer the tip portion through the lumen so that the element is positioned within the occlusion, wherein the at least one actuation mechanism is manipulated in a first direction to transition the element from the first state to a second state within the occlusion, and wherein the element in the second state is imparted one or more fore and aft motions to dislodge and scrape the occlusion.

Optionally, the first state corresponds to the element being in a contracted configuration and the second state corresponds to the element being in an expanded configuration.

Optionally, the at least one actuation mechanism includes first and second knobs, wherein the first knob is manipulated to transition the element from the first state to the second state, and wherein the second knob is manipulated to impart the one or more fore and aft motions to the element relative to the tip portion.

Optionally, the handle is moved fore and aft to cause the tip portion and therefore the element to be moved fore and aft.

Optionally, the at least one actuation mechanism includes a knob that is manipulated to transition the element from the first state to the second state.

Optionally, the device further comprises a delivery catheter and an aspiration catheter, wherein the tip portion is positioned within the delivery catheter and the delivery catheter is positioned within the aspiration catheter, and wherein a negative pressure is applied at a proximal end of the aspiration catheter to aspirate the dislodged and scraped occlusion.

Optionally, the at least one actuation mechanism is manipulated in a second direction opposite to the first direction to transition the element from the second state to the first state, and wherein the handle is used to retract the element in the first state from the lumen.

Optionally, the element has proximal, distal and center portions, wherein the proximal portion is shaped as a first funnel having a first neck directed proximally along a longitudinal axis of the tip portion and the distal portion is shaped as a second funnel having a second neck directed distally along the longitudinal axis, wherein respective cup edges of the first and second funnels are attached across a central axis to form the center portion, said central axis lying approximately orthogonal to the longitudinal axis.

Optionally, the element has a three dimensional geometric shape in the second state, and wherein the three dimensional geometric shape is one or a combination of spherical, elliptical, conical, polygonal, cylindrical, stent, chalice cup, umbrella, concave, convex, half-sphere, sphere, windsock, dumbbell, star, polygon, or lever shapes.

In some embodiments, the present specification discloses a method of using a device to remove an occlusion from a lumen within a patient's body, wherein the device comprises a handle coupled to a proximal end of a tip portion through one or more telescoping tubes, and an element mounted on the tip portion, and wherein the element is in a first state, the method comprising: positioning the tip portion through a delivery catheter; positioning the delivery catheter through an aspiration catheter; steering, using the handle, the tip portion through the lumen so that the element is positioned within the occlusion; transitioning, by manipulating at least one actuation mechanism on the handle in a first direction, the element from the first state to a second state; and imparting one or more fore and aft motions to the element in order to dislodge and scrape the occlusion.

Optionally, the first state corresponds to the element being in a contracted configuration and the second state corresponds to the element being in an expanded configuration.

Optionally, the at least one actuation mechanism includes first and second knobs, wherein the first knob is manipulated to transition the element from the first state to the second state, and wherein the second knob is manipulated to impart the one or more fore and aft motions to the element relative to the tip portion.

Optionally, the handle is moved fore and aft to cause the tip portion and therefore the element to be moved fore and aft.

Optionally, the at least one actuation mechanism includes a knob that is manipulated to transition the element from the first state to the second state.

Optionally, the method further comprises applying a negative pressure at a proximal end of the aspiration catheter to aspirate the dislodged and scraped occlusion.

Optionally, the method further comprises: transitioning, by manipulating the at least one actuation mechanism on the handle in a second direction opposite to the first direction, the element from the second state to the first state; and retracting, using the handle, the element in the first state from the lumen.

Optionally, the element has proximal, distal and center portions, wherein the proximal portion is shaped as a first funnel having a first neck directed proximally along a longitudinal axis of the tip portion and the distal portion is shaped as a second funnel having a second neck directed distally along the longitudinal axis, wherein respective cup edges of the first and second funnels are attached across a central axis to form the center portion, said central axis lying approximately orthogonal to the longitudinal axis.

Optionally, the element has a three dimensional geometric shape in the second state, and wherein the three dimensional geometric shape is one or a combination of spherical, elliptical, conical, polygonal, cylindrical, stent, chalice cup, umbrella, concave, convex, half-sphere, sphere, windsock, dumbbell, star, polygon, or lever shapes.

In some embodiments, the present specification discloses a device for removing clot from a lumen within a patient's body, comprising: a handle having a distal end, wherein the distal end is coupled to a proximal end of a tip portion through one or more telescoping tubes, wherein the handle includes at least one actuation mechanism; and an element mounted at the tip portion, wherein the element is in a first state, wherein the handle is configured to steer the tip portion through the lumen so that the element is positioned within the clot, wherein the at least one actuation mechanism is manipulated in a first direction to transition the element from the first state to a second state and from the second state to a third state within the clot, and wherein the element in the second state and/or the third state is imparted one or more fore and aft motions to dislodge and scrape the clot.

Optionally, the second state corresponds to a first radial force that a first size of the element applies to the clot and the third state corresponds to a second radial force that a second size of the element applies to the clot, and wherein the second radial force is different from the first radial force.

Optionally, each of the first and second radial force is in a range of 2 Newtons to 20 Newtons.

In some embodiments, the present specification discloses a method of using a device to remove an occlusion from a lumen within a patient's body, wherein the device comprises a handle coupled to a proximal end of an elongated member through a plurality of telescoping tubes, wherein a distal end of the elongated member has a tip portion mounted with a proximal element and a distal element, and wherein the proximal and distal elements are in a first state, the method comprising: positioning the tip portion through a delivery catheter; positioning the delivery catheter through an aspiration catheter; steering, using the handle, the tip portion through the lumen so that the proximal and distal elements are positioned within or beyond the occlusion; transitioning, by manipulating a first physically manipulable interface on the handle in a first direction, the distal element from the first state to a second state; transitioning, by manipulating a second physically manipulable interface on the handle in a first direction, the proximal element from the first state to a second state; and moving, by manipulating a third physically manipulable interface on the handle, the proximal element fore and aft axially along the tip portion in order to dislodge, curettage and capture the occlusion between the proximal and distal elements; transitioning, by manipulating the first and second physically manipulable interfaces on the handle in a second direction opposite to the first direction, the distal and proximal elements from the second state to the first state; and removing, using the handle, the proximal element, the captured occlusion and the distal element from the lumen.

Optionally, the first state corresponds to each of the proximal and distal elements being in a contracted configuration and the second state corresponds to each of the proximal and distal elements being in an expanded configuration.

Optionally, the method further comprises applying a negative pressure at a proximal end of the aspiration catheter to aspirate at least a portion of the dislodged occlusion prior to removing the proximal element, the captured occlusion and the distal element from the lumen.

Optionally, a length of the delivery catheter is in a range of 80 cm to 160 cm.

Optionally, a length of the delivery catheter is 120 cm.

Optionally, the aspiration catheter is of 16 Fr and has a length in a range of 70 cm to 160 cm or the aspiration catheter is of 20 Fr and has a length in a range of 60 cm to 150 cm or the aspiration catheter is of 24 Fr and has a length in a range of 50 cm to 130 cm.

Optionally, the aspiration catheter is of 16 Fr and has a length of 112 cm or the aspiration catheter is of 20 Fr and has a length 106 cm or the aspiration catheter is of 24 Fr and has a length of 90 cm.

Optionally, the aspiration catheter of 20 Fr has a distal end with a 270° bend.

Optionally, the aspiration catheter of 24 Fr has a flexible distal end.

Optionally, in the second state the distal element has a first diameter and the proximal element has a second diameter, and wherein the first diameter is 16 mm and the second diameter is 20 mm or the first diameter is 5 mm and the second diameter is 20 mm.

Optionally, in the second state each of the proximal and distal elements has an outer diameter ranging from 5 mm to 30 mm, preferably 10 mm to 25 mm, and more preferably 10 mm to 20 mm.

Optionally, in the second state each of the proximal and distal elements has a maximum outer diameter of 16 mm.

Optionally, the delivery catheter is of 9 Fr.

Optionally, a length of the delivery catheter is in a range of 40 cm to 120 cm.

Optionally, a length of the delivery catheter is 80 cm.

Optionally, the aspiration catheter is of 16 Fr and has a length of in a range of 45 cm to 80 cm.

Optionally, the aspiration catheter is of 16 Fr and has a length of 65 cm.

Optionally, in the second state the distal element has a first diameter and the proximal element has a second diameter, and wherein the first diameter is 16 mm and the second diameter is 14 mm.

Optionally, in the second state a diameter of the distal element is 16 mm and a diameter of the proximal element is 8 mm.

Optionally, in the second state each of the proximal and distal elements has an outer diameter ranging from 3 mm to 20 mm.

Optionally, in the second state the proximal element has a maximum outer diameter of 16 mm and the distal element has a maximum outer diameter of 20 mm.

Optionally, a distal end of the handle includes a fourth physically manipulable interface which can be manipulated to increase or decrease a length of the delivery catheter.

In some embodiments, the present specification discloses a method of using a device to remove an occlusion from a lumen within a patient's body, wherein the device comprises a handle coupled to a proximal end of an elongated member through at least one telescoping tube, wherein a distal end of the elongated member has a tip portion mounted with a proximal element and a distal element, and wherein the proximal and distal elements are in a first state, the method comprising: positioning the tip portion through a delivery catheter; positioning the delivery catheter through an aspiration catheter; steering, using the handle, the tip portion through the lumen so that the proximal and distal elements are positioned within or beyond the occlusion; simultaneously transitioning, by manipulating a first physically manipulable interface on the handle in a first direction, the proximal and distal elements from the first state to a second state; and moving the proximal and distal elements fore and aft in order to dislodge and curettage the occlusion; applying a negative pressure at a proximal end of the aspiration catheter to aspirate at least a portion of the dislodged occlusion; simultaneously transitioning, by manipulating the first physically manipulable interface on the handle in a second direction opposite to the first direction, the distal and proximal elements from the second state to the first state; and removing, using the handle, the proximal and distal elements from the lumen.

Optionally, the first state corresponds to each of the proximal and distal elements being in a contracted configuration and the second state corresponds to each of the proximal and distal elements being in an expanded configuration.

Optionally, the proximal and distal elements are moved fore and aft using the handle.

Optionally, the proximal and distal elements are moved fore and aft by manipulating a second physically manipulable interface on the handle.

Optionally, a distance between the proximal and distal elements is fixed and ranges from 2 cm to 3 cm.

Optionally, in the second state each of the proximal and distal elements opens incrementally to one of 20 different sizes, and wherein each of the 20 different sizes is capable of withstanding a same applied pressure in the range of 0 to 25 Newton.

Optionally, the tip portion is guided through the lumen using a guidewire, and wherein the guidewire has a diameter of 0.018 mm.

Optionally, the aspiration catheter is of 7 to 8 Fr and has a length of 135 cm.

Optionally, the elongated member is of 5 Fr and has a length of 145 cm.

The aforementioned and other embodiments of the present specification shall be described in greater depth in the drawings and detailed description provided below.

BRIEF DESCRIPTION OF THE DRAWINGS

The accompanying drawings illustrate various embodiments of systems, methods, and embodiments of various other aspects of the disclosure. Any person with ordinary skills in the art will appreciate that the illustrated element boundaries (e.g. boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another and vice versa. Furthermore, elements may not be drawn to scale. Non-limiting and non-exhaustive descriptions are described with reference to the following drawings. The components in the figures are not necessarily to scale, emphasis instead being placed upon illustrating principles.

FIG. 3 illustrates the expanded or released position of the proximal and distal bodies from the delivery catheter;

FIG. 4 illustrates advancing the proximal body of the retrieval device axially along the delivery wire to trap and compress a thrombus;

FIG. 5 illustrates the removal of a thrombus using the deployed proximal and distal bodies of an embodiment of the retrieval device;

FIG. 15 illustrates an embodiment having an active segment having a section spanning the length of a thrombus, and a delivery segment containing incorporation structure that is suture material between the proximal and distal bodies;

FIG. 16 illustrates an active segment having a section spanning the length of a thrombus, and a delivery segment containing incorporation structure that is collapsible sinusoidal wire material between the proximal and distal bodies;

FIG. 27 illustrates removal of the thrombus using the access catheter containing suction;

FIG. 29A is a perspective view of a retrieval device with contracted/unexpanded distal and proximal elements, in accordance with an embodiment of the present specification;

FIG. 29B is a perspective view of the retrieval device of FIG. 29A with expanded distal and proximal elements, in accordance with an embodiment of the present specification;

FIG. 29C is a perspective view of the retrieval device of FIG. 29A with flexible elements between the distal and proximal elements retracted to reduce the distance between the distal and proximal elements, in accordance with an embodiment of the present specification;

FIG. 33A is a side elevation view of a tip portion of a retrieval device with a bag covering the tip portion, in accordance with some embodiments of the present specification;

FIG. 33B is a side elevation view of a tip portion of FIG. 33A with the bag pulled away to uncover the tip portion, in accordance with some embodiments of the present specification;

FIG. 33C is a side elevation view of a tip portion of FIG. 33B with the bag pulled back to cover the tip portion, in accordance with some embodiments of the present specification;

FIG. 34A is a side elevation view of proximal and distal elements of a tip portion in unexpanded states, in accordance with some embodiments of the present specification;

FIG. 34B is a side elevation view of proximal and distal elements of the tip portion of FIG. 34A in expanded states, in accordance with some embodiments of the present specification;

FIG. 37A shows a first stage in a procedure of removing a clot in a nerve vessel using a retrieval device, in accordance with some embodiments of the present specification;

FIG. 37B shows a second stage in the procedure of removing the clot in the nerve vessel using the retrieval device, in accordance with some embodiments of the present specification;

FIG. 37C shows a third stage in the procedure of removing the clot in the nerve vessel using the retrieval device, in accordance with some embodiments of the present specification;

FIG. 37D shows a fourth stage in the procedure of removing the clot in the nerve vessel using the retrieval device, in accordance with some embodiments of the present specification;

FIG. 37E shows a fifth stage in the procedure of removing the clot in the nerve vessel using the retrieval device, in accordance with some embodiments of the present specification;

FIG. 37F shows a sixth stage in the procedure of removing the clot in the nerve vessel using the retrieval device, in accordance with some embodiments of the present specification;

FIG. 38 is a flowchart of a plurality of exemplary steps of retrieving an occlusion by using the retrieval device of FIGS. 37A through 37F, in accordance with some embodiments of the present specification;

FIG. 40B shows first, second and third views of the first conventional device shown in FIG. 40A being sequentially retracted from a hot dog;

FIG. 40C shows first, second and third views illustrating a comparison of thrombectomy capabilities of the conventional devices and the retrieval device of the present specification;

DETAILED DESCRIPTION

Figure 1:
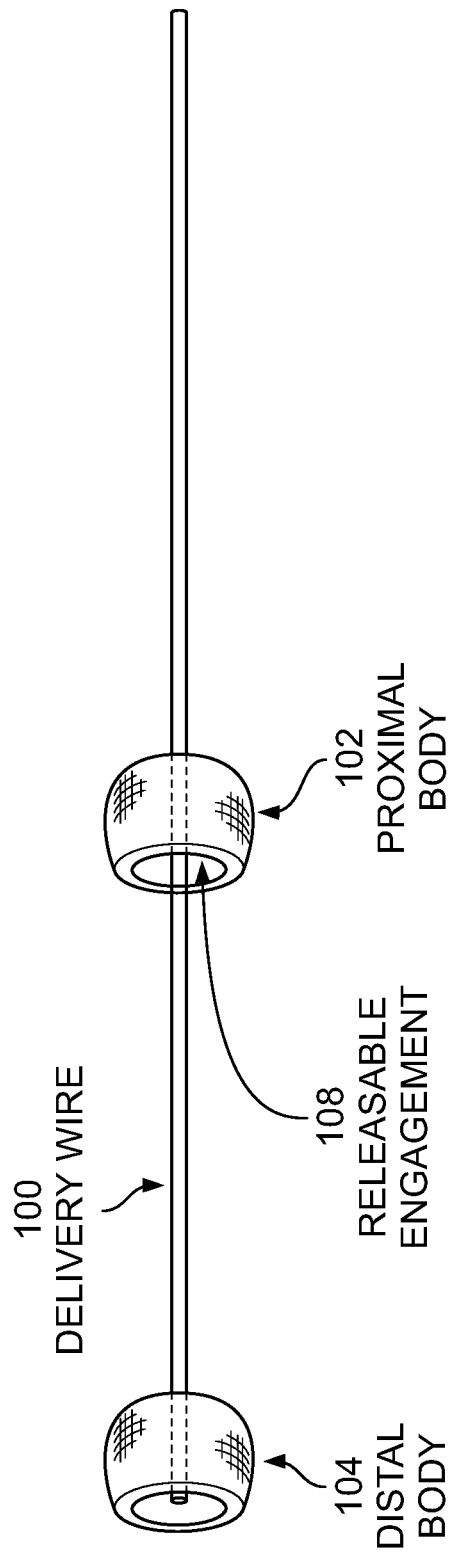
FIG. 1 illustrates a deployment stage of an embodiment of the retrieval device, showing the proximal and distal bodies deployed on a delivery wire.

In various embodiments, the retrieval devices of the present specification may be a catheter-delivered tool used to remove a foreign body, such as a thrombus or clot, from an artery, vein, nerve, duct, or other interior physical space. The retrieval device may be interchangeably referred to herein as "the device" or a "removal device", the "removal" or "retrieval" of the foregoing may be modified by a variety of terms such as "thrombus," "occlusion," "foreign body," etc. The retrieval device may be used as a foreign body retriever and as a thrombectomy device in the arterial, venous and neural systems. The device may be used in the vascular system and in non-vascular structures such as ureters, ducts, airways, and any other accessible space that contains a material (biologic or foreign) that necessitates removal or retrieval.

In various embodiments, the retrieval devices of the present specification are configured to be used in: all venous structures including dural venous sinuses, coronary arteries, cardiac chambers, all arteries, all ducts, ureters, urethra and fistulas.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise", "include", "have", "contain", and forms thereof, are not necessarily limited to members in a list with which the words may be associated. Thus, they are intended to be equivalent in meaning and be open-ended in that an item or items following any one of these words is not meant to be an exhaustive listing of such item or items, or meant to be limited to only the listed item or items. It should be noted herein that any feature or component described in association with a specific embodiment may be used and implemented with any other embodiment unless clearly indicated otherwise.

It must also be noted that as used herein and in the appended claims, the singular forms "a," "an," and "the" include plural references unless the context dictates otherwise. Although any systems and methods similar or equivalent to those described herein can be used in the practice or testing of embodiments of the present disclosure, the preferred, systems and methods are now described.

The term "clot", "occlusion", "blockage", or "thrombus" shall each be used to refer to material in a patient's veins or arteries that is blocking the flow of blood or material in any of a patient's anatomy that is blocking the flow of any fluid, such as urine.

It should be appreciated that each of the embodiments disclosed herein may be used in one or more of the following medical procedures: a) septal heart repairs in which a catheter is manipulated to the patient's heart in order to permanently place two connected patches in a hole to cover both the left and right atrial sides, b) pulmonary embolisms in which a catheter is manipulated proximate a blood clot that is lodged in an artery in the lung thereby blocking blood flow to part of the lung, c) deep vein thrombosis in which a catheter is manipulated proximate a blood clot that is lodged in a vein, often in the patient's legs, thereby blocking blood flow, d) repairing fistulas, e) removing fistula thrombus, f) removing stones from the patient's gastrointestinal system, g) removing stones from the patient's genitourinary system, h) removing foreign bodies from any location in the patient's body, or i) filter thrombus removal.

FIG. 1 depicts the deployed retrieval device with a distal body 104, which in this embodiment is a body mounted to the delivery wire 100 such that it remains in a fixed position. Referring to all embodiments disclosed herein, it should be noted that prior to deployment of the delivery wire 100, a guide wire may be used to position any element of the system disclosed herein, including a delivery catheter 202, guide catheter 204, and delivery wire 100 into the preferred position within a vessel or other interior. The "bodies" referred to herein may be a mesh, and they may be made of nitinol or other suitable expandable biocompatible material. The mesh construct of the distal 104 and proximal 102 bodies may reduce the risk of distal embolization of portions of a clot since the mesh construct may capture embolic material within its interstices. The distal body 104 may, in embodiments, have differently-sized mesh or may comprise a selectively permeable material, or it may be non-permeable. A proximal body 102 is also shown. The proximal body 102 is mounted to the delivery wire 100 and is temporarily affixed thereto such that it remains in a fixed position. The temporary affixed aspect referred to above is releasable such that upon release the proximal body 102 may move along the wire, which is referred to herein as "axial movement" along the wire, while remaining engaged to the wire 100. This aspect is referred to as being in "releasable engagement" or being "releasably engaged" to the delivery wire 100. Such releasable engagement may be achieved, for example, by using breakable connection 108, which in embodiments, may be an electrolytically or heat removable/disconnectable connection or mechanical connection that can be selectively disconnected by the clinician. In the case of an electrolytically or heat removable/disconnectable connection, for example, the clinician may apply a current to the connection, (in embodiments via the wire which may be conductive) wherein the electrical current breaks or melts the connection. The connection may include, without limitation, a breakable connection 108, linking a proximal body 102 to the delivery wire 100, that may be eroded and/or disintegrated through the application of electrical current. The breakable connection 108 may be preloaded onto the retrieval device in order to secure the proximal body 102 in a preferred location and/or configuration. The breakable connection may have a plurality of shapes and designs, including but not limited to a straight post extending from the delivery wire 100 to the proximal 102 or other body, a loop configuration of the breakable connection passing through the material of the proximal 102 or other body, and/or a "nail" configuration in which a straight post extends from the delivery wire to the proximal 102 or other body, wherein the post has an enlarged end, or nail head, within the body that may be eroded by the application of electric current to release the body. Embodiments of the present invention include a proximal 102 or other body that may be secured to the delivery wire 100 using more than one breakable connection 108. In an example, a proximal body 102 may be secured with multiple breakable connections, each having a different length and a different release threshold, allowing the breakable connections to be sequentially released. In embodiments, more than one proximal body may be secured to the delivery wire 100 using a breakable connection 108. Melting of a breakable connection may be caused by the application of electrical current, fluid, and/or chemical compounds. Melting may occur in a physical member that is used to secure the proximal or distal body and/or may occur within an adhesive that binds the physical member to the proximal, and/or the delivery wire 100. Breakable connection techniques and methods, including but not limited to those shown in U.S. Pat. Nos. 5,683,451, 5,855,578, 6,245,076, 8,273,116. and U.S. patent applications 20070100414A1, 20090062726A1, and 20100268251A1, may be used to release a proximal body and/or distal body, as described herein. In the case of a mechanically breakable connection, the breakable connection 108 may be made of a suture, brace, thread or other material that is able to be broken upon application of force to the breakable connection 108. In embodiments, the distal motion of a catheter, such as the delivery catheter, with a force above the threshold holding force of the breakable connection 108 may cause the connection 108 to break or release, thus allowing the body 102 to move along the wire in the manners described herein. The "bodies" referred to herein may be of various geometric shapes including a disc or sphere. In embodiments, the distal body 104 and/or proximal body 102 may be an inflatable device, including but not limited to an inflatable balloon. In embodiments, a retrieval device, as described herein, may include a distal body 104 and a proximal body 102 made of differing materials, for example a proximal body 102 may be an inflatable balloon and a distal body 104, on the same retrieval device, may be made of a mesh material. In embodiments, by adjusting the manufactured radial force, body diameter, and strength of the bodies, foreign body extraction, as described herein, may also be used for the removal of stones, pulmonary emboli, or some other type of obstruction. In embodiments, a proximal and/or distal body may have variable radial force, or stiffness across sub-regions of the body itself. For example, the upper hemisphere of a spherical body may have a difference radial force characteristic than the lower hemisphere of the body. In embodiments, the proximal and distal bodies may be substantially the same. In other embodiments, the proximal and distal bodies may be heterogeneous, having different compositions and characteristics including, without limitation, shape, size (e.g., thickness, diameter), configuration, pore size (e.g., mesh pore size), coating, or some other differing characteristic. In embodiments, the proximal and/or distal bodies may have anti-platelet, or some other type of, coatings to reduce adhesion and provide a less thrombogenic environment during clinical application. The proximal and/ or distal bodies, and any material (e.g., wires) between these bodies, may be coated with control release agents including, but not limited to, thrombolytic agents.

The "delivery wire" 100 referred to herein may be a wire or a hypo tube. The delivery wire 100 may not require a coaxial system of catheters as disclosed herein in embodiments.

The "delivery catheter" 202 referred to herein may be referred to as a microcatheter, and may form a plurality of shape configurations based on the clinical application in which it is used, for example, which type of vessel the delivery catheter is used within, the vessel size, the vessel shape, or some other application characteristic. In embodiments, a delivery wire and/or hypo tube may be used within a microcatheter. For purposes of this disclosure, the microcatheter 202 is commonly called a "delivery catheter", although it should be understood that the terms can be used interchangeably.

Figure 2:
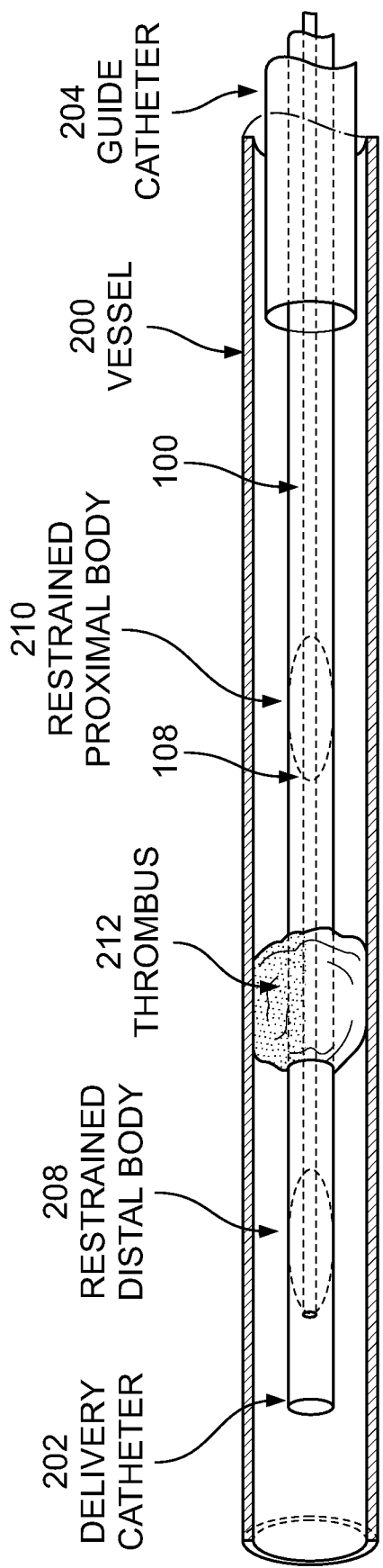
FIG. 2 illustrates the pre-deployment stage of the proximal and distal bodies, where the proximal and distal bodies are restrained or unexpanded.

Referring to FIG. 2, prior to deployment of the distal 208 and proximal 210 bodies (which are shown as being restrained or in their unexpanded form and thus having different reference numerals from the FIGS. 1, and 3-5) the delivery catheter 202 surrounds the delivery wire and restrains both bodies 208, 210. In embodiments, a guide catheter 204 is navigated into place, in embodiments, over a guide wire, said guide wire in some embodiments being removed. The delivery catheter 202 may be passed through an object, such as a thrombus or clot 212, the bodies 208, 210 may be released from the delivery catheter 202 either by retracting the delivery catheter 202 or advancing the wire 100, such that expandable bodies are no longer restrained by the delivery catheter 202. The distal body 104 remains fixed to the delivery wire 100, but the proximal body 102 (once released from its releasable engagement) can freely move along its axis and longitudinally along the delivery wire 100 when pushed by the delivery catheter 202. Also, the delivery wire 100 "pushing" the body (210 or 102 once expanded) must be understood as relative pushing. That is, the retraction of the delivery wire 100 while the delivery catheter 202 is kept in place may serve to move the proximal body 102 axially along the wire. The term "pushing" as is used herein will refer to both forms of movement mentioned above. Once the proximal and distal bodies are positioned adjacent to both sides of the clot (which has been referred to herein as "surrounded" or "surrounding" the clot) by movement of the proximal body 102, the clot may be removed by retrieving the device from the cavity and pulling the clot free. The terms "clot," "thrombus," "occlusion," "occlusive substance" and "foreign body" may be used interchangeably herein.

In embodiments, the freedom of movement of the proximal body 102 on the delivery wire 100 axially may allow for the compression of the occlusive substance and obviate the need for pre-measuring or estimating the required distance between the distal and proximal bodies prior to entering the vessel 200; sizing may take place in situ within the vessel 200 upon the interventionist encountering it.

In embodiments of the present disclosure, the retrieval device may consist of a distal body 104 and a proximal body 102, each of which in embodiments may be collapsible geometric forms. Although the distal and proximal bodies are presented for diagrammatic purposes as spherical, the distal and proximal bodies may also be other geometric forms such as a disc, cone, oblong-shaped form, etc. As mentioned above, the distal and proximal bodies may be a mesh in structure. The mesh cell size may be manufactured to have different sizes based on factors such as the expected properties of the target foreign matter to be removed, such as the density of the matter. The distal body 104 is mounted on a delivery wire 100 such that it remains fixed. In embodiments, the mounting of the proximal body 102 occurs by running the wire through one of the mesh opening. In other embodiments, the proximal body 102 itself may have an opening through which the wire may pass. In either case of mounting the proximal body 102, the body is able to slide along the wire in an axial direction along the wire. This may be referred to herein as "slidably mounted". In some embodiments, the distal body 104 may be slidably mounted in the way described above. As described above, the proximal body may be detachable (thus releasably engaged) using mechanical, electrolytic or some other type of control release format. In embodiments, the proximal body 102 will be slidable along the wire one released while the distal body 104 remains fixed. In other embodiments, both the proximal and distal bodies may be releasably engaged and thus slidable or movable along the delivery wire 100. Still in other embodiments, the proximal body 102 may be comprised of multiple bodies, and the distal body 104 may be comprised of multiple bodies. The mesh material of the distal and proximal bodies may have advantages over other material types, including but not limited to inflatable balloons. Inflatable material may be susceptible to rupture, such as that caused by over inflation. The clinical setting may also be associated with complications related to the use of inflatable balloons within a lumen. For example, a calcified thrombus may increase the risk of balloon rupture. In another example, if an occlusion itself includes metallic material, this may also increase the risk of rupture or other malfunction of an inflatable balloon. Rupture of a balloon may in turn increase the risk of an air embolus forming within the vessel or cavity of intervention. In embodiments, the mesh material of the distal and proximal bodies may allow for the bodies to expand upon release to the diameter and configuration of the cavity in which it is placed, such as a vessel 200 in which a thrombus 212 is located. Such meshes may be made of a shape memory substance such as nitinol. For example, a body made of nitinol mesh may expand to a first dimension outside of a vessel 200 or catheter, but may be designed to expand to a continuum of smaller dimensions than the first dimensions corresponding to different lumen sizes. In this way the bodies may fit the unique variations in diameter found in a lumen at the point of release and/or point of placement near an occlusion, such as a thrombus. Mesh material may also allow for improved distal flow during an intervention. The irregularity and/or texture of the expanded mesh material may facilitate the mesh material becoming entangled or otherwise incorporated with a clot or occlusive substance, thereby increasing adhesion of the distal and/or proximal body with the occlusion and facilitating its removal.

In embodiments, when the proximal body 102 is released, it may be free to move/slide on its axis along the delivery wire 100 in a longitudinal and/or rotational fashion. Referring to FIG. 3 when the distal body 104 is placed distal to the target thrombus 212 for retrieval and the proximal body 102 is placed proximal to the thrombus 212, the distal and proximal bodies will straddle and contain the thrombus 212 intended for removal from the vessel. The proximal body 102 may now be advanced in the direction of the thrombus 212 in a variety of mechanical fashions. As shown in FIG. 4, a coaxially placed microcatheter, also referred to herein as a "delivery catheter" 202, may be pushed forward (once the proximal body is released) and used to physically advance the proximal body 102 to ultimately capture and compress the thrombus 212. Alternatively, the delivery catheter 202 may be used to hold the proximal body 102 in a fixed position while the delivery wire 100 is withdrawn thus moving the fixed distal body 104 towards the proximal body 102 and ultimately capturing and compressing the thrombus 212. As shown in FIG. 5, once the thrombus 212 is captured/compressed between the distal body 104 and the proximal body 102, the entire retrieval device may be removed from the patient via withdrawal of the delivery wire 100 by, for example, withdrawing the proximal and distal bodies with the compressed material back to, and against, the delivery catheter and then removing the delivery catheter, bodies and compressed material through the guide catheter. Once this is removed, the guide catheter may be withdrawn from the vessel.

Figure 6:
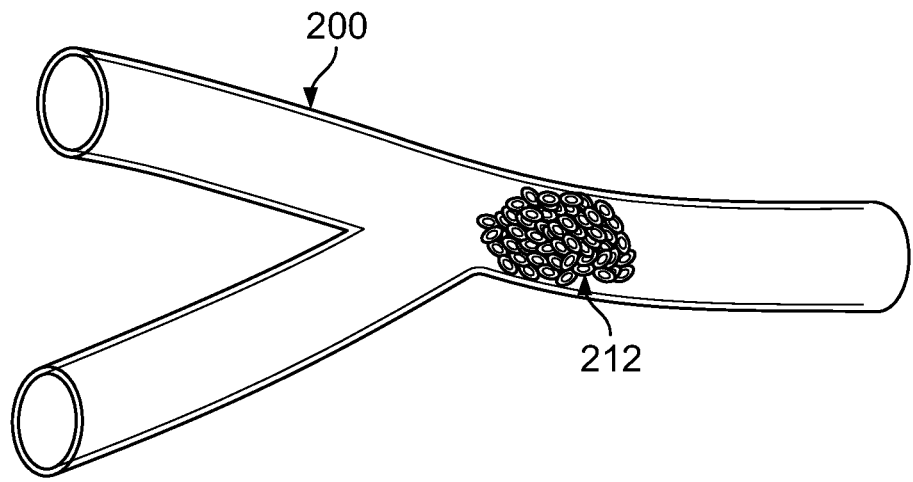
FIG. 6 illustrates a deployment stage of an embodiment of the retrieval device, further showing a thrombus lodged in an artery.
Figure 7:
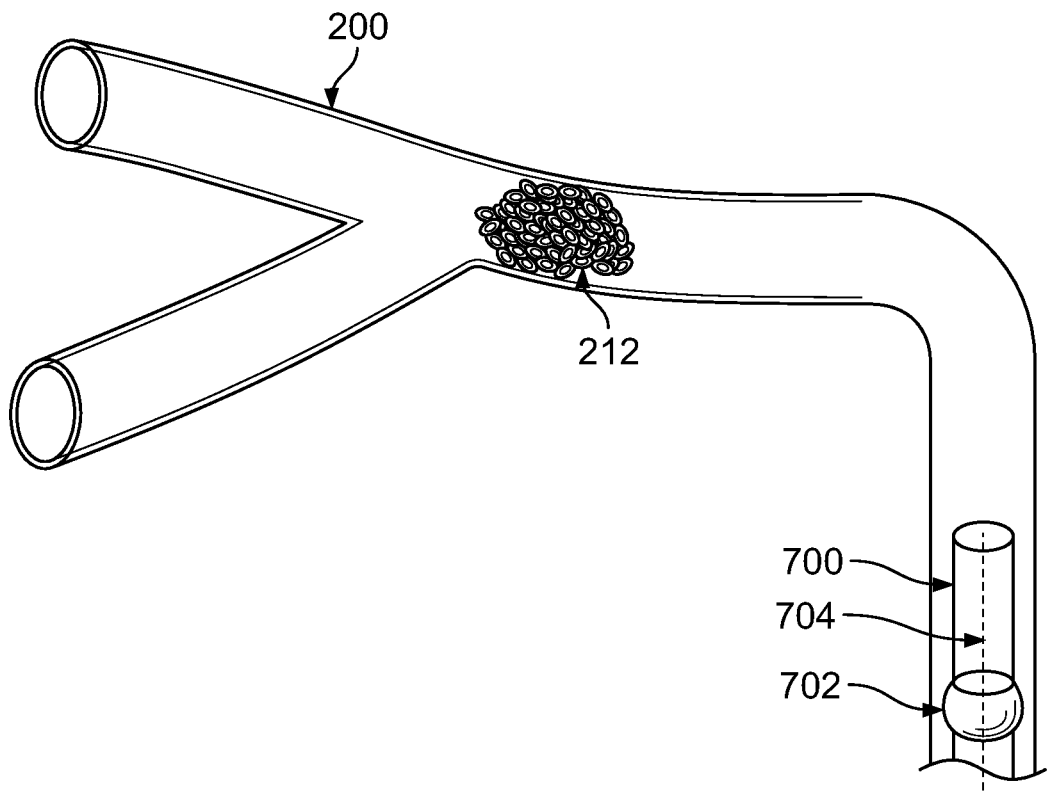
FIG. 7 illustrates a deployment stage of an embodiment of the retrieval device, further showing a guide catheter.
Figure 8:
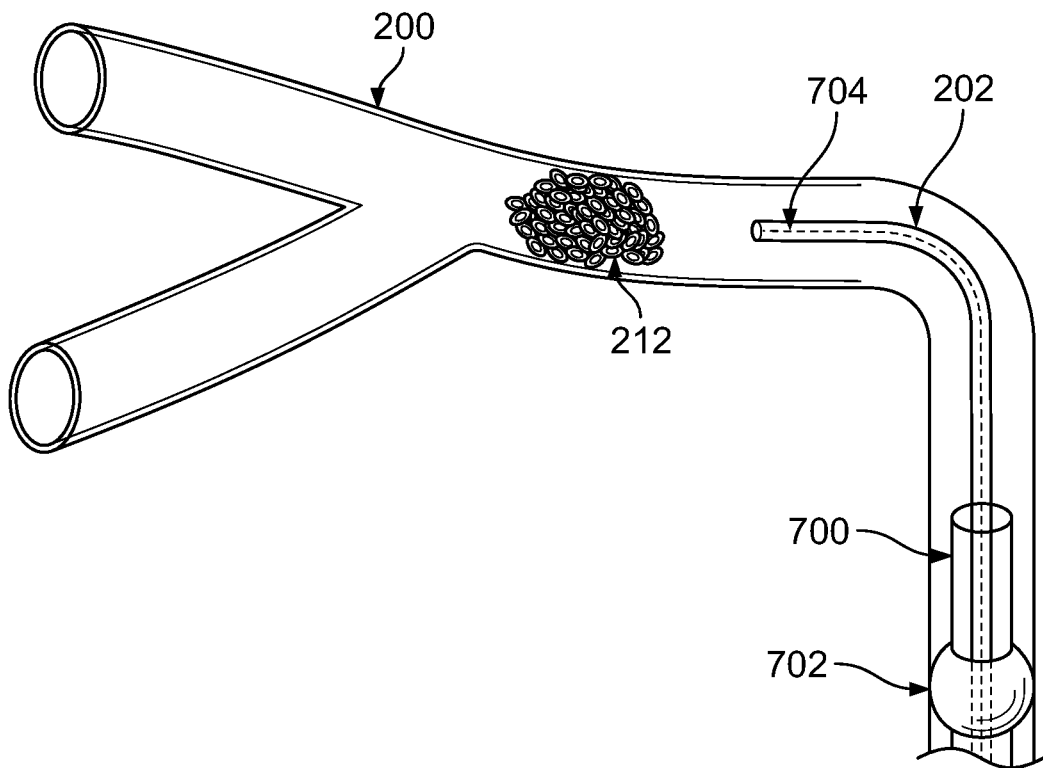
FIG. 8 illustrates the guide catheter of FIG. 7 with balloon inflated thus arresting anterograde blood flow through vessels.
Figure 9:
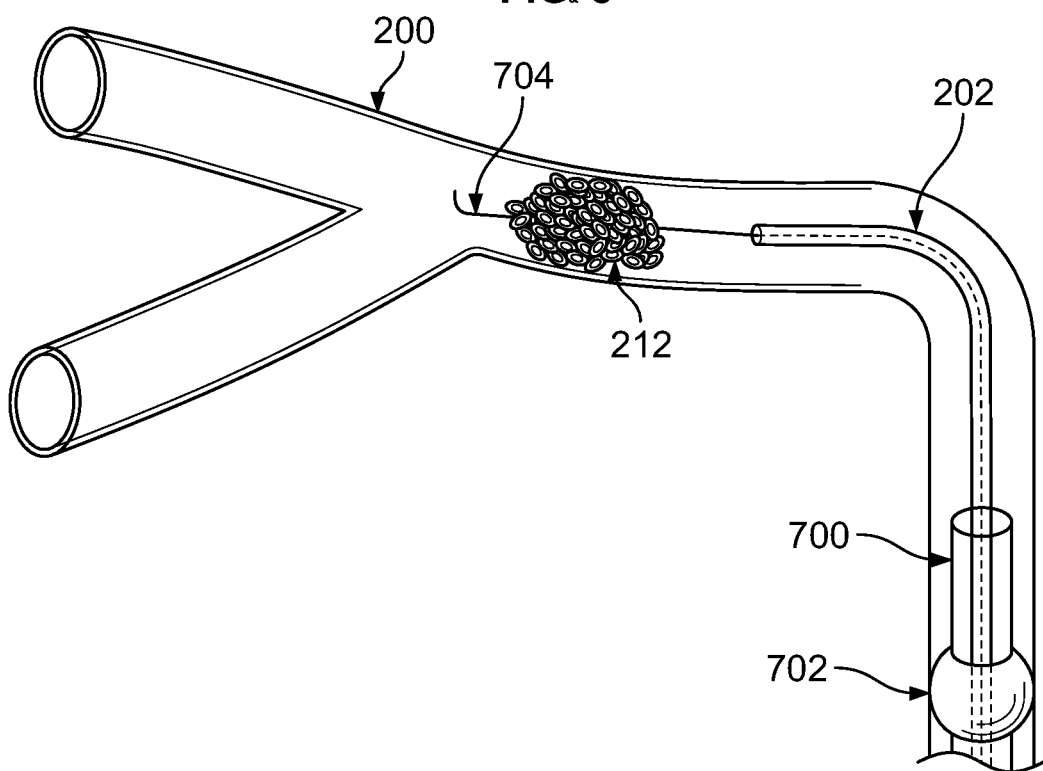
FIG. 9 illustrates a delivery catheter positioned proximal to the thrombus with the delivery wire across the thrombus.
Figure 10:
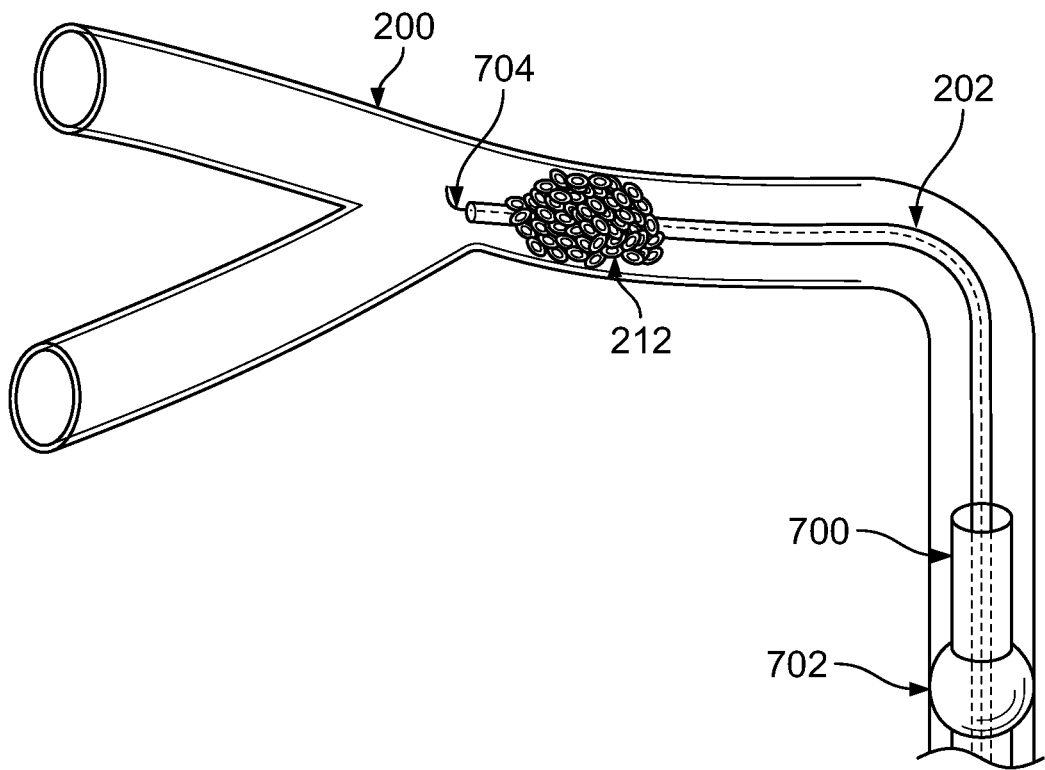
FIG. 10 illustrates a delivery catheter advanced over the delivery wire and across the thrombus.
Figure 11:
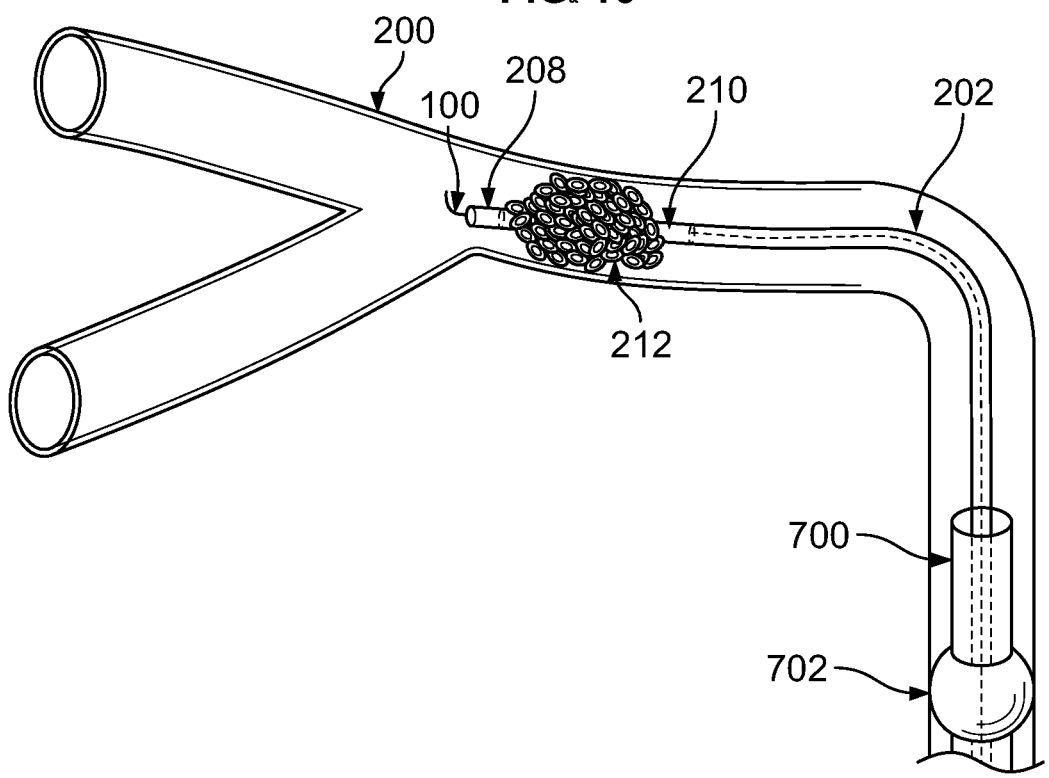
FIG. 11 illustrates the retrieval device advanced through the delivery catheter and positioned, with the bodies still restrained, proximal and distal to the thrombus.
Figure 12:
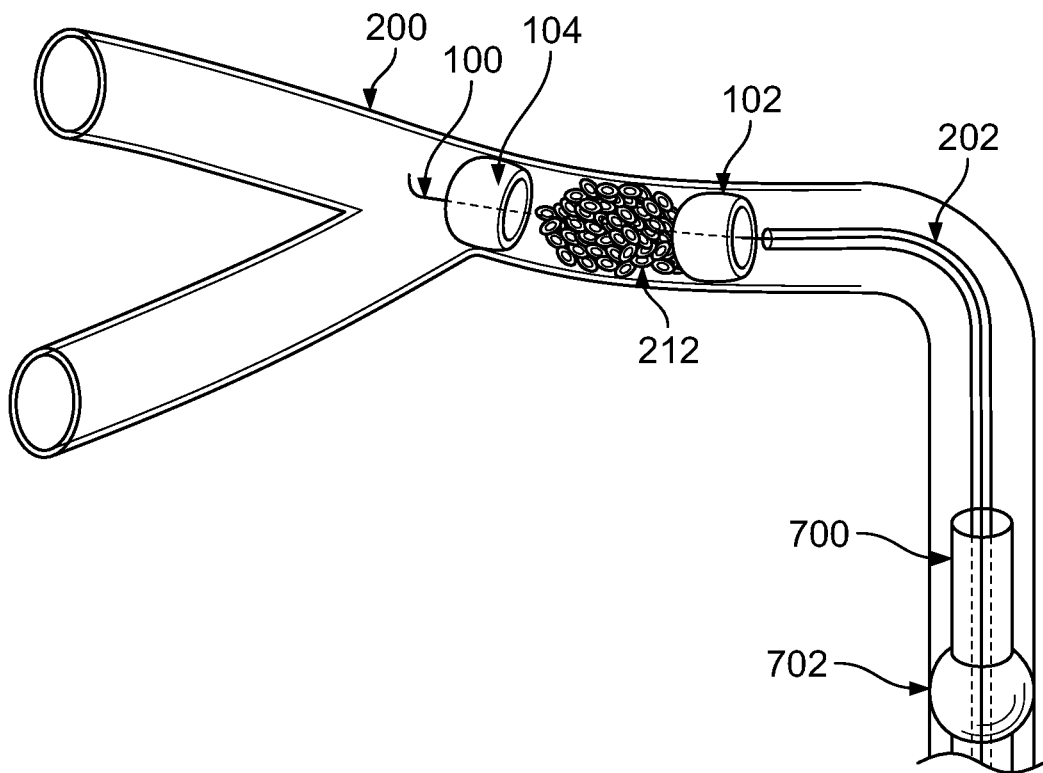
FIG. 12 illustrates the delivery catheter withdrawn proximally thus deploying the proximal and distal mesh bodies proximal and distal to the thrombus.
Figure 13:
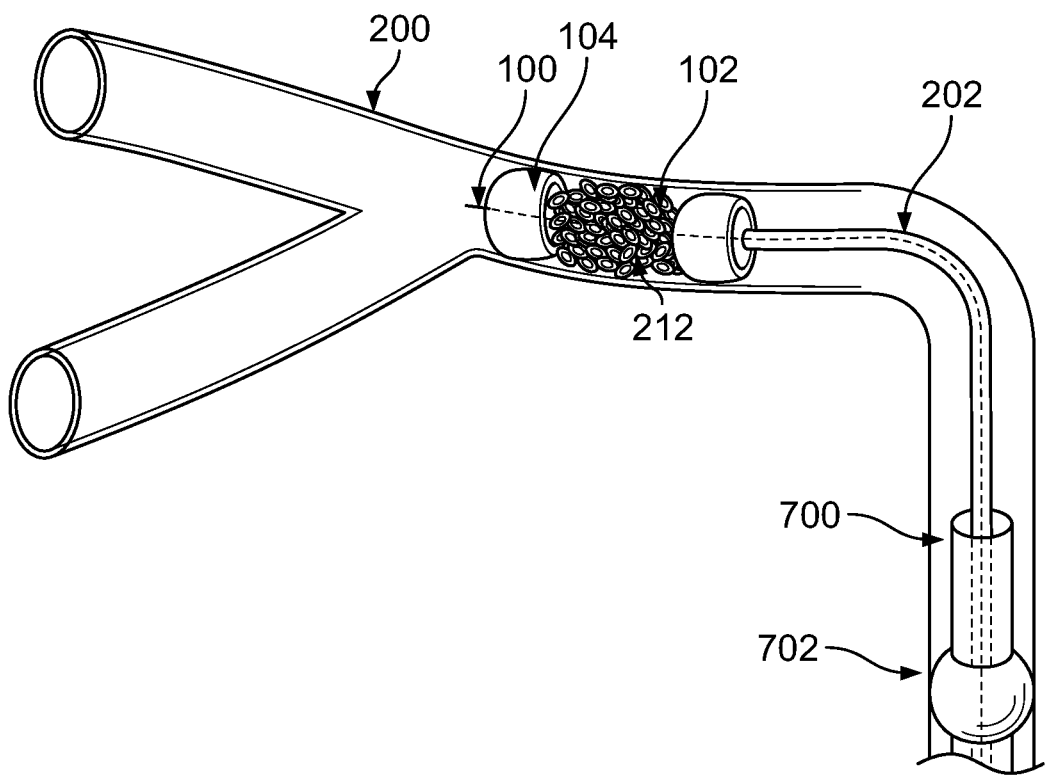
FIG. 13 illustrates the proximal body released from its engagement with the delivery wire and advanced axially along the delivery wire by advancing the delivery catheter to trap and compress the thrombus between the proximal and distal bodies.
Figure 14:
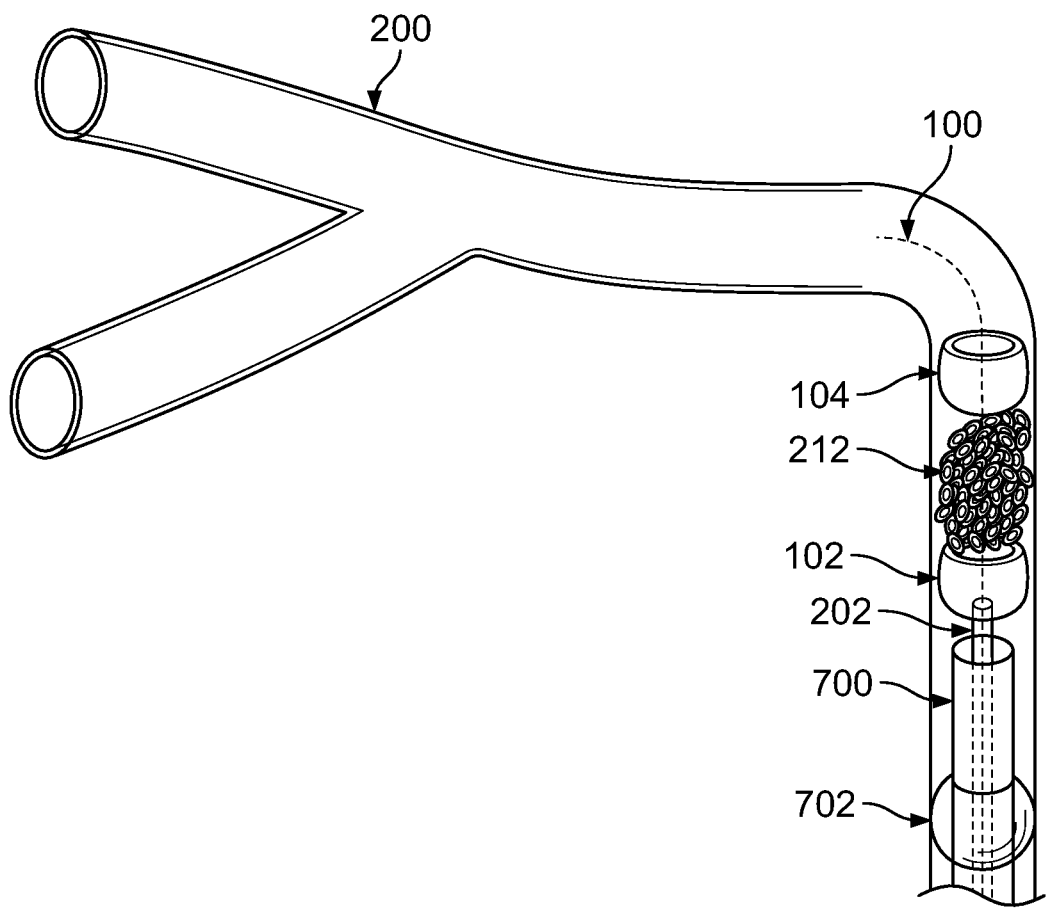
FIG. 14 illustrates the delivery catheter with the bodies and compressed thrombus being removed as a single unit while suction is applied to the guide catheters.

In embodiments of the present disclosure, the retrieval device may be employed as part of the removal of an occlusive object or substance from a human vessel, such as performing arterial thrombectomy. This procedure may include the following generalized steps. FIG. 6 shows an occlusion in the proximal left internal carotid artery (ICA). FIG. 7 shows an embodiment having a guide catheter 700 with a balloon 702 ("balloon catheter"). In embodiments, suction may be applied through the guide catheter 700, in effect utilizing the guide catheter 700 as a suction catheter, as a given intervention may require. The balloon 702 is deflated an inserted into the ICA over a guide wire 704. FIG. 8 shows a delivery catheter 202 advanced through the balloon catheter over the guide wire 704, which has been advanced. FIG. 9 shows a guide wire 704 being advanced through and distal to the occlusion 212. FIG. 10 shows the delivery catheter 202 being advanced through and distal to the occlusion over the guide wire 704. The guide wire 704 is then removed (not shown) and FIG. 11 shows the retrieval device (delivery with distal 208 and proximal 210 bodies mounted on a delivery wire 100 as described herein) inserted into the delivery catheter 202 and still retrained (unexpanded) in the delivery catheter 202. In FIG. 12 the delivery catheter 202 has been withdrawn (moved relative to the delivery wire 100) such that the proximal 102 and distal 100 bodies expand on either side of the occlusion 212. The proximal body 102 having been released is then advanced distally (shown in FIG. 13) by force of the delivery catheter 202 (either by pushing the delivery catheter 202 or by pulling the delivery wire 100 while restraining the position delivery catheter 202). FIG. 14 shows withdrawal of the retrieval device from the ICA, balloon 702 still inflated to arrest anterograde flow.

The retrieval device may remove both organized and unorganized thrombi since, in embodiments, the bodies of the retrieval device do not need to be incorporated into the thrombus 212 to affect its removal. The retrieval device may also remove calcified, atherosclerotic material since, in embodiments, the bodies of the retrieval device do not need to be incorporated into the material to affect its removal. The retrieval device may be used centrally and peripherally by selecting the appropriate diameter and characteristics of the bodies, such as appropriate radial force or stiffness, appropriate shape, whether the bodies are substantially identical or homogenous, mesh opening size in the bodies, and the like.

The methods, system and apparatus, as described herein, may have a plurality of sizes loaded within a common catheter, and a clinician may self-load, for example, different and/or additional proximal bodies, as described herein, rather than having to fully replace a deployed catheter for a second catheter-based device and system. This may reduce manufacturing costs and improve intervention efficiency.

FIGS. 15 and 16 show embodiments having a structure to incorporate into the thrombus 212, referred to herein as an "incorporation structure". In some embodiments, the incorporation structure is part of the delivery wire 100, in others it is separate. Referring to FIGS. 15 and 16, the delivery wire 100 (which in all embodiments disclosed herein may be a hypo tube) comprises a segment having characteristics different from that of the main segment of the delivery wire 100, or a structure mounted to the delivery wire 100 that may expand. In the case where the incorporation structure is part of the delivery wire 100, the segment will be referred to herein as the "active segment" while the remainder of wire will be referred to as the "delivery segment". The active segment is the segment having a section intended to span the length of the thrombus 212. In embodiments, the active segment comprises a cross-sectional shape that differs from the delivery segment. In embodiments, the delivery segment contains a suture material 1500 between the proximal 102 and distal 100 bodies. The suture material 1500 gathers and moves along the delivery wire 100 as the proximal body 102 is advanced. Once the proximal body 102 is in position, the suture material 1500 will be gathered in the area between the two bodies which will enhance incorporation characteristics of the active area. Note that the active area in the above example is the area between the two bodies, which in this case, has suture material 1500 gathered therebetween. As mentioned above, in embodiments the incorporation structure can be an additional expandable structure between the proximal 102 and distal 100 bodies that expands and incorporates into the thrombus 212. The incorporation structure may comprise other mechanisms to enhance thrombus-incorporation, such as flanges, hooks, sutures, sinusoidal wire 1600, or some other material configuration.

In embodiments, the delivery wire 100 may include a distal body 104 that may be affixed, mounted, adhered or otherwise connected to a delivery wire 100 or hypo tube as described herein. Prior to deployment, such as a thrombectomy, the distal body 104 may be affixed, mounted, adhered or otherwise connected to the delivery wire 100 or hypo tube in a collapsed or compressed state. Compression of the distal body 104 may be provided by the delivery catheter 202, and/or multiple catheters which surround the distal body 104 and delivery wire 100 (as described herein). Once the delivery catheter 202 is inserted through an object, such as a thrombus, the distal body 104 may be released from inside the delivery catheter 202 as described herein, thus expanding. Following removal of the delivery catheter 202, suction may be applied to the thrombus or other blockage. (It is to be noted that a suction step, as described herein, may be applied to any of the embodiments of this disclosure, and may be applied through the guide catheter, access catheter, specialized suction catheter, or some other type of catheter). In an example, the Seldinger technique may be initiated using a large bore suction catheter that is advanced over the delivery wire 100 (or a guide wire) and positioned proximal to the thrombus 212, with the distal body 104 distally positioned to the thrombus. Suction may be applied to remove all or a portion of the thrombus. The positioning of the distal body 104, on the distal side of the thrombus, may be used to retract the thrombus in the direction of the suction device, thereby increasing the effectiveness of the suction device in removing the thrombus. The distal body 104 may also provide distal protection from distal embolization during the suction device's placement and/or during the suctioning procedure. Note that in the above example, a proximal body has not yet been included in the procedure. There are situations and thus embodiments where an optional proximal body 102 may be added to the procedure, for example, by slidably mounting a proximal body 102 to the delivery wire 100. As such, in embodiments the inclusion of a proximal body 102 is optional.

In some clinical scenarios the suction procedure may result in only a partial removal of the thrombus 212 or other obstruction. In such scenarios, mechanical removal of the thrombus 212, using a distal body and an added proximal body 102, may be advantageous and/or required. Following the application of suction within the guide catheter 700, a proximal body 102 may be added to the delivery wire 100, where this proximal body 102 is proximal to the thrombus 212 or other obstruction. Once the proximal body 102 is placed on the delivery wire 100, it may be advanced towards the distal end of the delivery wire 100 by advancing the delivery wire 100. In another example, the proximal body 210, in a restrained position, may be advanced towards the distal end of the delivery wire 100 using a hypo tube that is placed within the delivery catheter 202 over the delivery wire. As the hypo tube is pushed towards the distal end of the delivery wire 100, the proximal body 210 may be moved axially to a desired location. Once the proximal body 210 is in the desired physical position, relative to the thrombus 212 or other obstruction, the proximal body 210 may be released from inside the delivery catheter 202 to form the expanded proximal body 102 in a manner already described herein. The coaxially placed hypo tube may be pushed forwards and used to physically advance the proximal body 102 to ultimately capture and compress the thrombus 212. Once the thrombus 212 is captured/compressed between the distal body 104 and the proximal body 102, the entire retrieval device may be removed from the body via coaxially placed catheters/tubes thus permitting removal of the thrombus 212 from its prior resting place within the vessel.

Figure 17A:
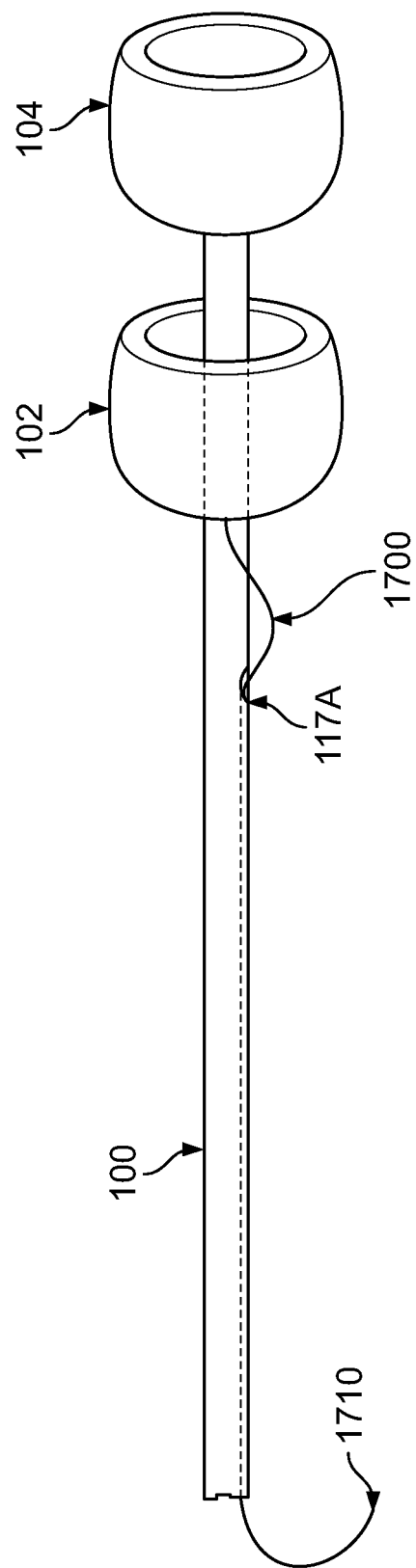
FIG. 17A illustrates the retrieval device with a single tether arrangement attached to the proximal body.
Figure 17B:
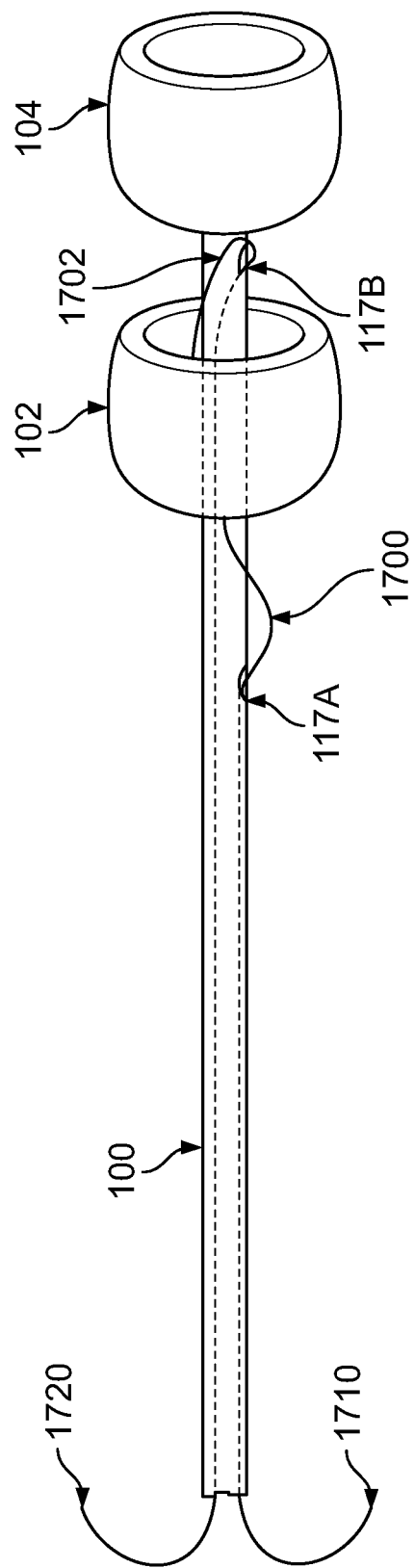
FIG. 17B illustrates the retrieval device with a double tether arrangement attached to the proximal body.

Referring to FIGS. 17A and 17B, the proximal body may be moved along the delivery wire via application of force to a tether or multiple tethers. As shown in FIG. 17A, a single proximal tether 1700 may be attached to the proximal body 102, the proximal body 102 being slidably mounted and in releasable engagement to a delivery wire (or hypo tube), as described herein. The proximal tether 1700 may be pulled to move the proximal body back, proximally along the wire 100 after the proximal body 102 has been released and positioned in the manner described herein. The proximal tether 1700 may run parallel and within the delivery catheter (not shown) or, as shown in FIG. 17A, the proximal tether 1700 may run within a hollowed-out portion of the delivery wire or hypo tube and emerge through an opening 117A. The proximal end 1710 of the proximal tether 1700 is accessible to the interventionist who can pull it to pull back, proximally to the proximal body 102 at least to the point adjacent to the opening 117A.

FIG. 17B shows a two-tether embodiment. As with the embodiment shown in FIG. 17A, the tethers may run parallel and within the delivery catheter (not shown) or, as shown in FIG. 17B, the proximal tether 1700 and distal tether 1702 may run within a hollowed-out portion of the delivery wire or hypo tube and emerge through openings 117A and 117B, where the proximal tether 1700 emerges from opening 117A and the distal tether 1702 emerges from opening 117B. Movement of the proximal body via the proximal tether, in the proximal direction, is the same as mentioned above. In this embodiment, the interventionist can pull the end of the distal tether 1720 to move the proximal body 102 adjacent to the opening 117B, which results in a distal movement of the proximal body 102 without the need for distal movement via the delivery catheter as described herein.

Figure 18:
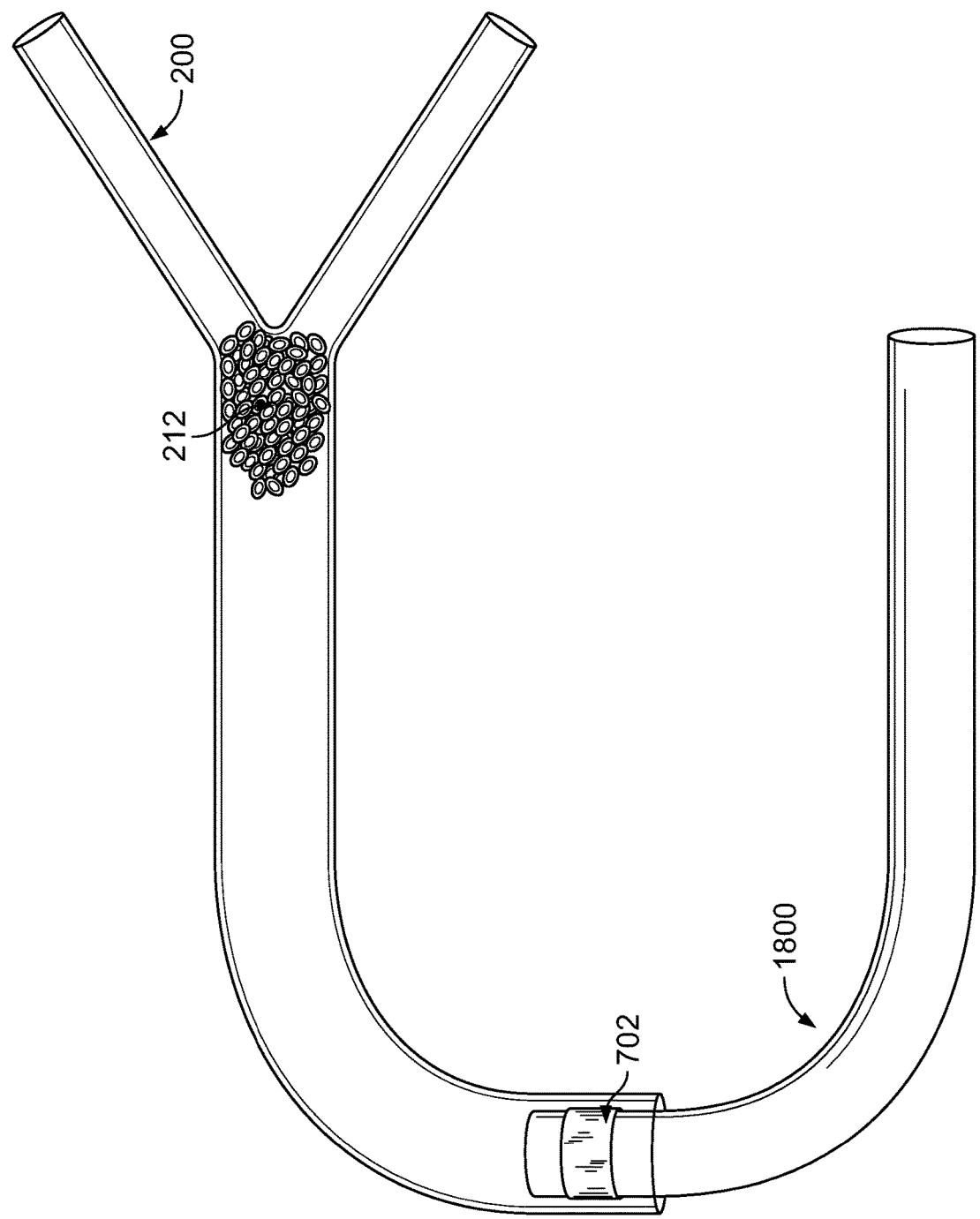
FIG. 18 illustrates a deployment stage of the retrieval device, showing the placement of a temporary balloon occlusion guide catheter into common carotid artery.
Figure 19:
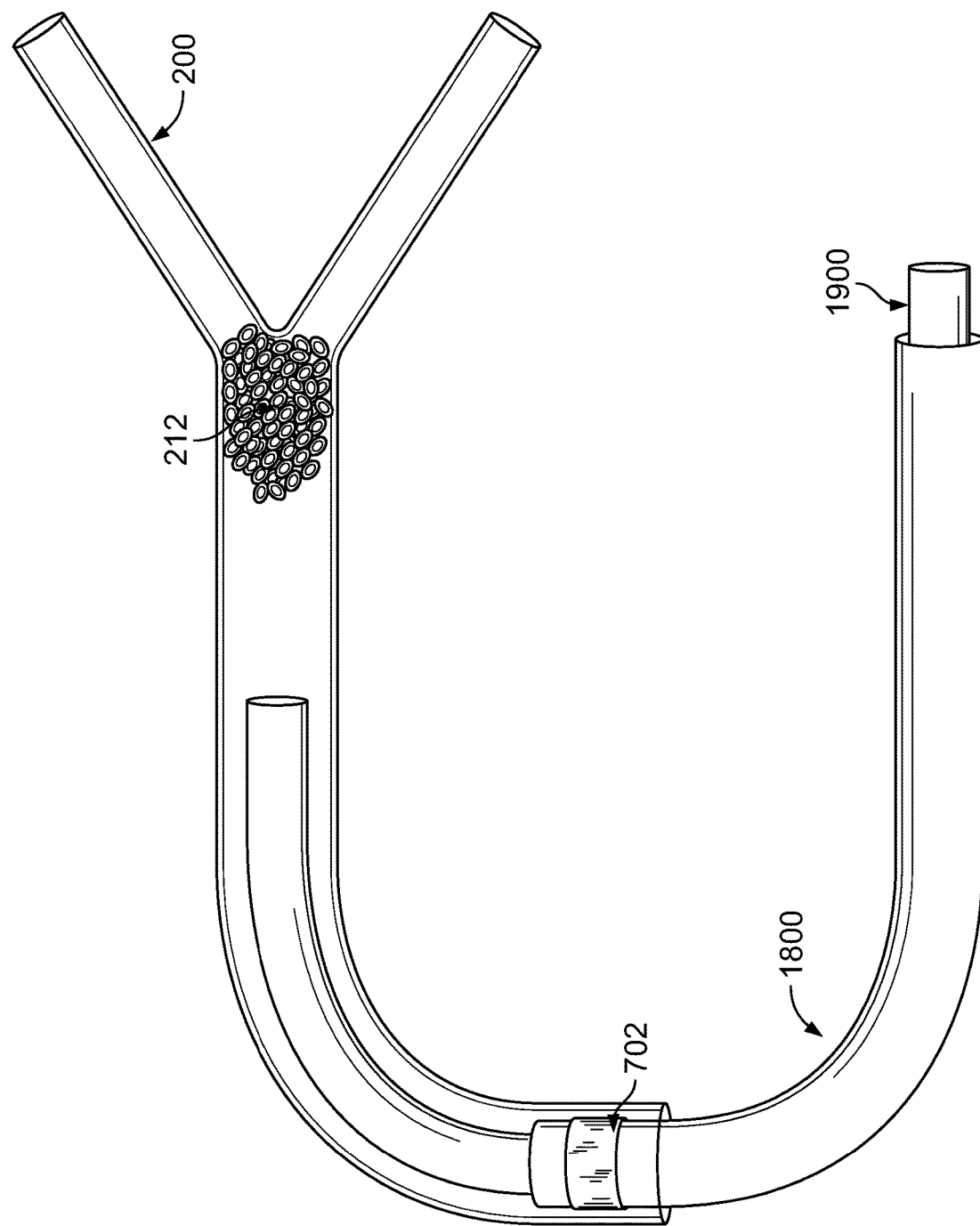
FIG. 19 illustrates an advancing access catheter into a vessel.
Figure 20:
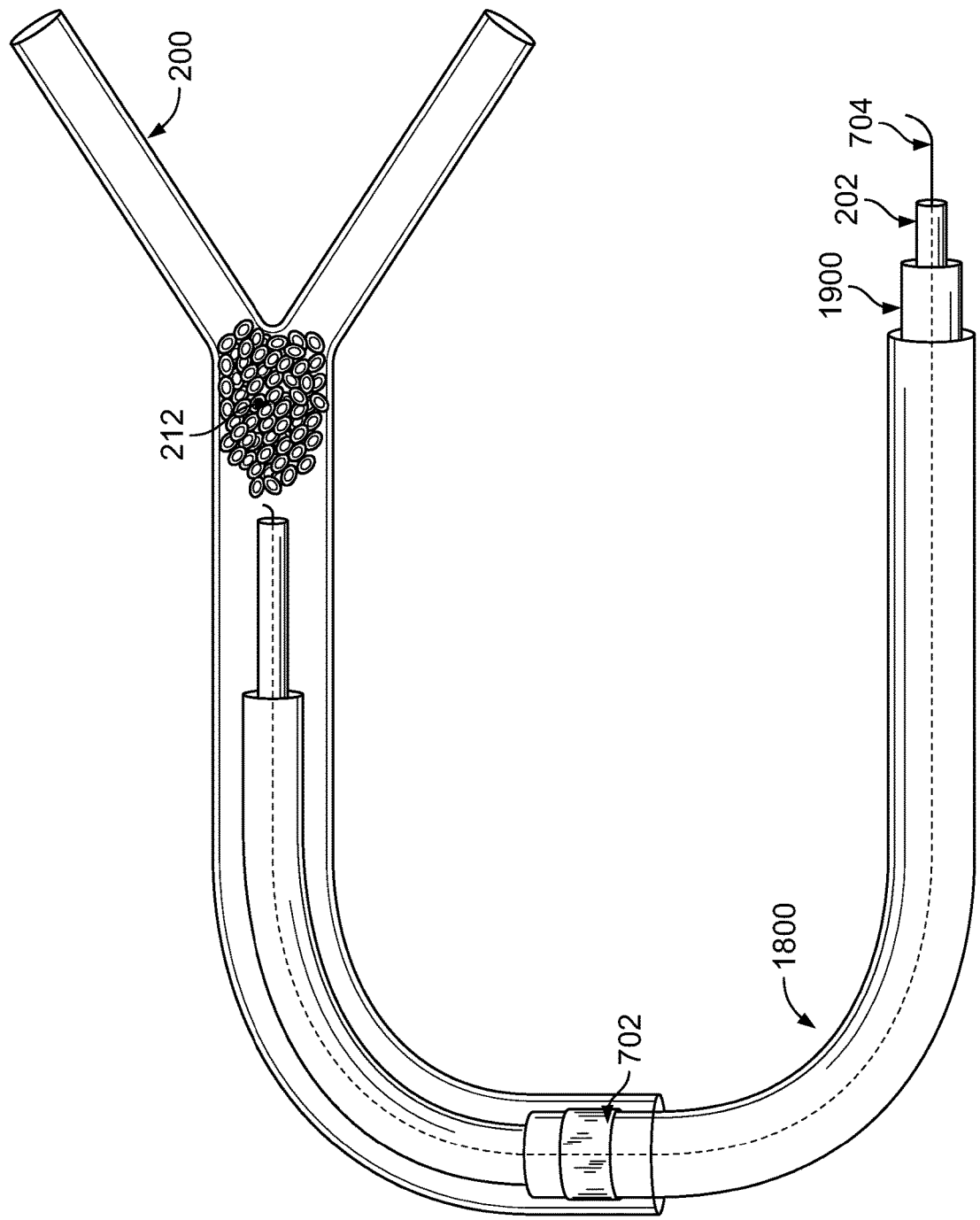
FIG. 20 illustrates advancing the delivery catheter and delivery wire to the origin of an occlusion.
Figure 21:
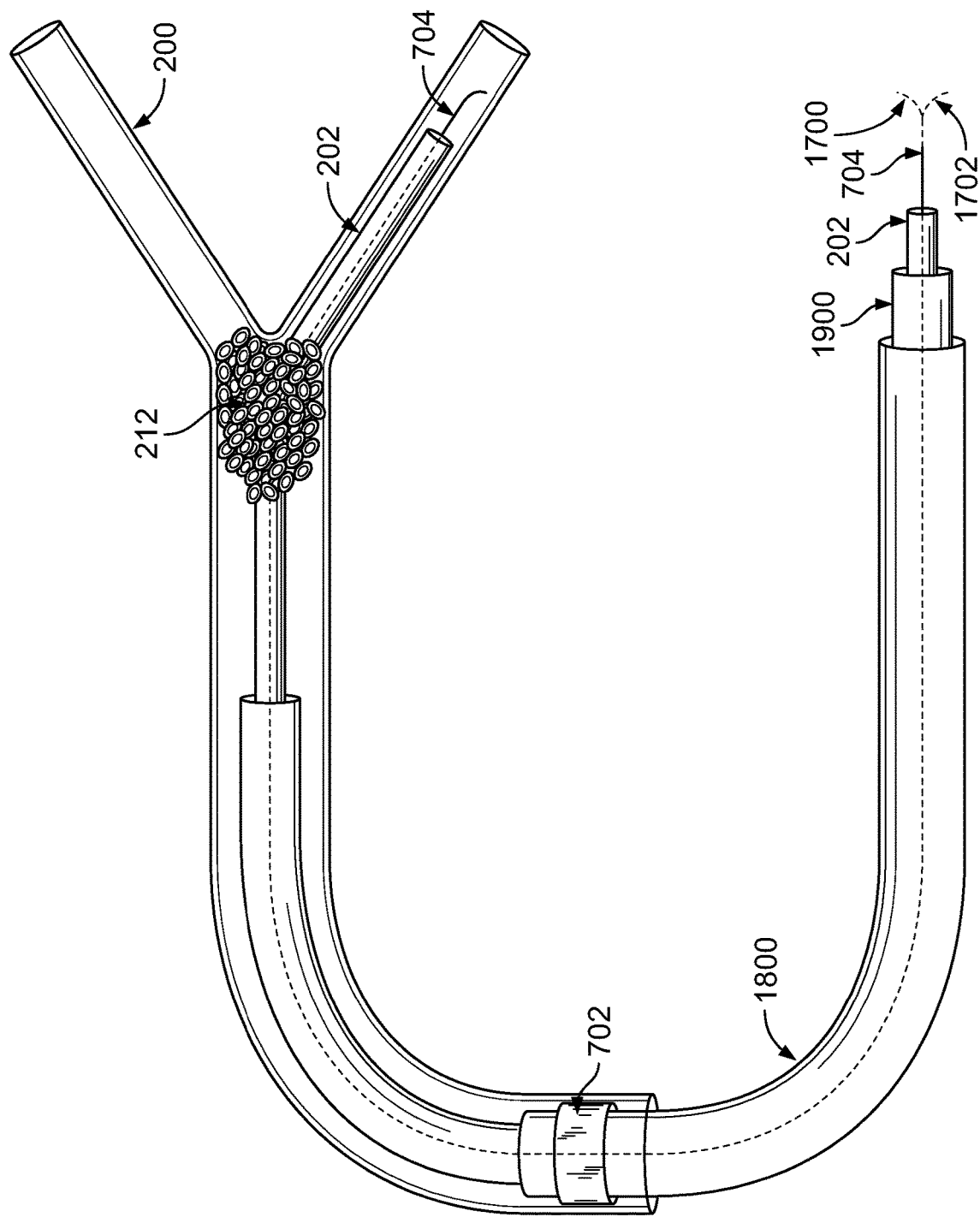
FIG. 21 illustrates temporary inflation of a balloon on a guide catheter to arrest anterograde flow.
Figure 22:
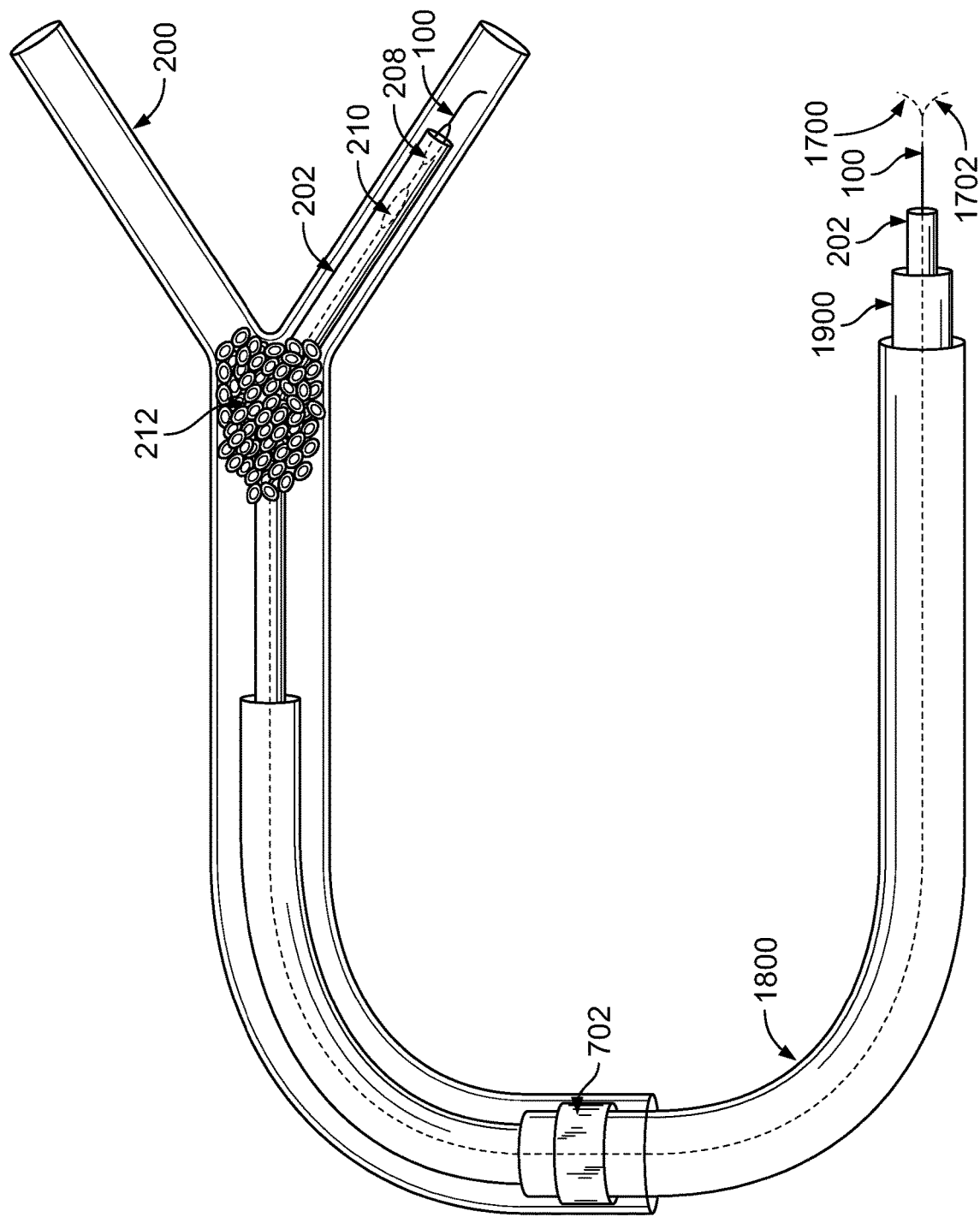
FIG. 22 illustrates advancing the delivery wire, with the retrieval device loaded thereon, and delivery catheter across the thrombus and positioning the tip of the delivery catheter distal to the thrombus.

In addition to the steps of deployment mentioned above, the following steps may also or alternatively be followed for using the retrieval device in embodiments. FIG. 18 shows the common carotid artery (CCA) having an occlusion therein 212. A guide catheter 1800 having a flow arrest balloon 702 is inserted into the CCA (in embodiments over a guide wire). FIG. 18 shows the flow arrest balloon 702 as deflated. FIG. 19 shows the advancement of an access catheter 1900 distally through the guide catheter 1800 (in embodiments over a guide wire (not shown)). FIG. 20 shows the distal advancement of a delivery catheter 202 via a guide wire 704 to the origin of the inclusion (i.e., the base of the thrombus 212). FIG. 21 shows the flow arrest balloon 702 being temporarily inflated to arrest anterograde flow in the CCA as well as the delivery catheter 202 being advanced distal to the occlusion 212 via the guide wire 704 and, in this case, in M1. The guide wire 704 is removed (not shown). The delivery wire 100 with restrained proximal 210 and restrained distal 208 bodies thereon is inserted into and through the delivery catheter 202 with the tip emerging the delivery catheter as shown in FIG. 22. In this example, the delivery wire 100 has within it a proximal tether 1700 and a distal tether 1702.

Figure 23:
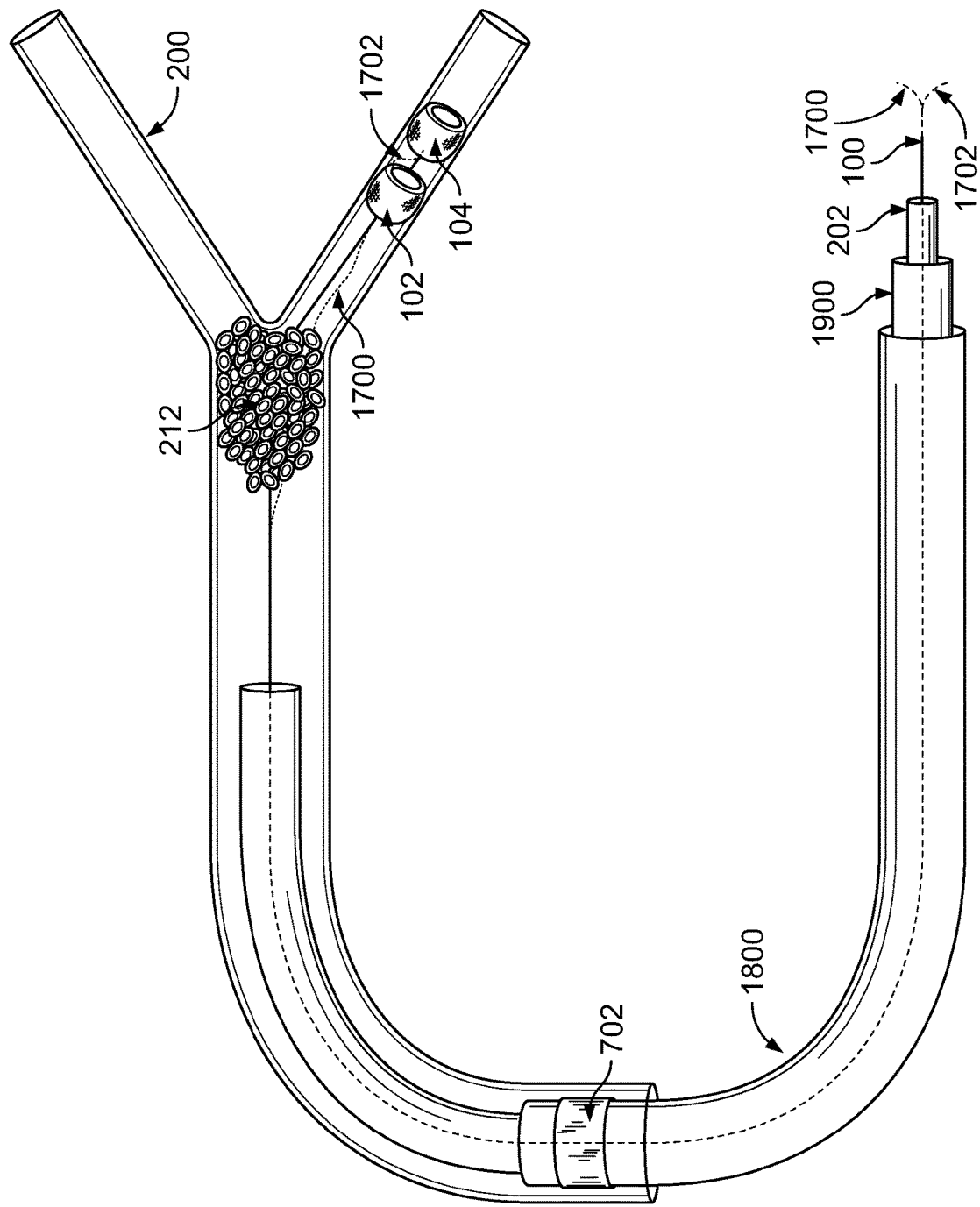
FIG. 23 illustrates deploying the bodies of the retrieval device and advancing the bodies device through the delivery catheter and deploying the bodies distal to the thrombus.

In FIG. 23, the proximal 102 and distal 104 bodies are deployed distally to the occlusion 212, the deployment being in the manner described herein. The delivery catheter 202 is withdrawn from patient to increase open luminal area in access catheter 1900, which allows for better suction when suction is applied to access catheter 1900. FIG. 23 also shows the proximal tether 1700 and the distal tether 1702, as described herein, attached to the proximal body 102. FIG. 23 also shows the deflation of flow arrest balloon 702 on the guide catheter 1800 to end flow arrest. Due to mesh construct of the proximal 102 and distal 104 bodies which are now deployed, anterograde flow into vessels will be re-established with protection (established via the expanded proximal 102 and distal 104 bodies) from distal embolization of occlusion when flow is re-established. Suction may be applied to the access catheter 1900 at this point. The proximal body 102 may be released from its releasable engagement 108 as described herein, while the distal body 104 remains fixed to the wire.

With both the proximal 102 and distal 104 bodies providing protection (most commonly initially in an M2 branch for an M1 occlusion or covering the M1 bifurcation for an ICA terminus) an interventionist may slowly pull the delivery wire 100 in a proximal direction. This will draw both bodies proximally (see FIGS. 23-25). The proximal 102 and distal 104 bodies will open to a larger diameter when they transition from M1 to M2 and in the process of being withdrawn proximally will begin the thrombectomy process (see FIG. 25).

Figure 24:
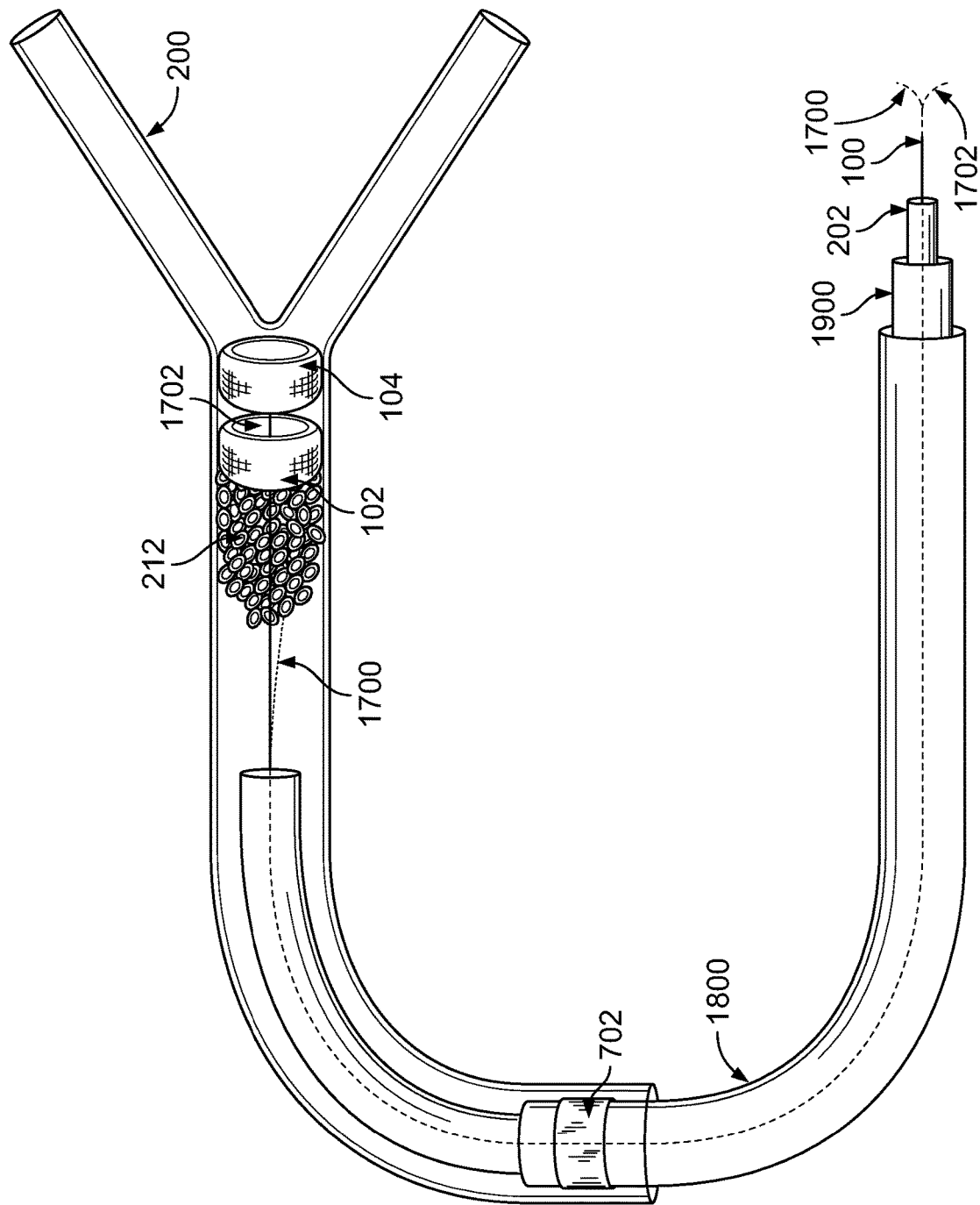
FIG. 24 illustrates the proximal and distal bodies drawn proximally to the thrombus and opening to a larger diameter when transitioning from M1 to M2 and in the process of being withdrawn proximally.
Figure 25:
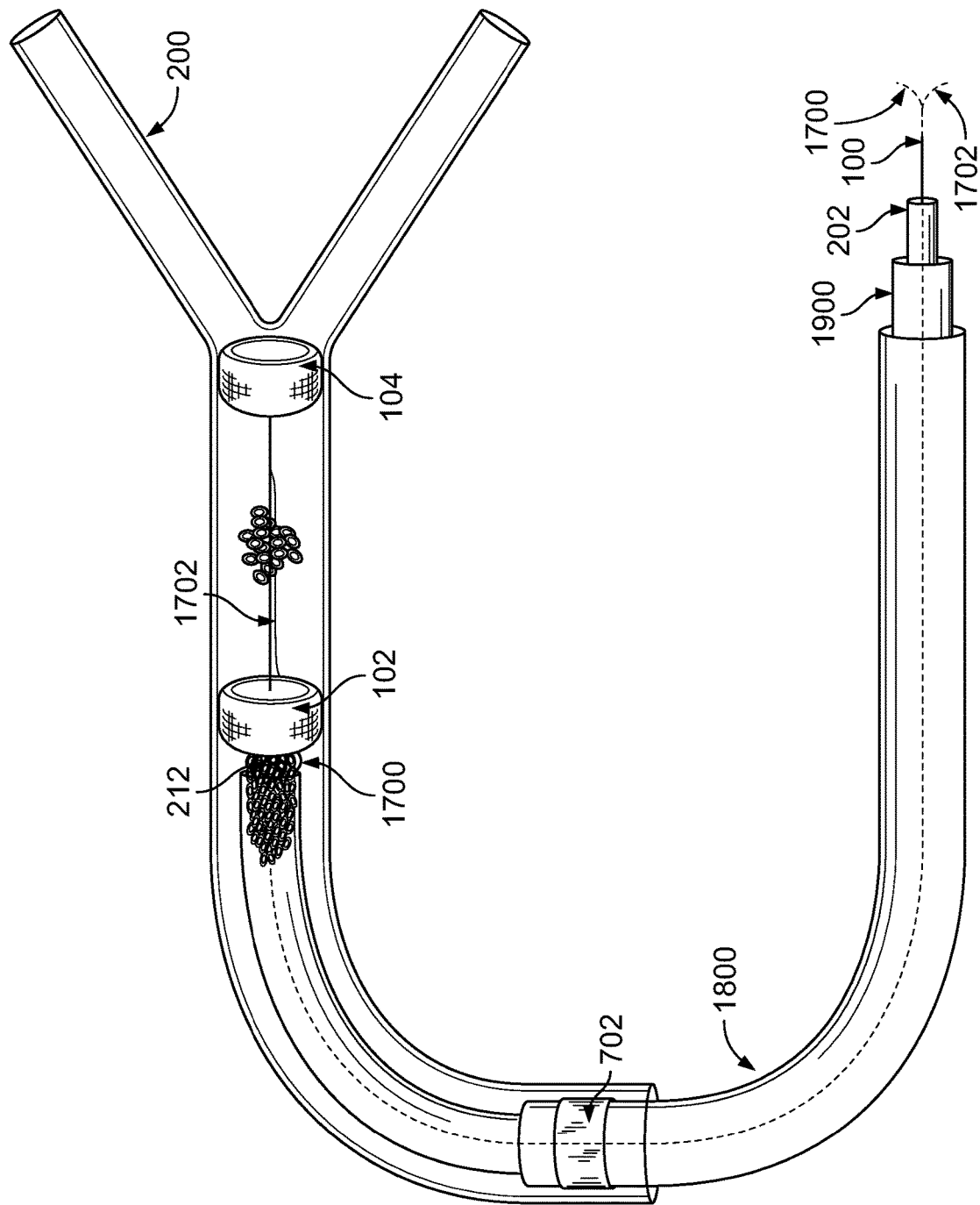
FIG. 25 illustrates the proximal body being moved proximally by the tether.

Once the distal body 104 opens at the M1 bifurcation, both superior and inferior M2 protection has been established (see FIGS. 24 and 25). Using a proximal tether 1700 and a distal tether 1702 that connect to the proximal body 102 and exit from the delivery wire 100 either via an opening in the outer surface or via the opening on the end of the delivery wire 100 (see FIGS. 17A and 17B), the proximal body 102 can be moved along the M1 and possibly ICA lumen back and forth (i.e., proximally and distally axially along the delivery wire) by pulling the ends of the tethers 1710, 1720 as described herein and as desired by the clinician to mobilize occlusion and loosen and draw it proximally towards the suction device. If the initial placement of the proximal body 102 is determined to be too far in the distal direction, the interventionist may use the proximal tether 1700 that is attached to the proximal body 102 to pull the proximal body 102 back in the proximal direction to place it farther from the distal end of the retrieval device. This allows the interventionist to adjust the proximal body's position along the wire 100 instead of only being able to advance the proximal body 102 in the distal direction. In an example, the proximal body 102 may have a Kevlar tether that exits the delivery wire (or hypo tube) 100 at an opening distance about 1-2 cm proximal to the proximal side of the proximal body 102 to which it is attached. Therefore, while the two bodies are initially adjacent to each other, the proximal body 102, once electrolytically detached, can be withdrawn a distance proximally along the delivery wire 100 axis 1-1.5 cm by pulling on the proximal tether 1700. (All distances herein may be adjusted according to the need). It may be advanced by pushing it forward with the delivery catheter 202 and/or a second, distal tether 1702 may exit the wire at opening 117B distally to the proximal body 102 which when pulled can pull the proximal body 102 distally back towards the distal body and adjacent to the opening 117B. Therefore, by pulling proximal tether 1700 and/or the distal tether 1702 the proximal body 102 may slide backwards and forwards along the delivery wire 100. In this example, this configuration provides the proximal body 102 with 1-1.5 cm of travel distance back and forth along the delivery wire 100. Despite anterograde flow, the distal body 104 may provide protection against distal embolization of loosened/floating occlusion thus eliminating/reducing the risk of distal embolization of this material (see FIG. 25).

Figure 26:
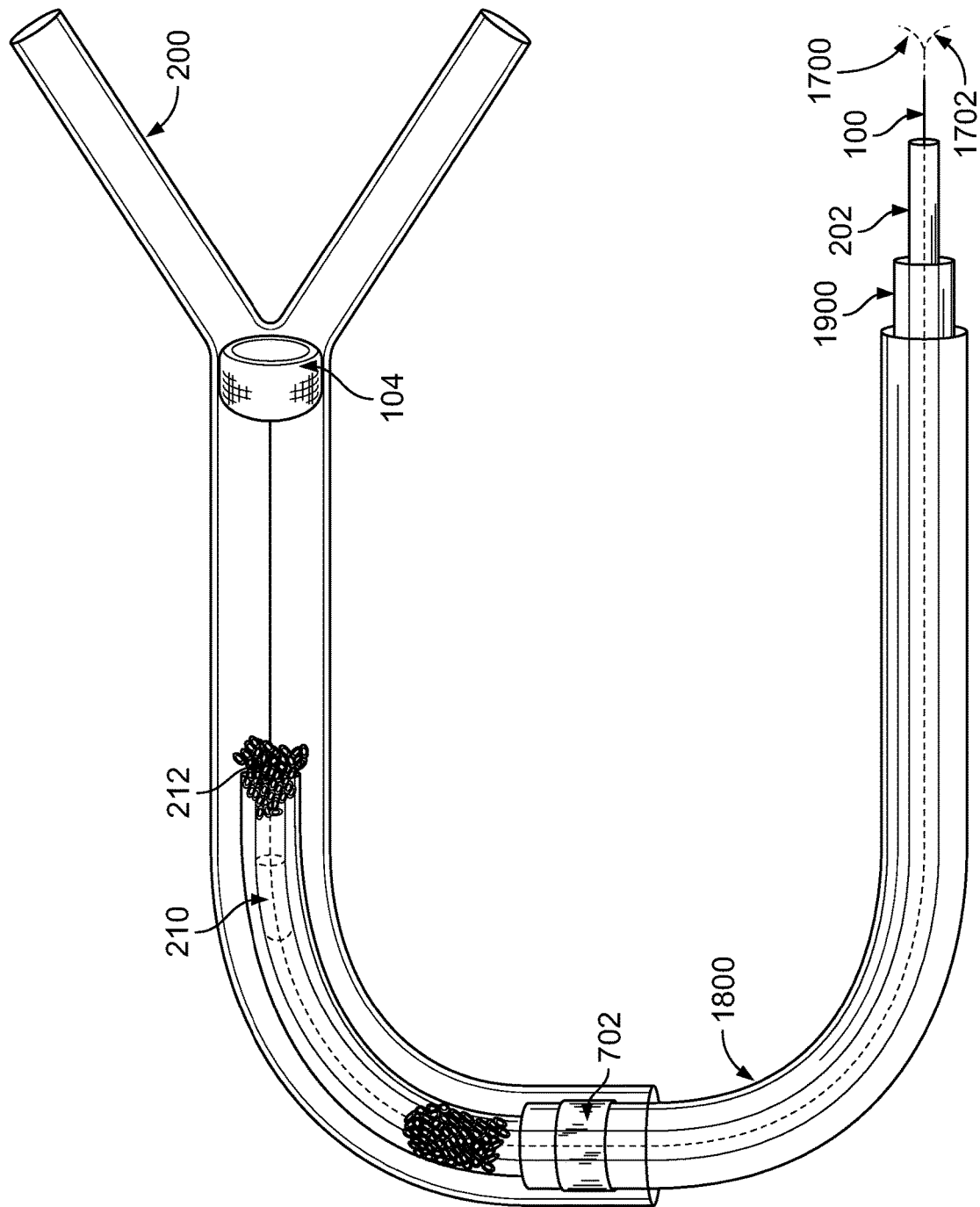
FIG. 26 illustrates withdrawing the thrombus towards the access catheter containing suction.

Once the thrombus 212 has been removed/evacuated through the access catheter 1900, the proximal and distal bodies can be removed by withdrawing them through the delivery catheter 202. This process will also mechanically draw any thrombus 212 that sits on the tip of the access catheter 1900 (cleans the catheter tip) into the catheter 1900 so that it does not embolize off the catheter tip and back into the intracranial circulation (see FIGS. 25-27).

In embodiments, the following steps may be followed for using the retrieval device, as described herein, for a foreign body (e.g., lost coil or fractured filter) capture and extraction intervention, such as an aneurysm coil lodged at an M1 bifurcation (proximal and distal bodies may be sized according to vessel size where the foreign body is located):

Guide catheter 1800 already in ICA from coiling procedure.

Advance a delivery catheter 202 distal to the foreign body.

Advance the retrieval device through the delivery catheter 202 (the "retrieval device", again is the delivery wire 100 with the proximal and distal bodies mounted thereon in a manner described in this disclosure).

When the distal body 104 reaches the end of the delivery catheter 202, the interventionist may optionally detach the releasable engagement of proximal body 102 so it is free to move axially along the delivery wire 100.

Pull the proximal tether 1700 and draw the proximal body 102 proximally in the delivery catheter 202 so that there is a space, in some embodiments a 1 cm space, between the two non-deployed bodies which are still constrained within the delivery catheter 202.

Slowly retract the delivery catheter 202 proximally. This will allow the distal body 104 to open in the vessel 200 distal to the foreign body.

Holding the wire in place, continue drawing the delivery catheter 202 proximally until the proximal body 102 is unsheathed. The proximal body 102 will now be opened proximal to the foreign body/coil.

The foreign body is now trapped/isolated between the distal and proximal bodies.

While holding the distal body 104 in place by holding the delivery wire 100, the proximal body 102 can now be approximated along the wire to the distal body 104 by either using the tethers as described herein or by simply pushing it forward with the delivery catheter 202 or drawing the distal body 104 proximally.

The foreign body/coil is now trapped between the two bodies and can be removed from the vessel 200. By pulling the entire system down to or into the guide catheter 1800.

In another embodiment, the present specification describes a medical device for retrieval and removal of at least one occlusion from a patient's blood vessel(s) and, in embodiments, bronchial pathways. The device may also be used in the vascular system of a patient, and in non-vascular structures such as ureters, ducts, airways, and any other accessible space that contains a material (biologic or foreign) that necessitates removal or retrieval. In one embodiment, each of the devices disclosed herein may be used to perform a procedure in order to resolve, treat, or address a deep vein thrombosis or a pulmonary embolism or perform any type of thrombectomy.

Figure 28A:
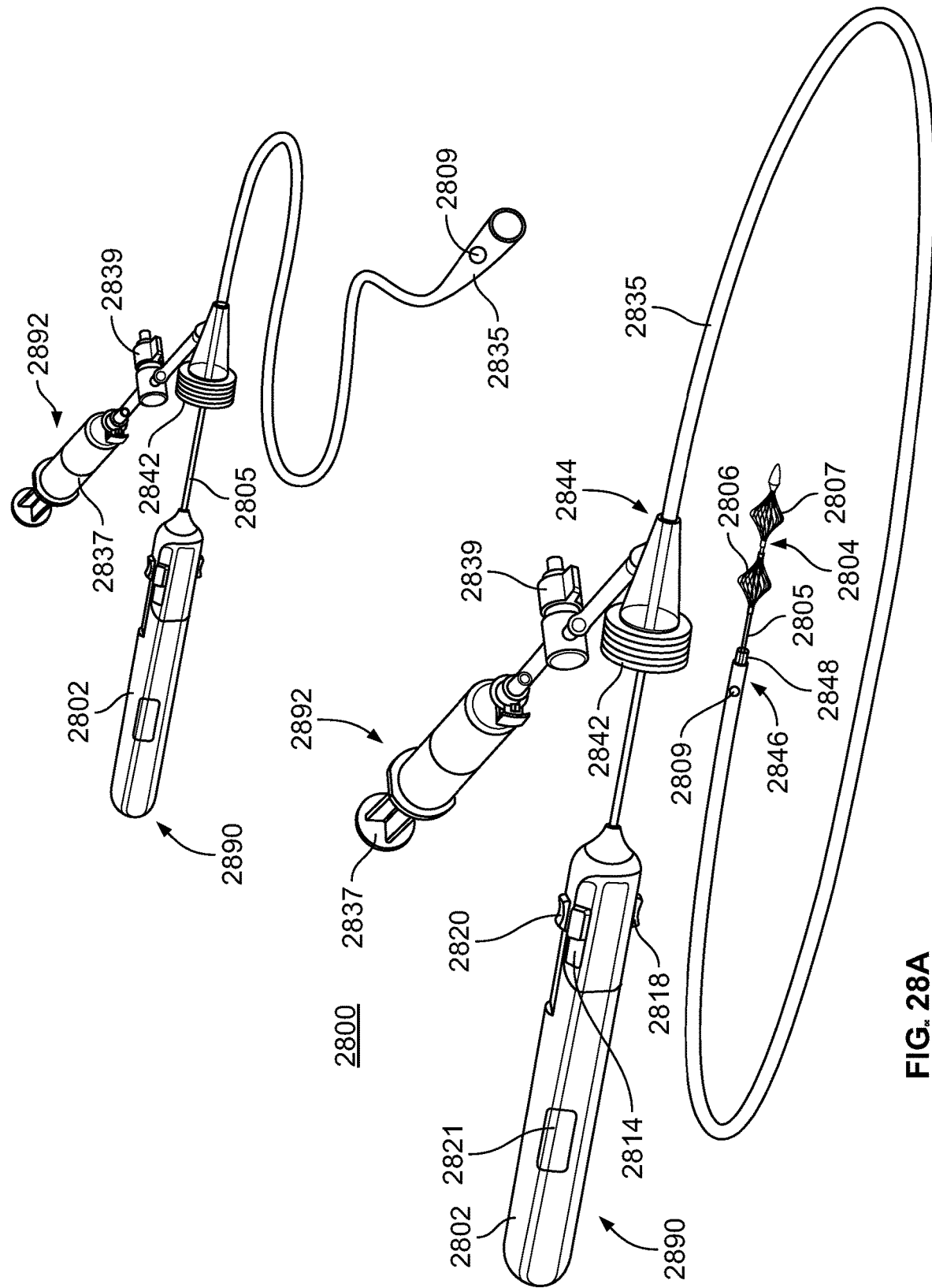
FIG. 28A is a perspective view of a retrieval device, in accordance with an embodiment of the present specification.
Figure 28B:
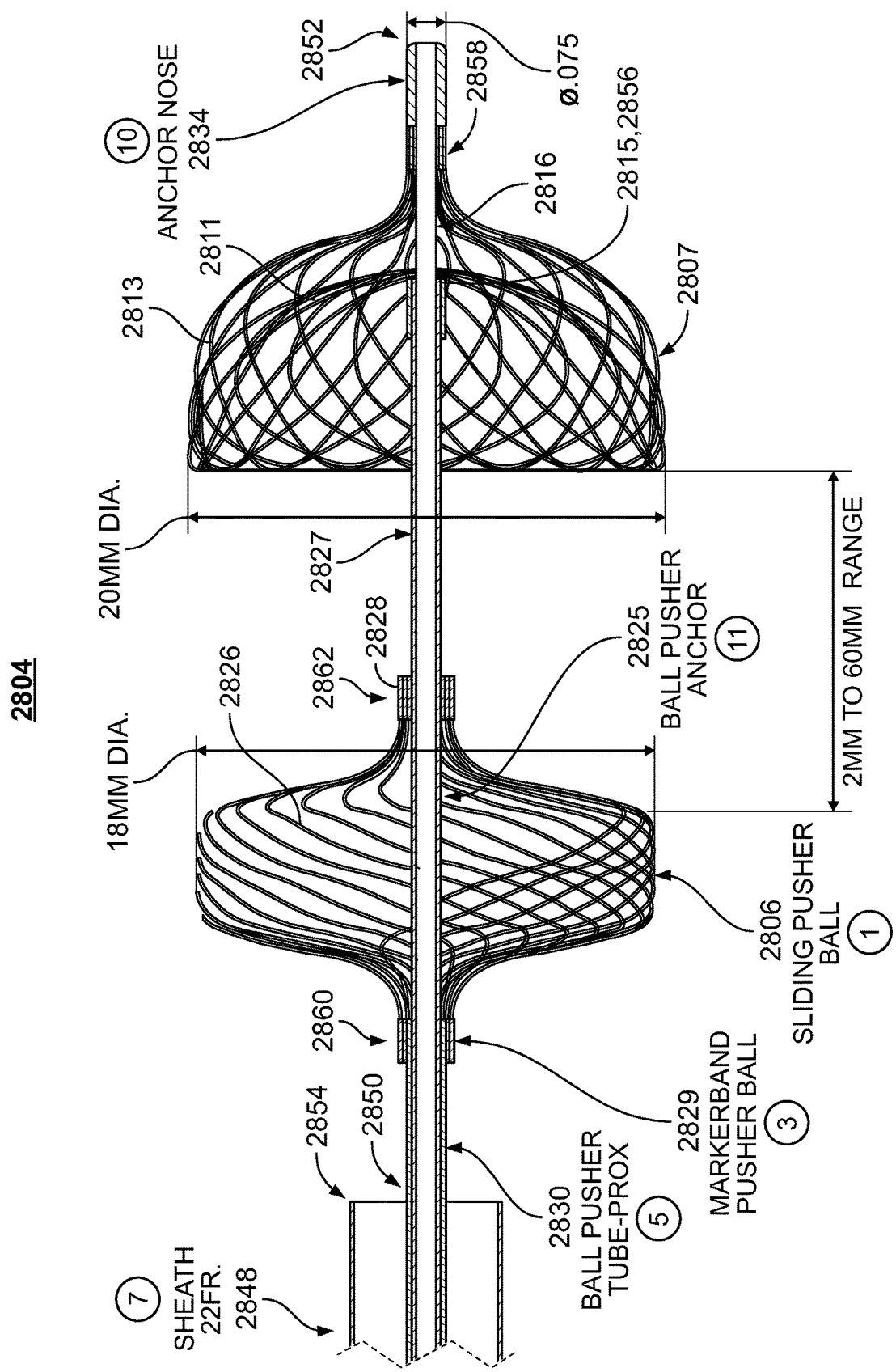
FIG. 28B is an exploded view of a distal tip portion of the device shown in FIG. 28A.
Figure 28C:
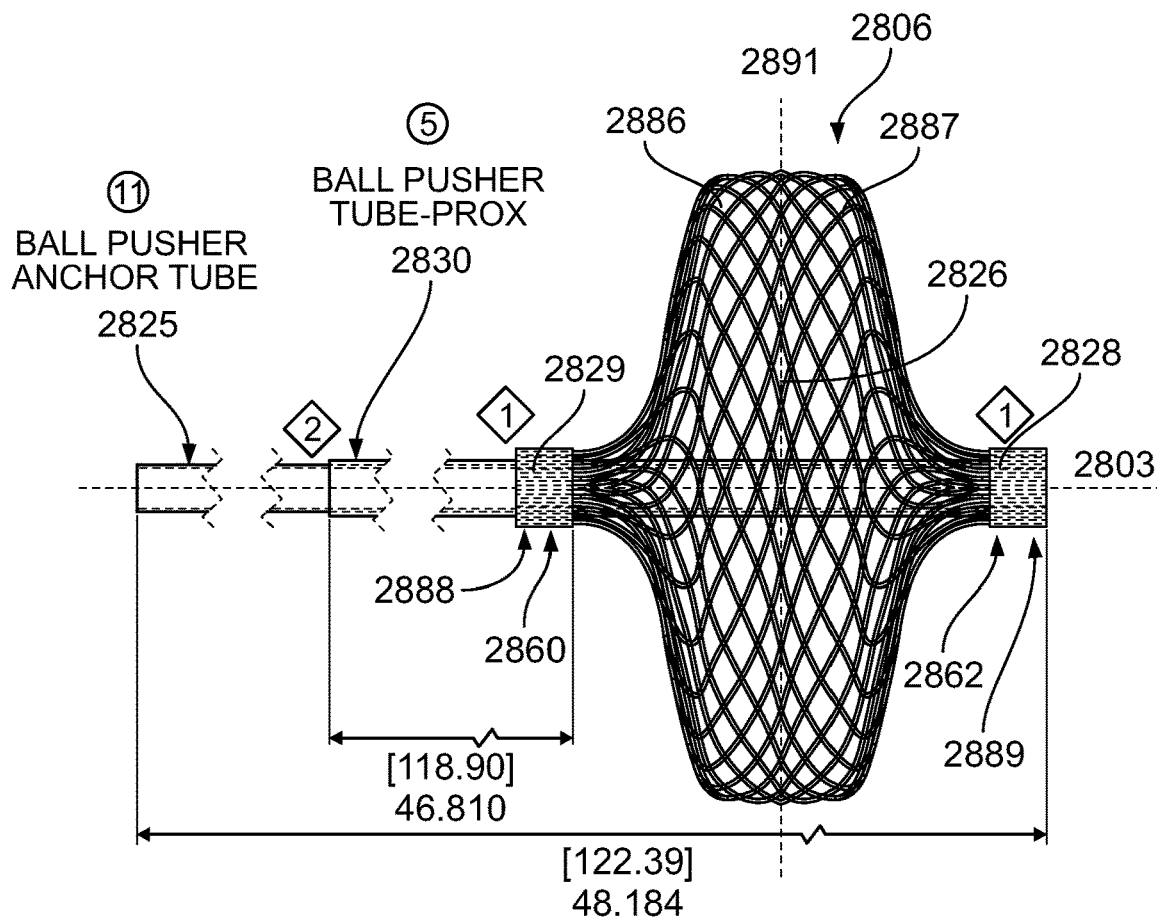
FIG. 28C is a side elevation view of an exemplary proximal element of the device shown in FIG. 28A.
Figure 28D:
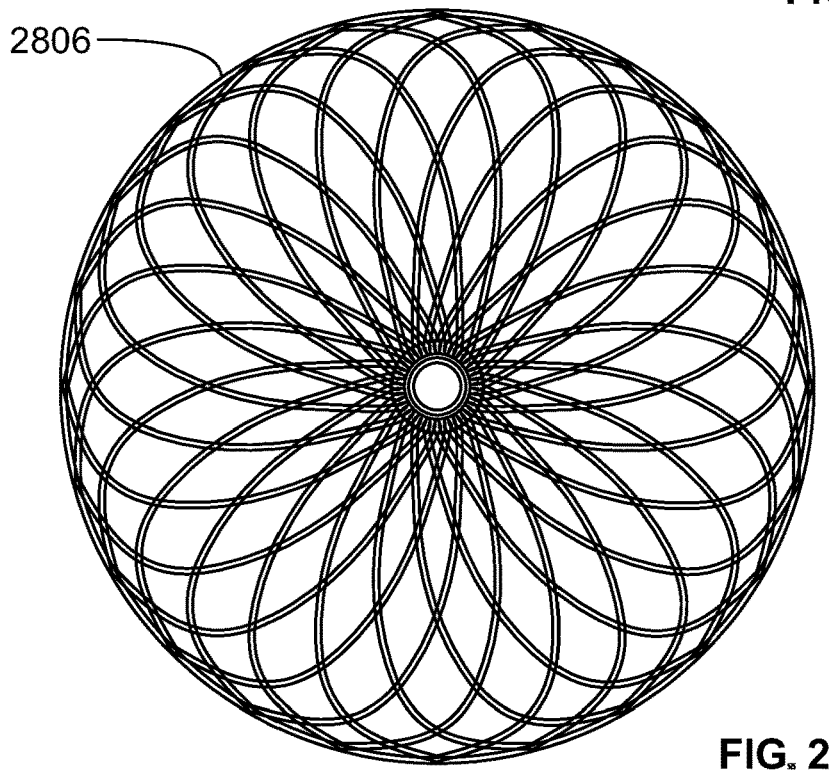
FIG. 28D is a front plan view of the proximal element shown in FIG. 28C, in an expanded state.
Figure 28F:
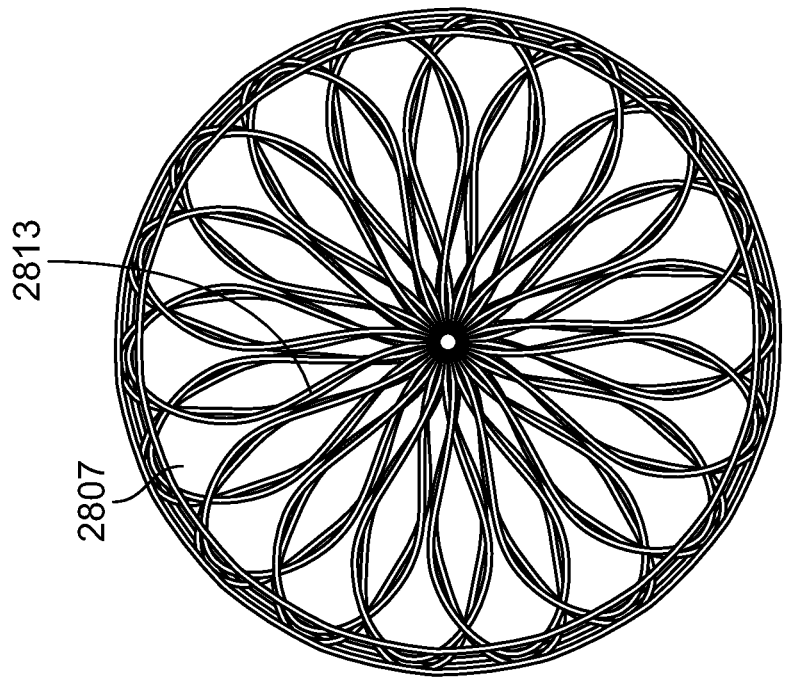
FIG. 28F is a front plan view of the distal element shown in FIG. 28E in an expanded state.
Figure 28E:
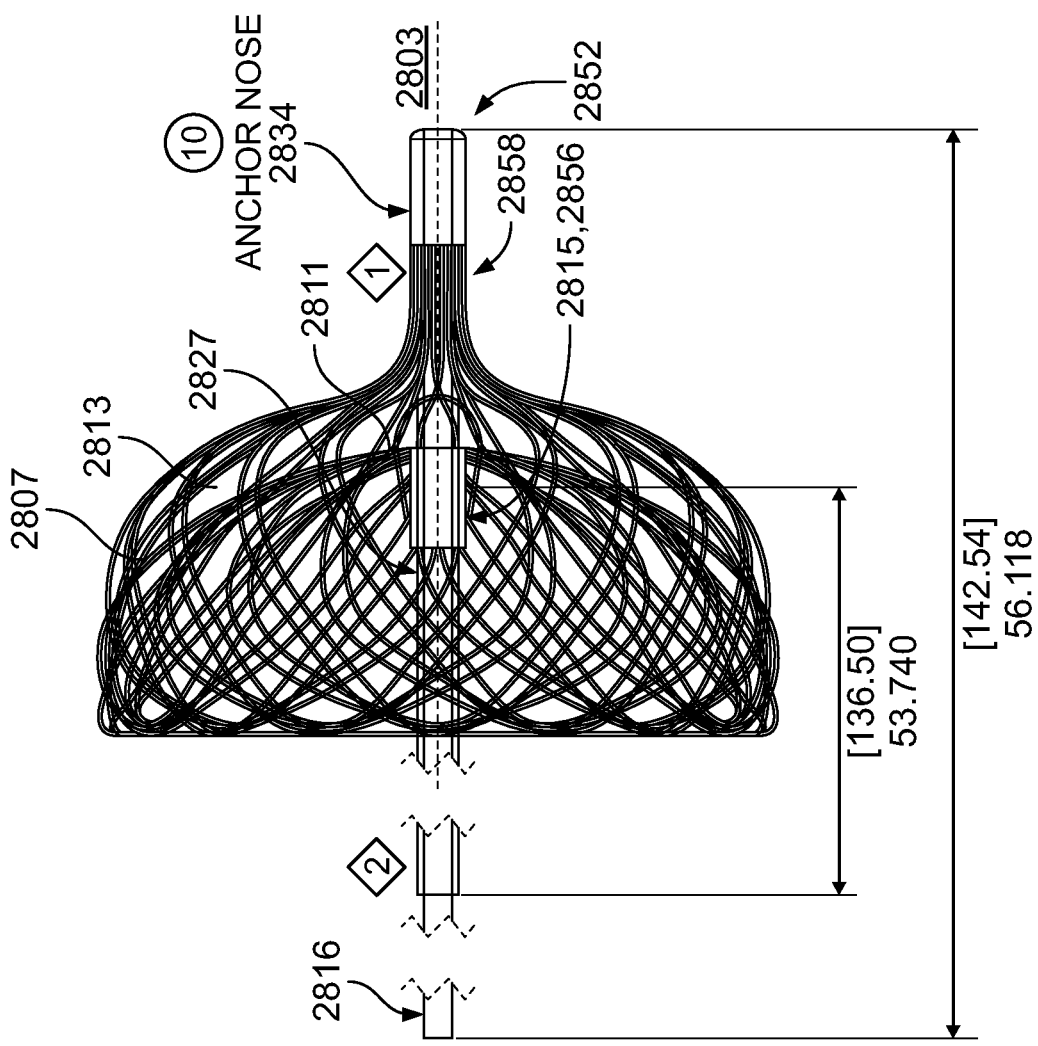
FIG. 28E is a side elevation view of an exemplary distal element assembly of the device shown in FIG. 28A.
Figure 28G:
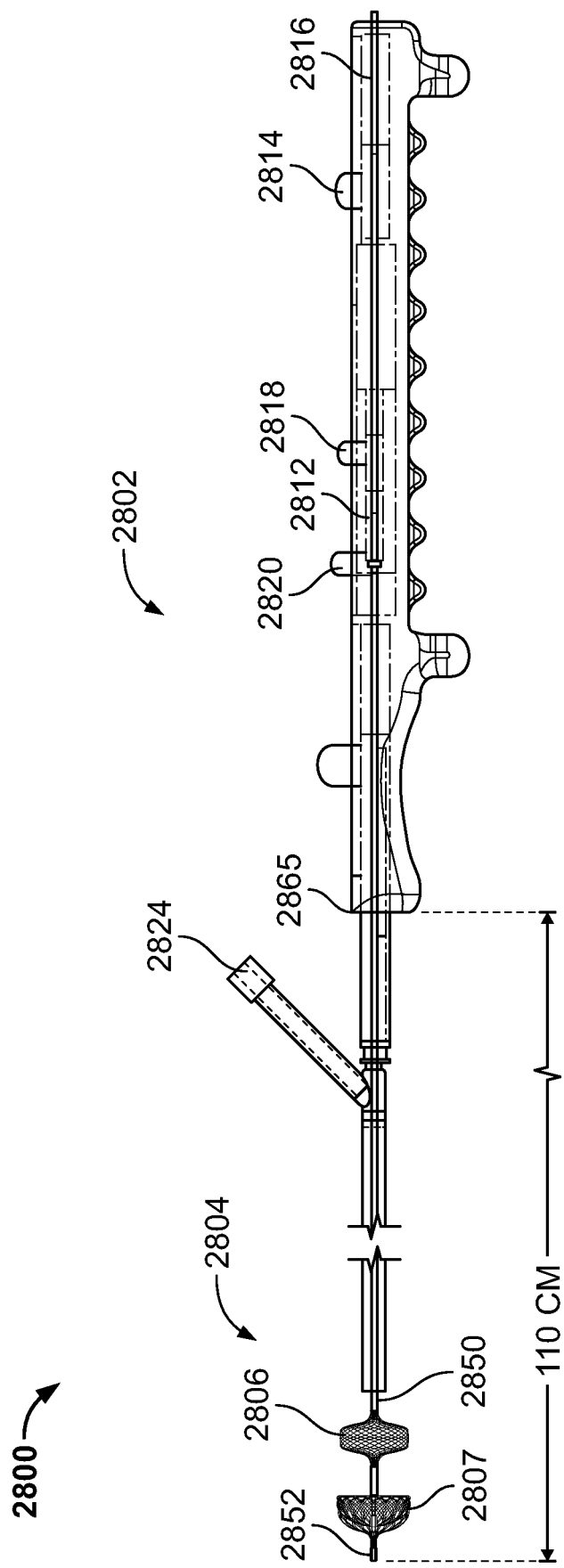
FIG. 28G is another perspective view of the retrieval device shown in FIG. 28A.

FIG. 28A illustrates a retrieval device, in accordance with an embodiment of the present specification. FIG. 28B illustrates an expanded view of a distal tip portion of the device shown in FIG. 28A. FIG. 28C illustrates a proximal element of the device shown in FIG. 28A. FIG. 28D illustrates a front/top view of the proximal element shown in FIG. 28C, in an expanded state. FIG. 28E illustrates a mechanically expanded distal element of the device shown in FIG. 28A. FIG. 28F illustrates a front/top view of the distal element shown in FIG. 28E in an expanded state. FIG. 28G illustrates another view of the retrieval device shown in FIG. 28A and FIG. 28J illustrates a retrieval device, in accordance with another embodiment of the present specification.

Referring simultaneously to FIGS. 28A through 28G and FIG. 28J, device 2800 comprises a first unit 2890 that includes a handle 2802 coupled to a proximal end of an elongated member 2805 having a plurality of telescoping tubes, such as at least four telescoping tubes, wherein a distal end of the elongated member 2805 has a tip portion 2804. The handle 2802 is configured to steer the tip portion 2804 in proximity to an occlusion. The device 2800 further comprises a second unit 2892 that includes an aspiration catheter 2835 having a suction source such as, for example, a syringe 2837, a one-way valve 2839 and a port 2842 (FIG. 28A), where the port 2842 is coupled to a proximal end 2844 of the aspiration catheter 2835. In one embodiment the one-way valve 2839 is configured to direct suction through the aspiration catheter 2835. For use during a procedure, the tip portion 2804 is placed into a delivery catheter 2848 and thereafter the delivery catheter 2848 is inserted into the aspiration catheter 2835, and follows through to port 2842, so that at least the tip portion 2804 projects distally from a distal end 2846 of the aspiration catheter 2835.

Figure 28H:
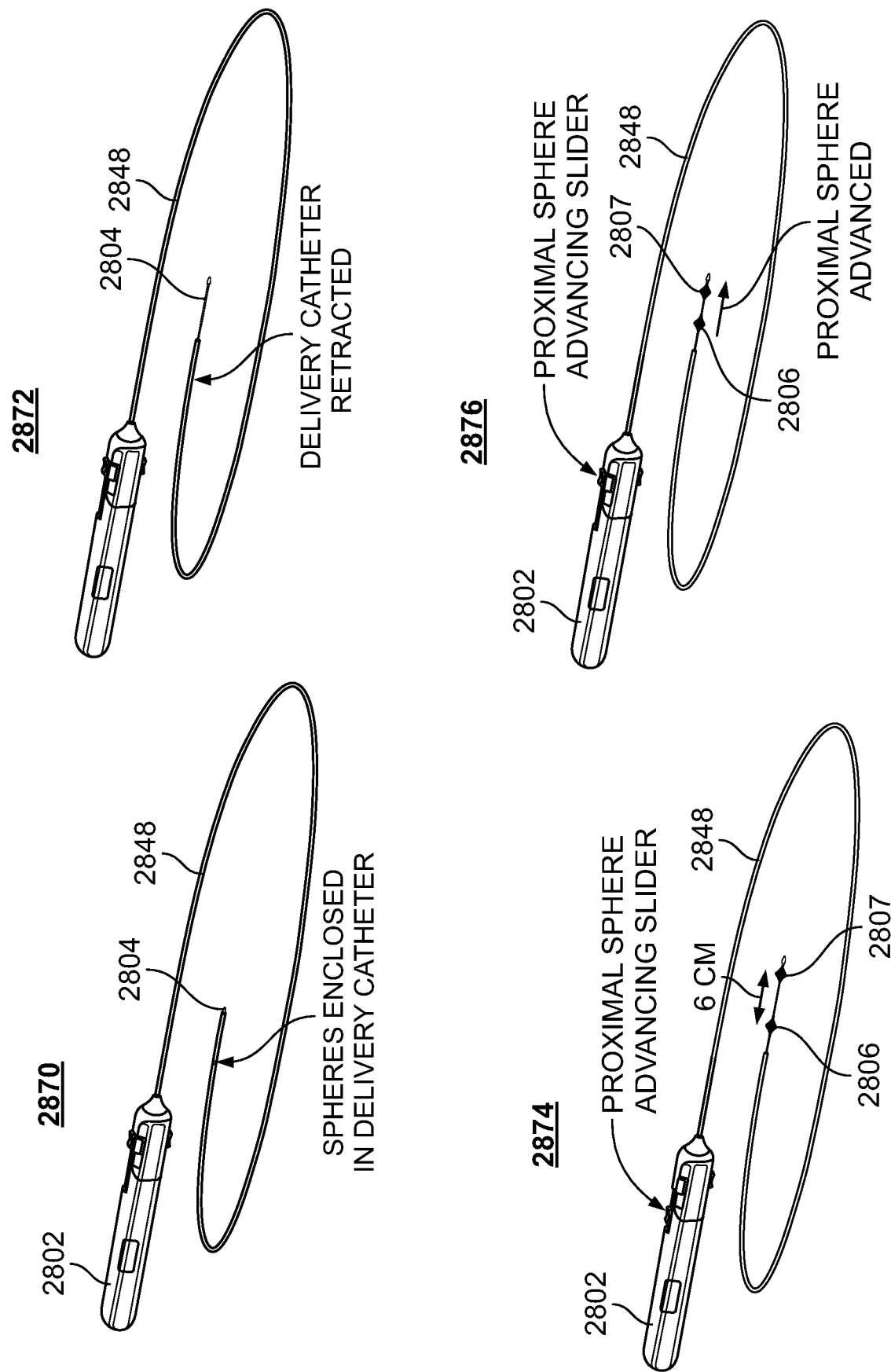
FIG. 28H represents first, second, third, and fourth views of the retrieval device of FIG. 28A being manipulated to maneuver a tip portion, in accordance with some embodiments of the present specification.
Figure 28I:
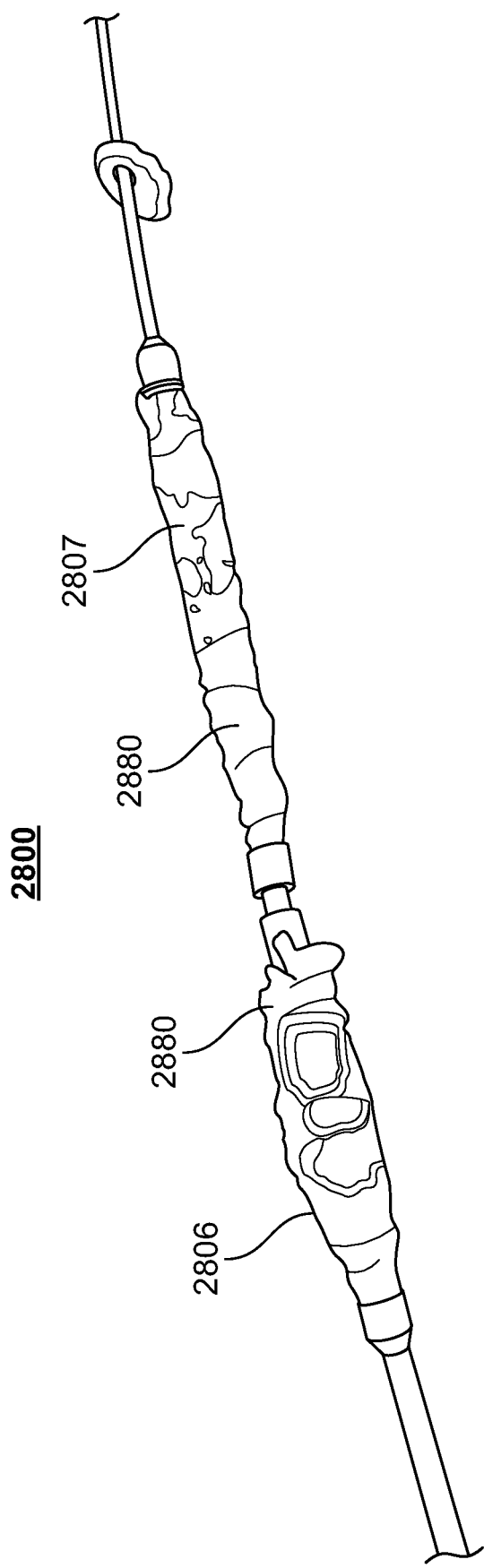
FIG. 28I is an illustration of an occlusion captured between and embedded in mesh lattices of proximal and distal elements of the retrieval device of FIG. 28A, in accordance with an embodiment of the present specification.
Figure 28J:
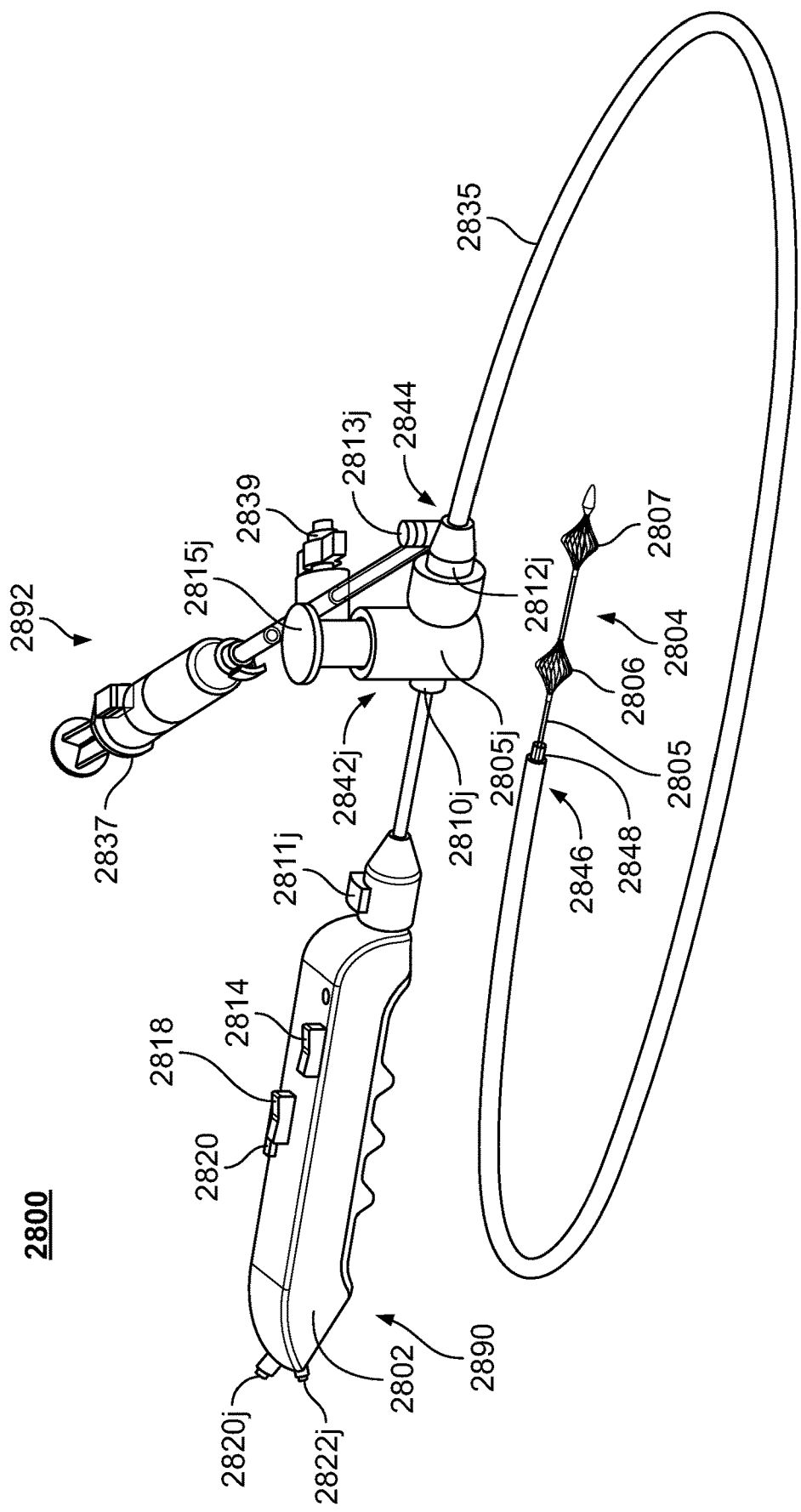
FIG. 28J is a perspective view of a retrieval device, in accordance with another embodiment of the present specification.

In some embodiments, as shown in FIG. 28J, instead of the port 2842 the device 2800 includes a hemostasis valve hub 2842j. The valve hub 2842j is defined by an enclosure 2805j, a first opening 2810j in a first end of the enclosure 2805j, a second opening 2812j in a second end of the enclosure 2805j, and an actuator 2815j extending upward out of the enclosure 2805j. In embodiments, the proximal end 2844 of the aspiration catheter 2835 is coupled to the second opening 2812j. When the actuator 2815j is depressed, the valve hub 2842j is configured to receive the elongated member 2805 through the first opening 2810j and allow the elongated member 2805 to pass through the second opening 2812j and through the aspiration catheter 2835. When the actuator 2815j is not depressed, the valve hub 2842j is configured to create a seal around a surface of the elongated member 2805. In embodiments, the suction source 2837 is coupled to a portion of the valve hub 2842j and is in pressure communication with the aspiration catheter 2835.

In accordance with aspects of the present specification, the device 2800 is configured to enable an operator to single-handedly operate/actuate the handle portion 2802 (using first, second and third physically manipulable interfaces such as, for example, knobs, sliders, buttons or other actuation mechanisms 2814, 2818 and 2820) in order to mechanically expand, contract, or move a proximal member 2806 and/or a distal member 2807, as further discussed below. In one embodiment, a first slider, knob, button, or other actuation mechanism 2814 is configured to mechanically expand or mechanically contract the proximal member 2806, a second slider, knob, button, or other actuation mechanism 2818 is configured to mechanically expand or mechanically contract the distal member 2807, and a third slider, knob, button, or other actuation mechanism 2820 is configured to axially move the proximal member 2806 relative to the distal member 2807, to axially move the proximal member 2806 while maintaining the distal member 2807 stationary, or to axially move the distal member 2807 while maintaining the proximal member 2806 stationary.

It is preferred that the proximal and distal members 2806, 2807 disclosed herein are not self-expandable or self-contractable but, rather, only expand or contract when a pressure is manually applied or released using the physically manipulable interfaces (such as, for example, knobs, sliders, buttons or other actuation mechanisms) integrated into the handle 2802.

In one embodiment, as shown in FIG. 28A, the first slider, knob, button, or other actuation mechanism 2814, the second slider, knob, button, or other actuation mechanism 2818, and the third slider, knob, button, or other actuation mechanism 2820 are positioned in an arc around an external surface of the handle 2802 such that each of the first, second, and third actuation mechanisms are at the same location, or within 3 inches, axially along the length of the handle. In another embodiment, as shown in FIG. 28J, the first slider, knob, button, or other actuation mechanism 2814, the second slider, knob, button, or other actuation mechanism 2818, and the third slider, knob, button, or other actuation mechanism 2820 are positioned on a flat external surface of the handle 2802 such that each of the first, second, and third actuation mechanisms are positioned adjacent to each other. In some embodiments, as shown in FIG. 28J, a proximal end of the handle 2802 includes a first guidewire port 2820j and a second flush port 2822j. Also, in some embodiments, as shown in FIG. 28J, a distal end of the handle 2802 includes a fourth physically manipulable interface such as, for example, a slider, knob, button, or other actuation mechanism 2811j used to slidably advance or retract the delivery catheter 2848. The physically manipulable interface 2811j allows for a greater length of the delivery catheter 2848 to be passed through the hemostasis valve hub 2842j. In some embodiments, pressing the physically manipulable interface 2811j allows the user to move or slide the physically manipulable interface 2811j towards or away from the tip portion 2804 thereby increasing or decreasing the length of the delivery catheter 2848 passing through the valve hub 2842j. Further, in some embodiments, as shown in FIG. 28J, the proximal end 2844 of the aspiration catheter 2835 (or the distal end of the valve hub 2842j) includes a port 2813j for injecting saline or a contrasting agent, when required.

In another embodiment, the handle comprises one or more actuation mechanisms to deliver medications and, in particular, can deliver tPA (tissue Plasminogen Activator) and/or activate an aspiration while providing distal embolic protection because of the stationary position of the distal member. In one embodiment, a method of treatment would include infusing tPA into at least one lumen positioned within the catheter. Preferably the infusion is performed at the outset of the pulmonary embolism or deep vein thrombosis treatment process, while the proximal and/or distal members are still housed within the catheter, thereby covering the unexpanded proximal and/or distal members in tPA. Alternatively, the infusion is performed at the outset of the pulmonary embolism or deep vein thrombosis treatment process, while the proximal and/or distal members are still housed within the catheter, directed through the distal end of the catheter, and injected directly into the clot prior to inserting and expanding the proximal and/or distal members.

In another embodiment, the catheter and handle, in combination, are configured to deliver ultrasonic energy to a clot in order to accelerate lytic dispersion, drive medications deeper into the clot, speed the breakdown of the clot, and/or degenerate or unwind the fibrin quicker. In one embodiment, the catheter comprises an ultrasonic core in parallel with the elongated wire extending axially through the catheter lumen. The ultrasonic core is in electrical communication with a control unit positioned external to the catheter. The proximal end of the handle would preferably have one or more leads in electrical communication with the ultrasonic core that would extend outward from the handle and be configured to connect to the control unit. During the pulmonary embolism or deep vein thrombosis treatment process, the ultrasonic energy would be activated, using the control unit, at the beginning of the treatment upon delivery of the medications, as described above.

In embodiments, an ultrasonic core energy generator runs through the center of the catheter. In embodiments, the ultrasonic core energy generator includes a control unit configured to manage the generator. A proximal end of the retrieval device 2800 includes leads plug into the control unit, in embodiments.

In accordance with some aspects of the present specification, the first and second units 2890, 2892 are manufactured as separate standalone units or devices. This is advantageous in that a physician may use the first unit 2890 with any third-party aspiration catheter. In some embodiments, the aspiration catheter 2835 is available with a plurality of external diameters such as, but not limited to, 12 Fr, 16 Fr, 20 Fr, and 24 Fr (where Fr represents French scale or gauge system). In some embodiments, the syringe 2837 has an exemplary, non-limiting, volume of 60 cubic centimeters.

In some embodiments, for use in treatment of pulmonary embolism a length of the delivery catheter 2848 is in a range of 80 cm to 160 cm, preferably 120 cm. In some embodiments, for use in treatment of pulmonary embolism the aspiration catheter 2835 has different lengths for different external diameters. For example, an aspiration catheter of 16 Fr has a length in a range of 70 cm to 160 cm, preferably 112 cm, an aspiration catheter of 20 Fr has a length in a range of 60 cm to 150 cm, preferably 105 cm or 106 cm, and an aspiration catheter of 24 Fr has a length in a range of 50 cm to 130 cm, preferably 90 cm. Also, in some embodiments, for use in treatment of pulmonary embolism (PE), the aspiration catheter of 20 Fr has a distal end or tip with a customizable 270° bend whereas the aspiration catheter of 24 Fr has a flexible or bendable distal end or tip. In some embodiments, for use in treatment of pulmonary embolism (PE), the suction source 2837 is a syringe having a volume ranging from 1 cc to 100 cc, and preferably a volume of 60 cc. In some embodiments, for use in treatment of deep vein thrombosis (DVT) a length of the delivery catheter 2848 is in a range of 40 cm to 120 cm, preferably 80 cm. In some embodiments, for use in treatment of deep vein thrombosis a length of a 16 Fr aspiration catheter 2835 is in a range of 45 cm to 80 cm, preferably 65 cm. In some embodiments, for use in treatment of deep vein thrombosis, the suction source 2837 is a syringe having a volume ranging from 1 cc to 100 cc, and preferably a volume of 60 cc. In some embodiments, for use in treatment of right heart/atrium, the 24 Fr aspiration catheter has a length of 90 cm. In some embodiments, for use in treatment of IVC/SVC (Inferior Vena Cava/Superior Vena Cava), the 24 Fr aspiration catheter has a length of 90 cm. In some embodiments, at least one pressure transducer or sensor 2809 (such as, for example, a fiber-optic pressure sensor, electro-mechanical pressure sensor and hydraulic pressure sensor) is positioned at a distal end of aspiration catheter 2835. In some embodiments, the at least one pressure transducer or sensor 2809 is in the form of an elongated member that is co-extruded into the aspiration catheter 2835 so that the elongated member runs along a full length of the aspiration catheter 2835. In embodiments, the pressure transducer or sensor 2809 is in electrical communication with electronic circuitry located in a handle 2802 of the first unit 2890. In embodiments, the handle 2802 includes a pressure display 2821. In various embodiments, the pressure transducer or sensor 2809 is configured to sense a pressure change or drop and, in particular, provide the physician with an indication that, as the occlusion is removed, there is an associated change of pressure indicative of a right side drop in right heart pressure. A right side drop in right heart pressure indicates that a problematic occlusion is being successfully removed.

Referring again to FIGS. 28A to 28J, in embodiments, tip portion 2804 of device 2800 has a proximal end 2850 and a distal end 2852. During operation of the device 2800, the tip portion 2804 is inserted into, for example, a blood vessel for removing an occlusion while the handle portion 2802 remains in an operator/user's hands. During insertion of the device 2800 into the blood vessel, the distal end 2852 of the tip portion 2804 enters the blood vessel first and is placed in close proximity to the occlusion within the blood vessel by using the handle 2802 to maneuver the insertion of the tip portion 2804 in a desired position in the blood vessel. The tip portion 2804 comprises a distal member, element or body 2807, which in an embodiment, is a mechanically expandable, rigid anchor fixedly attached proximate the distal end 2852 of the tip portion 2804, and a proximal member, element or body 2806, which in an embodiment is a mechanically expandable pusher ball that is slidably mounted proximate the proximal end 2850 of the tip portion 2804. The mechanical expansion is in contrast to a non-mechanical expansion occurring because a shape memory material is naturally configured to adopt a pre-defined shape without mechanical force requiring to be applied.

In some alternate embodiments, the proximal element or body 2806 is configured as a mechanically expandable, rigid anchor fixedly attached proximate to the proximal end 2850 of the tip portion 2804 while the distal element or body 2807 is configured as a mechanically expandable pusher ball that is slidably or moveably mounted proximate the distal end 2852 of the tip portion 2804.

In various embodiments, the proximal and distal elements 2806, 2807 are substantially curved structures. In some embodiments, each of the proximal and distal elements 2806, 2807 is a three-dimensional (3D) shape. In some embodiments, the proximal and distal elements 2806, 2807 are independent of one another yet mounted on a single delivery system or device 2800. In one embodiment, the proximal 2806 member and the distal member 2807 are braided structures made of interwoven wires such that each structure has a plurality of open areas (allowing egress from outside the member into the internal volume of the member) formed by the braid. The open areas, relative to the total surface area of the proximal or distal member 2806, 2807, is in a range of 1% to 99% of the total surface area. In one embodiment, the proximal member 2806 has a greater percentage of open surface area than the distal member 2807, thereby allowing the proximal member 2806 to capture more clot material and the distal member 2807 to function more as a barrier to material flowing away from the device. The proximal member 2806 and/or distal member 2807 may be of any shape, including linear, spherical, spheroid, elliptical, ellipsoid, conical, polygonal, cylindrical, stent, chalice cup, umbrella, concave structure, convex structure, half-sphere, sphere, windsock, dumbbell, star, polygon, lever, disc, or a combination of such shapes.

In one embodiment, as shown in FIG. 28C, the proximal member 2806 is structurally shaped as a first funnel 2886 having a neck 2888 directed along an axis 2803 in a proximal direction and a second funnel 2887 having a neck 2889 directed along the axis 2803 in a distal direction wherein the cup edge of the first funnel 2886 and the second 2887 are attached (in the form of contiguous wires) across a center axis 2891. Alternatively or additionally, in some embodiments, the distal member 2807 is also structurally shaped similar to the proximal member 2806 in terms of including a first funnel having a first neck directed along the axis 2803 in a proximal direction and a second funnel having a second neck directed along the axis 2803 in a distal direction wherein the cup edges of the first funnel and the second funnel are attached, optionally, in the form of contiguous wires, across a center axis). In some embodiments, when either of or both of the proximal element 2806 and/or the distal element 2807 is mechanically expanded, a proximal portion and a distal portion of the respective element expands first followed by a center portion. In some embodiments, each of the respective proximal, distal and center portions of the proximal element 2806 and the distal element 2807 may expand at different rates. In some embodiments, the proximal element 2806 and the distal element 2807 may be heterogeneous, having different characteristics including, without limitation, radial force (as described further below), shape, size (for example, thickness, diameter), pore size (for example, mesh pore size or open areas as described above), and external coating. In some embodiments, the proximal and distal elements 2806, 2807 may be substantially similar in terms of the compositions and characteristics.

In some embodiments, the proximal and distal elements 2806, 2807 have similar braided structures that transition from a substantially linear structure to a substantially disc structure, adopting one or more three dimensional geometric shapes (spherical, spheroid, elliptical, ellipsoid, conical, polygonal, cylindrical, stent, chalice cup, umbrella, concave structure, convex structure, half-sphere, sphere, windsock, dumbbell, star, polygon, lever, disk or a combination of such shapes) during the transition. That is, the proximal element 2806 is defined by a first braid structure while the distal element 2807 is defined by a second braid structure, wherein the second braid structure is equivalent to the first braid structure, in embodiments. In other embodiments, the second braid structure is not equivalent to the first braid structure.

Figure 28K:
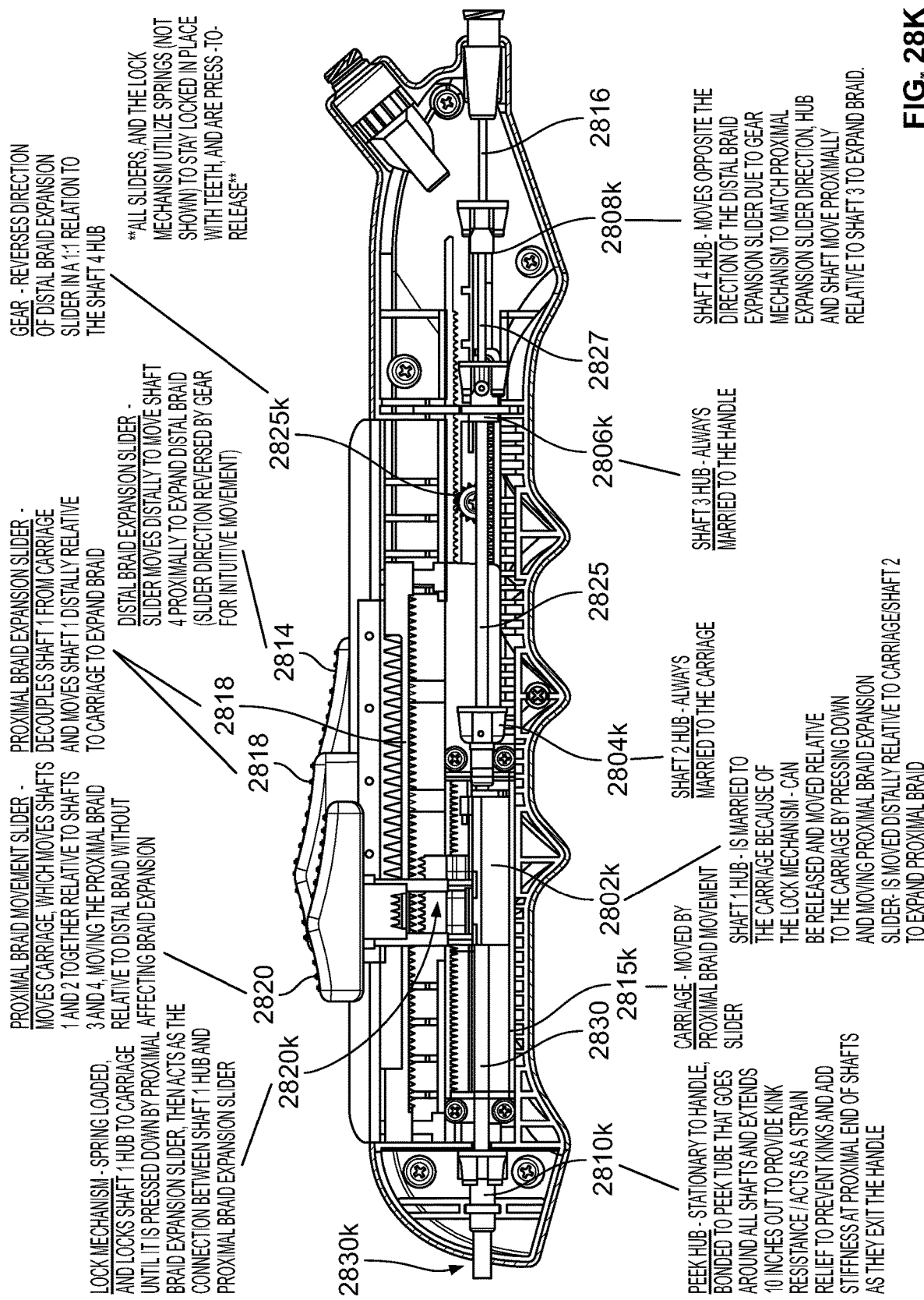
FIG. 28K is a longitudinal cross-sectional view of a handle of a retrieval device, in accordance with another embodiment of the present specification.
Figure 28L:
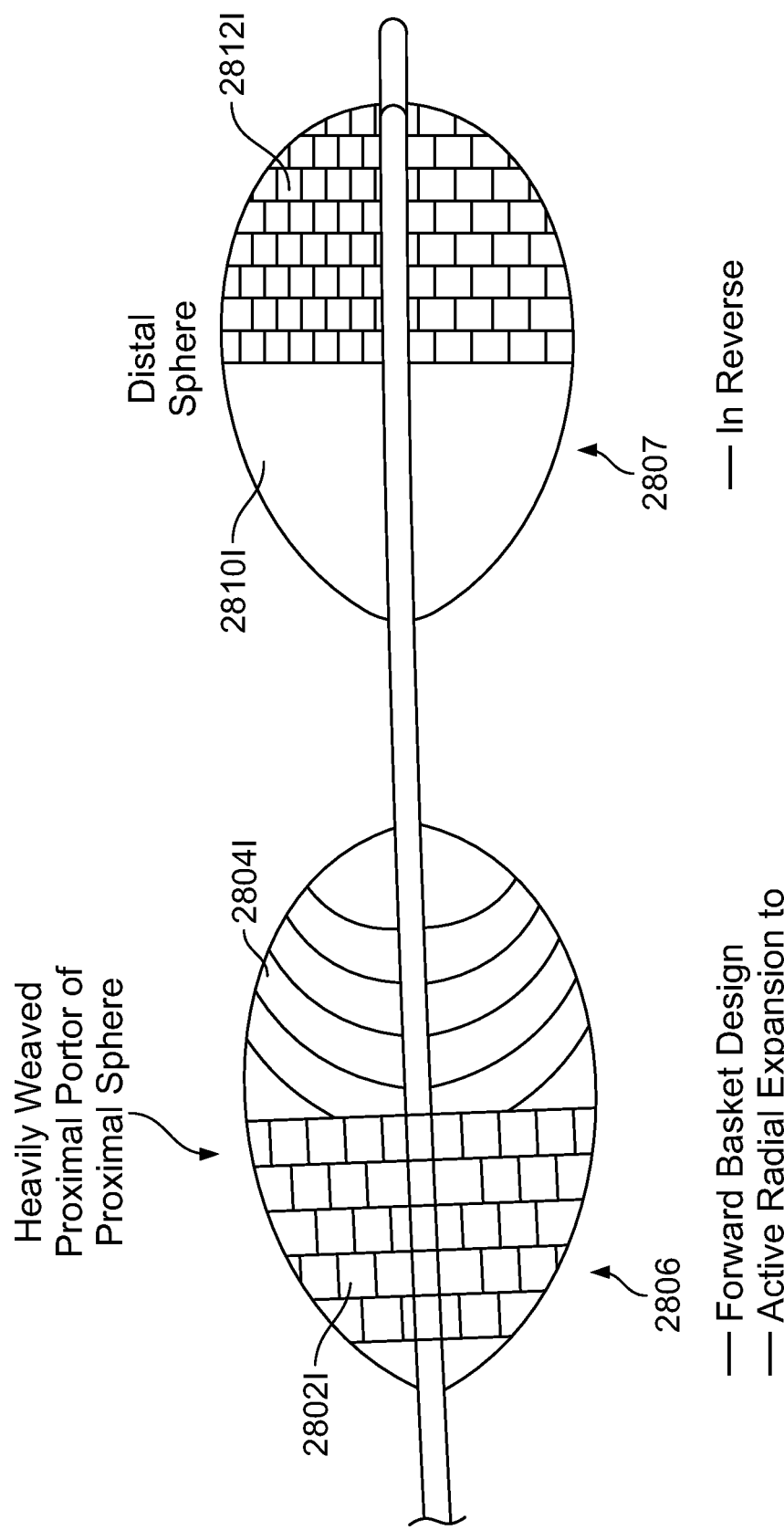
FIG. 28L shows proximal and distal elements of the retrieval device of FIG. 28A, in accordance with an embodiment of the present specification.

As shown in FIG. 28L, the proximal element 2806 has a proximal portion 2802*l* and a distal portion 2804*l*. In some embodiments, the proximal portion 2802*l* has a denser braid relative to the distal portion 2804*l*. That is, the proximal portion 2802l is defined by a braid or weave pattern that is more stiff, rigid, or dense as compared to the distal portion 2804*l*. The proximal element 2806 has a braid or weave that results in an active radial expansion. In some embodiments, the proximal portion 2802*l* represents 30-70% of the total surface area of the proximal element 2806 while the distal portion 2804*l* represents 70-30% of the total surface area of the proximal element 2806. The distal element 2807 has a proximal portion 2810*l* and a distal portion 2812*l*. In contrast to the proximal element 2806, the proximal portion 2810*l* of the distal element 2807 has a less dense (stiff/rigid) braid than the distal portion 2812*l* of the distal element 2807. The distal element 2807 has a braid or weave that results in an active radial expansion. In some embodiments, the distal portion 2812*l* represents 30-70% of the total surface area of the distal element 2807 and the proximal portion 2810*l* represents 70-30% of the surface area of the distal element 2807. Thus, in some embodiments, the proximal element 2806 is defined by a first braid structure while the distal element 2807 is defined by a second braid structure, wherein the second braid structure is equivalent to the first braid structure rotated 180 degrees. In embodiments, the different braid structures enable scraping of unwanted material or occlusion from a vessel wall as well as effective trapping of the unwanted material or occlusion within and/or between the proximal and distal elements 2806, 2807 so that the material or occlusion is easily removed.

The tip portion 2804 is at least partially enclosed within the delivery catheter 2848 (as shown in view 2870 of FIG. 28H) which when retracted (as shown in view 2872 of FIG. 28H) exposes at least the distal element 2807 and the proximal element 2806 when the device 2800 is inserted and maneuvered within the vascular system or non-vascular structures, by using the handle portion 2802.

As stated above, in some embodiments, the distal element 2807 may be curved and take the form of a cylinder, stent, chalice cup, umbrella, concave structure, half-sphere, sphere, windsock, dumbbell, star, polygon, lever, or any other suitable shape configured for holding an occlusion and aiding retrieval of the occlusion. In some embodiments, the elongated member 2805, including the tip portion 2804, comprises four flexible telescoping tubes, that when manipulated together enable an operator/doctor to expand or contract the distal and proximal elements 2807, 2806 and move the proximal element 2806 axially, relative to the distal element 2807 and vice versa, in order to dislodge and remove the occlusion. View 2874 of FIG. 28H illustrates the proximal and distal elements 2806, 2807 fully expanded by manipulating the flexible telescoping tubes using the handle 2802. In an embodiment, the proximal element (pusher ball) 2806 is configured to move relative to the distal element (rigid anchor) 2807 via manipulation of the flexible telescoping tubes to enable dislodging and removal of the occlusion, as is explained in detail with reference to FIGS. 29A through 29D. View 2876 of FIG. 28H illustrates the proximal element 2806 being moved axially towards the distal element 2807 by manipulating the flexible telescoping tubes using the handle 2802.

In some embodiments, the distal and/or proximal elements 2807, 2806 are fabricated from a Nitinol wire mesh having a plurality of mesh pores, lattices or cells. In some less preferred embodiments, the distal and/or proximal elements 2807, 2806 are inflatable devices including, but not limited to, inflatable balloons. In some embodiments, the distal and proximal elements 2807, 2806 are fabricated from different materials. In some embodiments, the distal element 2807 is a wire mesh while the proximal element 2806 is an inflatable balloon. In some embodiments, the distal element 2807 is an inflatable balloon while the proximal element 2806 is a wire mesh.

In some embodiments, each of the proximal element 2806 and the distal element 2807 may be characterized by their ability to apply a variable radial force by virtue of the mechanical expansion being applied to each structure and the elements' stiffness or rigidity across sub-regions or portions of the respective elements 2806, 2807. For example, in some embodiments, the expansion of each of the proximal and distal elements 2806, 2807 to a first size (defined by an area or volume encompassed by the element) may be characterized by a first radial force that first size can apply to surrounding materials. The expansion of each of the proximal and distal elements 2806, 2807 to a second size (defined by an area or volume encompassed by the element that is larger than the first size) may be characterized by a second radial force that second size can apply to surrounding materials, where the second radial force is different from the first radial force. In some embodiments, each of the first and second radial forces are in a range of 5 Newtons to 25 Newtons, preferably 10 Newtons to 14 Newtons. The mechanical expansion allows for the intermittent, controlled expansion of the proximal and distal elements 2806, 2807 so that they can adopt and retain the shape of a first size (having a first area or volume), a second size (having a second area or volume), a third size (having a third area or volume), or a fourth size (having a fourth area or volume) under the control of the user and throughout the length of a procedure where the fourth size is bigger than the third size which is bigger than the second size which is bigger than the first size.

In some embodiments, each of the proximal element 2806 and the distal element 2807 may be characterized by their ability to resist an application of a radial force, thereby maintaining its expanded shape, by virtue of the mechanical expansion being applied to each structure and the elements' stiffness or rigidity across sub-regions of the respective elements 2806, 2807. For example, in some embodiments, the expansion of each of the proximal and distal elements 2806, 2807 to a first size (defined by an area or volume encompassed by the element) may be characterized by an ability to resist (and therefore avoid collapse or compression of the first size) from a first radial force. The expansion of each of the proximal and distal elements 2806, 2807 to a second size (defined by an area or volume encompassed by the element that is larger than the first size) may be characterized by an ability to resist (and therefore avoid collapse or compression of the second size) from a second radial force that is different from the first radial force. In some embodiments, each of the first and second radial forces are in a range of 5 Newtons to 25 Newtons, preferably 9 to 20 Newtons, more preferably 10 Newtons to 14 Newtons. The mechanical expansion allows for the intermittent, controlled expansion of the proximal and distal elements 2806, 2807 so that they can adopt and retain the shape of a first size (having a first area or volume), a second size (having a second area or volume), a third size (having a third area or volume), or a fourth size (having a fourth area or volume) under the control of the user and throughout the length of a procedure where the fourth size is bigger than the third size which is bigger than the second size which is bigger than the first size. It should further be appreciated that at least one of the proximal and distal elements 2806, 2807 area adapted to not collapse or compress when positioned against blood flow that applies a hydrostatic pressure in a range of 80 mm Hg to 250 mm Hg. This is particularly valuable in arterial clot removal where the hydrostatic pressure level often causes other structures, particularly self-expanding structures, to compress or collapse.

In one embodiment, a physician uses any of the embodiments disclosed herein by a) placing the distal element distal to the occlusion, b) placing the proximal element proximal to the occlusion, c) expand each of the proximal and distal elements to a diameter, width, or volume that is greater than or equal to the diameter, width or volume of the vessel lumen it is positioned within of vessel (if greater than, it may be equal to or up to 150%, preferably around 110% to 130%, more preferably 120%), d) sandwich the thrombus between the distal and proximal elements, e) apply aspiration, f) move the proximal element to pull the thrombus to the catheter, g) partially collapse the proximal and distal elements to move both toward the catheter, h) collapse both elements to pull them back into the catheter, with the thrombus, and remove the catheter from the patient. The distal element may optionally act as embolic protection to protect against clot material breaking free and flowing away from the procedure site.

In some embodiments, the proximal element 2806 and the distal element 2807 may have anti-platelet coating to reduce adhesion and provide a less thrombogenic environment during clinical application. In some embodiments, the proximal element 2806 and the distal element 2807 and any material (for example, wires and/or tubes) between these elements, may be coated with control release agents including, but not limited to, thrombolytic agents.

Preferably, the distal element 2807 is rigid and holds/maintains a predefined shape after expansion. In particular, it is preferred that, when deployed within a patient's vessel, a degree of fixation achieved by the distal element 2807 is greater than that achieved by the proximal element 2806, making the proximal element 2806 comparatively more mobile than the distal element 2807. Having a distal member that is less susceptible to collapse and/or more resistant to force, ensures that the distal member can anchor and fix the device within the vessel and provide the opposing leverage to ensure the proximal member, when axially moved, can pull the clot material toward the open catheter. In alternate embodiments, however, the proximal element 2806 is rigid and holds/maintains a predefined shape after expansion while the distal element 2807 is relatively more mobile than the proximal element 2806. In such embodiments, the degree of fixation achieved by the proximal element 2806 is greater than that achieved by the distal element 2807. Consequently, in such embodiments, the proximal element 2806 is less susceptible to collapse and/or more resistant to force, ensuring that the proximal element 2806 can anchor and fix the device within the vessel and provide the opposing leverage to ensure the distal element 2807, when axially moved, can pull the clot material toward the open catheter.

Fixation may be achieved by means of radial opposition against a patient's vessel wall, engagement within or beyond a distal portion of an occlusion requiring removal, deployment around distal anatomical features (such as a vascular bifurcation or curve in the vasculature), or any combination of these. Aspects that may selectively enhance or impede the relative fixation enabled by the proximal and distal elements 2806, 2807 include radial force or stiffness, expanded diameter, braid density, braid wire size, deployed length, deployed shape, wire geometry and surface finish, surface treatments and coatings, or other means that allow for amplification or dampening of frictional engagement of the elements 2806, 2807 with the occlusion and surrounding vasculature.

In embodiments, the proximal element 2806 is equally or less stiff/rigid than the distal element 2807 by a ratio of less than or equal to 1:10. In embodiments, the relative stiffness or rigidity relationship is inverted with the distal element 2807 being equally or less stiff than the proximal element 2806 by a ratio of less than or equal to 1:10. By modulating the manufactured relative radial force, stiffness or rigidity of the proximal and distal elements 2806, 2807, a desired balance of relative anchoring force to maceration potential can be achieved.

As previously stated, higher stiffness, rigidity or degree of fixation of the distal element 2807, relative to the proximal element 2806, provides an effective anchoring function when positioned within a vascular system or non-vascular structures. During a procedure, the anchored distal element 2807 provides an opposing anchoring force when the proximal element 2806, having relatively lesser stiffness, rigidity or degree of fixation, is moved or pushed axially towards the distal element 2807 to dislodge an occlusion. This provides an operator an improved ability to apply pressure, through the pushing manipulation of the proximal element 2806, in order to dislodge the occlusion. Thus, in various embodiments, by adjusting the characteristics (of the proximal and distal elements 2806, 2807) such as the radial force, shape, size (for example, thickness, diameter), pore size (for example, mesh pore size in embodiments where at least one of the two elements 2806, 2807 is fabricated from a wire mesh) and external coating a desired stiffness, rigidity or flexibility of the retrieval device 2800 may be obtained. With the desired stiffness, rigidity or flexibility the retrieval device 2800 may be adapted to extract or remove a variety of obstructions such as, for example, stones, pulmonary emboli and deep vein clots.

In sum, the distal member has a higher degree of rigidity and greater degree of porosity as compared to the proximal member. This is achieved by the distal member having at least one of a shape, wire thickness, average pore size, total porosity, total open surface area to total surface area ratio, and/or coating that is different from the proximal member. As a result, when expanded to any number of a plurality of sizes, the distal member is preferably more resistant to changing its size or shape upon application of an external force as compared to the proximal member. In some embodiments, that external force is in a range of 1 newton to 50 Newtons and any increment therein, more preferably 8 newton to 20 Newton, even more preferably 9 newton to 15 newton. Additionally, as a result, when expanded to the same size as the proximal member, the distal member is preferably less porous, meaning that it has less open surface area relative to total surface area, than the proximal member.

In embodiments, the elongated member 2805, including the tip portion 2804, comprises a plurality of telescoping tubes (also referred to, alternatively, as shafts), such as 1-6 or preferably 4, which are also described with reference to FIGS. 29A-29D. As shown in FIG. 28B (in an expanded form), a first tube 2830 is shown projecting distally from a distal end 2854 of the delivery catheter 2848. The first tube 2830 is coupled with a second tube 2825 that is coupled with a third tube 2827 which, in turn, is coupled with a fourth/ anchor tube 2816. The fourth/anchor tube 2816 forms the distal end 2852 of the tip portion 2804. In an embodiment, the four tubes 2830, 2825, 2827 and 2816 are arranged as a coaxial array of telescopic tubes, all of which are designed to be able to move axially relative to one another. In an embodiment, the first tube 2830 is concentrically positioned around the second tube 2825, the second tube 2825 is concentrically positioned around the third tube 2827, and the third tube 2827 is concentrically positioned around the fourth tube 2816. In embodiments, the four telescoping tubes 2830, 2825, 2827 and 2816 can be axially expanded or contracted relative to each other by using the handle portion 2802. In an embodiment, the telescoping tubes 2830, 2825, 2827 and 2816 are made of Nitinol.

In an embodiment, the distal element 2807 has a proximal end 2856 and a distal end 2858. As shown, the distal end 2858 is fixedly connected on the fourth tube 2816 at the anchor nose 2834, while the proximal end 2856 is fixedly connected to a point 2815 on the third tube 2827 in both expanded and non-expanded states of the distal element 2807. In embodiments, the wire mesh 2813 is only attached at points 2834 and 2815, respectively, of an exterior surface of the fourth tube 2816 and the third tube 2827, while the remaining portion of the wire mesh 2813 is unattached and therefore free to expand or contract. In some embodiments, in a non-expanded or collapsed state, the distal element 2807 (comprising a plurality of wires) forms a generally tubular wire mesh 2813 and is concentrically positioned around a lumen of the fourth tube 2816. It should be appreciated that, while the term "tube" is used to describe the telescoping structures, any type of cylindrical, hollow wire, solid wire, or other elongated structure may be used and the term "tube" or "shaft" is just intended to cover each of these structures.

Upon axial compression of the third tube 2827 relative to the fourth tube 2816, the wire mesh 2813 expands radially around the lumen of the fourth tube 2816. Similarly, upon axial decompression of the third tube 2827 relative to the fourth tube 2816, the wire mesh 2813 is induced to compress or contract radially around the lumen of the fourth tube 2816. In some embodiments, in order to expand or contract the distal element 2807 the fourth tube 2816 is moved axially while the first, second and third tubes 2830, 2825, 2827 remain stationary. In some embodiments, initial expansion of the distal element 2807, as induced by relative axial motion of the third tube 2827 and the fourth tube 2816, is such that the distal element 2807 first takes a shape similar to that of the proximal element 2806 (the shape of the proximal element 2806 being substantially elliptical, in one embodiment). Further relative axial movement of the third tube 2827 and the fourth tube 2816 induces an inversion in at least a portion of the wire mesh 2813 such that the proximal end 2856 collapses inside the distal end 2858, forming a chalice or a cup/concave shape as shown in FIGS. 28B and 28E. Consequently, in some embodiments, the expanded distal element 2807 has a shape substantially equivalent to a semi-sphere or cone with an interior surface 2811 folded into the semi-sphere to form a chalice or cup-like structure which may be used to hold an occlusion before removal from a patient's body. In an embodiment a distance between the two attachment points 2834 and 2815 of the wire mesh 2813 ranges approximately from 1 mm to 100 mm.

Stated differently, relative axial movement of the third tube 2827 and the fourth tube 2816 causes the proximal end 2856 and the distal end 2858 to move closer to each other, the material comprising the distal element 2807 and extending between the ends 2856 and 2858 is compressed and therefore expands outward. In contrast, as the proximal end 2856 and the distal end 2858 move away from each other, the material comprising the distal element 2807 and extending between the ends 2856 and 2858 is stretched and therefore collapses down to, and elongates along, a body lumen. Thus, the distal element 2807 expands by having the proximal end 2856 move distally and contracts by having the proximal end 2856 move proximally relative to the distal end 2858.

In some embodiments, the anchor nose 2834 is configured as a corkscrew structure such that, as the tip portion 2804 is advanced towards a clot (within a vessel lumen) the tip portion 2804 is rotated to "screw into" and break up the clot material.

Referring now to FIGS. 28B, 28C and 28D, in an embodiment, the proximal element 2806 has a proximal end 2860 and a distal end 2862. The distal end 2862 of the proximal element 2806 is fixedly attached to the second tube 2825 at a point 2828, while the proximal end 2860 is fixedly attached to the first tube 2830 at a point 2829 in both expanded and non-expanded states of the proximal element 2806. In various embodiments, in a non-expanded state, the proximal element 2806 (comprising a plurality of wires) forms a wire mesh 2826 concentrically positioned around a lumen of the second tube 2825.

In embodiments, a portion of the wire mesh 2826 is only attached at points 2828 and 2829, of an exterior surface of the second tube 2825 and the first tube 2830, respectively, while the remaining portion of the wire mesh 2826 is unattached and therefore free to expand or contract. Upon axial compression of the first tube 2830 relative to the second tube 2825, the wire mesh 2826 is induced to expand radially around the lumen of the second tube 2825. Similarly, upon axial decompression of the first tube 2830 relative to the second tube 2825, the wire mesh 2826 is induced to compress or contract radially around the lumen of the second tube 2825. In some embodiments, in order to expand or contract the proximal element 2806 the first tube 2830 is moved axially while the second, third, and fourth tubes 2825, 2827, 2816 remain stationary. Stated differently, relative axial movement of the first tube 2830 and the second tube 2825 causes the proximal end 2860 and the distal end 2862 to move closer to each other, whereby the material comprising the proximal element 2806 and extending between the ends 2860 and 2862 is compressed and therefore expands outward. In contrast, as the proximal end 2860 and the distal end 2862 move away from each other, the material comprising the proximal element 2806 and extending between the ends 2860 and 2862 is stretched and therefore collapses down to, and elongates along, a body lumen. Thus, the proximal element 2806 expands by having the proximal end 2860 move distally and contracts by having the proximal end 2860 move proximally relative to the distal end 2862.

In an embodiment, in an expanded state the proximal element 2806 approximates an elliptical shape wherein, at least a portion of the wire mesh 2826 lies approximately perpendicular to the lumen of the second tube 2825. In an embodiment, a diameter of an expanded proximal element 2806 is approximately 18 mm. In some embodiments, a fully expanded proximal element 2806 is substantially elliptical or disc-shaped as shown in FIGS. 28C and 28D, while in a transient or less expanded state the proximal element 2806 may take different curved shapes such as, for example, substantially spherical. In some embodiments, a fully expanded proximal element 2806 may be substantially spherical shaped while in a transient or less expanded state the proximal element 2806 may take a substantially elliptical shape.

As previously discussed, in various embodiments, in an expanded state the proximal element 2806 may take the form of a cylinder, stent, chalice cup, umbrella, concave structure, half-sphere, sphere, windsock, dumbbell, star, polygon, lever, or any other suitable shape configured for aiding retrieval of the occlusion. It should be appreciated that in an expanded state, in some embodiments, the proximal element 2806 may take on a first shape while the distal element 2807 may take on a second shape. In some embodiments, the first shape is different from the second shape. In some embodiments, the first and second shapes are substantially similar. In some embodiments, the proximal and/or distal elements 2806, 2807 can be turned and rotated as motorized units. In such an embodiment, a small motor positioned in or proximate the handle is coupled to each of the proximal and/or distal elements 2806, 2807 and, upon actuation, the motor causes one of or both the proximal and/or distal elements 2806, 2807 to move or rotate.

Referring now to FIGS. 28A, 28G and 28J, in an embodiment, the handle portion 2802 comprises a groove 2812 running longitudinally along a length of the handle 2802. In an embodiment a distance between a distal end 2865 of the handle portion 2802 and the distal end 2852 of the tip portion 2804 is in a range of 0.5 mm to 110 cm, preferably 1 mm to 100 mm. A first actuator, knob, slider or button 2814, configured to enable the user to mechanically expand or contract the distal element 2807, is coupled with the third tube 2827 and is slidably fitted into the groove 2812 such that the first slider 2814 may be slid forward (that is, distally) towards the tip portion 2804 or backwards (that is, proximally) away from the tip portion 2804. The fourth tube 2816 is connected to the distal element 2807 at point 2834 while the third tube 2827 is connected to the distal element 2807 at point 2815. A sliding movement of the third tube 2827 relative to the fourth tube 2816 induces and aids in the expansion and contraction of the distal element 2807.

It should be appreciated that, in alternate embodiments, the first actuator, knob, slider or button 2814 is coupled to the fourth tube 2816 so that a sliding movement of the fourth tube 2827 (using the first actuator, knob, slider or button 2814) relative to the third tube 2827 induces and aids in the expansion and contraction of the distal element 2807. In other words, the first actuator, knob, slider or button 2814 may be coupled to either the third tube 2827 or the fourth tube 2816 in order to impart a sliding movement of the third and fourth tubes 2827, 2816 relative to each other.

Sliding the first knob 2814 within the groove 2812 towards the tip portion 2804 causes the third tube 2827 to telescope into the fourth tube 2816 thereby inducing an axial compression of the third tube 2827 relative to the fourth tube 2816 and consequently of the distal element 2807 between the proximal and distal ends 2856, 2858 of the wire mesh 2813. This causes the wire mesh 2813 (and therefore the distal element 2807) to expand radially around the lumen of the fourth tube 2816 and assume an expanded chalice, cup/concave shape having a diameter greater than a diameter in an unexpanded state. This kind of mechanical expansion of the distal element 2807 is preferred as this expansion provides a user control over the diameter of the distal element 2807 in an expanded state and, also provides a rigid structure that is less susceptible to collapse when placed under pressure. Providing a physician control over the expansion size means that a physician may set one of a plurality of different expansion sizes and, upon setting that expansion size, the proximal or distal element maintains that expansion size even upon application of an external force in the ranges disclosed herein, such as 9 newtons to 15 newtons. In one embodiment, a proximal element and/or distal element (first expansion member and/or second expansion member) expands upon moving the at least one actuation mechanism (slider, knob, lever, etc.) distally and wherein said expansion causes at least one of the first expandable member and the second expandable member to transform from a substantially linear configuration to a first shape, second shape or third shape depending on how far the at least one actuation mechanism has been moved distally. The first shape, second shape or third shape is at least one of a spherical shape, an elliptical shape, a conical shape, a polygonal shape, a cylindrical shape, a shape of a stent, a shape of a chalice cup, a shape of an umbrella, a concave shape, a convex shape, a half-sphere shape, a windsock shape, a dumbbell shape, a star shape, or any combination of said shapes. The first shape has a first outer surface and a furthest distance from the first outer surface to the elongated member is defined by a first distance; the second shape has a second outer surface and a furthest distance from the second outer surface to the elongated member is defined by a second distance; the third shape has a third outer surface and a furthest distance from the third outer surface to the elongated member is defined by a third distance and the third distance is greater than the second distance and wherein the second distance is greater than the first distance. The first shape is configured to maintain said first distance even upon an application of an external force to the first outer surface in a range of 9 newtons to 15 newtons, wherein the second shape is configured to maintain said second distance even upon an application of an external force to the second outer surface in a range of 9 newtons to 15 newtons, and wherein the third shape is configured to maintain said third distance even upon an application of an external force to the third outer surface in a range of 9 newtons to 15 newtons.

Similarly, sliding the first knob 2814 within the groove 2812 away from the tip portion 2804 causes the third tube 2827 to telescope and expand out of the fourth tube 2816 thereby inducing an axial decompression of the distal element 2807 between the proximal and distal ends 2856, 2858 of the wire mesh 2813. This causes the wire mesh 2813 (and therefore the distal element 2807) to contract radially around the lumen of the fourth tube 2816 and assume an unexpanded substantially cylindrical shape having a diameter lesser than a diameter in an expanded state.

In some embodiments, the distal element 2807 assumes a substantially cylindrical shape when in a fully collapsed or unexpanded state, a substantially elliptical shape when in a partially expanded state and a concave, umbrella, half-sphere, sphere, windsock, dumbbell, star, polygon, chalice or cup-like shape when in a fully expanded state.

In some embodiments, the first knob 2814 locks (cannot be moved further forward) in a position in the groove 2812 when the distal element 2807 has expanded to a maximum diameter, which in an embodiment is approximately 25 mm. Thus, sliding the first knob 2814 forward enables the user to expand the distal element 2807 to a plurality of intermediate diameters and up to a maximum permissible diameter. In some embodiments, the first knob 2814 is provided with a "clutch" feature so that, when opposing pressure is experienced from walls of a blood vessel during expansion of the distal element 2807, the "clutch" clicks in so that the user does not over expand. This feature is advantageous since it prevents the user from damaging the blood vessel due to over expansion of the distal element 2807.

In various embodiments, the distal element 2807 may expand to a diameter depending upon an application/functional use of the device 2800. For example, for use in treatment of pulmonary/large vessel having a diameter of up to 20 mm, the diameter of an expanded distal element 2807 ranges from 10 mm to 25 mm; for use in treatment of peripheral or deep vein thrombosis vessel having a diameter ranging from 5 mm to 10 mm, the diameter of an expanded distal element 2807 ranges from 3 mm to 12 mm; for use in treatment of neuro vessels, the diameter of an expanded distal element 2807 ranges from 2 mm to 10 mm; for use in retrieval of an occlusion in the inferior vena cava (IVC) vessels, the diameter of an expanded distal element 2807 ranges from 35 mm to 40 mm. In some embodiments, for use in treatment of pulmonary embolism, each of the proximal and distal elements 2806, 2807 has an outer diameter ranging from 3 mm to 16 mm. In some embodiments, for use in treatment of pulmonary embolism, each of the proximal and distal elements has a maximum outer diameter of 16 mm. In some embodiments, for use in treatment of pulmonary embolism, the delivery catheter is of 9 Fr. In some embodiments, for use in treatment of deep vein thrombosis, each of the proximal and distal elements 2806, 2807 has an outer diameter ranging from 3 mm to 20 mm. In some embodiments, for use in treatment of deep vein thrombosis, the proximal element 2806 has a maximum outer diameter of 16 mm and the distal element 2807 has a maximum outer diameter of 20 mm.

In an embodiment, for application of the retrieval device 2800 in treatment of pulmonary embolism the proximal element 2806 is designed with a larger diameter as compared to the distal element 2807. In an embodiment, if a diameter of the distal element 2807 is 16 mm, diameter of the proximal element 2806 is 20 mm, as the internal diameter of a patient's blood vessels tapers down distally. In another embodiment, if a diameter of the distal element 2807 is 5 mm, then a diameter of the proximal element 2806 is 20 mm. In an embodiment, for application of the retrieval device 2800 in treatment of deep vein thrombosis the proximal element 2806 is designed with a smaller diameter as compared to the distal element 2807. In an embodiment, if a diameter of the distal element 2807 is 16 mm, then a diameter of the proximal element 2806 is 14 mm, as in this case, the internal diameter of a patient's blood vessels is larger proximally. In another embodiment, if a diameter of the distal element 2807 is 16 mm then a diameter of the proximal element 2806 is 8 mm.

In various embodiments, in fully expanded state, each of the proximal and distal elements 2806, 2807 has a diameter ranging from 5 mm to 30 mm, preferably 10 mm to 25 mm, and more preferably 10 mm to 20 mm.

In embodiments, the groove 2812 contains a series of interlocking features along its length such that the first knob 2814 can be selectively engaged or disengaged from a locked position in the handle 2802 at a plurality of expanded diameters for the distal element 2807.

Additionally, the handle portion 2802 includes a second actuator, knob, slider or button 2818 configured to enable the user to mechanically expand or contract the proximal element 2806. Additionally, the handle portion 2802 includes a third actuator, knob, slider or button 2820 configured to enable the user to mechanically slide the proximal element 2806 forward towards the distal element 2807 or backwards away from the distal element 2807 that remains stationary. Alternatively, the third actuator, knob, slider or button 2820 is configured to enable the user to mechanically slide the distal element 2807 back towards the proximal element 2806 or forwards away from the proximal element 2806 that remains stationary. The second and third knobs 2818, 2820 are slidably fitted into the groove 2812. In some embodiments, the second slider 2818 is coupled with the first tube 2830 to enable the user to mechanically expand or contract the proximal element 2806. Alternatively, the second slider 2818 may be coupled with the second tube 2825 to enable the user to mechanically expand or contract the proximal element 2806.

In some embodiments, the third slider 2820 is coupled with the first and second tubes 2830, 2825 such that a sliding movement of the third slider 2820 towards or away from the tip portion 2804 causes the proximal element 2806 to slide towards or away from the distal element 2807 (while the third and fourth tubes 2827, 2816 remain stationary). In alternative embodiments, the third slider 2820 is coupled with the third and fourth tubes 2827, 2816 such that a sliding movement of the third slider 2820 towards or away from the tip portion 2804 causes the distal element 2807 to slide away from or towards the proximal element 2806 (while the first and second tubes 2830, 2825 remain stationary).

In some embodiments, the first tube 2830 is connected to the proximal element 2806 at the point 2829 while the second tube 2825 is connected to the proximal element 2806 at the point 2828. A sliding movement of the first tube 2830 relative to the second tube 2825 aids in the expansion and contraction of the proximal element 2806. Upon axial compression of the first tube 2830 relative to the second tube 2825, the wire mesh 2826 is induced to expand radially around the lumen of the second tube 2825.

In some embodiments, when the second slider 2818 is moved or slid in the groove 2812 towards the tip portion 2804, this causes the first tube 2830 to telescope into the second tube 2825, thereby inducing an axial compression of the first tube 2830 relative to the second tube 2825. Consequently, the proximal element 2806 is caused to expand to a desired diameter. When the second slider 2818 is moved away from the tip portion 2804 the first tube 2830 is caused to telescope out of the second tube 2825 thereby inducing an axial decompression (or elongation) of the first tube 2830 relative to the second tube 2825 between the proximal and distal ends 2829, 2828 of the wire mesh 2826. This causes the wire mesh 2826 (and therefore the proximal element 2806) to contract radially around the lumen of the second tube 2825 and assume an unexpanded shape having a diameter lesser than a diameter in an expanded state or assume a fully unexpanded state.

In some embodiments, when the third slider 2820 is moved in the groove 2812 towards the tip portion 2804, the proximal element 2806 is caused to slide distally away from the handle 2802 and towards the distal element 2807, whereas when the third knob 2820 is moved away from the tip portion 2804 the proximal element 2806 is caused to slide proximally towards the handle portion 2802 and away from the distal element 2807.

In an embodiment, a diameter of a fully expanded proximal element 2806 is approximately 18 mm. In various embodiments, the proximal element 2806 may expand to a diameter depending upon an application/functional use of the device 2800. For example, for use in treatment of a pulmonary/large vessel having a diameter of up to 20 mm, the diameter of an expanded proximal element 2806 ranges from 10 mm to 25 mm; for use in treatment of a peripheral/DVT vessel having a diameter ranging from 5 mm to 10 mm, the diameter of an expanded proximal element 2806 ranges from 3 mm to 12 mm; for use in treatment of neuro vessels, the diameter of an expanded proximal element 2806 ranges from 2 mm to 10 mm; for use in retrieval of an occlusion in the inferior vena cava (IVC) vessels, the diameter of an expanded proximal element 2806 ranges from 35 mm to 40 mm.

In some embodiments, the second slider 2818 locks (and thus, cannot be moved further forward) in a position in the groove 2812 when the proximal element 2806 has expanded to a maximum diameter. Thus, sliding the second slider 2818 forward enables the user to expand the proximal element 2806 to a plurality of intermediate diameters and up to a maximum permissible diameter. In some embodiments, the second slider 2818 is provided with a "clutch" feature so that, when opposing pressure is experienced from walls of a blood vessel during expansion of the proximal element 2806, the "clutch" clicks in so that the user does not over expand. This feature is advantageous since it prevents the user from damaging the blood vessel due to over expansion of the proximal element 2806.

In various embodiments, the third slider 2820 may be configured to move synchronously along with the second slider 2818 toward the tip portion 2804 and/or in an opposing direction away from the tip portion 2804 for dislodging an occlusion and placing it in the distal element 2807. In some embodiments, the groove 2812 has a series of interlocking features along its length such that the second slider 2818 can be selectively engaged or disengaged from a locked position in the handle 2802 at a plurality of expanded diameters for the proximal element 2806.

In some embodiments, the device 2800 utilizes a lead-screw mechanism for continuous adjustment of the diameters of the proximal and distal elements 2806, 2807, so that the corresponding second slider 2818 and first slider 2814 may be advanced or retracted to an infinitely variable number of positions in the groove 2812 and may be held in a desired position by using a friction based locking mechanism, in order for the proximal and distal elements 2806, 2807 to attain a desired diameter. In an embodiment, a non-backdriving thread pattern in the lead-screw is used to provide a friction-brake when not actuated by the user, enabling continuous adjustment of the diameters of expanded proximal and distal elements 2806, 2807.

In embodiments, the fourth tube 2816 and the third tube 2827 are telescoped together to cause the distal element 2807 to expand or contract, and the second tube 2825 and the first tube 2830 are telescoped together, to cause the proximal element 2806 to expand or contract. In an embodiment, by moving the third slider 2820, leading to advancing or retracting of the second tube 2825 and the first tube 2830 together as one, the relative positions of the proximal element 2806 and the distal element 2807 may be adjusted in an expanded or collapsed state. In an alternate embodiment, by moving the third slider 2820 which leads to advancing or retracting of the third tube 2827 and the fourth tube 2816 together as one, the relative positions of the proximal element 2806 and the distal element 2807 may be adjusted in an expanded or collapsed state.

In an embodiment, a distance between the proximal element 2806 and the distal element 2807 ranges between 2 mm to 60 mm. Stated differently, the third knob 2820 may be actuated to cause the proximal element 2806 to move distally towards the distal element 2807 until a minimum distance between the proximal and distal elements 2806, 2807 is 2 mm. Similarly, the third slider may be actuated to cause the proximal element 2806 to move proximally and away from the distal element 2807 until a maximum distance between the proximal and distal elements 2806, 2807 is 60 mm. In embodiments, the second slider 2818 may be positioned at several different locations/positions along the length of the groove 2812, wherein each of the locations/positions corresponds to a different degree of expansion of the proximal element 2806, and hence a different shape of the proximal element 2806.

In some embodiments, a minimum distance between the proximal and distal elements 2806, 2807 ranges from 0 to 5 mm and a maximum distance between the proximal and distal elements 2806, 2807 ranges from 60 mm to 400 mm.

In some embodiments, the first tube 2830 extends from the handle portion 2802 to the proximal element 2806 and is co-axial with the second tube 2825, while the third tube 2827 extends from the handle portion 2802 to the distal element 2807 and is co-axial with the fourth tube 2816 which is fixedly attached to the anchor nose 2834. In some embodiments, the second tube 2825 and the fourth tube 2816 provide a fixed distal position of the corresponding wire mesh (proximal or distal elements 2806, 2807 respectively) against which the telescoping first tube 2830 and the third tube 2827 actuate to expand the proximal or distal elements 2806, 2807, respectively. The anchor nose 2834 provides a termination and fixation point for the distal element 2807 and, in an embodiment, performs a secondary function of a radiopaque marker. In various embodiments, diameters of the telescoping tubes 2830, 2825, 2827 and 2816 range from 0.010 mm to 1 mm for neurovascular and peripheral applications, and 1 mm to 3 mm for pulmonary and larger applications. In some embodiments, the fourth tube 2816 may be a solid wire instead of a hollow tube. In an embodiment, a fully expanded distal element 2807 may be concave in shape or may be shaped like a chalice, cup, or a half-sphere as shown in FIGS. 28E and 28F, while in a less expanded state the distal element 2807 may take different shapes.

Referring back to FIGS. 28A-28G, and 28J, in an embodiment, in order to retrieve an occlusion from a lumen of a patient, the delivery catheter 2848 is positioned near the occlusion (using the handle 2802) and the tip portion 2804 is positioned within, or all the way through, the occlusion. Once the occlusion matter is captured between the proximal element 2806 and the distal element 2807, the syringe 2837 is actuated to generate suction at an aspiration line 2824 and aspirate the occlusion matter through the aspiration catheter 2835.

Thus, in various embodiments, the proximal and distal elements 2806, 2807 expand to a particular diameter and a particular radial force, thereby allowing trapping and curettage of thrombus or clot material from a vessel lumen and wall. In some embodiments, the retrieval device 2800 utilizes its adjustable radial forces and its adjustable size to actively curettage the wall of an artery or vein. In some embodiments, the retrieval device 2800 enables removal of thrombus by simultaneously capturing, compressing, dragging and curetting thrombotic material from vessel walls. In one embodiment, the proximal element is configured to capture, and/or contain, a size of clot or thrombus material in a volume range of 1 mm to 100 cm.

In some embodiments, the handle portion 2802 includes a plurality of gradations such as, for example and by way of example only, three gradations of low, medium and high, five gradations ranging from low to high or eight gradations ranging from low to high. Each gradation is indicative of a corresponding predefined diameter of the proximal and distal elements in expanded states. The three slide buttons 2814, 2818, 2820 can be actuated to any one of the plurality of gradations and then détente to that position.

While in some embodiments, the handle portion 2802 includes three buttons 2814, 2818, 2820 to manipulate the proximal and distal elements 2806, 2807, in alternate embodiments fewer than three buttons may be used. For example, in some embodiments, a clinician's use of the device 2800 is monitored over a predefined number of uses or operations of the device 2800 while performing mechanical thrombectomy procedures. Based on the monitoring, a preferred sequence of deployment of the proximal and distal elements 2806, 2807 is determined and data indicative of the deployment sequence is stored in a memory (residing within the handle portion 2802 or remote from the handle portion 2802).

As a non-limiting illustration, the deployment sequence may include (after placing the device 2800 proximate an occlusion) expanding the distal element first followed by expanding the proximal element. Consequently, a first button (when actuated) is programmed to carry out the deployment sequence and a second button is then used to reciprocate the proximal element axially. Thus, in this illustration, only two buttons are required to manipulate the proximal and distal elements 2806, 2807. In another case scenario, the deployment sequence may include expanding the distal element, expanding the proximal element and then moving the proximal element axially fore and aft for a cycle of 5 reciprocations. Consequently, a first button (when actuated) is programmed to carry out the deployment sequence. Of course, in some embodiments, second and third buttons may still be used manually after the deployment sequence has been completed by the programmed button. In some embodiments, an Artificial Intelligence (AI) algorithm implements the deployment sequence, once the device 2800 is placed in-vivo, to automatically expand the proximal and distal elements and/or move the proximal element axially.

It should also be appreciated that the three buttons 2814, 2818, 2820 may be sliders, knobs, levers, dials, push buttons or a combination thereof. For example, first and second knobs may be used to expand/contract the proximal and distal elements respectively while a push button may be used to move the proximal element axially. In another example, first, second and third levers may be actuated to generate pump actions to expand/contract the proximal and distal elements and to move the proximal element axially. In yet another example, first and second dials may be actuated clockwise/counter-clockwise to expand/contract the proximal and distal elements respectively while a slider button may be used to move the proximal element axially. Push buttons may use servos and ball screws to expand/contract the proximal and distal elements and to move the proximal element axially. Knobs may be circumferentially designed on the handle portion 2802.

In some embodiments, the distal and/or proximal elements 2807, 2806 are self-expanding Nitinol wire meshes. In some embodiments, the self-expanding distal and/or proximal elements 2807, 2806 are restrained by the handle portion 2802. In some embodiments, the self-expanding distal and/or proximal elements 2807, 2806 are constrained by a sheath or ring that covers the tip portion 2804. The self-expanding distal and/or proximal elements 2807, 2806 expand when the constraining sheath or ring is removed. Thus, in some embodiments, the self-expanding distal and/or proximal elements 2807, 2806 are configured for expansion based on removal of a constraining or resisting member.

In some embodiments, the retrieval device 2800, within the catheter 2835, has a hypo tube and a central wire is positioned within the hypo tube. The distal element 2807 is positioned on the wire while the proximal element 2806 is positioned on the hypo tube at a fixed location. Once the device 2800 is in place, the central wire is passed out of the catheter 2835 and the distal element 2807 becomes unconstrained and automatically pops open to a preset size or outer diameter (self-expanding). With the central wire and distal element 2807 in place, the hypo tube is then moved axially. Because the hypo tube is over the wire, moving the hypo tube automatically moves the proximal element 2806 relative to the distal element 2807. The hypo tube is moved until the proximal element 2806 also pops open. The physician then moves the hypo tube relative to the wire (which is fixed in place) to move the proximal element 2806 relative to the distal element 2807 and scrub out the clot/occlusion.

FIG. 28K illustrates a longitudinal cross-sectional view of the handle 2802 of the retrieval device 2800, in accordance with some embodiments of the present specification. Referring again to FIGS. 28A, 28J and 28K, the handle 2802 is coupled to the proximal end of the elongated member 2805 having a first shaft or tube 2830, a second shaft or tube 2825, a third shaft or tube 2827, and a fourth shaft or tube 2816, that are concentrically positioned relative to each other. In an embodiment, the first tube 2830 is concentrically positioned around the second tube 2825, the second tube 2825 is concentrically positioned around the third tube 2827, and the third tube 2827 is concentrically positioned around the fourth tube 2816.

As shown in FIG. 28B, the proximal element 2806 has a proximal end 2860 and a distal end 2862. The distal end 2862 of the proximal element 2806 is fixedly attached to the second tube 2825 at a point 2828, while the proximal end 2860 is fixedly attached to the first tube 2830 at a point 2829. Similarly, the distal element 2807 has a proximal end 2856 and a distal end 2858. As shown, the distal end 2858 is fixedly connected on the fourth tube 2816, while the proximal end 2856 is fixedly connected to a point 2815 on the third tube 2827.

As shown, the handle 2802 includes first, second and third physically manipulable interfaces such as, for example sliders 2814, 2818 and 2820. Each of a first hub 2802k, second hub 2804k, third hub 2806k, and fourth hub 2808k enable respective first, second, third and fourth tubes 2830, 2825, 2827, 2816 to be coupled to the handle 2802. A fifth hub 2810k is stationary to the handle 2802, is bonded to a PEEK (Polyether ether ketone) tube that goes around all the tubes 2830, 2825, 2827, 2816, and extends a predefined length distally from a proximal end 2830k of the handle 2802 in order to provide kink resistance or act as a strain relief to prevent kinks and add stiffness at proximal ends of the tubes 2830, 2825, 2827, 2816 as the exit the proximal end 2830k of the handle 2802.

In an embodiment, the first slider 2814 is coupled to the fourth tube 2816 such that a sliding movement of the first slider 2814 (along a length of the handle 2802) causes the fourth tube 2816 to move axially while the first, second and third tubes 2830, 2825, 2827 remain stationary thereby causing the distal element 2807 to expand or contract. In some embodiments, sliding the first slider 2814 distally (towards the tip portion 2804) causes the fourth tube 2816 and therefore the distal end 2858 to move proximally causing the distal element 2807 to expand whereas sliding the first slider 2814 proximally (away from the tip portion 2804) causes the fourth tube 2816 and therefore the distal end 2858 to move distally causing the distal element 2807 to compress or contract. Thus, the movement of the first slider 2814 causes the fourth tube 2816 to move relative to the third tube 2827. In alternate embodiments, however, the first slider 2814 may be configured to move the third tube 2827 relative to the fourth tube 2816.

The second slider 2818 is coupled to the first tube 2830 such that a sliding movement of the second slider 2818 (along the length of the handle 2802) causes the first tube 2830 to move axially while the second, third and fourth tubes 2825, 2827, 2816 remain stationary thereby causing the proximal element 2806 to expand or contract. In some embodiments, sliding the second slider 2818 distally (towards the tip portion 2804) causes the first tube 2830 and therefore the proximal end 2860 to move distally thereby causing the proximal element 2806 to expand whereas sliding the second slider 2818 proximally (away from the tip portion 2804) causes the first tube 2830 and therefore the proximal end 2860 to move proximally thereby causing the proximal element 2806 to compress or contract. Thus, the movement of the second slider 2818 causes the first tube 2830 to move relative to the second tube 2825. In alternate embodiments, however, the second slider 2818 may be configured to move the second tube 2825 relative to the first tube 2830.

The third slider 2820 is coupled to the first and second tubes 2830, 2825 such that a sliding movement of the third slider 2820 (along the length of the handle 2802) causes the first and second tubes 2830, 2825 to move axially while the third and fourth tubes 2827, 2816 remain stationary thereby causing the proximal element 2806 to move relative to the distal element 2807 (that remains stationary). In some embodiments, sliding the third slider 2820 distally (towards the tip portion 2804) causes the proximal element 2806 to move towards the distal element 2807 whereas sliding the third slider 2820 proximally (away from the tip portion 2804) causes the proximal element 2806 to move away from the distal element 2807.

In alternate embodiments, the third slider 2820 may be coupled to the third and fourth tube 2827, 2816 such that a sliding movement of the third slider 2820 (along the length of the handle 2802) causes the third and fourth tube 2827, 2816 to move axially while the first and second tubes 2830, 2825 remain stationary thereby causing the distal element 2807 to move relative to the proximal element 2806 (that remains stationary). In some embodiments, sliding the third slider 2820 distally (towards the tip portion 2804) causes the distal element 2807 to move away from the proximal element 2806 whereas sliding the third slider 2820 proximally (away from the tip portion 2804) causes the distal element 2807 to move towards the proximal element 2806.

In some embodiments, by default, a spring loaded locking mechanism 2820k keeps the first and second hubs 2802k, 2804k locked/coupled to a carriage 2815k. Sliding movement of the third slider 2820 moves the carriage 2815k causing the first and second tubes 2830, 2825 to be moved in unison (relative to the third and fourth tubes 2827, 2816) resulting in the axial movement of the proximal element 2806 relative to the distal element 2807 without affecting expansion/contraction of the proximal element 2806.

In some embodiments, the three sliders 2814, 2818, 2820 and the locking mechanism utilize springs to stay locked in place with teeth on a rail, and must be pressed/depressed to release or unlock.

Depressing the second slider 2818 causes the locking mechanism 2820k to decouple the first and second tubes 2830, 2825 from the carriage 2815k and engage the second slider 2818 with the first tube 2830. Consequently, the sliding movement of the second slider 2818 causes the first tube 2830 to move axially thereby expanding or contracting the proximal element 2806. Once released, the locking mechanism 2820k is actuated again and, therefore, the third slider 2820 can be used to move both first and second tubes 2830, 2825 and therefore the entire proximal element 2806.

Thus, the second slider 2818 expands or contracts the proximal element 2806 by moving the first tube 2830 while the second tube 2825 remain stationary. The second slider 2818 is configured to open or expand the proximal element 2806 incrementally and mechanically to one of a plurality of predefined geometric shapes, dimensions, sizes, diameters or volumes, each of which (other than the linear shape) is capable of withstanding a same or different applied pressure in the range of 0 to 25 Newton. In some embodiments, the plurality of geometric shapes includes at least two of linear, ellipsoid, spheroid, spherical or disk shape. In some embodiments, the second slider 2818 includes a plurality of teeth on a rail that allows the proximal element 2806 to be opened or expanded incrementally. As discussed earlier, the second slider 2818 is spring loaded, such that it needs to be depressed in order to move or slide the second slider 2818 to have a desired geometric shape, dimension, size, diameter or volume of the proximal element 2806. In other words, the dimensional increments are built in and represented, in some embodiments, by corresponding iconography on the handle 2802 to visually represent the plurality of predefined geometric shapes, dimensions, sizes, diameters or volumes of the proximal element 2806. Additionally, since a procedure using the retrieval device 2800, to remove an occlusion or unwanted material from a vessel lumen, is typically carried out under fluoroscopy, the physician can see the internal diameter of the vessel lumen, feel the tactile feedback (generated due to the second slider 2818 having the plurality of teeth on the rail that allows the proximal element 2806 to be opened or expanded incrementally) versus the outer diameter of the expanded proximal element 2806 and have a visual reference.

In an embodiment, the fourth tube 2816 is configured to move in a direction opposite to a direction of movement of the first tube 2830. In the absence of the opposing movement of the first and second tubes 2830, 2816, if the first slider 2814 is moved distally the fourth tube 2816 will also move distally causing the distal element 2807 to contract while if the first slider 2814 is moved proximally then the fourth tube 2816 will also move proximally causing the distal element 2807 to expand. This movement of the first slider 2814 and the fourth tube 2816, however, is less intuitive to the user (since movement of the second slider 2818 distally causes the proximal element 2806 to expand and vice versa). Therefore, a gear 2825k reverses the direction of movement of the first slider 2814 in a 1:1 relation to the fourth hub 2808k and therefore the fourth tube 2816. Consequently, movement of the first slider 2814 distally causes the fourth tube 2816 to move proximally causing the distal element 2807 to expand while movement of the first slider 2814 proximally causes the fourth tube 2816 to move distally causing the distal element 2807 to contract.

Thus, the first slider 2814 expands or contracts the distal element 2807 by moving the fourth tube 2816 while the first, second and third tubes 2830, 2825, 2827 remain stationary. The first slider 2814 is configured to open or expand the distal element 2807 incrementally and mechanically to one of a plurality of predefined geometric shapes, dimensions, sizes, diameters or volumes, each of which (other than the linear shape) is capable of withstanding a same or different applied pressure in the range of 0 to 25 Newton. In some embodiments, the first slider 2814 includes a plurality of teeth on a rail that allows the distal element 2807 to be opened or expanded incrementally. In some embodiments, the first slider 2814 is spring loaded, such that it needs to be depressed in order to move or slide the first slider 2814 to have a desired geometric shape, dimension, size, diameter or volume of the distal element 2807. In other words, the dimensional increments are built in and represented, in some embodiments, by corresponding iconography on the handle 2802 to visually represent the plurality of predefined geometric shapes, dimensions, sizes, diameters or volumes of the distal element 2807. Additionally, since a procedure using the retrieval device 2800, to remove an occlusion or unwanted material from a vessel lumen, is typically carried out under fluoroscopy, the physician can see the internal diameter of the vessel lumen, feel the tactile feedback (generated due to the first slider 2814 having the plurality of teeth that allows the distal element 2807 to be opened or expanded incrementally) versus the outer diameter of the expanded distal element 2807 and have a visual reference.

Lock and Key System

Figure 28M:
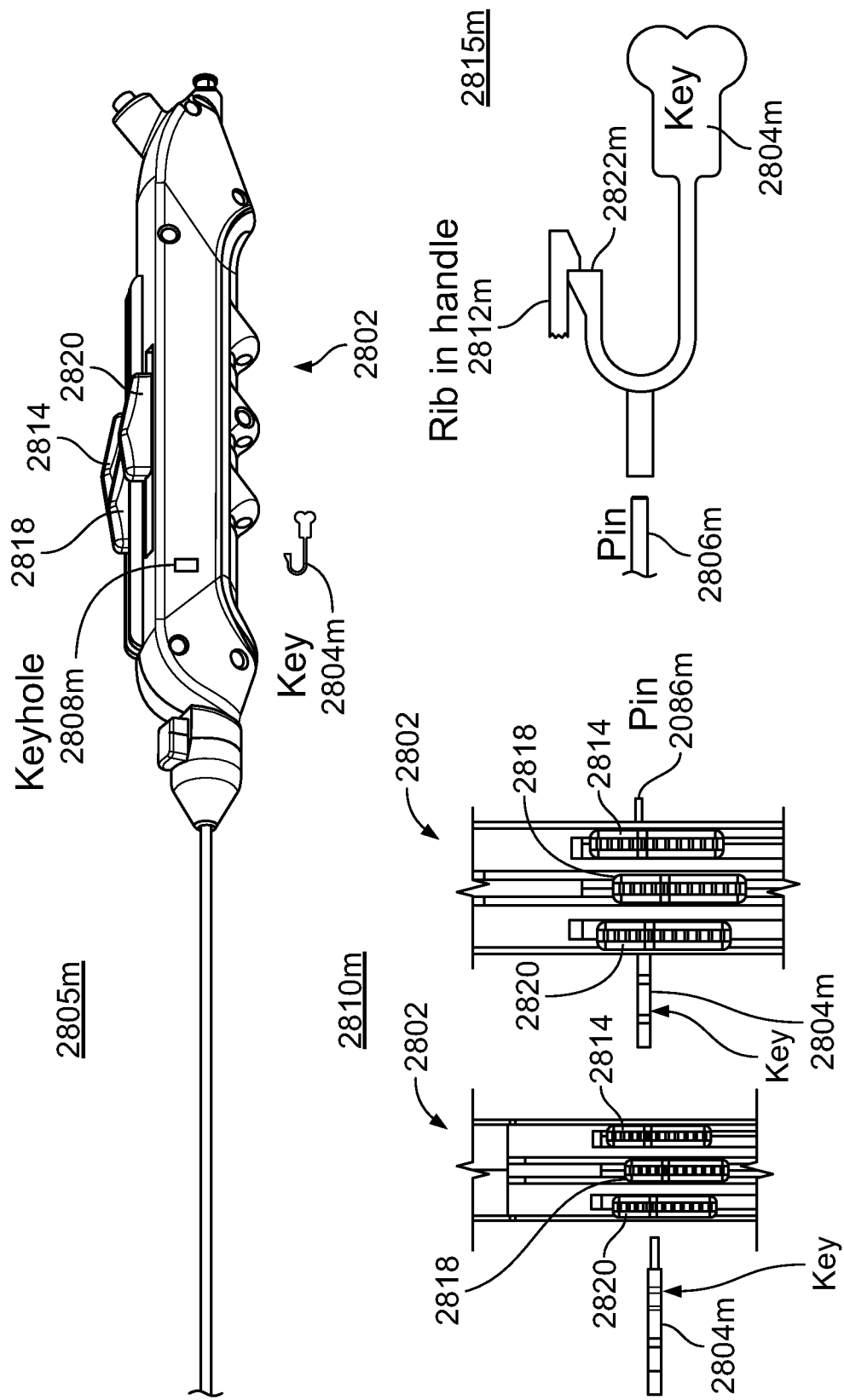
FIG. 28M shows first, second and third views of using a key to unlock a handle of a retrieval device, in accordance with an embodiment of the present specification.

As shown in a first view 2805*m* of FIG. 28M, the retrieval device 2800 is provided to the user (for example, upon purchase), with the handle 2802 locked or inactivated, which can only be activated or unlocked upon using an associated key 2804*m*. In some embodiments, a pin 2806*m* is placed in the handle 2802, during assembly, such that the pin 2806*m* passes through the first, second and third sliders 2814, 2818, 2820 thereby preventing the sliders from being actuated or moved. As shown in a second view 2810*m*, in order to activate the handle 2802 (and, therefore, be able to actuate the sliders 2814, 2818, 2820), a key 2804*m* that is uniquely configured to pass through a first side of a keyhole 2808*m* (in the handle 2802) to cause the pre-placed pin 2806*m* to be pushed out and protrude from a second side (opposite to the first side) of the keyhole 2808*m*. The protruding pin 2806*m* may then be grabbed by a user and pulled out by the user thereby unlocking, or allowing the sliders 2814, 2818, 2820 to freely move. In some embodiments, as shown in a third view 2815*m*, the key 2804*m* is designed such that a surface 2822*m* of the key 2804*m* abuts or engages with a rib 2812*m* in the handle 2802 upon insertion through the first side of the keyhole 2808*m*. Thus, the key 2804*m* is characterized to one-way snap fit into the handle 2802 so that it cannot be removed without breaking (since the surface 2822*m* abutting the rib 2812 provides substantial resistance when an attempt is made to pull the key 2804*m* out of the first side of the keyhole 2808*m*). It should be appreciated that the keyhole is preferably uniquely designed such that handles may have one of a plurality of differently sized, shaped, or configured keyholes and therefore require a similarly and complementarily designed key to successfully pass through the keyhole and push out the pin.

Figure 43:
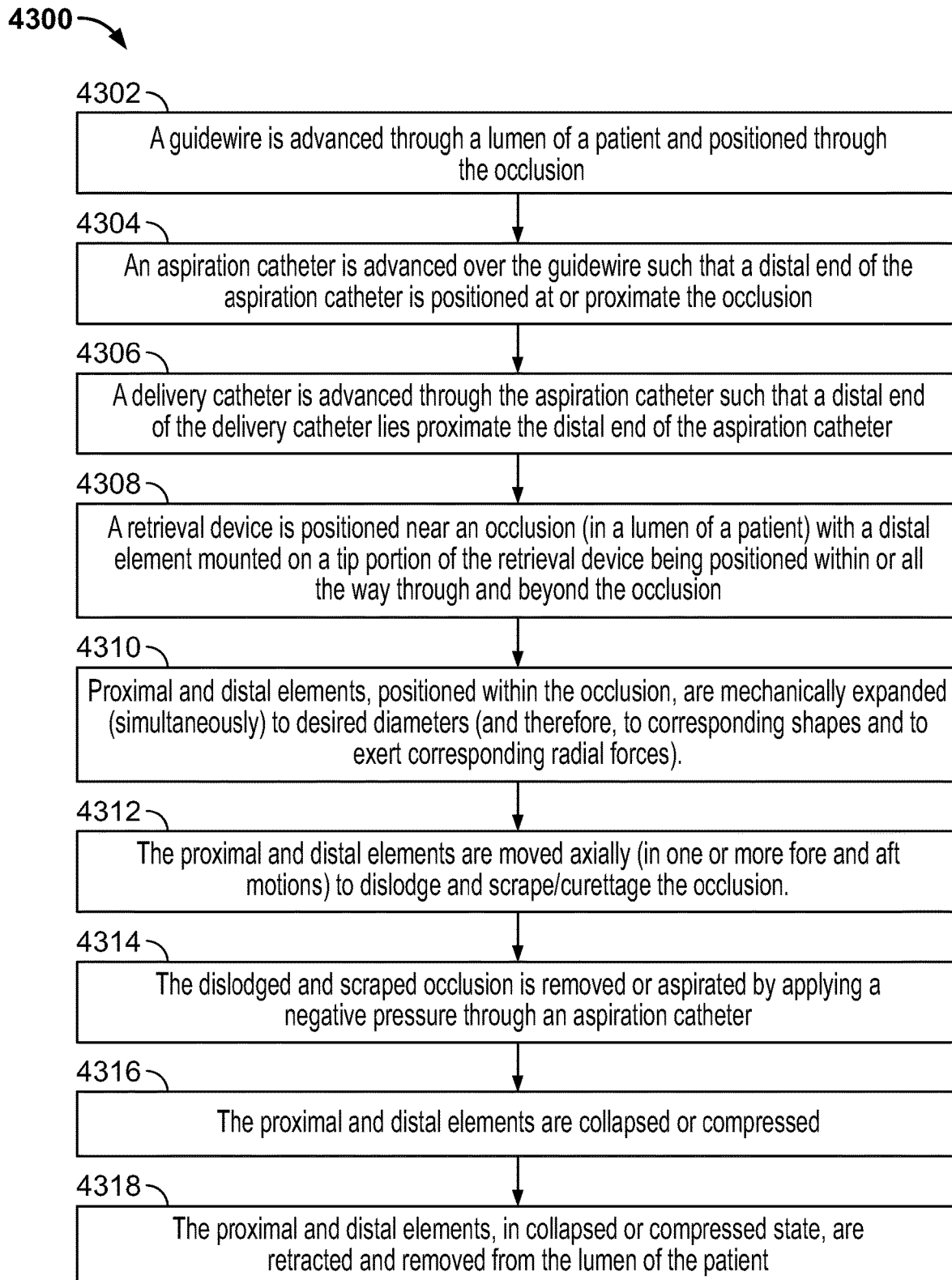
FIG. 43 is a flowchart of a plurality of exemplary steps of a method of using a retrieval device configured to remove an occlusion from peripheral arterial vessels (and therefore treat peripheral arterial disease), in accordance with an embodiment of the present specification.

Simultaneously Expandable and Contractable/Compressible Proximal and Distal Elements FIG. 43 is a flowchart of a plurality of exemplary steps of a method 4300 of using a retrieval device configured to remove an occlusion from peripheral arterial vessels (and therefore treat peripheral arterial disease), in accordance with an embodiment of the present specification. In accordance with some embodiments, the method 4300 enables removing the occlusion from a lumen having an internal diameter ranging from 1 mm to 14 mm. In some embodiments, the method 4300 enables removing the occlusion from a lumen having an internal diameter less than 3 mm, and even those less than 1 mm, wherein the lumen is one of, but not limited to, biliary ducts, fistula declotting, brain blood vessels, upper and lower extremities, ureter, appendicular artery and peripheral arterial vessels (particularly in the hands, arms, forearms, thighs, legs and feet).

For the method 4300, a retrieval device of the present specification, such as, for example, the device 2800, is configured or adapted for performing thrombectomy procedures in biliary ducts, fistula declotting, hepatic bile ducts, brain blood vessels, upper and lower extremities, ureter, appendicular artery and peripheral arterial vessels (particularly in the hands, arms, forearms, thighs, legs and feet) in order to treat peripheral arterial disease (PAD) and thromboembolic processes related to all arterial and hematologic pathologies. In such embodiments of the retrieval device, the handle 2802 is coupled to a proximal end of the elongated member 2805 through at least one telescoping tube, wherein a distal end of the elongated member 2805 has the tip portion 2804 mounted with proximal and distal elements 2806, 2807. In some embodiments, the handle 2802 may include a physically manipulable interface such as, for example, a knob, slider or button that is used to expand/open and contract/close both the proximal and distal elements 2806, 2807 simultaneously. In some embodiments, a distance between the proximal and distal elements 2806, 2807 is predefined/fixed and ranges from 2 cm to 6 cm. The physically manipulable interface such as a slider has a plurality of teeth on a rail to enable the proximal and distal elements 2806, 2807 to expand or open incrementally to a plurality of shapes, dimensions, sizes, volumes or outer diameters. In some embodiments, the proximal and distal elements 2806, 2807 may be expanded to shapes, dimensions, sizes, volumes or outer diameters corresponding to up to 20 increments. In some embodiments, the proximal and distal elements 2806, 2807 may be expanded to shapes, dimensions, sizes, volumes or outer diameters on a continuous basis without set increments. In some embodiments, each of the plurality of shapes, dimensions, sizes, volumes or outer diameters of the proximal and distal elements 2806, 2807 is capable of withstanding a same applied pressure in the range of 0 to 25 Newton. Alternatively, in some embodiments, each of the plurality of shapes, dimensions, sizes, volumes or outer diameters of the proximal and distal elements 2806, 2807 is capable of withstanding different applied pressure in the range of 0 to 25 Newton.

The dimensional increments, for simultaneously expanding the proximal and distal elements 2806, 2807 are built in and represented, in some embodiments, by corresponding iconography on the handle 2802 to visually represent the plurality of predefined geometric shapes, dimensions, sizes, diameters or volumes of the proximal and distal elements 2806, 2807. Additionally, since a procedure using the retrieval device, to remove an occlusion or unwanted material from a vessel lumen, is typically carried out under fluoroscopy, the physician can see the internal diameter of the vessel lumen, feel the tactile feedback (generated due to the slider having the plurality of teeth on the rail) versus the outer diameter of the expanded proximal and distal elements 2806, 2807 and have a visual reference. In some embodiments, the retrieval device with simultaneously expandable and contractable/compressible proximal and distal element 2806, 2807 is configured to use a guidewire having a diameter of 0.014 in or 0.018 in, an aspiration catheter 2835 of 7 to 8 Fr and having a length of 135 cm, and an elongated member 2805 of 5 Fr having a length of 145 cm. In some embodiments, in a fully expanded state, a diameter of each of the proximal and distal elements ranges from 5 mm to 30 mm, preferably 10 mm to 25 mm, and more preferably 10 mm to 20 mm.

Optionally, in some embodiments, the handle 2802 may include another physically manipulable interface such as, for example, a knob, slider or button that is used to axially move the proximal and distal element 2806, 2807 together.

For use during the procedure, in some embodiments, a tip portion of the retrieval device (with proximal and distal elements that can be expanded and contracted simultaneously) is placed into a delivery catheter and thereafter the delivery catheter is inserted into the aspiration catheter, and follows through to a valve hub, so that at least the tip portion projects distally from a distal end of the aspiration catheter.

Referring now to FIG. 43, in an embodiment, at step 4302, in order to retrieve an occlusion from the lumen of a patient, a guidewire is advanced through the lumen of the patient and positioned through the occlusion. In some embodiments, the guidewire has a diameter of 0.014 in or 0.018 in. At step 4304, the aspiration catheter is advanced over the guidewire such that a distal end of the aspiration catheter is positioned at or proximate the occlusion. At step 4306, the delivery catheter is advanced through the aspiration catheter such that a distal end of the delivery catheter lies proximate the distal end of the aspiration catheter.

At step 4308, the retrieval device (with proximal and distal elements that can be expanded and contracted simultaneously) is positioned near the occlusion with the distal element mounted on the tip portion of the retrieval device is positioned within or all the way through and beyond the occlusion. In some embodiments, this ensures that the proximal and distal elements, in compressed or non-expanded state, are positioned within the occlusion.

At step 4310, the proximal and distal elements, positioned within the occlusion, are mechanically expanded, simultaneously, to desired diameters (and therefore, to corresponding shapes and to exert corresponding radial forces). In an embodiment, a slider on a handle of the retrieval device is actuated to cause the wire mesh structures of the proximal and distal elements to expand out concurrently. In some embodiments, upon expansion, the proximal and distal elements are configured to resist compression from an applied force in a range of 0 to 25 Newtons.

At step 4312, the proximal and distal elements are moved axially (in one or more fore and aft motions) to dislodge and scrape/curettage the occlusion. In some embodiments, the occlusion can also be trapped into the mesh lattices of the proximal and distal elements.

In some embodiments, the handle is moved fore and aft to cause the tip portion and therefore the proximal and distal elements to be moved fore and aft in order to dislodge and curettage the occlusion. In another embodiment, another slider provided on the handle is actuated to axially move the proximal and distal elements together relative to the tip portion. In some embodiments, the proximal and distal elements are configured to be moved axially in a range from 1 mm to 8 cm and preferably at least 6 cm.

At step 4314, the dislodged and scraped occlusion is removed or aspirated by applying a negative pressure through the aspiration catheter. In some embodiments, the fore and aft movement of the proximal and distal elements further directs the dislodged and scraped occlusion towards the aspiration catheter.

At step 4316, the proximal and distal elements are collapsed or compressed simultaneously. In some embodiments, the slider is actuated to cause the proximal and distal elements to collapse or compress. Finally, at step 4318, the proximal and distal elements, in collapsed or compressed state, are retracted and removed from the lumen of the patient.

FIG. 29A illustrates a retrieval device 2900 with unexpanded proximal and distal elements, in accordance with an embodiment of the present specification. FIG. 29B illustrates the retrieval device 2900 with expanded proximal and distal elements, in accordance with an embodiment of the present specification. FIG. 29C illustrates the retrieval device 2900 with a plurality of telescoping tubes maneuvered to reduce a distance between the proximal and distal elements, in accordance with an embodiment of the present specification. Referring to FIGS. 29A, 29B and 29C, in some embodiments, the distal element 2902 and the proximal element 2904 are affixed to a set of first, second, third and fourth telescoping tubes 2906, 2908, 2910 and 2912, wherein the first tube 2906 is shown extending beyond a delivery catheter 2914.

In embodiments, the telescoping tubes 2906, 2908, 2910 and 2912 are capable of being retracted or expanded axially relative to each other, thereby decreasing or increasing, respectively, a distance between the distal element 2902 and the proximal element 2904. The retraction and expansion of the telescoping tubes 2906, 2908, 2910 and 2912 as well as the expansion and contraction of the distal and proximal elements 2902, 2904, in an embodiment, is carried out by means of a handle of the retrieval device 2900. In embodiments, an axial compression between respective proximal and distal ends of the of the distal and proximal elements 2902, 2904 causes the elements 2902, 2904 to expand radially about a longitudinal axis and obtain a diameter greater than a diameter in an unexpanded state.

FIG. 29A shows the distal and proximal elements 2902, 2904 completely unexpanded, while the elements are shown fully expanded in FIGS. 29B and 29C. As shown in FIG. 29B, by using a handle (not shown in FIG. 29), the first tube 2906 is extended, the second tube 2908 is retracted, the third tube 2910 is extended and the fourth tube 2912 is retracted thereby increasing a distance between the distal and proximal elements 2902, 2904. As shown in FIG. 29C, the first tube 2906 is extended further while the third tube 2910 is retracted to decrease the distance between the distal and proximal elements 2902, 2904.

In some embodiments, to remove an occlusion, the distal element 2902 is positioned within, or all the way through, the occlusion so that the distal element 2902 is held fixed in a position within or beyond a distal end of the occlusion while the proximal element 2904 precedes a proximal end of the occlusion. Subsequently, the proximal element 2904 is moved back and forth axially along a longitudinal axis to dislodge and trap the occlusion between the distal and proximal elements 2902, 2904. Thus, by maneuvering the handle, the distance between the distal and proximal elements 2902, 2904 can be increased/decreased to dislodge the occlusion and trap the occlusion between the distal and proximal elements 2902, 2904. This is described in detail in subsequent paragraphs with reference to FIGS. 30A-30H.

Referring back to FIGS. 28A through 28J, in some embodiments, the retrieval device 2800 is configured to be maneuvered using the handle portion 2802 such that the size, shape and relative position of both the proximal and distal elements 2806, 2807 as well as the radial force being applied by both the proximal and distal elements 2806, 2807 may be adjusted.

Figure 30A:
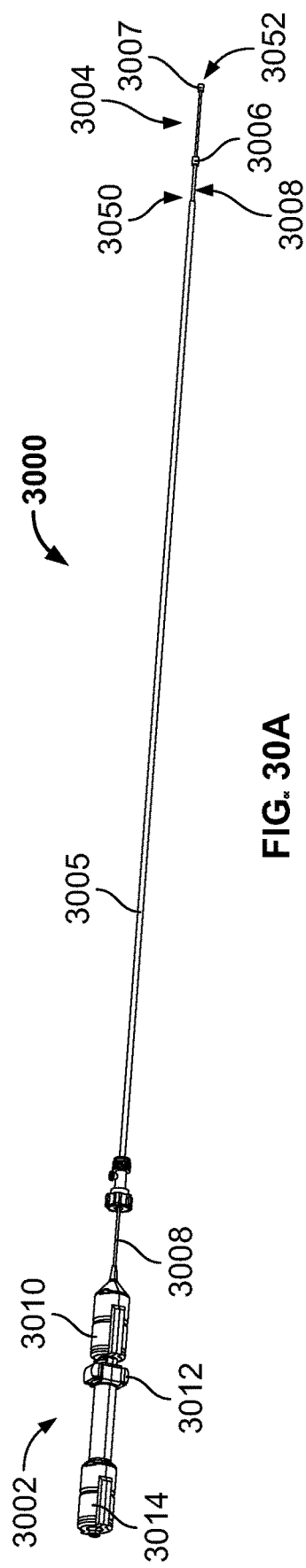
FIG. 30A is a perspective view of a retrieval device, in accordance with an embodiment of the present specification.
Figure 30B:
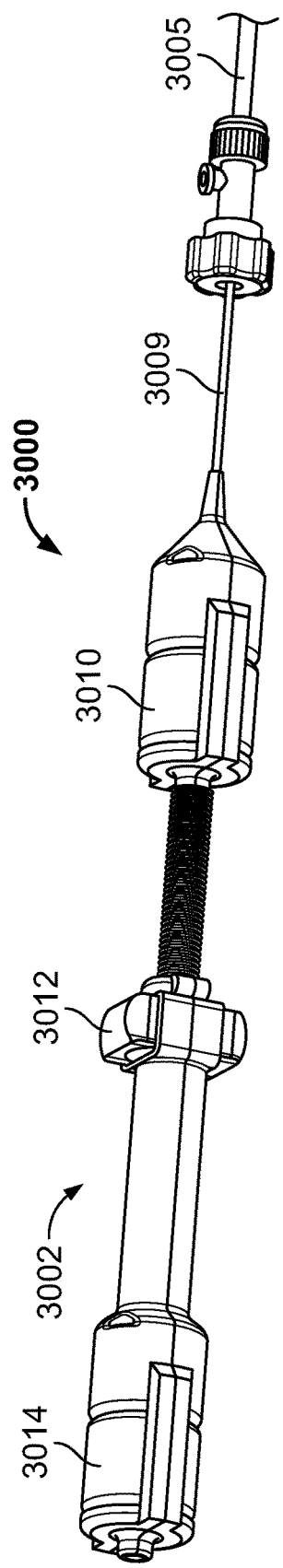
FIG. 30B is a perspective view of an expanded handle portion of the retrieval device shown in FIG. 30A, in accordance with an embodiment of the present specification.
Figure 30C:
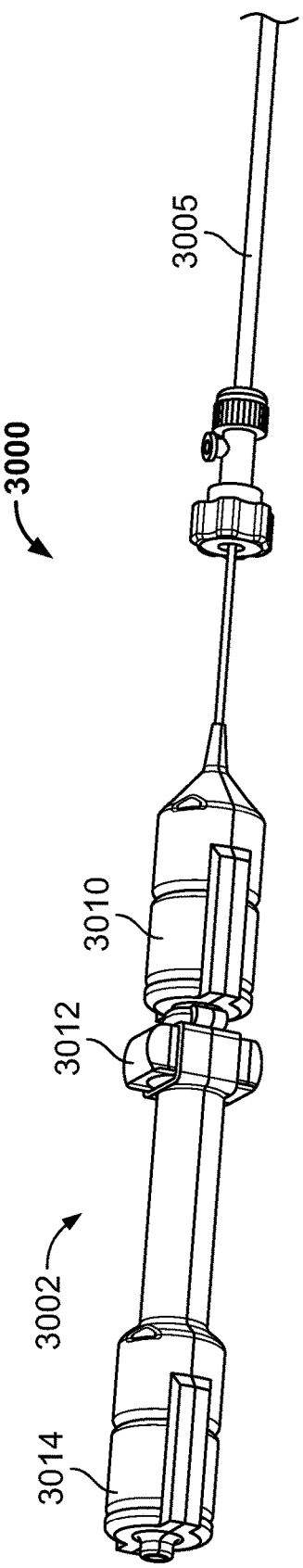
FIG. 30C is a perspective view of a compressed handle portion of the retrieval device shown in FIG. 30A, in accordance with an embodiment of the present specification.

FIG. 30A illustrates a retrieval device 3000, in accordance with an embodiment of the present specification. FIG. 30B illustrates an expanded handle portion of the retrieval device 3000, in accordance with an embodiment of the present specification. FIG. 30C illustrates a compressed handle portion of the retrieval device 3000, in accordance with an embodiment of the present specification. Referring to FIGS. 30A, 30B and 30C, the device 3000 comprises a handle portion 3002 and a tip portion 3004. The tip portion has a proximal end 3050 and a distal end 3052. During operation of the device 3000, the tip portion 3004 is inserted into a body lumen for removing an occlusion while the handle portion 3002 remains in an operator/user's hands to maneuver the insertion of the tip portion 3004 in a desired position in the body lumen. During insertion of the device 3000 into the body lumen, the distal end 3052 of the tip portion 3004 enters the body first and is placed within, beyond or in close proximity of the occlusion within a blood vessel of the body by using the handle 3002.

The tip portion 3004 comprises a distal element or body 3007, which in an embodiment, is a mechanically expandable, rigid anchor fixedly attached to the distal end 3052 of the tip portion 3004, and a proximal element or body 3006, which in an embodiment is a pusher ball that is slidably mounted on the proximal end 3050 of the tip portion 3004. The tip portion 3004 is at least partially covered with a sheath 3005 which may be retracted exposing at least the distal element 3007 and proximal element 3006 when the device 3000 is inserted and maneuvered within a vasculature of a person, by using the handle portion 3002.

In some embodiments, the distal element 3007 can take the form of a cylinder, stent, chalice cup, umbrella, concave structure, half-sphere, sphere, windsock, dumbbell, star, polygon, lever, or any other suitable shape configured for holding an occlusion and aiding retrieval of the occlusion. In some embodiments, the tip portion 3004 comprises flexible elements or tubes 3008 that extend all the way back to the handle portion 3002 and can be maneuvered together to enable an operator/doctor to expand or contract the distal and proximal elements 3007, 3006 as well as slide the proximal element 3006 (towards or away from the distal element 3007) for removing the occlusion. In an embodiment, the flexible elements 3008 comprise four flexible telescoping tubes as described earlier with reference to FIGS. 29A-29C.

Referring to FIGS. 30A, 30B and 30C, in embodiments, the proximal element 3006 is enabled to move relative to the distal element 3007 for removal of the occlusion. The handle portion 3002 comprises a first knob 3010 configured to actuate the proximal element 3006, a second knob 3012 configured as a 'press and hold' button, a third knob 3014 configured to actuate the distal element 3007 and flexible elements 3008 which extend up to the tip portion 3004. The flexible elements 3008 enable the proximal element 3006 and the distal element 3007 to move relative to each other for removal of the occlusion as is described with reference to FIGS. 29A, 29B and 29C.

Figure 30D:
FIG. 30D is an illustration of expanded proximal and distal elements of the retrieval device shown in FIG. 30A, in accordance with an embodiment of the present specification.
Figure 30E:
FIG. 30E is an illustration of collapsed/contracted proximal and distal elements of the retrieval device shown in FIG. 30A, in accordance with an embodiment of the present specification.

In some embodiments, the distal element 3007 is expanded to a plurality of intermediate diameters (and up to a maximum permissible diameter) by rotating the third knob 3014 in an anticlockwise direction. Rotating the third knob 3014 in a clockwise direction contracts the distal element 3007 back to the plurality of intermediate diameters and eventually to a non-expanded/collapsed state from the expanded state. In some embodiments, the proximal element 3006 is expanded to a plurality of intermediate diameters (and up to a maximum permissible diameter) by rotating the first knob 3010 in an anticlockwise direction. Rotating the first knob 3010 in a clockwise direction contracts the proximal element 3006 back to the plurality of intermediate diameters and eventually to a non-expanded/collapsed state from the expanded state. FIG. 30D illustrates fully expanded proximal and distal elements 3006, 3007, in accordance with an embodiment of the present specification. FIG. 30E illustrates fully collapsed proximal and distal elements 3006, 3007, in accordance with an embodiment of the present specification.

Figure 30F:
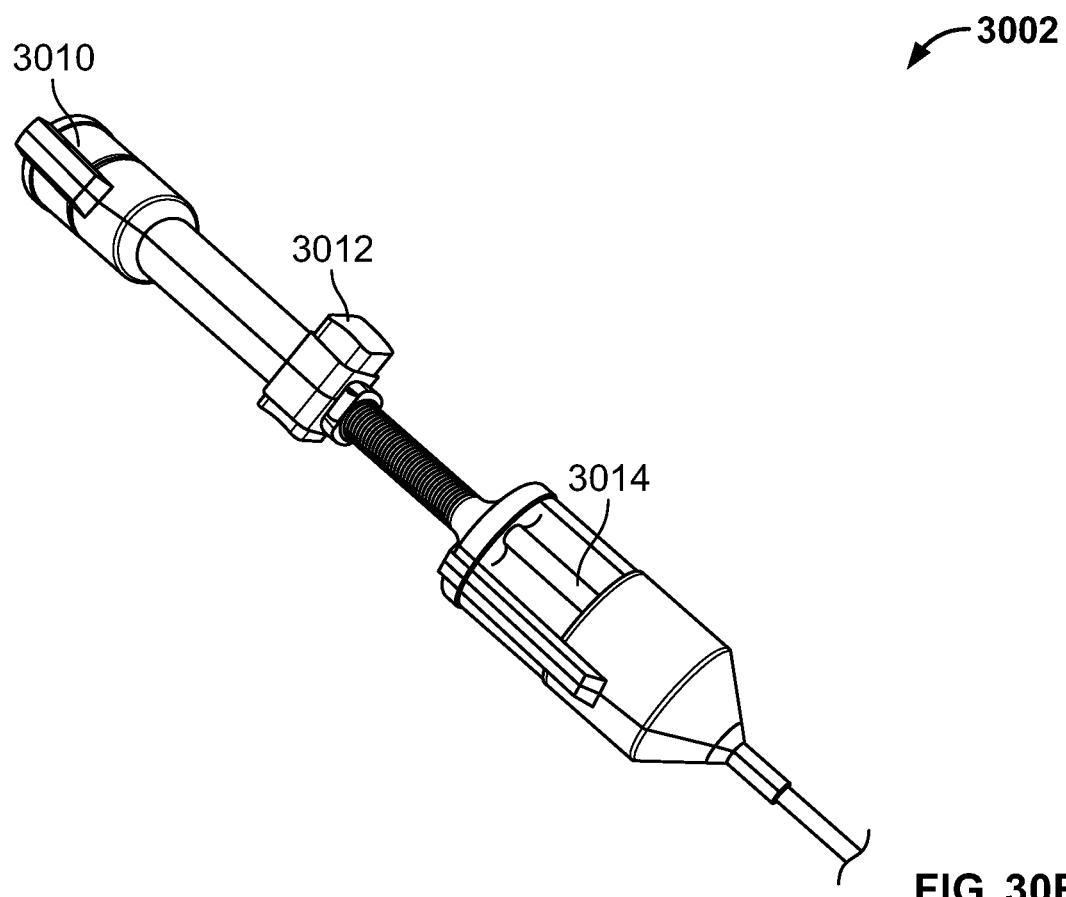
FIG. 30F is an illustration of an embodiment of the expanded handle portion of the retrieval device, in accordance with an embodiment of the present specification.
Figure 30G:
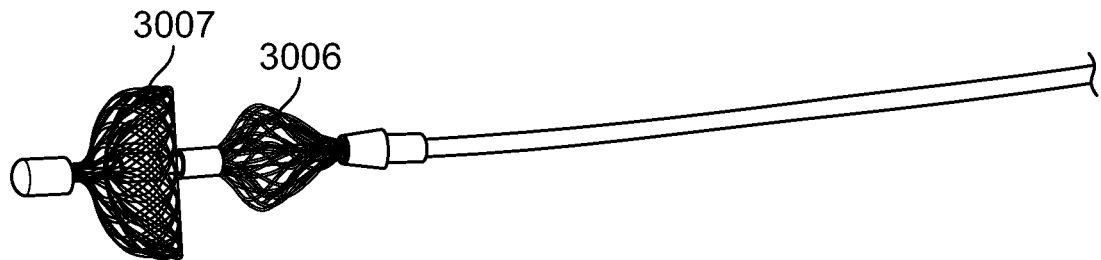
FIG. 30G is a perspective illustration of a compressed distance between the proximal and distal elements as a result of expanding the handle portion shown in FIG. 30F, in accordance with an embodiment of the present specification.
Figure 30H:
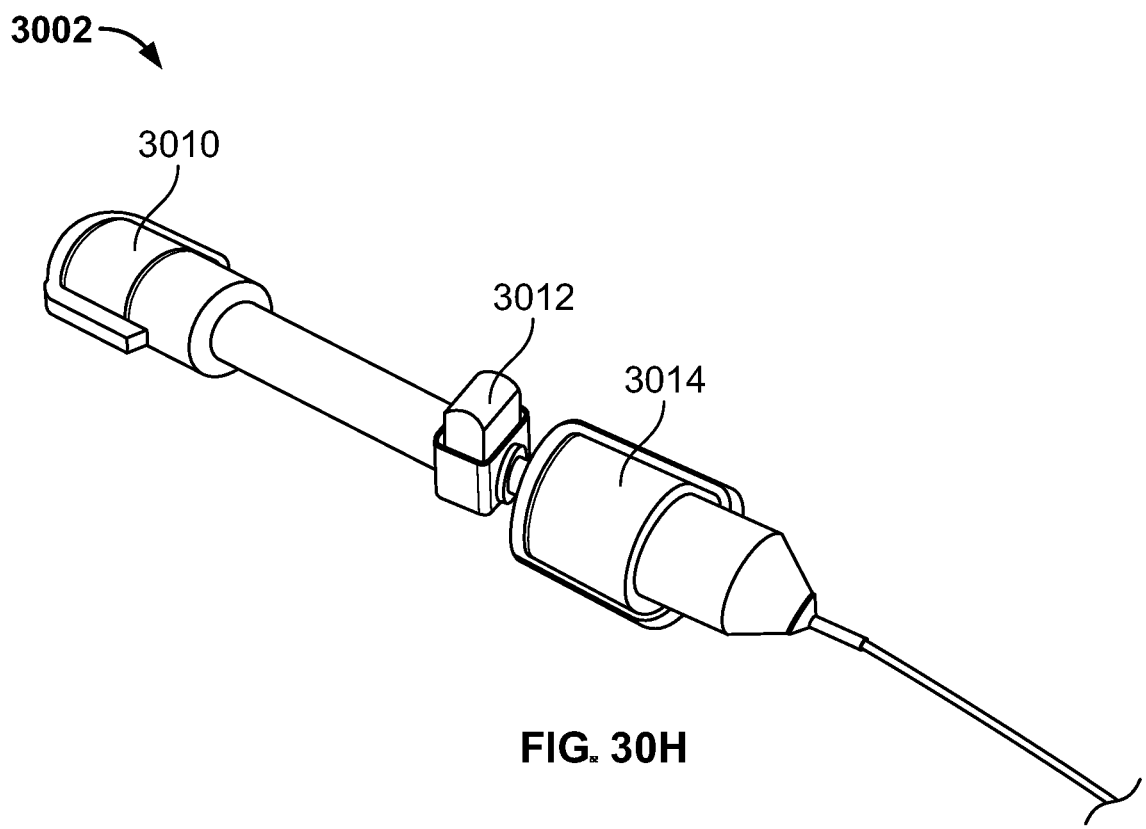
FIG. 30H is an illustration of the handle portion shown in FIG. 30F in a compressed state causing the distance between the proximal and distal elements to expand, in accordance with an embodiment of the present specification.

A distance between the proximal and distal elements 3006, 3007 may be decreased by pressing the second knob 3012 and moving the first knob 3010 towards the tip portion 3004. As the distance between the second knob 3012 and the first knob 3010 increases, the distance between the proximal and distal elements 3006, 3007 decreases. FIGS. 30B and 30F illustrate an expanded handle portion 3002 wherein the first knob 3010 is moved away from the second knob 3012, while FIGS. 30C and 30H illustrate a compressed handle portion 3002 wherein the first knob 3010 is moved towards the second knob 3012 to lie proximate to the second knob 3012. As the distance between the second knob 3012 and the first knob 3010 decreases, the distance between the proximal and distal elements 3006, 3007 increases. FIG. 30G illustrates a compressed or reduced distance between the proximal and distal elements 3006, 3007 as a result of the expanded handle portion shown in FIGS. 30B and 30F. A user may use the second knob 3012 along with the first knob 3010 to cause a relative movement between the proximal and distal elements 3006, 3007 for dislodging an occlusion, and causing the occlusion to be lodged between the proximal and distal elements 3006, 3007 for removal from a patient's body.

In some embodiments, a protective bag covers a tip portion of a retrieval device of the present specification. The protective bag may be removed from the tip portion and re-draped over the tip portion as needed. FIGS. 33A, 33B and 33C show a tip portion 3304 of a retrieval device (such as, the retrieval device 2800, 2900 or 3000). As described earlier in the specification, the tip portion 3304 has four telescoping tubes (such as the tubes 2906, 2908, 2910 and 2912 of FIG. 29A) that, in some embodiments, have respective lumens.

As shown in FIG. 33A, when proximal and distal elements 3306, 3308 are in fully collapsed or contracted states, the tip portion 3304 including the proximal and distal elements 3306, 3308, is enclosed or covered by a bag 3305. A first tether 3310, such as a wire, is attached to an internal surface of the bag 3305 at its distal end 3314. In some embodiments, the first tether 3310 extends from the distal end 3314 of the bag 3305 through the respective lumens of the four telescoping tubes and up to a handle (such as, the handle 2802 of FIG. 28A) of the retrieval device. Second and third tethers 3312a, 3312b (which may also be wires) are attached to proximal ends 3313a, 3313b of the bag 3305. In some embodiments, the second and third tethers 3312a, 3312b extend from the proximal ends 3313a, 3313b of the bag 3305 to the handle of the retrieval device.

As shown in FIG. 33B, once the tip portion 3304 is positioned for removal of an occlusion, a force is applied proximally on the first tether 3310 causing the first tether 3310 to be pulled towards the handle and away from the tip portion 3304 thereby causing the bag 3305 to collapse and be retracted into the lumen of at least one of the four telescoping tubes. This results in exposing the proximal and distal elements 3306, 3308 that can now be expanded.

Referring now to FIG. 33C, once the occlusion is dislodged and trapped between the proximal and distal elements 3306, 3308, the proximal and distal elements 3306, 3308 are fully collapsed or contracted. Subsequently, a force is applied proximally on the second and third tethers 3312a, 3312b causing them to be pulled towards the handle and away from the tip portion 3304 thereby causing the collapsed bag 3305 of FIG. 33B to be pulled out of the lumen and be wrapped or covered over the tip portion 3304 again. Thereafter, the tip portion 3304 may be removed or pulled out along with the occlusion trapped between the proximal and distal elements 3306, 3308.

It should be appreciated that the bag 3305 in FIGS. 33A and 33C enables the tip portion 3304 to be atraumatic during insertion and retrieval of the tip portion 3304 into a vascular lumen or a non-vascular structure of a patient. Additionally, the bag in FIG. 33C encompasses the occlusion, trapped between the proximal and distal elements 3306, 3308, and acts as a further measure of ensuring that the trapped occlusion is not lost during removal of the tip portion 3304 from the body of the patient.

In some embodiments, structurally, leading portions of the proximal and distal elements are different from trailing portions of the proximal and distal elements. FIG. 34A shows a tip portion 3404 of a retrieval device (such as, the retrieval device 2800, 2900 or 3000) having proximal and distal elements 3406, 3408 fully collapsed or in unexpanded state, while FIG. 34B shows the tip portion 3404 with the proximal and distal elements 3406, 3408 fully expanded, in accordance with some embodiments of the present specification.

The proximal element 3406 has a leading portion 3406a and a trailing portion 3406b. Similarly, the distal element 3407 has a leading portion 3408a and a trailing portion 3408b. In some embodiments, the leading portions 3406a, 3408a are solid (such as, for example, made of a biocompatible fabric) while the trailing portions 3406b, 3408b are wire meshes having a plurality of cells. This causes the leading portions 3406a, 3408a to be more rigid, stiff or firm compared to the trailing portions 3406b, 3408b. In some embodiments, the leading portions 3406a, 3408a as well as the trailing portions 3406b, 3408b are wire meshes. However, the leading portions 3406a, 3408a have a plurality of cells of a first size while the trailing portions 3406b, 3408b have a plurality of cells of a second size. In some embodiments, the first size is smaller compared to the second size causing the leading portions 3406a, 3408a to be more rigid, stiff or firm compared to the trailing portions 3406b, 3408b.

In various embodiments, the leading and trailing portions may or may not be substantially halves of the respective proximal and distal elements. It should be appreciated that the more rigid, stiff or firm leading portions 3406a, 3408a enable the tip portion 3404 to be effectively slid through an occlusion, bareback.

Figure 35:
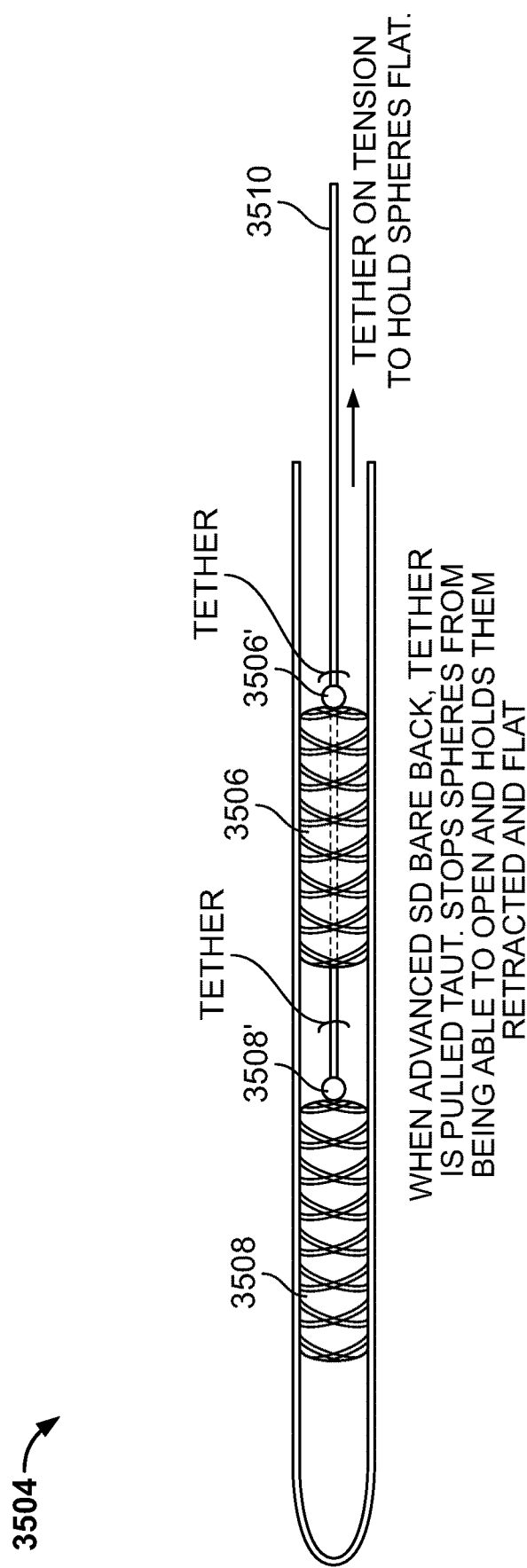
FIG. 35 is a side elevation view of proximal and distal elements of a tip portion in unexpanded states and attached to a tether, in accordance with some embodiments of the present specification.

FIG. 35 shows a tip portion 3504 of a retrieval device (such as, the retrieval device 2800, 2900 or 3000) with proximal and distal elements 3506, 3508 in fully collapsed or unexpanded state, in accordance with some embodiments of the present specification. A tether 3510, such as a wire, is coupled or attached to trailing or proximal ends 3506', 3508' of the respective proximal and distal elements 3506, 3508. The tether 3510 extends from the trailing or proximal ends 3506', 3508' all the way to a handle of the retrieval device. While advancing the tip portion 3500, bareback, in a patient's body the tether 3510 is pulled proximally towards the handle and thereby kept taut. This prevents the proximal and distal elements 3506, 3508 from expanding inadvertently thereby holding them retracted and flat.

Figure 31A:
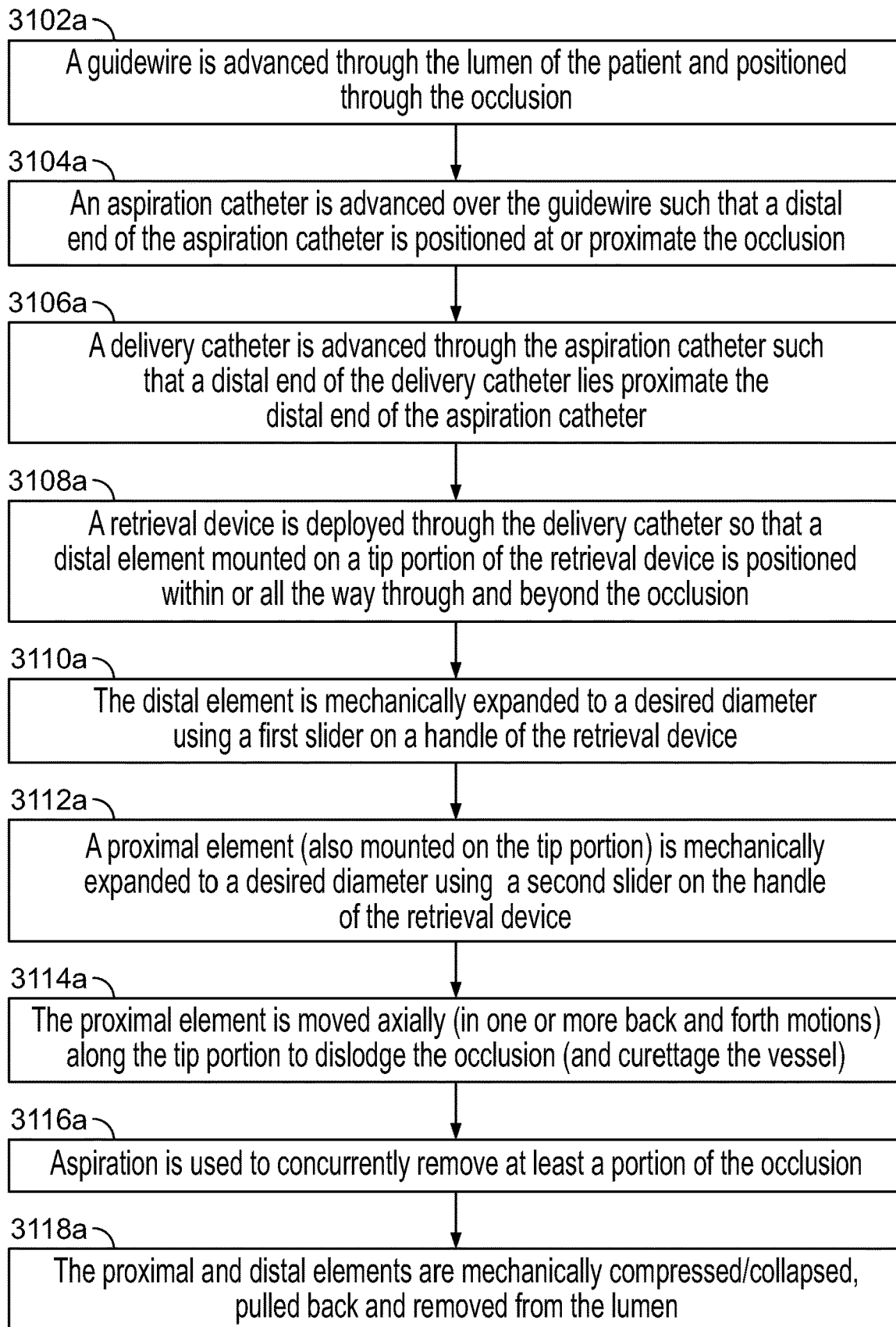
FIG. 31A is a flowchart of a plurality of exemplary steps of treating pulmonary embolism (PE) by using the retrieval device shown in FIGS. 28A-G and 28J-28L, in accordance with an embodiment of the present specification.

FIG. 31A is a flowchart of a plurality of exemplary steps of treating pulmonary embolism (PE) by using any of the retrieval devices 2800, 2900 or 3000, in accordance with an embodiment of the present specification. In some embodiments, treatment of PE involves removing an occlusion from a lumen of a patient's pulmonary vessel.

At step 3102a, a guidewire is advanced through the lumen of the patient and positioned through the occlusion. At step 3104a, an aspiration catheter is advanced over the guidewire such that a distal end of the aspiration catheter is positioned at or proximate the occlusion. At step 3106a, a delivery catheter is advanced through the aspiration catheter such that a distal end of the delivery catheter lies proximate the distal end of the aspiration catheter. At step 3108a, a retrieval device is deployed through the delivery catheter so that a distal element mounted on a tip portion of the retrieval device is positioned within or all the way through and beyond the occlusion.

At step 3110a, the distal element is mechanically expanded to a desired diameter using a first slider on a handle of the retrieval device. In some embodiments, the distal element is a mechanically expandable and rigid anchor fixedly attached proximate a distal end of the tip portion.

At step 3112a, a proximal element (also mounted on the tip portion) is mechanically expanded to a desired diameter using a second slider on the handle of the retrieval device.

At step 3114a, the proximal element is moved axially (in one or more back and forth motions) along the tip portion to dislodge the occlusion (and curettage the vessel). In some embodiments, the axial fore and aft movement of the proximal element results in capturing at least a portion of the occlusion between the proximal and distal elements. The proximal element is moved using a third slider on the handle of the retrieval device. In some embodiments, as shown in FIG. 28I, an occlusion 2880 can be trapped into the mesh lattices of the distal element 2807 and the proximal element 2806 of the retrieval device 2800, for example.

In various embodiments, the anchoring of the rigid distal element proximate the distal end of the tip portion followed by a mechanical expansion of the distal element using the first slider (as opposed to a Nitinol temperature-based expansion) provides the distal element a required minimum degree of rigidity to anchor in place within the lumen and/or preferably wedged into the occlusion. Persons of ordinary skill in the art would appreciate that if the distal element is not rigid and not solidly anchored, the retrieval device may not have sufficient leverage to dislodge the occlusion.

In some embodiments, the anchoring of the distal element to the tip portion and the occlusion (in embodiment where the distal element is positioned within the occlusion) while attaining a required degree of rigidity locks the distal element in a desired location with respect to the occlusion, and allows the proximal element to move back and forth longitudinally with respect to the distal element to dislodge the occlusion.

In an embodiment, the distal element is positioned and expanded within the occlusion (like a fishing hook), and in another embodiment the distal element is positioned and expanded distal to (or beyond) the occlusion. In an embodiment the proximal element is expanded proximal to (prior to) or within the occlusion, such that the proximal element can be moved all the way into the expanded (concave or cup-shaped) distal element to generate a vice-like grip and trap the occlusion between the proximal and distal elements. In some embodiments, once the occlusion is trapped between the proximal and distal elements, the distance between the proximal element and the distal element may be reduced further such that the proximal element moves all the way into or proximate the distal element.

At step 3116a, aspiration is used to concurrently remove at least a portion of the occlusion. In some embodiments, aspiration is performed by applying negative pressure at a proximal end of the aspiration catheter.

At step 3118a, the proximal and distal elements are mechanically compressed/collapsed, pulled back and removed from the lumen.

In some embodiments, the portion of the occlusion captured between the proximal and distal elements is removed by pulling out the proximal element, the portion of the occlusion and the distal element together from the lumen of the patient.

In some embodiments, a first portion of the occlusion captured between the proximal and distal elements is removed by pulling out the proximal element, the first portion of the occlusion and the distal element while a remaining second portion is aspirated using an aspiration catheter. In various embodiments, the exact technique of removing the occlusion varies depending upon factors such as, but not limited to, the anatomical location of the occlusion within the patient's body, and the complexity and density of the occlusion. However, in various embodiments, removal of the occlusion involves some degree of moving the proximal element relative to the distal element to dislodge, trap and aspirate the occlusion.

Figure 31B:
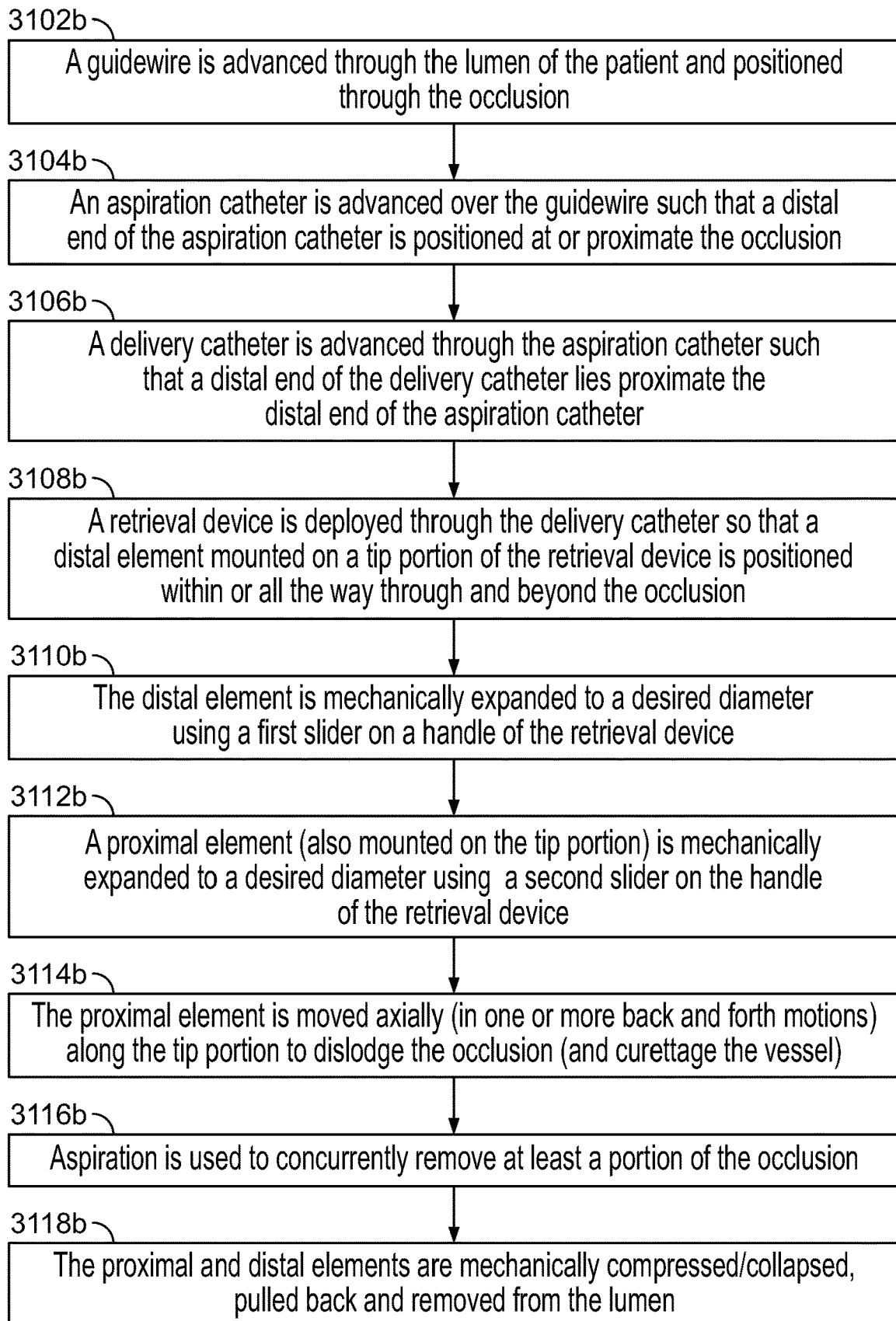
FIG. 31B is a flowchart of a plurality of exemplary steps of treating deep vein thrombosis (DVT) by using the retrieval device shown in FIGS. 28A-G and 28J-28L, in accordance with an embodiment of the present specification.

FIG. 31B is a flowchart of a plurality of exemplary steps of treating deep vein thrombosis (DVT) by using any of the retrieval devices 2800, 2900 or 3000, in accordance with an embodiment of the present specification. In some embodiments, treatment of DVT involves removing an occlusion from a lumen of a patient's deep vein/vessel.

At step 3102b, a guidewire is advanced through the lumen of the patient and positioned through the occlusion. At step 3104b, an aspiration catheter is advanced over the guidewire such that a distal end of the aspiration catheter is positioned at or proximate the occlusion. At step 3106b, a delivery catheter is advanced through the aspiration catheter such that a distal end of the delivery catheter lies proximate the distal end of the aspiration catheter. At step 3108b, a retrieval device is deployed through the delivery catheter so that a distal element mounted on a tip portion of the retrieval device is positioned within or all the way through and beyond the occlusion.

At step 3110b, the distal element is mechanically expanded to a desired diameter using a first slider on a handle of the retrieval device. In some embodiments, the distal element is a mechanically expandable and rigid anchor fixedly attached proximate a distal end of the tip portion.

At step 3112b, a proximal element (also mounted on the tip portion) is mechanically expanded to a desired diameter using a second slider on the handle of the retrieval device.

At step 3114b, the proximal element is moved axially (in one or more back and forth motions) along the tip portion to dislodge the occlusion (and curettage the vessel). In some embodiments, the axial fore and aft movement of the proximal element results in capturing at least a portion of the occlusion between the proximal and distal elements. The proximal element is moved using a third slider on the handle of the retrieval device. In some embodiments, as shown in FIG. 28I, an occlusion 2880 can be trapped into the mesh lattices of the distal element 2807 and the proximal element 2806 of the retrieval device 2800, for example.

In various embodiments, the anchoring of the rigid distal element proximate the distal end of the tip portion followed by a mechanical expansion of the distal element using the first slider (as opposed to a Nitinol temperature-based expansion) provides the distal element a required minimum degree of rigidity to anchor in place within the lumen and/or preferably wedged into the occlusion. Persons of ordinary skill in the art would appreciate that if the distal element is not rigid and not solidly anchored, the retrieval device may not have sufficient leverage to dislodge the occlusion.

In some embodiments, the anchoring of the distal element to the tip portion and the occlusion (in embodiment where the distal element is positioned within the occlusion) while attaining a required degree of rigidity locks the distal element in a desired location with respect to the occlusion, and allows the proximal element to move back and forth longitudinally with respect to the distal element to dislodge the occlusion.

In an embodiment, the distal element is positioned and expanded within the occlusion (like a fishing hook), and in another embodiment the distal element is positioned and expanded distal to (or beyond) the occlusion. In an embodiment the proximal element is expanded proximal to (prior to) or within the occlusion, such that the proximal element can be moved all the way into the expanded (concave or cup-shaped) distal element to generate a vice-like grip and trap the occlusion between the proximal and distal elements. In some embodiments, once the occlusion is trapped between the proximal and distal elements, the distance between the proximal element and the distal element may be reduced further such that the proximal element moves all the way into or proximate the distal element.

At step 3116b, aspiration is used to concurrently remove at least a portion of the occlusion. In some embodiments, aspiration is performed by applying negative pressure at a proximal end of the aspiration catheter.

At step 3118b, the proximal and distal elements are mechanically compressed/collapsed, pulled back and removed from the lumen.

In some embodiments, the portion of the occlusion captured between the proximal and distal elements is removed by pulling out the proximal element, the portion of the occlusion and the distal element together from the lumen of the patient.

In some embodiments, a first portion of the occlusion captured between the proximal and distal elements is removed by pulling out the proximal element, the first portion of the occlusion and the distal element while a remaining second portion is aspirated using an aspiration catheter. In various embodiments, the exact technique of removing the occlusion varies depending upon factors such as, but not limited to, the anatomical location of the occlusion within the patient's body, and the complexity and density of the occlusion. However, in various embodiments, removal of the occlusion involves some degree of moving the proximal element relative to the distal element to dislodge, trap and aspirate the occlusion.

Figure 32A:
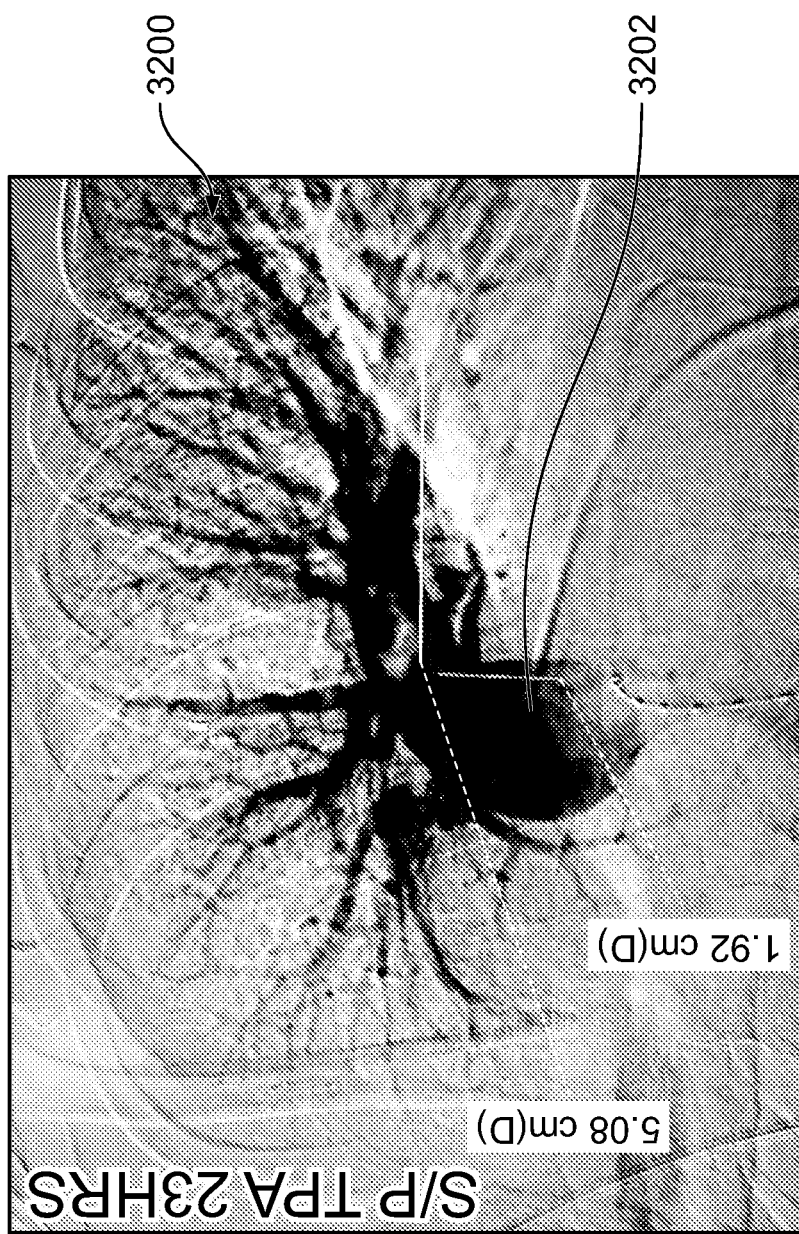
FIG. 32A illustrates a human pulmonary artery with a chronic blood clot on a left side of said artery.
Figure 32B:
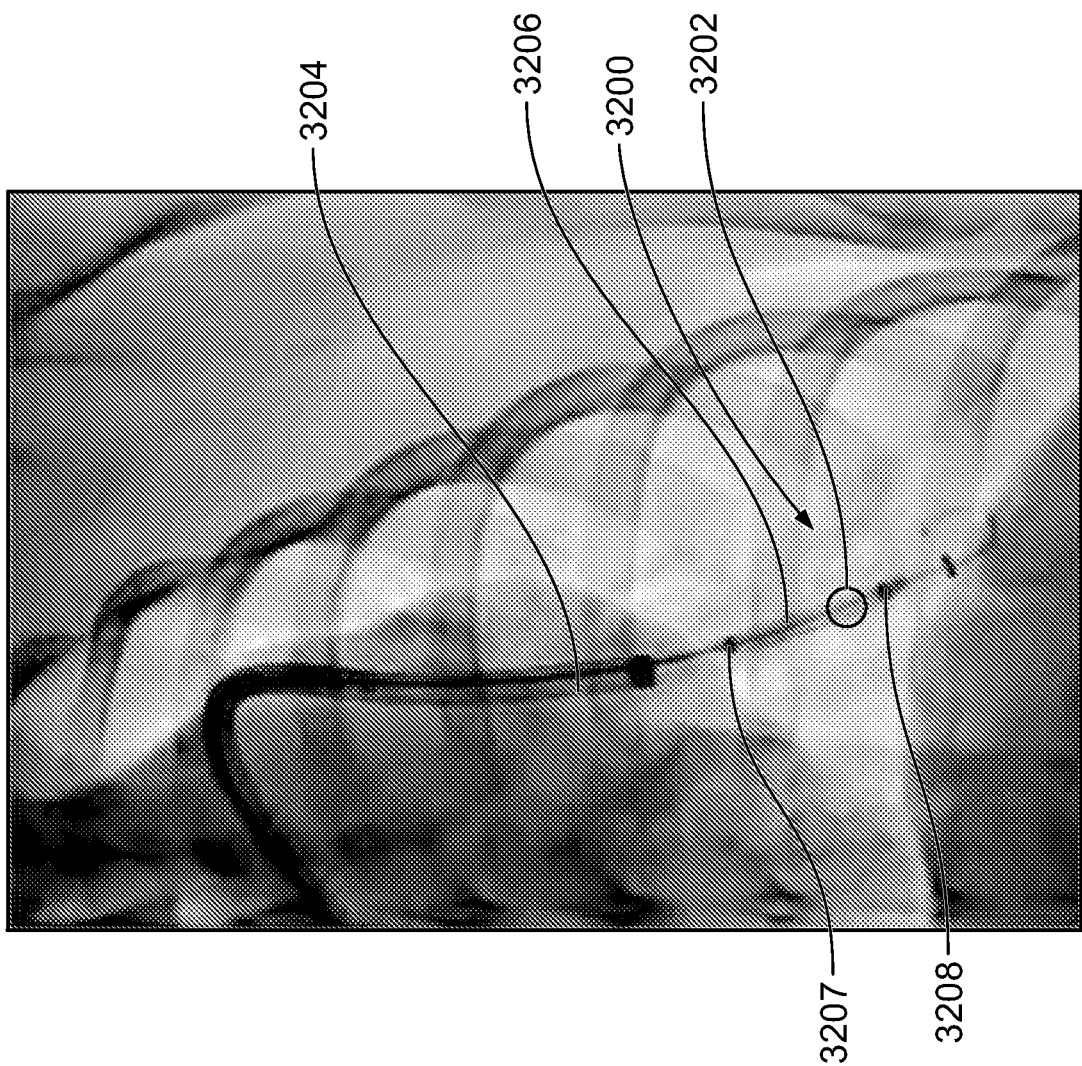
FIG. 32B illustrates a retrieval device such as that shown in FIGS. 28A-28G, inserted into the pulmonary artery shown in FIG. 30A.
Figure 32C:
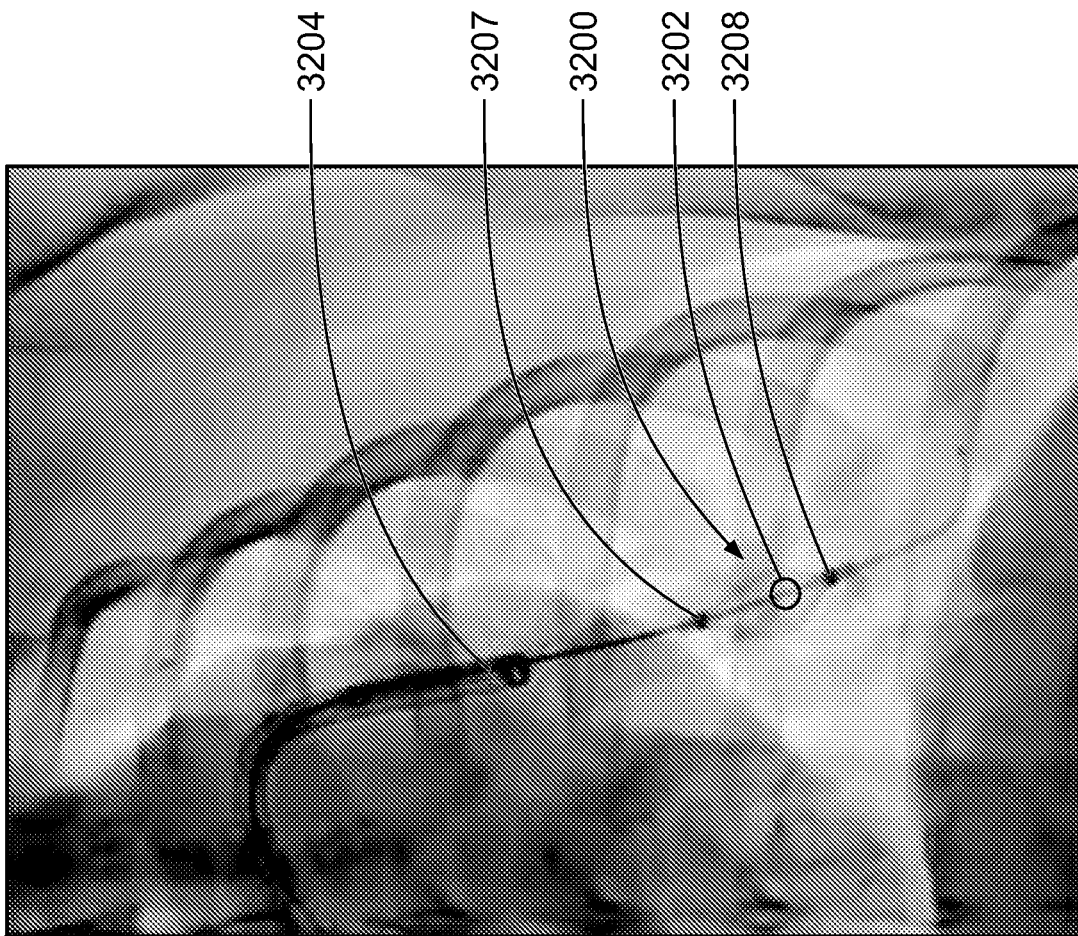
FIG. 32C illustrates an expanded distal element holding the blood clot, which can be removed from the pulmonary artery by withdrawing the retrieval device.

FIG. 32A illustrates a human pulmonary artery 3200 with a blood clot 3202 on a left side of the artery 3200. FIG. 32B illustrates a retrieval device 3204 of the present specification, inserted into the pulmonary artery 3200 with a tip portion 3206 of the retrieval device 3204 positioned within the clot 3202. The tip portion has proximal and distal elements 3207, 3208. FIG. 32C illustrates an expanded distal element 3208 holding the blood clot 3202, which can be removed from the pulmonary artery 3200 by withdrawing the retrieval device 3204.

In various embodiments, the retrieval device 3204 is one of devices 2800, 2900 or 3000 of the present specification.

As shown in FIG. 32B, the tip portion 3206 of the device 3204 is lodged into the blood clot 3202. Next (as also described earlier in the specification with respect to FIGS. 28A-28G and 30A-30H), proximal and distal elements 3207, 3208 are expanded and the blood clot 3202 is trapped in the expanded distal element 3208, which takes a concave shape upon expansion, by moving the proximal element 3207 relative to the distal element 3208. In an embodiment, the distal element 3208 does not expand fully to form a cup like structure, instead the distal element 3208 expands until an outer wall of the expanded distal element 3208 touches internal walls of the artery 3200.

In other words, a distal element expands to a diameter equal to an internal diameter of a vein/artery/lumen into which a tip portion of a retrieval device is inserted and creates a radial force to macerate an occlusion which can then be removed by pulling out the retrieval device from the vasculature.

FIGS. 37A through 37F illustrate various stages in a procedure of removing a clot 3702 in a nerve vessel 3705 using a retrieval device 3700, in accordance with some embodiments of the present specification. In some embodiments, a tip portion 3704 of the retrieval device 3700 includes proximal and distal elements 3710, 3712 that are self-expanding elements of Nitinol wire mesh or of woven Nitinol fabric. The proximal element 3710 is the only component of the device 3700 that is actuated (using a knob on a handle of the device 3700) to move axially in order to dislodge and mobilize the clot 3702. The distal element 3712 is fixedly mounted on the tip portion 3704 and provides embolic protection. In various embodiments, the proximal and distal elements 3710, 3712 are three dimensional geometric shapes and may be approximately spherical, elliptical or cylindrical in shape when in fully expanded states.

At step 3750*a* (FIG. 37A), the tip portion 3704 is introduced into the nerve vessel 3705 and the proximal and distal elements 3710, 3712 extended from, for example, an aspiration catheter 3715 (or from a delivery catheter or sheath) and positioned so that the clot 3702 lies between the proximal and distal elements 3710, 3712. The proximal element 3710 is moved axially to dislodge and mobilize the clot 3702. In some embodiments, the proximal and distal elements 3710, 3712 are flexible to self-expand and contract in accordance with a diameter of a lumen of the nerve vessel 3705. As shown in FIG. 37A, the distal element 3712 provides embolic protection.

At step 3750*b* (FIG. 37B), the proximal element 3710 is begun to be retracted into the aspiration catheter 3715 and is fully retracted into the aspiration catheter 3715 at step 3750*c* (FIG. 37C). As shown in FIGS. 37B and 37C, the proximal element 3710 self-contracts into the aspiration catheter 3715.

At step 3750*d* (FIG. 37D), the dislodged clot 3702 is aspirated through the aspiration catheter 3715. Next, at step 3750*e* (FIG. 37E), the tip portion 3704 is begun to be retracted back into the aspiration catheter 3715 while the distal element 3712 self-contracts into the aspiration catheter 3715. Finally, at step 3750*f* (FIG. 37F), the tip portion 3704 is fully retracted into the aspiration catheter 3715 and the device 3700 is removed, along with the clot 3702 from the nerve vessel 3705.

FIG. 38 is a flowchart of a plurality of exemplary steps of retrieving an occlusion by using the retrieval device 3700 (of FIGS. 37A through 37F), in accordance with some embodiments of the present specification. In an embodiment, in order to retrieve an occlusion from a lumen of a patient's nerve vessel, at step 3802, an aspiration catheter (or a delivery catheter or a sheath) of the retrieval device is positioned near the occlusion with a distal end of a tip portion of the retrieval device, protruding from the aspiration catheter (or delivery catheter or sheath), being positioned within or all the way through and beyond the occlusion. In an embodiment, a handle of the retrieval device is used to maneuver and position the tip portion.

At step 3804, as the tip portion is positioned, a distal element, which is fixedly attached to the distal end of the tip, and a proximal element, slidably coupled to a proximal end of the tip portion, self-expand to respective first and second diameters. In some embodiments, the first and second diameters are same and in accordance with a diameter of the lumen of the nerve vessel. In some embodiments, the first and second diameters are dissimilar.

In an embodiment, the distal element is positioned within the occlusion, and in another embodiment the distal element is positioned distal to (or beyond) the occlusion. In an embodiment the proximal element is positioned proximal to (prior to) or within the occlusion, such that the proximal element can be moved all the way up to the expanded distal element to generate a vice-like grip and trap the occlusion between the proximal and distal elements. In some embodiments, once the occlusion is trapped between the proximal and distal elements, the distance between the proximal element and the distal element may be reduced further such that the proximal element moves proximate the distal element.

At step 3806 the proximal element is moved axially (in one or more to and fro motions) along the tip portion to dislodge the occlusion in a manner that captures the occlusion between the proximal and distal elements.

At step 3808, in some embodiments, the occlusion captured between the proximal and distal elements is removed by retracting the proximal element, aspirating the occlusion and thereafter retracting the distal element into the aspiration catheter. The distal and proximal elements self-contract into the aspiration catheter as they are retracted. In other words, first the proximal element is retracted into the aspiration catheter, then the occlusion (dislodged and captured between the distal and proximal elements) is aspirated through the aspiration catheter and finally the distal element is also retracted into the aspiration catheter.

In some embodiments, a first portion of the occlusion captured between the proximal and distal elements is removed by pulling out the proximal element, the first portion of the occlusion and the distal element while a remaining second portion is aspirated using the aspiration catheter. In various embodiments, the exact technique of step 3808 varies depending upon factors such as, but not limited to, the anatomical location of the occlusion within the patient's body, and the complexity and density of the occlusion. However, in various embodiments, step 3808 involves some degree of moving the proximal element relative to the distal element to dislodge and trap the occlusion.

In some embodiments, a retrieval device of the present specification is configured to have at least one of the proximal and distal elements be formed of first and second braids respectively and positioned on a tip portion of the device. The first and second braids are coupled onto a shaft that is torqued. As the shaft is untorqued, each of the first and second braids expands and pulls together to form a football shape. Thus, in some embodiments, a centrifugal force applied to the shaft (via the handle) causes the shaft to spin or rotate in order to untorque and expand the first and second braids.

In some embodiments, a portion of the first or second braid is covered so that as the covered braid expands, the cover acts as a funnel for aspiration or curettage of the clot material. In some embodiments, a proximal portion of the first or second braid is covered while the distal portion is open or not covered. Since the open portion is distal, affected aspiration is directed, isolated or focused onto fluid/clot distal to the tip portion.

It should be appreciated that in preferred embodiments a retrieval device of the present specification is characterized by a) a proximal element and a distal element being able to expand or open as well as contract or close independently, b) the proximal and distal elements not being self-expanding/self-contracting but rather only expand or contract mechanically by the application/removal of force, and c) the proximal element being configured to move relative to the distal element or vice-versa. However, in less preferred embodiments, a retrieval device of the present specification is characterized by a) a single physically manipulable interface such as, for example, a knob, slider or button being configured to expand or contract the proximal and distal elements concurrently, b) the proximal and distal elements being configured to partially self-expand, and/or c) the proximal and distal elements being configured to move axially together in a coordinated fashion.

Key Characteristics of a Retrieval Device

In various embodiments, a retrieval device (such as, the devices 2800, 2900, 3000, 3304, 3504 and 3700) of the present specification is configured to have a plurality of characteristics, such as follows:

In some embodiments, the retrieval device includes proximal and distal elements that are three dimensional (3D) geometric shapes. In some embodiments, the proximal and distal elements are independently expandable, compressible, and moveable relative to each other yet mounted on a single delivery system.

In some embodiments, each geometric shape (proximal and distal elements) can independently expand even while the other geometric shape or element cannot expand, is blocked or is being moved. The retrieval device enables active (controlled) mechanical expansion of each of the proximal and distal elements by the user.

In some embodiments, the retrieval device includes a handle system at a proximal end, wherein the handle system includes three sliders, levers, dials, or buttons that allow for the independent expansion/contraction of the distal element, independent expansion/contraction of the proximal element, and independent axial movement of the proximal element relative to the distal element.

In some embodiments, the handle includes a plurality of gradations such as, for example, three gradations of low, medium and high, five gradations ranging from low to high or eight gradations ranging from low to high. Each gradation is indicative of a corresponding predefined diameter of the proximal and distal elements in expanded states. The three slide buttons can be actuated to any one of the plurality of gradations and then détente to that position.

In some embodiments, handle or axial force (that is, the pulling or pushing force that comes into force due to actuation of each of the three slide buttons) ranges from 0 to 20 Newtons and generally up to 60 Newtons, preferably from 9 to 15 Newtons. In other words, the handle or axial force is a force required to, for example, pull on one of the shafts to expand the braid wires of any of the proximal or distal elements. In embodiments, therefore, the proximal and distal elements are capable of delivering controlled radial force.

In some embodiments, the retrieval device enables one geometric shape (that is, the proximal element) to move linearly fore and aft while another tandem geometric shape (that is, the distal element) remains in place. Thus, the proximal element is configured to independently move forward and backward along a wire/lumen even while the distal element cannot expand, is blocked, is stationary or is being moved in a different direction.

In some embodiments, the geometric shapes (proximal and distal elements) can perform multiple passes without re-sheathing—that is, position the elements, expand the elements, drag out embolic material, flatten the elements, position the elements, expand the elements, drag out embolic material and so on. Stated differently, the retrieval device is capable of multiple (thrombus related) extraction passes without the need to re-sheath or reintroduce the device.

In some embodiments, a minimum distance between the proximal and distal elements ranges from 0 to 5 mm and a maximum distance between the proximal and distal elements 2806, 2807 ranges from 60 mm to 400 mm.

In some embodiments, the retrieval device enables an operator to actively adjust the respective diameters of the individual geometric shapes (proximal and distal elements) across a range of diameters.

In some embodiments, each geometric shape (proximal and distal elements) is configured to independently apply a radial force preferably in a range of 10 Newtons to 14 Newtons. More generally, each of the proximal and distal elements can be mechanically expanded to allow for controlling an amount of radial force applied ranging from 0 to 40 Newtons and, in some embodiments, generally ranging from 0 to 25 Newtons. Therefore, each element can be expanded to reach a radial force level and maintain the element at the reached radial force level without further action. It should be appreciated that force is a function of a length of contact of each of the proximal and distal elements with a vessel wall. For example, in a 5 mm vessel, the length of contact of an element could be 0.9 inches while in a 12 mm vessel, the length of contact of the element could be 0.6 inches. However, the degree of radial force is not likely the same across an entire length of contact (in fact, it may be more at some portions and less in other portions of the contact length). Therefore, "radial force" refers to an average force applied along the length of contact and is not necessarily equal along the entire length of contact.

In some embodiments, the retrieval device enables the operator to actively adjust the exerted radial forces of the individual geometric shapes (proximal and distal elements) across a range of diameters and/or within a fixed diameter.

In some embodiments, the retrieval device enables each geometric shape (proximal and distal elements) to be simultaneously and independently adjusted with respect to size, shape, location and radial force relative to the other.

In some embodiments, the retrieval device provides continuous distal embolic protection (using the distal element) while simultaneously engaging in remote proximal thrombectomy (using the proximal element). The distal embolic protection is enabled because the distal element opposes to the vessel wall and contains pores ranging from 0.01 inches to 0.08 inches, preferably 0.02 inches to 0.06 inches, encompassing a cross-sectional area of a blood vessel and thereby substantially blocking anything flowing out.

In some embodiments, the geometric shapes enable maceration of embolic material to fit through an aspiration catheter.

In some embodiments, the retrieval device can utilize linear travel and geometric shape apposition and compression to capture thrombus and remove it from arteries and veins. Thus, the proximal and distal elements can move relative to each other allowing capture and mechanical removal of material.

In some embodiments, the retrieval device can effectively be manually expanded into thrombus to capture material within a geometric shape (proximal element and/or distal element) itself prior to material extraction. In other words, the retrieval device can trap thrombus within the confines of the proximal and/or distal elements allowing for mechanical removal of thrombus.

In some embodiments, the distal element can independently invaginate on itself (to form a chalice) in order to capture embolic material mechanically. The distal element envelopes the embolic material when inverted and then when flattened, the embolic material is exposed. In other words, the distal element encloses at least a portion of the clot material by inverting a portion of the distal element.

In some embodiments, each geometric shape (proximal and distal elements) is configured to independently apply a pull force capable of removing, scraping, or dislodging clot material from a vessel wall thereby minimizing a need for aspiration. Thus, in some embodiments, the retrieval device enables removal of thrombus with minimal reliance on aspiration.

In some embodiments, both geometric shapes (proximal and distal elements) can be collectively used to apply a compressive force (on a thrombus) ranging from 0 Newtons to 60 Newtons, preferably in a range of 9 Newtons to 15 Newtons.

In some embodiments, the geometric shapes (proximal and distal elements) are configured to exert the radial, compressive, and pull forces using atraumatic surfaces.

In some embodiments, the retrieval device enables the geometric shapes (proximal and distal elements) adjusted so that a wide range of vessel lumen diameters can be treated using a single adjustable device.

In some embodiments, the retrieval device anchors itself distally to provide for a more stationary wire that improves the ability to advance catheters into distal anatomy and through tortuous vasculature.

In a preferred embodiment, the retrieval device does not rely on or require passive expansion of a self-expanding material in order to perform its thrombectomy functions. In other words, the geometric shapes (proximal and distal elements) expand reliably and mechanically to a particular diameter and a particular radial force, thereby allowing trapping and curettage of material from the vessel lumen and wall.

In some embodiments, the retrieval device utilizes its adjustable radial forces and its adjustable size to actively curettage the wall of an artery or vein.

In some embodiments, the retrieval device enables removal of thrombus by simultaneously capturing, compressing, dragging and curetting thrombotic material from vessel walls. In other words, the fore and aft (forward and backward) movement of the proximal element relative to the distal element enables curettage to separate and mobilize thrombus from vessel wall.

In some embodiments, the retrieval device can be used equally as well and in the same manner for extraction of acute, sub-acute and organized chronic thrombus in any anatomic location.

In some embodiments, the retrieval device includes a completed aspiration system.

In some embodiments, the retrieval device is capable of performing mechanical removal of PE and DVT.

In some embodiments, the single retrieval device is configured to perform both PE and DVT procedures.

In embodiments, the retrieval device minimizes blood loss and tPA during extraction of thrombus from a vessel lumen.

Braid wire parameters for proximal and distal elements—in some embodiments, each of the proximal and distal elements is a geometric mesh structure of braid wire. In some embodiments, a braid includes 32 wires of 0.006 inches diameters each, 8 Pics (or PPI) per inch, of super elastic Nitinol and pattern: two over two under—resulting in mesh structure having a cell size of 0.92 inches×0.92 inches.

In various embodiments, following are some of the key parameters of the braid wire forming the geometric mesh structures (having a plurality of cells) of the proximal and distal elements:

Braid diameters: ranging from 3 mm to 20 mm and up to 30 mm in some embodiments

Number of wires: in various embodiments a braid includes 16, 24, 32 or 48 wires

Wire diameter: in various embodiments, a diameter of a wire in a braid ranges from 0.002 inches to 0.02 inches.

Wire shape: in various embodiments, a shape of a wire in a braid includes square, rectangular or triangular (any of these shaped wires may be twisted for additional cutting surfaces).

Wire material: Nitinol, Stainless Steel

Patterns: over one under one, one under over two and two over two under.

Pics (or PPI) per inch: ranges from 6 to 16 in various embodiments.

Cell size in a mesh structure: in various embodiments, a cell size of a mesh structure varies according to the Pics per inch as follows:

| Pics Per Inch | Cell Size (inches × inches) |
|---|---|
| 8 | .092 × .092" |
| 9 | .072 × .072" |
| 10 | .065 × .065" |
| 12 | .051 × .051" |

Exemplary Live Animal Experimentation Using a Retrieval Device of the Present Specification A retrieval device, such as the device 2800, 2900 or 3000, of the present specification was introduced into venous structures of an 821*b* live swine to perform thrombectomy test procedures. Table A summarizes values of a plurality of parameters associated with the test procedures. Once a tip portion was positioned for removal of an occlusion within the venous structures, proximal and distal elements were expanded, the proximal element slid to dislodge the occlusion and thereafter trapped between the proximal and distal elements (in accordance with the method of FIGS. 31A and 31B).

A first test procedure was performed in the animal's right internal jugular vein (RIJV) having an initial diameter of 4.5 mm. During the first test, a handle force of 15.1 N was applied, the distal element was expanded to a diameter of 5 mm to exert a radial force of 13 N on the walls of the RIJV. After the first test, a post test diameter of the RIJV was measured to range between 4 mm and 5 mm.

A second test procedure was performed in the animal's left internal jugular vein (LIJV) having an initial diameter of 5 mm. During the second test, a handle force of 15 N was applied, the distal element was expanded to a diameter of 8 mm to exert a radial force of 13 N on the walls of the LIJV. After the second test, a post test diameter of the LIJV was measured to be 5 mm.

A third test procedure was performed in the animal's right external jugular vein (REJV) having an initial diameter of 8 mm. During the third test, a handle force of 10 N was applied, the distal element was expanded to a diameter of 11 mm to exert a radial force of 10 N on the walls of the REJV. After the third test, a post test diameter of the REJV was measured to range between 8 mm and 9 mm.

A fourth test procedure was performed in the animal's left external jugular vein (LEJV) having an initial diameter of 9 mm. During the fourth test, a handle force of 11 N was applied, the distal element was expanded to a diameter of 11 mm to exert a radial force of 11 N on the walls of the LEJV. After the fourth test, a post test diameter of the LEJV was measured to range between 7 mm and 8 mm.

A fifth test procedure was performed in the animal's right common iliac vein (RCIV) having an initial diameter of 14 mm. During the fifth test, a handle force of 7 N was applied, the distal element was expanded to a diameter of 16 mm to exert a radial force of 14 N on the walls of the RCIV. After the fifth test, a post test diameter of the RCIV was measured to be 14.5 mm.

A total of 5 retrieval device cycles, where each cycle comprises expanding the proximal element, capturing material, moving the proximal element, pulling out the material and moving the proximal element back, were performed in each of the first, second, third, fourth and fifth test procedures.

TABLE A

| Test | 1 | 2 | 3 | 4 | 5 |
|---|---|---|---|---|---|
| Location | RIJV | LIJV | REJV | LEJV | RCIV |
| Handle Force | 3.4 lbs (15.1N) | 3.4 lbs (15N) | 2.2 lbs (10N) | 2.5 lbs (11N) | 1.5 lbs (7N) |
| Radial Force | 13N | 13N | 10N | 11N | 14N |
| Vessel Initial Diameter | 4.5 mm | 5 mm | 8 mm | 9 MM | 14 mm |
| Sphere Expanded Diameter | 5 mm | 8 mm | 11 mm | 11 MM | 16 mm |
| Cycles | 5 | 5 | 5 | 5 | 5 |
| Post Test Vessel Diameter | 4-5 mm | 5 mm | 8-9 mm | 7-8 mm | 14.5 mm |

Post procedures, H&E staining of the cross-sections of the venous structures (RIJV, LIJV, REJV, LEJV and RCIV) were performed by a veterinary pathologist as part of a histopathology study that used a left iliac vein as control vessel. Table B summarizes results of the pathology evaluation, as follows:

TABLE B

| File ID | Vessel ID | Pathology Evaluation |
|---|---|---|
| 1056122 | #1 Left Iliac Vein | Linear tangential section of blood vessel: Normal vasculature (control vessel) |
| 1056125 | #2 Right Common Iliac Vein | Linear tangential sections of blood vessel: The several sections of tangential blood vessels appear normal with post-mortem blood pooling. Scattered loss of endothelial lining in some of the vessels. (experimental vessel) |
| 1056123 | #3 Left External Jugular Vein | Linear tangential sections of blood vessel: The several sections of tangential blood vessels appear normal with some post-mortem blood pooling. (experimental vessel) |
| 1056077 | #4 Left Internal Jugular Vein | Linear tangential sections of blood vessel: The several sections of tangential blood vessels appear normal with post-mortem blood pooling. Scattered loss of endothelial lining in some of the vessels. (experimental vessel) |
| 1056121 | #5 Right External Jugular Vein | Linear tangential sections of blood vessel: The several sections of tangential blood vessels appear normal and are expanded by pooling of blood and early fibrin clot formation. Scattered loss of endothelial lining in some of the vessels. (experimental vessel) |
| 1056079 | #6 Right Internal Jugular Vein | Linear tangential sections of blood vessel: The several sections of tangential blood vessels appear normal with some pooling of blood and early fibrin clot formation. Scattered loss of endothelial lining in some of the vessels. (experimental vessel) |

Figures 36A, 36B:
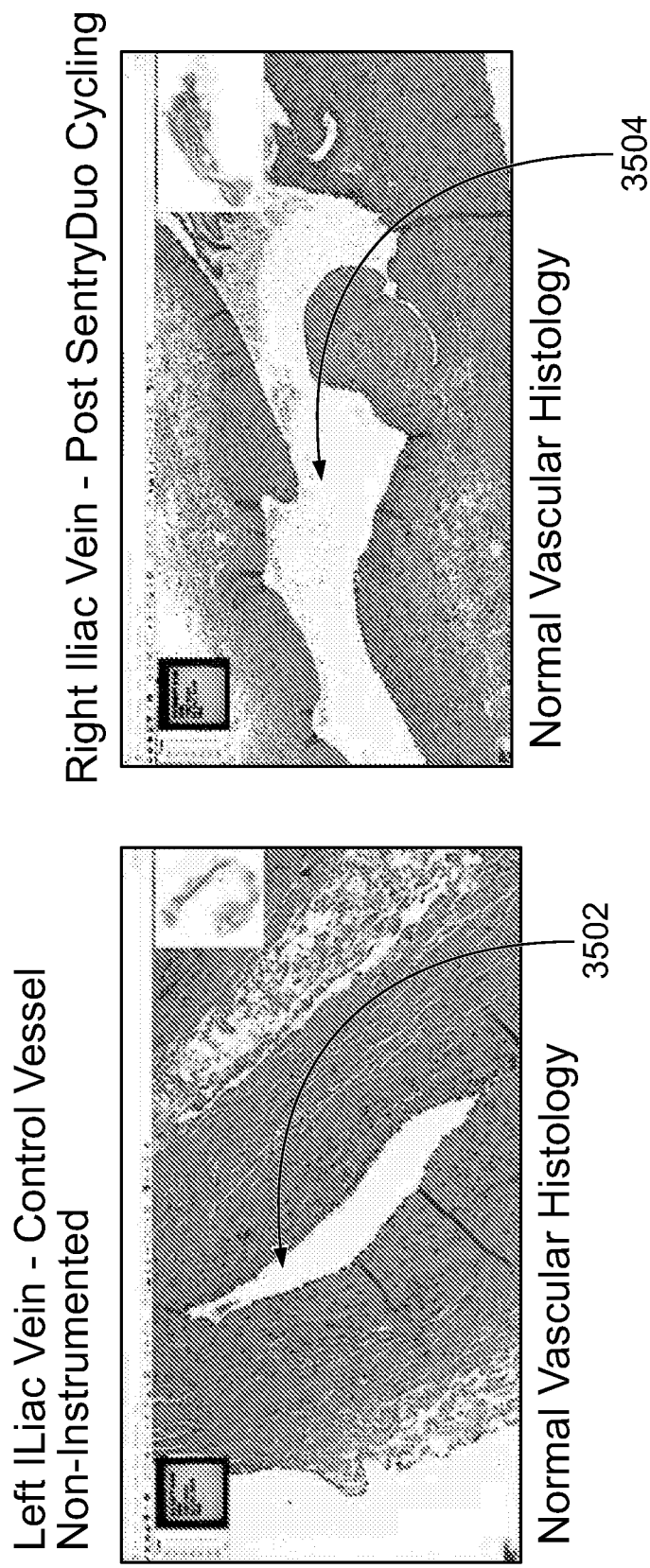
FIG. 36A illustrates a linear tangential section of a left iliac vein that has not been subjected to an experimental thrombectomy procedure.
FIG. 36B illustrates a linear tangential section of a right iliac vein after an experimental thrombectomy procedure.

In all specimens, the vascular integrity was intact and the histology of vascular elements essentially normal. The blood pooling and clotting were observed to be recent events and were considered to be artifactual as there was no definitive pathology associated with the veins. In some of the blood vessels, there was scattered endothelial cell loss, which was considered most likely also artifactual and due to venous extraction and handling. As an example, FIG. 36B illustrates a linear tangential section of the right iliac vein 3604 of the animal after a test procedure, in comparison to FIG. 36A that illustrates a linear tangential section of the left iliac vein 3602 that has not been subjected to the thrombectomy test procedure. FIG. 36B is illustrative of a normal vascular histology when compared with the histology of the vein (control vessel) of FIG. 36A.

Experimental Use Case Study 1

Figure 39A:
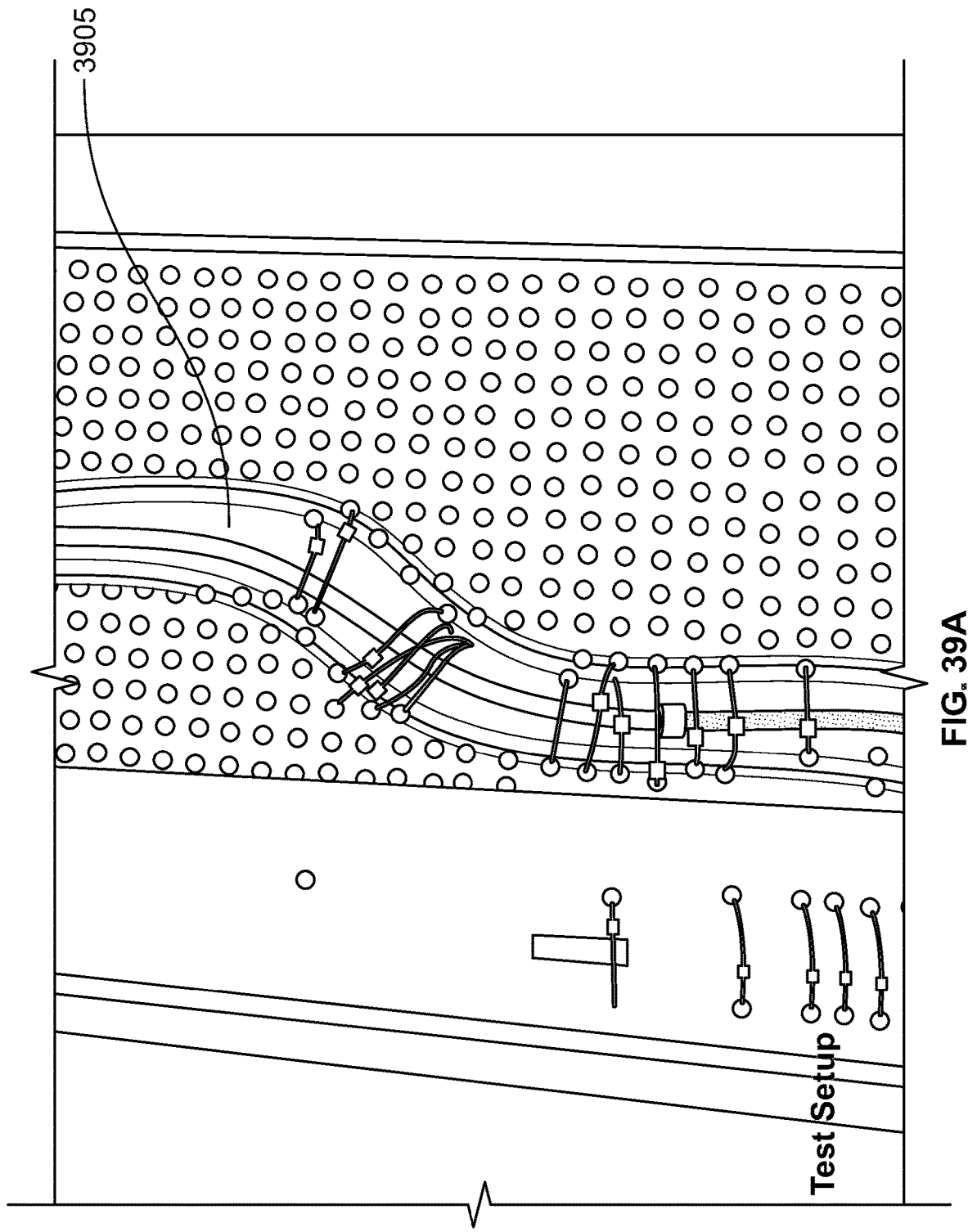
FIG. 39A shows a linear continuous flow model representative of a blood vessel for performing experimental thrombectomy using a retrieval device, in accordance with some embodiments of the present specification.

FIG. 39A shows a linear continuous flow model 3905 representative of a blood vessel for performing experimental thrombectomy using a retrieval device, in accordance with some embodiments of the present specification. The model 3905 has a proximal access hemostatic valved port that permits introduction of an aspiration catheter and a delivery catheter (such as, the aspiration catheter 2835 and delivery catheter 2848 of FIG. 28A). The model 3905 also includes a distally located filter or collection trap that can capture distal emboli that occur during thrombectomy.

Figure 39B:
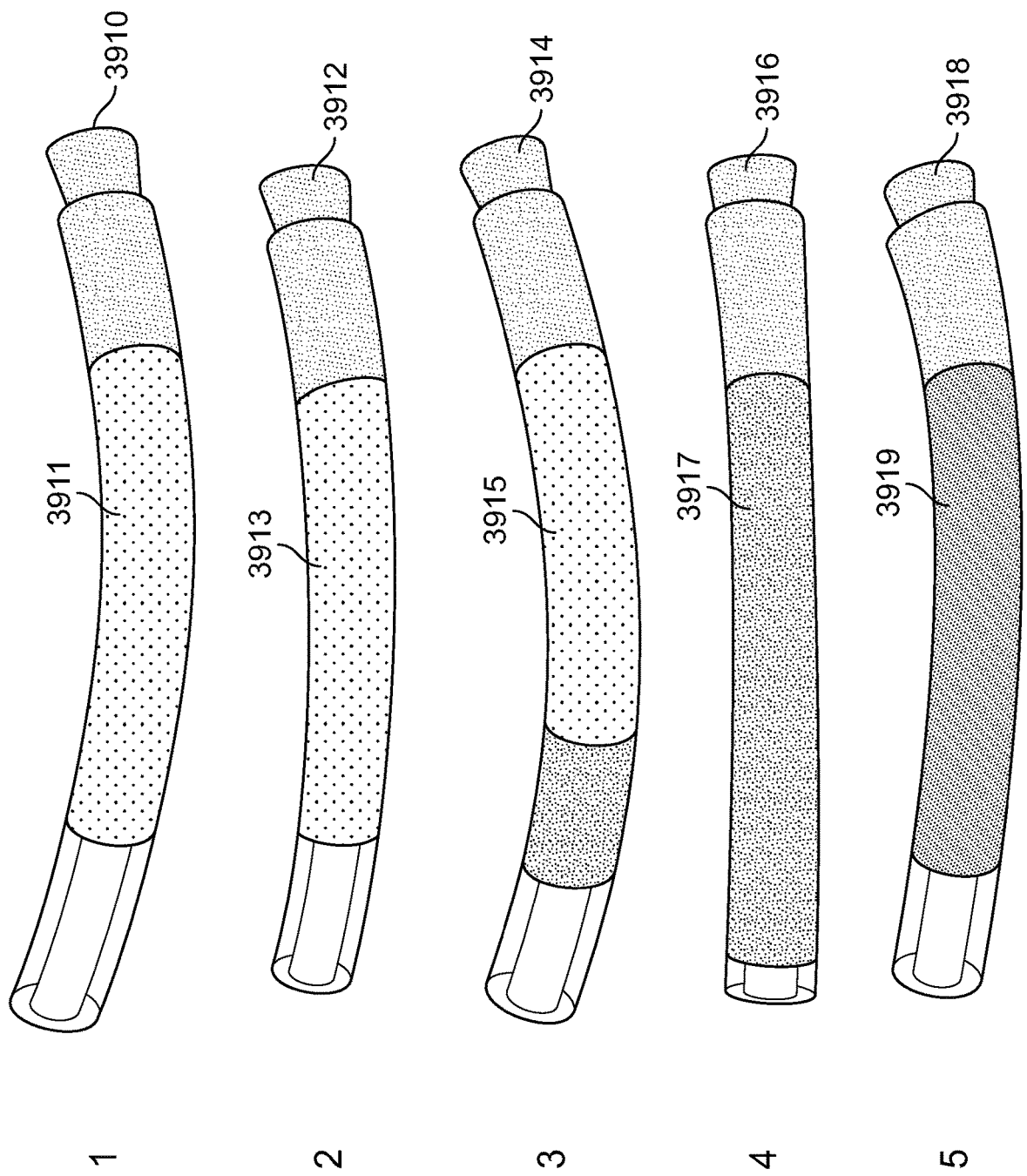
FIG. 39B shows a plurality of exemplary tubes with artificial thrombus/clot, in accordance with some embodiments of the present specification.

The model 3905 allows incorporation of a pre-made tube, of a predefined internal diameter, with mechanically characterized artificial thrombus spliced into the tube. A pre-made tube with artificial thrombus is also referred to collectively as a 'cartridge'. FIG. 39B shows example cartridges consisting of tubes 3910, 3912, 3914, 3916 and 3918 with artificial thrombus 3911, 3913, 3915, 3917 and 3919, respectively. In embodiments, an artificial thrombus is manufactured using a predetermined recipe of egg albumin, flour, water and food coloring. The model 3905 further includes pressure transducers proximal and distal to a cartridge incorporated in the model 3905.

For the experimental use case study:
a) Fifteen cartridges are prepared such that each cartridge has a tube of 15 mm diameter and artificial thrombus or clot spliced into the tube. Weight of each of the empty tube cartridge (that is, without the thrombus) is recorded.
b) The fifteen cartridges are organized into first, second and third groups such that each group includes five cartridges.
c) The five cartridges of the first group are exposed to a microwave oven for 15 seconds, the five cartridges of the second group are exposed to a microwave oven for 30 seconds, and the five cartridges of the third group are exposed to a microwave oven for 45 seconds. Weight of each of the cartridges with microwaved thrombus is recorded.
d) Each of the fifteen cartridges with the microwaved thrombus is submerged in water for 30 minutes to saturate the microwaved thrombus with fluid. Weight of each of the cartridges with water saturated microwaved thrombus is recorded. Using, the weight of the empty tube cartridge and weight of the microwaved and water saturated cartridge, the approximate saturated thrombus weight is determined for each cartridge.
e) Modulus of Elasticity of the experimental artificial thrombus in each cartridge is determined after it is saturated. It should be appreciated, that each of the thrombi of the first group of five cartridges will have a first Modulus of Elasticity, each of the thrombi of the second group of five cartridges will have a second Modulus of Elasticity, and each of the thrombi of the third group of five cartridges will have a third Modulus of Elasticity. The third Modulus of Elasticity will be greater than the second Modulus of Elasticity which will be greater than the first Modulus of Elasticity. Thus, each group will have similar Modulus of Elasticity that increases from the first group through the second group and to the third group.
f) Place a cartridge into the non-pulsatile flow model 3805 that has a pressure transducer positioned proximal and distal to the occlusive thrombus cartridge.
g) The aspiration catheter is inserted through the hemostatic valve and positioned proximal to the thrombus cartridge.
h) The delivery catheter is inserted into the thrombus.
i) A pump, associated with the flow model 3905, is switched on in order to generate fluid flow through the model 3905.
j) Baseline pressures are measured proximal and distal to the occlusive thrombus cartridge.
k) A retrieval device (such as, the device 2800, 2900 or 3000) is inserted into the delivery catheter.
l) A tip portion of the retrieval device is unsheathed and a timer is started.
m) An operator now uses the retrieval device to extract the thrombus or clot. A continuous video recording is done of the thrombus extraction process in the tubing.
n) During the thrombus extraction process continuous pressure monitoring is performed both distal and proximal to the cartridge.
o) The timer is stopped when the thrombectomy is clinically completed.
Steps f) through o) are repeated for each of the fifteen cartridges.

The following exemplary data is derived as a result of the experimental steps performed above:
Time from deployment of the retrieval device in the thrombus/clot to clinical thrombectomy completion.
Time to achieve clinically significant pressure equalization across the thrombosed cartridge.
Mass by weight of the extracted thrombus/clot. This mass divided by the baseline clot mass will provide a percentage of clot that was removed by the retrieval device in a specific time.
Mass by weight of the distally embolized thrombus/clot that was captured by the filter. This mass divided by the baseline thrombus/clot mass will provide a percentage of the thrombus/clot that embolized distally during the thrombectomy procedure.

Steps a) to o) are repeated for first and second prior art devices to generate data comparable to the data pertaining to the retrieval device of the present specification. When compared with data of the first and second prior art devices, the retrieval device does the following:
Extracts thrombus/clot faster
Re-establishes acceptable pressure differences faster
Removes more thrombus/clot
Produces less distal embolization In some embodiments, additional cartridges are prepared that have increasing Moduli of Elasticity of the artificial thrombi. Thereafter, the retrieval device is separately deployed in each of the additional cartridges until a point of failure is reached—that is, the point where it is no longer possible to manually expand the proximal and distal elements and remove thrombus/clot material. The same approach is followed for the first and second prior art devices. Compared to the first and second prior art devices, the retrieval device of the present specification can open in thrombus/clot material that has a far greater Modulus of Elasticity than can the first and second prior art devices.

Experimental Use Case Study 2

This study uses a closed-loop anatomical flow model for performing experimental thrombectomy using a retrieval device of the present specification (such as, the device 2800, 2900 or 3000). The flow model has a proximal access hemostatic valved port that permits introduction of an aspiration catheter and a delivery catheter (such as, the aspiration catheter 2835 and delivery catheter 2848 of FIG. 28A). The model also includes a distally located filter or collection trap that can capture distal emboli that occur during thrombectomy.

The model allows incorporation of a pre-made tube, of a predefined internal diameter, with mechanically characterized artificial thrombus spliced into the tube. A pre-made tube with artificial thrombus is also referred to collectively as a 'cartridge'. In embodiments, an artificial thrombus is manufactured using a predetermined recipe of egg albumin, flour, water and food coloring. In accordance with an embodiment, the study uses an artificial thrombus, having a Modulus of Elasticity, that can be extracted by the retrieval device of the present specification but not by first and second prior art devices. The model further includes pressure transducers proximal and distal to a cartridge incorporated in the model.

For the experimental use case study:
a) A video recording is made of the thrombus/clot extraction procedure and of the thrombus/clot distal embolization.
b) Measure pressures during the procedure.
c) Measure resistance to device extraction once it is deployed against a native PA (Pulmonary Artery) vessel wall that does not have clot in it.
d) Record the volume of fluid aspirated from the aspiration catheter during thrombus extraction. The aforementioned study is repeated for the first and second prior art devices.

Comparative Studies of a Retrieval Device of the Present Specification with Respect to First and Second Conventional Devices In the foregoing studies, the retrieval device of the present specification refers to any of the devices 2800, 2900 or 3000. The foregoing studies are directed towards comparative abilities of the retrieval device of the present specification with respect to the first and second prior art devices to extract thrombus material that simulates sub-acute and organized thrombus encountered in Pulmonary Embolism (PE)/Deep Vein Thrombosis (DVT) clinical settings.

Figure 40A:
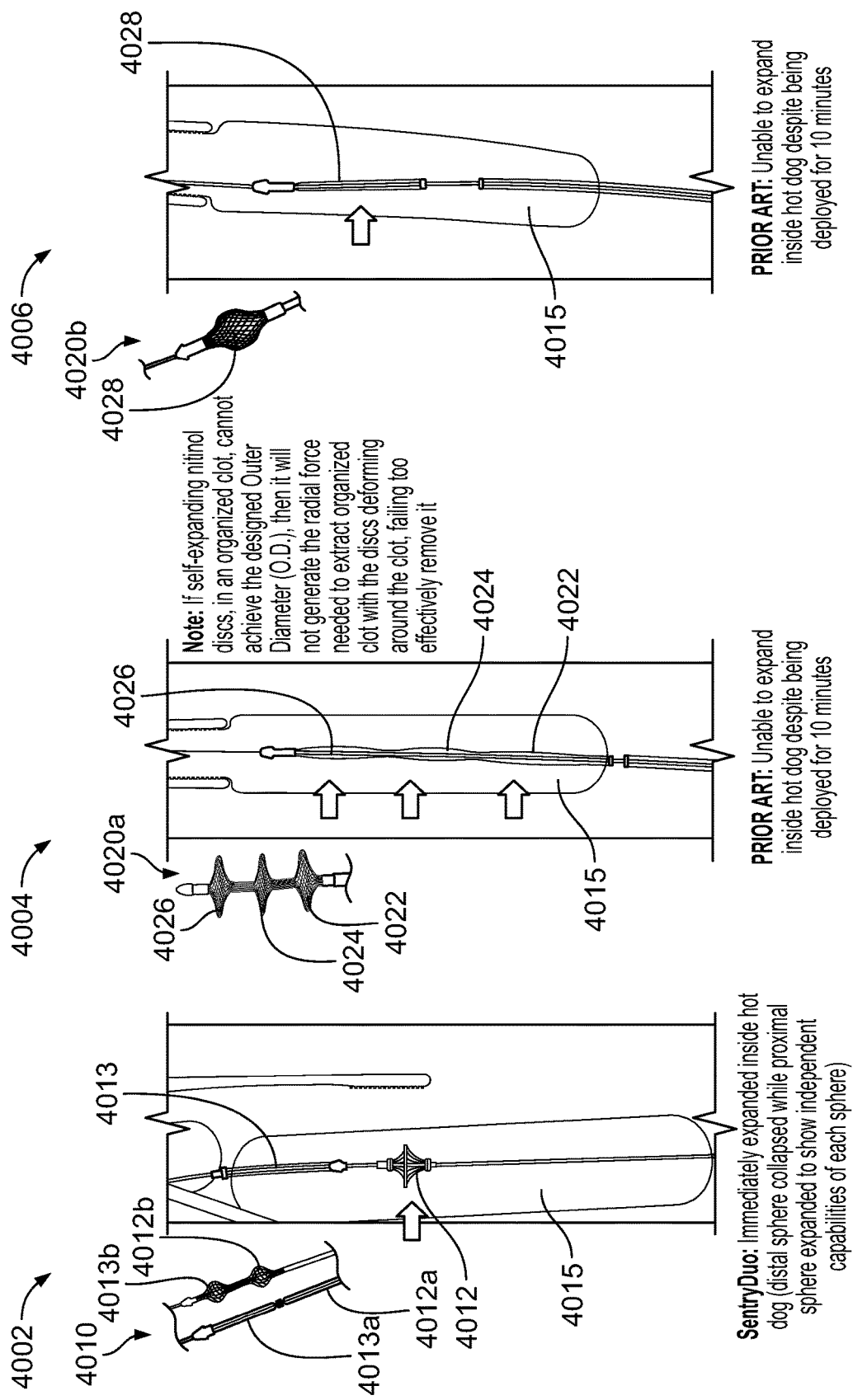
FIG. 40A shows first, second and third views illustrating deployment capability of a retrieval device of the present specification with respect to conventional, prior art devices.

FIG. 40A shows first, second and third views 4002, 4004 and 4006 illustrating deployment capability of a retrieval device 4010 of the present specification with respect to first and second prior art devices 4020a, 4020b. View 4002 shows the retrieval device 4010 with proximal and distal elements in collapsed state 4012a, 4013a and in expanded state 4012b, 4013b. As visible, the proximal element 4012 is expanded immediately inside a hot dog 4015 while the distal element 4013 is kept collapsed demonstrating independent maneuver capabilities of the proximal and distal elements 4012, 4013.

View 4004 shows the first prior art device 4020a deployed within the hot dog 4015. The first prior art device 4020a includes first, second and third self-expanding Nitinol discs 4022, 4024, 4026. However, none of the first, second and third discs 4022, 4024, 4026 are able to expand inside the hot dog 4015 despite being deployed for 10 minutes.

View 4006 shows the second prior art device 4020b deployed within the hot dog 4015. The second prior art device 4020b includes a self-expanding Nitinol basket 4028. However, the basket 4028 is unable to expand inside the hot dog 4015 despite being deployed for 10 minutes. Thus, the self-expanding Nitinol discs 4022, 4024, 4026 and basket 4028 of the first and second prior art devices cannot reliably expand into sub-acute and organized thrombus. Consequently, the discs and basket cannot achieve their designed outer diameters and therefore are unable to generate the radial force needed to extract sub-acute or organized thrombus. The discs and basket deform around the thrombus thereby failing to effectively remove it.

FIG. 40B shows first, second and third views 4032, 4034, 4036 of the first prior art device 4020a being sequentially retracted from the hot dog 4015. View 4032 shows the first disc 4022 being removed from the hot dog 4015. The first disc 4022 is unable to achieve its maximum outer diameter because the other two discs (second and third discs 4034, 4036) are constrained within the hot dog 4015. View 4034 shows the second disc 4024 being removed from the hot dog 4015. Both the first and second discs 4022, 4024 are unable to achieve their respective maximum outer diameters because the remaining third disc 4026 is still constrained within the hot dog 4015. View 4036 shows the third disc 4026 being removed from the hot dog 4015. Since none of the three discs are constrained, now each disc is able to achieve its designed maximum outer diameter.

It is observed from the study of FIG. 4B that the first prior art device 4020a is a contiguous three-disc design interconnected by two bands where the diameter of one disc affects the diameter of the adjacent disc. If the device 4020a is placed into firm or heterogeneous thrombus and one disc cannot open to its full discoid shape, then the other discs cannot fully expand as well. Thus, unlike the retrieval devices of the present specification, the three discs 4022, 4024, 4026 of the first prior art device 4020a are not functionally independent and cannot generate the radial force and fore/aft movement needed to remove organized fibrotic thrombus.

FIG. 40C shows first, second and third views 4042, 4044, 4046 illustrating a comparison of thrombectomy capabilities of the first prior art device 4020a, the second prior art device 4020b and the retrieval device 4010 of the present specification. The thrombectomy capabilities refer to the comparative abilities of the devices to extract thrombus material that simulates sub-acute and organized thrombus encountered in Pulmonary Embolism (PE)/Deep Vein Thrombosis (DVT) clinical settings.

View 4042 shows the first prior art device 4020a having failed to remove thrombus material (hot dog) due to its self-expanding Nitinol discs being unable to generate the radial force required to expand into the thrombus material. View 4044 shows the second prior art device 4020b having failed to remove thrombus material (hot dog) due to its self-expanding Nitinol basket being unable to generate the radial force required to expand into the thrombus material. View 4046 shows the retrieval device 4010 of the present specification being able to expand into organized thrombus (hot dog) and remove a significant amount of thrombus material 4048 due to the mechanical properties/characteristics of the retrieval device 4010.

Following are key take away from the studies of FIGS. 40A, 40B and 40C:
  a) Self-expanding nitinol disc/basket design of the first and second prior art devices cannot reliably expand into subacute and organized thrombus, failing to remove material as the radial force is inadequate.
  b) Self-expanding nitinol disc/basket of the first and second prior art devices achieves maximum radial force only if the disc/basket expands/forms to the deigned maximum Outer Diameter (O.D.). If disc/basket is partially opened, it will not generate the radial force to remove organized thrombus and will deform around the organized clot, failing to mechanically remove it.
  c) Active, controlled radial expansion of proximal and distal elements of the retrieval device of the present specification into organized clot, with independent movement of the proximal and distal elements axially, provides the needed radial force and mechanical potential to remove organized fibrotic thrombus.

Thus, the retrieval device of the present specification is characterized by at least the following:
  The proximal and distal elements can reliably expand and deploy on all thrombi.
  The proximal and distal elements can expand and deploy in firm subacute and chronic thrombus.
  Includes two thrombectomy elements (proximal and distal) in a single insertion.
  The proximal and distal elements can be deployed/expanded independently of one another.
  The proximal and distal elements can be simultaneously deployed at different diameters with the diameters controlled by the operator.
  Each of the proximal and distal elements can move independent of the other.
  The proximal and distal elements can be moved fore and aft within a vessel lumen to curettage thrombus from the vessel wall.
  Multiple passes can be conducted by the proximal and distal elements without re-sheathing the retrieval device.
  Diameters of the proximal and distal elements can be actively controlled and adjusted while also moving fore and aft.
  The retrieval device provides actively controlled wide range of proximal and distal element diameters, permitting access to both small and large diameter vessels.
  The retrieval device can actively capture and extract thrombus using the device apposition (compress, capture and remove).
  The retrieval device provides distal embolic protection during active thrombectomy.
  The retrieval device does not depend on aspiration to extract thrombus.
  The retrieval device is not tPA dependent.
  The retrieval device is proved to function atraumatically in porcine venous structures based on post procedure histologic microscopic analysis of vessel.
  The retrieval device is proven to effectively extract thrombus from porcine pulmonary arterial system in live animal studies.

A Retrieval Device Having a Single Element/Member

In some embodiments, a retrieval device of the present specification is configured to have a single element that has a three-dimensional shape and is mounted on a tip portion of the device. In some embodiments, the element takes a substantially spherical shape during an intermediate expanded state. When fully expanded, the element forms a chalice or cup shape. In some embodiments, the tip portion includes a first tube that is proximal to a handle of the device and a second tube that is distal to the handle of the device. In some embodiments, the first tube is configured to axially telescope into the second tube. In some embodiments, the element is a Nitinol mesh that has a proximal end and a distal end. The proximal end is coupled to the first tube and the distal end is coupled to the second tube.

In some embodiments, when a first knob, slider or button is slid forward towards the tip portion, the first tube moves axially into the second tube and the proximal end of the element moves distally (while the distal end of the element remains stationary) causing the element to expand into a substantially spherical shape. As the first knob or button is slid forward further, the proximal end of the element moves further close to the stationary distal end causing the element to take on a cup or chalice shape. Similarly, when the first knob or button is slid backward away from the tip portion, the first tube moves axially out of the second tube and the proximal end of the element moves proximally (while the distal end of the element remains stationary) causing the element to contract into a substantially cylindrical shape.

In some embodiments, when a second knob or button is slid forward towards the tip portion, the first and second tubes move distally together as one and the proximal and distal ends of the element move together distally causing the element to move distally away from the handle. Similarly, when the second knob or button is slid backward away from the tip portion, the first and second tubes move proximally together as one and the proximal and distal ends of the element move together proximally causing the element to move proximally towards the handle. Thus, sliding the second knob or button forward causes the element to move forward or distally while sliding the second knob or button backward causes the element to move backward or proximally.

Figure 41A:
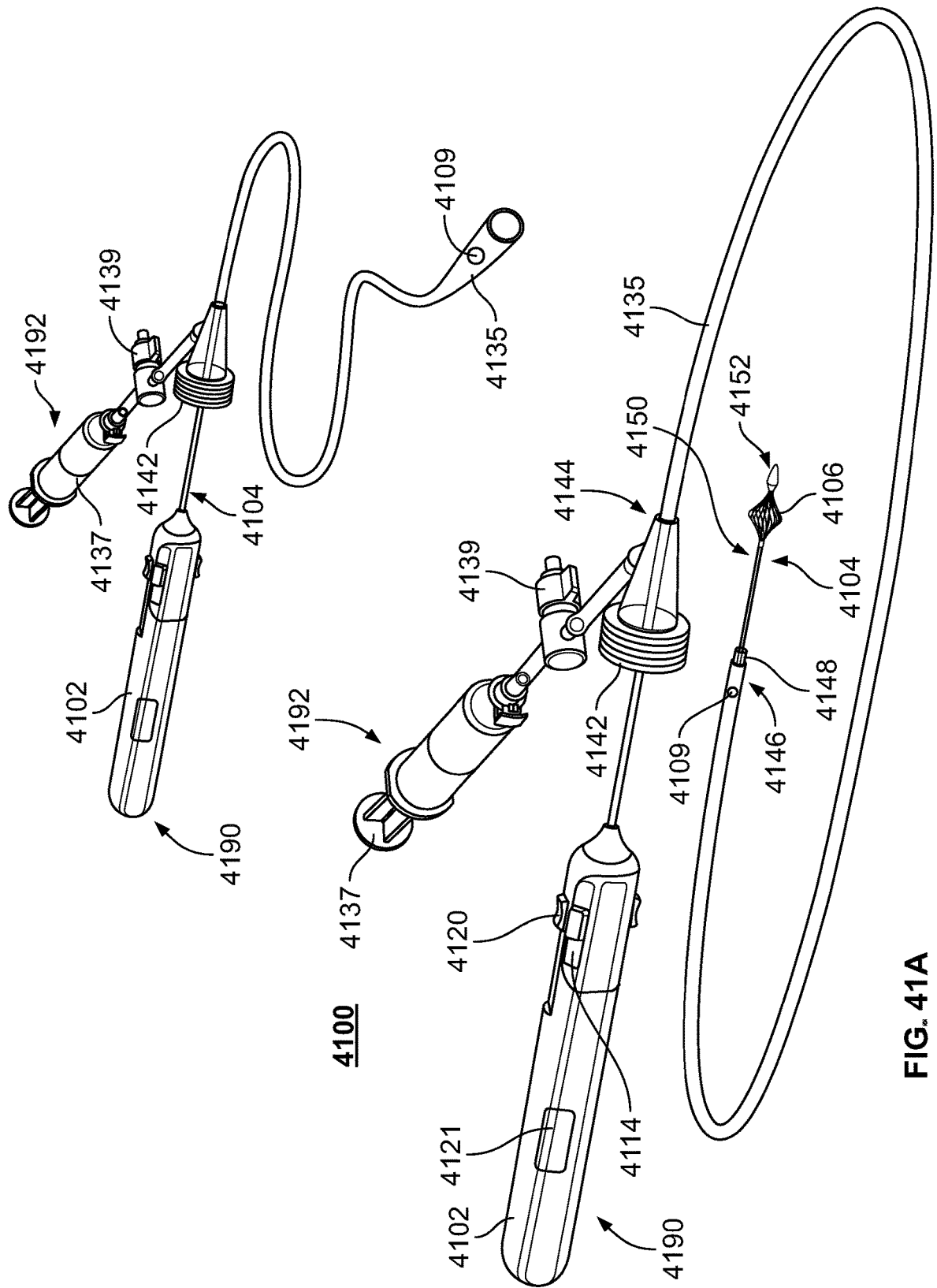
FIG. 41A illustrates a retrieval device having a single element or member, in accordance with some embodiments of the present specification.

FIG. 41A illustrates a retrieval device 4100, in accordance with some embodiments of the present specification. The device 4100 comprises a first unit 4190 that includes a handle 4102 coupled to a tip portion 4104 via telescoping tubes wherein the handle 4102 is configured to steer the tip portion 4104 in proximity to an occlusion. The device 4100 further comprises a second unit 4192 that includes an aspiration catheter 4135 having a syringe 4137, a one-way valve 4139 and a port 4142, where the port is coupled to a proximal end 4144 of the aspiration catheter 4135. In one embodiment the one-way valve is configured to direct suction through the aspiration catheter 4135. For use during a procedure, the tip portion 4104 is placed into a delivery catheter 4148 and thereafter the delivery catheter 4148 is inserted into the aspiration catheter 4135, and follows through to port 4142, so that at least the tip portion 4104 projects distally from a distal end 4146 of the aspiration catheter 4135.

In accordance with aspects of the present specification, the device 4100 is configured to enable an operator to single-handedly operate/actuate the handle portion 4102 in order to mechanically expand, contract, or move a member 4106. In one embodiment, a first slider, knob, button, or other actuation mechanism 4114 is configured to mechanically expand or mechanically contract the member 4106. The handle portion 4102 is further moved fore and aft to cause the tip portion 4104 and therefore the member 4106 to be moved fore and aft in order to curettage the occlusion. In another embodiment, an optional second slider, knob, button, or other actuation mechanism 4120 is configured to axially move the member 4106 relative to the tip portion

4104. In one embodiment, the first slider, knob, button, or other actuation mechanism 4114 and the second slider, knob, button, or other actuation mechanism 4120 are positioned in an arc around an external surface of the handle such that each of the first and second actuation mechanisms are at the same location, or within 3 inches, axially along the length of the handle.

In another embodiment, the handle 4102 comprises one or more actuation mechanisms to deliver medications and, in particular, deliver tPA (tissue Plasminogen Activator) and/or activate an aspiration. In one embodiment, a method of treatment would include infusing tPA into at least one lumen positioned within the catheter 4148. Preferably the infusion is performed at the outset of the pulmonary embolism or deep vein thrombosis treatment process, while the member 4106 is still housed within the catheter 4148, thereby covering the unexpanded member 4106 in tPA. Alternatively, the infusion is performed at the outset of the pulmonary embolism or deep vein thrombosis treatment process, while the member 4106 is still housed within the catheter 4148, directed through a distal end of the catheter 4148, and injected directly into the clot prior to inserting and expanding the member 4106.

In another embodiment, the catheter and handle, in combination, are configured to deliver ultrasonic energy to a clot in order to accelerate lytic dispersion, drive medications deeper into the clot, speed the breakdown of the clot, and/or degenerate or unwind the fibrin quicker. In one embodiment, the catheter comprises an ultrasonic core in parallel with the elongated wire extending axially through the catheter lumen. The ultrasonic core is in electrical communication with a control unit positioned external to the catheter. A proximal end of the handle would preferably have one or more leads in electrical communication with the ultrasonic core that would extend outward from the handle and be configured to connect to the control unit. During the pulmonary embolism or deep vein thrombosis treatment process, the ultrasonic energy would be activated, using the control unit, at the beginning of the treatment upon delivery of the medications, as described above.

In embodiments, an ultrasonic core energy generator runs through the center of the catheter. In embodiments, the ultrasonic core energy generator includes a control unit configured to manage the generator. A proximal end of the handle includes leads plug into the control unit, in embodiments.

In accordance with some aspects of the present specification, the first and second units 4190, 4192 are manufactured as separate standalone units or devices. This is advantageous in that a physician may use the first unit 4190 with any third-party aspiration catheter. In some embodiments, the aspiration catheter 4135 is available with a plurality of external diameters such as, but not limited to, 12 Fr, 16 Fr, 20 Fr, and 24 Fr (where Fr represents French scale or gauge system). In some embodiments, the syringe 4137 has an exemplary, non-limiting, volume of 60 cubic centimeters.

In some embodiments, for use in treatment of pulmonary embolism a length of the delivery catheter 4148 is in a range of 80 cm to 160 cm, preferably 120 cm. In some embodiments, for use in treatment of pulmonary embolism the aspiration catheter 4135 has different lengths for different external diameters. For example, an aspiration catheter of 16 Fr has a length in a range of 70 cm to 160 cm, preferably 112 cm, an aspiration catheter of 20 Fr has a length in a range of 60 cm to 150 cm, preferably 106 cm, and an aspiration catheter of 24 Fr has a length in a range of 50 cm to 130 cm, preferably 90 cm. In some embodiments, for use in treatment of deep vein thrombosis a length of the delivery catheter 4148 is in a range of 40 cm to 120 cm, preferably 80 cm. In some embodiments, for use in treatment of deep vein thrombosis a length of a 16 Fr aspiration catheter 4135 is 65 cm. In some embodiments, for use in treatment of right heart/atrium, the aspiration catheters can range from 24 Fr with a length of 90 cm to 28 Fr with a length of 70 cm. In some embodiments, for use in treatment of IVC/SVC (Inferior Vena Cava/Superior Vena Cava), the aspiration catheters can range from 24 Fr with a length of 90 cm to 28 Fr with a length of 70 cm. In some embodiments, at least one pressure transducer or sensor 4109 (such as, for example, a fiber-optic pressure sensor, electro-mechanical pressure sensor and hydraulic pressure sensor) is positioned at a distal end of aspiration catheter 4135. In some embodiments, the at least one pressure transducer or sensor 4109 is in the form of an elongated member that is co-extruded into the aspiration catheter 4135 so that the elongated member runs along a full length of the aspiration catheter 4135. In embodiments, the pressure transducer or sensor 4109 is in electrical communication with electronic circuitry located in a handle 4102 of the first unit 4190. In embodiments, the handle 4102 includes a pressure display 4121. In various embodiments, the pressure transducer or sensor 4109 is configured to sense a pressure change or drop and, in particular, provide the physician with an indication that, as the occlusion is removed, there is an associated change of pressure indicative of a right side drop in right heart pressure. A right side drop in right heart pressure indicates that a problematic occlusion is being successfully removed.

In embodiments, the tip portion 4104 has a proximal end 4150 and a distal end 4152. During operation of the device 4100, the tip portion 2804 is inserted into, for example, a blood vessel for removing an occlusion while the handle portion 4102 remains in an operator/user's hands. During insertion of the device 4100 into the blood vessel, the distal end 4152 of the tip portion 4104 enters the blood vessel first and is placed in close proximity to the occlusion within the blood vessel by using the handle 4102 to maneuver the insertion of the tip portion 4104 in a desired position in the blood vessel. The tip portion 2804 comprises the member, element or body 4106, which in an embodiment is a mechanically expandable pusher ball that is slidably mounted proximate the proximal end 4150 of the tip portion 4104. The mechanical expansion is in contrast to a non-mechanical expansion occurring because a shape memory material is naturally configured to adopt a pre-defined shape without mechanical force requiring to be applied.

In various embodiments, element 4106 is a substantially curved structure. In some embodiments, the element 4106 is a three-dimensional (3D) shape. In one embodiment, the element 4106 is a braided structure made of interwoven wires such that the structure has a plurality of open areas (allowing egress from outside the element into the internal volume of the element) formed by the braid. The open areas, relative to the total surface area of the element 4106 is in a range of 1% to 99% of the total surface area. In one embodiment, the element 4106 has a high percentage of open surface area thereby allowing the element 4106 to capture more clot material. The element 4106 may be of any shape, including spherical, elliptical, conical, polygonal, cylindrical, stent, chalice cup, umbrella, concave structure, convex structure, half-sphere, sphere, windsock, dumbbell, star, polygon, lever or a combination of such shapes.

Figure 41B:
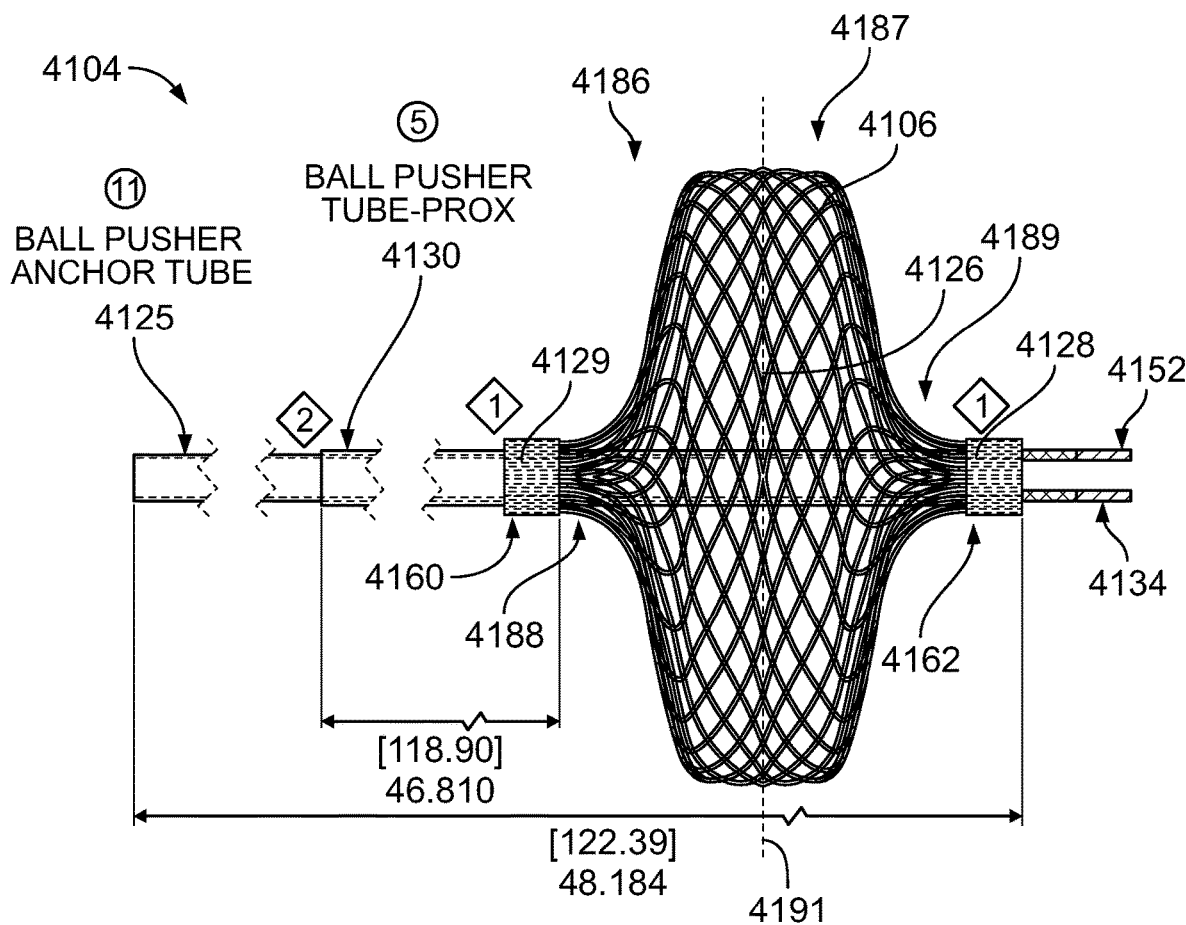
FIG. 41B is a side elevation view of an exemplary element of the device shown in FIG. 41A, in accordance with some embodiments of the present specification.
Figure 41C:
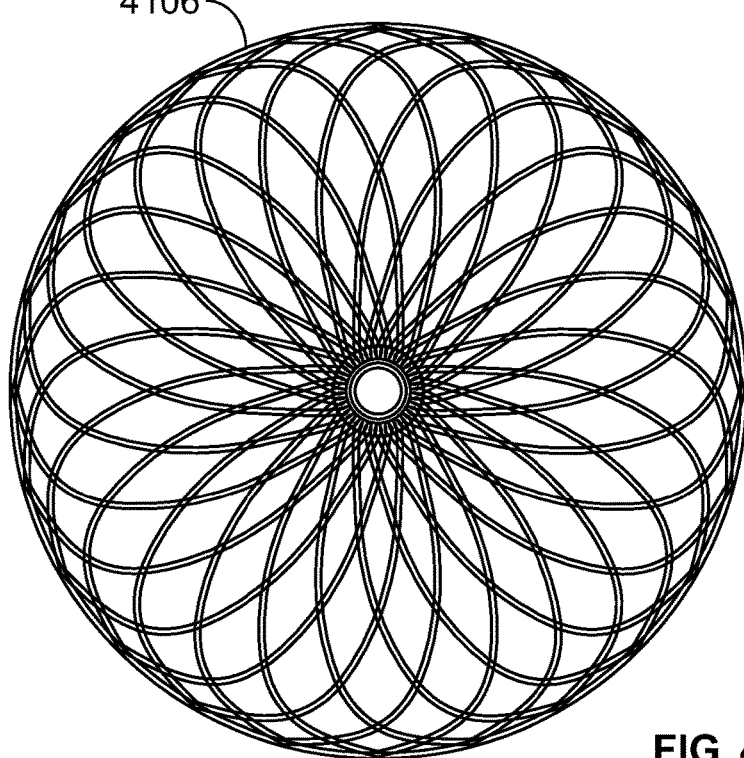
FIG. 41C is a front plan view of the element shown in FIG. 41B, in an expanded state, in accordance with some embodiments of the present specification.

In one embodiment, as shown in FIGS. 41B and 41C, the element 4106 is structurally shaped as a first funnel 4186 having a neck 4188 directed along a longitudinal axis of the tip portion 4104 in a proximal direction and a second funnel 4187 having a neck 4189 directed along the axis in a distal direction wherein the cup edge of the first funnel 4186 and the second 4187 are attached (in the form of contiguous wires) across a center axis 4191. In some embodiments, when the element 4107 is mechanically expanded, a proximal portion and a distal portion of the element expands first followed by a center portion. In some embodiments, each of the respective proximal, distal and center portions of the element 4106 may expand at different rates. In some embodiments, the element 4106 may be heterogeneous, having different characteristics including, without limitation, radial force, shape, size (for example, thickness, diameter), pore size (for example, mesh pore size or open areas as described above), and external coating.

Referring back to FIG. 41A, the tip portion 4104 is at least partially enclosed within the delivery catheter 4148 which when retracted exposes the element 4106 when the device 4100 is inserted and maneuvered within the vascular system or non-vascular structures, by using the handle portion 4102.

In some embodiments, the tip portion 4104 comprises at least two flexible telescoping tubes, that when manipulated together enable an operator/doctor to expand or contract the element 4106 and move the element 4106 axially, in order to dislodge and remove the occlusion.

In some embodiments, the element 4106 is fabricated from a Nitinol wire mesh having a plurality of mesh pores, lattices or cells. In some less preferred embodiments, the element 4106 is an inflatable device including, but not limited to, an inflatable balloon.

In some embodiments, element 4106 may be characterized by its ability to apply a variable radial force by virtue of the mechanical expansion being applied to the structure and the stiffness or rigidity across sub-regions of the element 4106. For example, in some embodiments, the expansion of the element 4106 to a first size (defined by an area or volume encompassed by the element) may be characterized by a first radial force that first size can apply to surrounding materials. The expansion of the element 4106 to a second size (defined by an area or volume encompassed by the element that is larger than the first size) may be characterized by a second radial force that second size can apply to surrounding materials, where the second radial force is different from the first radial force. In some embodiments, each of the first and second radial forces are in a range of 2 Newtons to 20 Newtons, preferably 4 Newtons to 12 Newtons. The mechanical expansion allows for the intermittent, controlled expansion of the element 4106 so that it can adopt and retain the shape of a first size (having a first area or volume), a second size (having a second area or volume), a third size (having a third area or volume), or a fourth size (having a fourth area or volume) under the control of the user and throughout the length of a procedure where the fourth size is bigger than the third size which is bigger than the second size which is bigger than the first size.

In some embodiments, the element 4106 may be characterized by its ability to resist an application of a radial force, thereby maintaining its expanded shape, by virtue of the mechanical expansion being applied to the structure and the stiffness or rigidity across sub-regions of the element 4106. For example, in some embodiments, the expansion of the element 4106 to a first size (defined by an area or volume encompassed by the element) may be characterized by an ability to resist (and therefore avoid collapse or compression of the first size) from a first radial force. The expansion of the element 4106 to a second size (defined by an area or volume encompassed by the element that is larger than the first size) may be characterized by an ability to resist (and therefore avoid collapse or compression of the second size) from a second radial force that is different from the first radial force. In some embodiments, each of the first and second radial forces are in a range of 2 Newtons to 20 Newtons, preferably 3 to 15 Newtons, more preferably 4 Newtons to 12 Newtons. The mechanical expansion allows for the intermittent, controlled expansion of the element 4106 so that it can adopt and retain the shape of a first size (having a first area or volume), a second size (having a second area or volume), a third size (having a third area or volume), or a fourth size (having a fourth area or volume) under the control of the user and throughout the length of a procedure where the fourth size is bigger than the third size which is bigger than the second size which is bigger than the first size. It should further be appreciated that the element 4106 is adapted to not collapse or compress when positioned against blood flow that applies a hydrostatic pressure in a range of 80 mm Hg to 250 mm Hg. This is particularly valuable in arterial clot removal where the hydrostatic pressure level often causes other structures, particularly self-expanding structures, to compress or collapse.

In one embodiment, a physician uses any of the embodiments disclosed herein by a) placing the element 4106 into the occlusion, b) expanding the element 4106 to a diameter, width, or volume that is greater than or equal to the diameter, width or volume of the vessel lumen it is positioned within of vessel (if greater than, it may be equal to or up to 150%, preferably around 110% to 130%, more preferably 120%), c) moving the element 4106 back and forth to scrape out the occlusion and direct the scraped occlusion to an aspiration catheter, d) applying aspiration, e) collapsing the element 4106 to pull it back into the catheter, with remaining non-aspirated thrombus, and f) removing the catheter from the patient.

In some embodiments, the element 4106 may have antiplatelet coating to reduce adhesion and provide a less thrombogenic environment during clinical application. In some embodiments, the element 4106 may be coated with control release agents including, but not limited to, thrombolytic agents.

In embodiments, the tip portion 4104 comprises a plurality of telescoping tubes, such as at least 2. As shown in FIG. 41B (in an expanded form), a first tube 4130 projects distally from a distal end of the delivery catheter 4148 (FIG. 41A). The first tube 4130 is coupled with a second tube 4125. The second tube 4125 forms the distal end 4152 of the tip portion 4104. In an embodiment, the two tubes 4130 and 4125 are arranged as a coaxial array of telescopic tubes, wherein the first tube 4130 is designed to be able to move axially relative to the second tube 4125 which is fixed relative to the handle portion 4102. In embodiments, the first tube 4130 can be axially expanded or contracted relative to the second tube 4125 by using the handle portion 4102. In an embodiment, the telescoping tubes 4130 and 4125 are made of Nitinol.

In an embodiment, the element 4106 has a proximal end 4160 and a distal end 4162. The distal end 4162 of the element 4106 is fixedly attached to the second tube 4125 at a point 4128, while the proximal end 4160 is fixedly attached to the first tube 4130 at a point 4129 in both expanded and non-expanded states of the element 4106. In various embodiments, in a non-expanded state, the element 4106 (comprising a plurality of wires) forms a wire mesh 4126 concentrically positioned around a lumen of the second tube 4125.

In embodiments, a portion of the wire mesh 4126 is only attached at points 4128 and 4129, of an exterior surface of the second tube 4125 and the first tube 4130, respectively, while the remaining portion of the wire mesh 4126 is unattached and therefore free to expand or contract. Upon axial compression of the first tube 4130 relative to the second tube 4125, the wire mesh 4126 is induced to expand radially around the lumen of the second tube 4125. Similarly, upon axial decompression of the first tube 4130 relative to the second tube 4125, the wire mesh 4126 is induced to compress or contract radially around the lumen of the second tube 4125. Stated differently, relative axial movement of the first tube 4130 and the second tube 4125 causes the proximal end 4160 to move closer to the distal end 4162, whereby the material comprising the element 4106 and extending between the ends 4160 and 4162 is compressed and therefore expands outward. In contrast, as the proximal end 4160 moves away from the distal end 4162, the material comprising the element 4106 and extending between the ends 4160 and 4162 is stretched and therefore collapses down to, and elongates along, a body lumen. Thus, the element 4106 expands by having the proximal end 4160 move distally and contracts by having the proximal end 4160 move proximally while the distal end 4162 remains stationary in both cases.

In an embodiment, in an expanded state the element 4106 approximates an elliptical shape wherein, at least a portion of the wire mesh 4126 lies approximately perpendicular to the lumen of the second tube 4125. In an embodiment, a diameter of an expanded element 4106 is approximately 16 mm. In some embodiments, a fully expanded element 4106 is substantially elliptical or disc-shaped as shown in FIGS. 41B and 41C, while in a transient or less expanded state the element 4106 may take different curved shapes such as, for example, substantially spherical. In some embodiments, a fully expanded element 4106 may be substantially spherical shaped while in a transient or less expanded state the element 4106 may take a substantially elliptical shape.

As previously discussed, in various embodiments, in an expanded state the element 4106 may take the form of a cylinder, stent, chalice cup, umbrella, concave structure, half-sphere, sphere, windsock, dumbbell, star, polygon, lever, or any other suitable shape configured for aiding retrieval of the occlusion. In some embodiments, the element 4106 can be turned and rotated as motorized units. In such an embodiment, a small motor positioned in or proximate the handle is coupled to the element 4106 and, upon actuation, the motor causes the element 4106 to move or rotate.

Figure 41D:
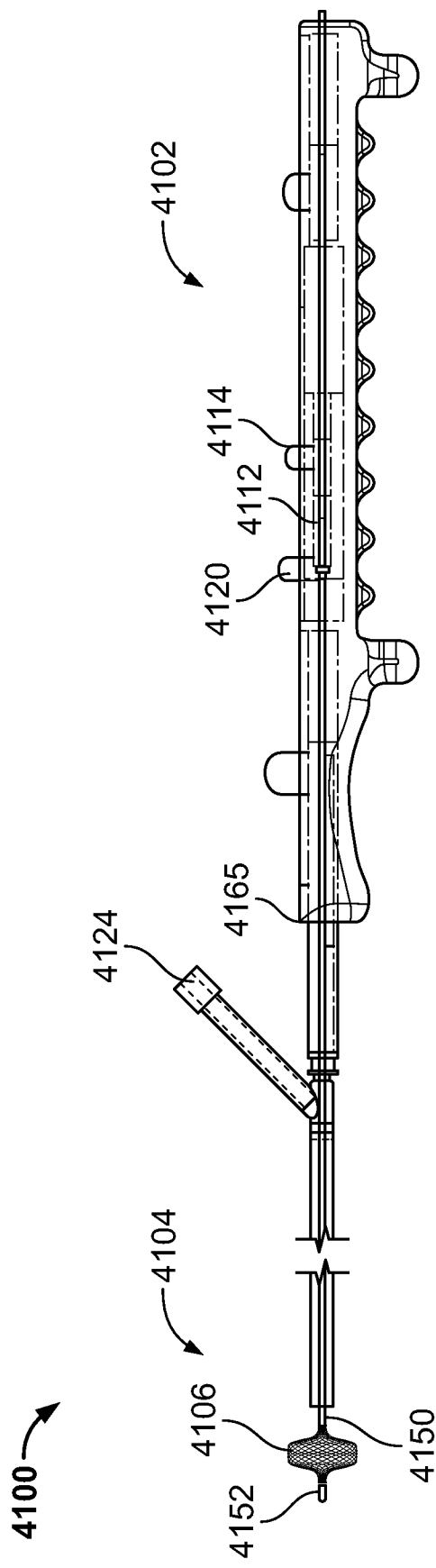
FIG. 41D is another perspective view of the retrieval device shown in FIG. 41A, in accordance with some embodiments of the present specification.

Referring now to FIGS. 41A and 41D, in an embodiment, the handle portion 4102 comprises a groove 4112 running longitudinally along a length of the handle 4102. In an embodiment a distance between a distal end 4165 of the handle portion 4102 and the distal end 4152 of the tip portion 4104 is in a range of 0.5 mm to 110 cm, preferably 1 mm to 100 mm. The handle portion 4102 includes a first actuator, knob or button 4114 configured to enable the user to mechanically expand or contract the element 4106. In some embodiments, the element 4106 is moved forward or backwards, within the occlusion, by moving the handle portion 4102 fore or aft thereby inducing a forward or backward motion of the tip portion 4104. In some embodiments, the handle portion 4102 includes an optional second actuator, knob or button 4120 configured to enable the user to mechanically slide the element 4106 forward distally from the handle portion 4102 or backwards proximally towards the handle portion 4102. The first and second knobs 4114, 4120 are slidably fitted into the groove 4112. The first knob 4114 is coupled with the first tube 4130 while the second knob 4120 is coupled with both the first and second tubes 4130, 4125.

Referring now to FIGS. 41B and 41D, when the first knob 4114 is moved or slid in the groove 4112 towards the tip portion 4104, this causes the first tube 4130 to telescope into the second tube 4125, thereby inducing an axial compression of the first tube 4130 relative to the second tube 4125. Consequently, the element 4106 is caused to expand to a desired diameter. When the first knob 4114 is moved away from the tip portion 4104 the first tube 4130 is caused to telescope out of the second tube 4125 thereby inducing an axial decompression (or elongation) of the first tube 4130 relative to the second tube 4125 between the proximal and distal ends 4129, 4128 of the wire mesh 4126. This causes the wire mesh 4126 (and therefore the element 4106) to contract radially around the lumen of the second tube 4125 and assume an unexpanded shape having a diameter lesser than a diameter in an expanded state or assume a fully unexpanded state.

When the second knob 4120 is moved in the groove 4112 distally towards the tip portion 4104, the element 4106 is caused to slide distally away from the handle 4102, whereas when the second knob 2820 is moved proximally away from the tip portion 4104 the element 4106 is caused to slide proximally towards the handle portion 4102.

In an embodiment, a diameter of a fully expanded element 4106 is approximately 16 mm. In various embodiments, the element 4106 may expand to a diameter depending upon an application/functional use of the device 4100. For example, for use in treatment of a pulmonary/large vessel having a diameter of in a range of 20 mm to 30 mm, the diameter of an expanded element 4106 ranges from 5 mm to 30 mm, preferably 10 mm to 25 mm, for use in treatment of a peripheral arterial/DVT vessel having a diameter ranging from 2 mm to 10 mm, the diameter of an expanded element 4106 ranges from 3 mm to 12 mm; for use in treatment of neuro vessels, the diameter of an expanded element 4106 ranges from 1 mm to 10 mm; for use in retrieval of an occlusion in the inferior vena cava (IVC) vessels, the diameter of an expanded element 4106 ranges from 35 mm to 40 mm; for use in treatment of biliary ducts, fistula declotting, hepatic bile ducts, brain blood vessels and peripheral arterial vessels (particularly in the hands and feet) having a lumen diameter less than 3 mm and even those less than 1 mm, the diameter of an expanded element 4106 ranges from 1 mm to 14 mm.

In some embodiments, the diameter of the element 4106, in a fully expanded state, ranges from 5 mm to 30 mm, preferably 10 mm to 25 mm, and more preferably 10 mm to 20 mm.

In some embodiments, the first knob 4114 locks (and thus, cannot be moved further forward) in a position in the groove 4112 when the element 4106 has expanded to a maximum diameter. Thus, sliding the first knob 4114 forward enables the user to expand the element 4106 to a plurality of intermediate diameters and up to a maximum permissible diameter. In some embodiments, the first knob 4114 is provided with a "clutch" feature so that, when opposing pressure is experienced from walls of a blood vessel during expansion of the element 4106, the "clutch" clicks in so that the user does not over expand. This feature is advantageous since it prevents the user from damaging the blood vessel due to over expansion of the element 4106.

In some embodiments, the groove 4112 has a series of interlocking features along its length such that the first knob 4114 can be selectively engaged or disengaged from a locked position in the handle 4102 at a plurality of expanded diameters for the element 4106.

In some embodiments, the device 4100 utilizes a lead-screw mechanism for continuous adjustment of the diameters of the element 4106 so that the first knob 4114 may be advanced or retracted to an infinitely variable number of positions in the groove 4112 and may be held in a desired position by using a friction based locking mechanism, in order for the element 4106 to attain a desired diameter. In an embodiment, a non-backdriving thread pattern in the lead-screw is used to provide a friction-brake when not actuated by the user, enabling continuous adjustment of the diameters of expanded element 4106. In embodiments, the first knob 4114 may be positioned at several different locations/positions along the length of the groove 4112, wherein each of the locations/positions corresponds to a different degree of expansion of the element 4106, and hence a different shape of the element 4106.

In an embodiment, by moving the second knob 4120, leading to advancing or retracting of the second tube 4125 and the first tube 4130 together as one, the element 4106 may be moved axially fore and aft along the tip portion 4104 in an expanded or collapsed state. In some embodiments, the element 4106 can be moved axially in a range from 1 mm to 8 cm, and preferably at least 6 cm.

In some embodiments, the first tube 4130 extends from the handle portion 4102 to the element 4106 and is co-axial with the second tube 4125. Referring to FIG. 41B, the anchor nose 4134 provides a termination point for the element 4106 and, in an embodiment, performs a secondary function of a radiopaque marker. In various embodiments, diameters of the telescoping tubes 4130 and 4125 range from 0.3 mm to 2 mm for neurovascular and peripheral applications, and 1 mm to 5 mm for pulmonary and larger applications.

Referring back to FIGS. 41A through 41D, in an embodiment, in order to retrieve an occlusion from a lumen of a patient, the delivery catheter 4148 is positioned near the occlusion (using the handle 4102) and the tip portion 4104 is positioned within, or all the way through, the occlusion. Once the occlusion matter is curetted using the element 4106, the syringe 4137 is actuated to generate suction at an aspiration line 4124 and aspirate the occlusion matter through the aspiration catheter 4135.

Thus, in various embodiments, the element 4106 expands to a particular diameter and a particular radial force, thereby allowing trapping and curettage of thrombus or clot material from a vessel lumen and wall. In some embodiments, the retrieval device 4100 utilizes its adjustable radial forces and its adjustable size to actively curettage the wall of an artery or vein. In some embodiments, the retrieval device 4100 enables removal of thrombus by simultaneously capturing, compressing, dragging and curetting thrombotic material from vessel walls. In one embodiment, the element 4106 is configured to capture, and/or contain, a size of clot or thrombus material in a volume range of 0.01 ml to 100 ml.

In some embodiments, the handle portion 4102 includes a plurality of gradations such as, for example and by way of example only, three gradations of low, medium and high, five gradations ranging from low to high or eight gradations ranging from low to high. Each gradation is indicative of a corresponding predefined diameter of the element 4106 in expanded states. The two slide buttons 4114 and 4120 can be actuated to any one of the plurality of gradations and then détente to that position.

While in some embodiments, the handle portion 4102 includes two buttons 4114 and 4120 to manipulate the element 4106, in alternate embodiments fewer than two buttons may be used. For example, in some embodiments, a clinician's use of the device 4100 is monitored over a predefined number of uses or operations of the device 4100 while performing mechanical thrombectomy procedures. Based on the monitoring, a preferred sequence of deployment of the element 4106 is determined and data indicative of the deployment sequence is stored in a memory (residing within the handle portion 4102 or remote from the handle portion 4102).

As a non-limiting illustration, the deployment sequence may include expanding the element 4106 and then moving the element 4106 axially fore and aft for a cycle of, say, 5 reciprocations. Consequently, a single button (when actuated) is programmed to carry out the deployment sequence. Of course, in some embodiments, the second button may still be used manually after the deployment sequence has been completed by the programmed button. In some embodiments, an Artificial Intelligence (AI) algorithm implements the deployment sequence, once the device 4100 is placed in-vivo, to automatically expand the element 4106 and/or move the element 4106 axially.

Figure 42:
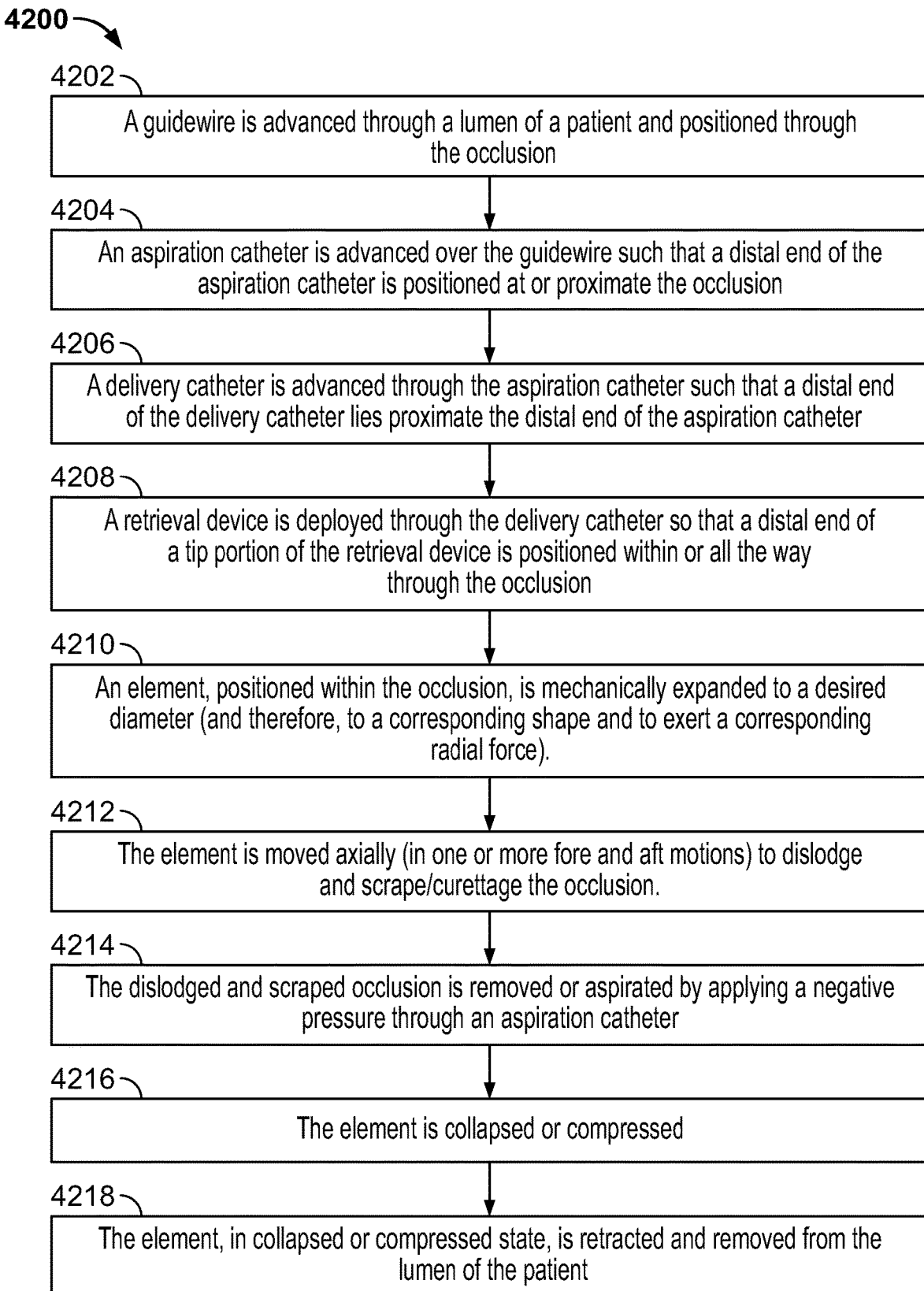
FIG. 42 is a flowchart of a plurality of exemplary steps of a method of treating peripheral arterial disease (PAD) by using the retrieval device of FIG. 41A, in accordance with an embodiment of the present specification.

FIG. 42 is a flowchart of a plurality of exemplary steps of a method 4200 of treating peripheral arterial disease (PAD) using the retrieval device 4100, in accordance with an embodiment of the present specification. In accordance with some embodiments, the method 4200 enables removing the occlusion from a lumen having an internal diameter less than 3 mm, and preferably less than 1 mm, wherein the lumen is one of, but not limited to, biliary ducts, fistula declotting, brain blood vessels, upper and lower extremities, ureter, appendicular artery and peripheral arterial vessels (particularly in the hands, arms, forearms, thighs, legs and feet).

Referring now to FIGS. 41A and 42, at step 4202, in order to retrieve an occlusion from the lumen of a patient, a guidewire is advanced through the lumen of the patient and positioned through the occlusion. At step 4204, the aspiration catheter 4135 is advanced over the guidewire such that a distal end of the aspiration catheter 4135 is positioned at or proximate the occlusion. At step 4206, the delivery catheter 4148 is advanced through the aspiration catheter 4135 such that a distal end of the delivery catheter 4148 lies proximate the distal end of the aspiration catheter 4135.

At step 4208, the retrieval device 4100 is deployed through the delivery catheter 4148 so that the distal end 4152 of the tip portion 4104 of the retrieval device 4100, protruding from the delivery catheter 4148 or sheath, is positioned within or all the way through and beyond the occlusion. This ensures that the element 4106, in a compressed or non-expanded state, is positioned within the occlusion.

At step 4210, the element 4106, positioned within the occlusion, is mechanically expanded to a desired diameter (and therefore, to a corresponding shape and to exert a corresponding radial force). In an embodiment, the first knob 4114 on the handle portion 4102 of the retrieval device 4100 is actuated to cause the wire mesh structure of the element 4106 to expand out. In some embodiments, upon expansion, the element 4106 is configured to resist compression from an applied force in a range of 0 Newtons to 25 Newtons.

At step 4212, the element 4106 is moved axially (in one or more fore and aft motions) to dislodge and scrape/curettage the occlusion. In some embodiments, the occlusion can also be trapped into the mesh lattices of the element 4106 of the retrieval device 4100, for example.

In some embodiments, the handle portion 4102 is moved fore and aft to cause the tip portion 4104 and therefore the element 4106 to be moved fore and aft in order to dislodge and curettage the occlusion. In another embodiment, the second knob 4120 is actuated to axially move the element 4106 relative to the tip portion 4104. In some embodiments, the element 4106 is configured to be moved axially in a range from 1 mm to 8 cm and preferably at least 6 cm.

At step 4214, the dislodged and scraped occlusion is removed or aspirated by applying a negative pressure through the aspiration catheter 4135. In some embodiments, the fore and aft movement of the element 4106 further directs the dislodged and scraped occlusion towards the aspiration catheter 4135.

At step 4216, the element 4106 is collapsed or compressed. In some embodiments, the first knob 4114 is actuated to cause the element 4106 to collapse or compress. Finally, at step 4218, the element 4106, in collapsed or compressed state, is retracted and removed from the lumen of the patient.

Removing Gallstones During an ERCP (Endoscopic Retrograde Cholangio-Pancreatography)

In accordance with some aspects, the retrieval devices of the present specification, comprising at least one mechanically expandable element, may be used to remove gallstones during an ERCP procedure.

During an ERCP procedure an endoscope is advanced from a patient's mouth, down the esophagus and into the duodenal section of the small intestines. Thereafter, the endoscope may be advanced proximate the patient's bile duct and a catheter is then advanced into the patient's a) bile duct, b) accessory pancreatic duct, c) main pancreatic duct, d) cystic duct, e) common hepatic duct, f) right hepatic duct, g) left hepatic duct. A contrasting agent is now injected, using the catheter, into the ducts in order to determine filling defects representative of occlusion such as stones or growth.

If one or more stones or other sludge are determined to be occluding the duct, a retrieval device of the present specification is advanced, over a wire, so that a tip portion is positioned proximate, into or all the way through the occlusion (depending upon the type of occlusion). Thereafter, the proximal and distal elements are mechanically expanded and maneuvered (using a handle and physically manipulable interfaces on the handle) to remove the occlusion.

Figure 44:
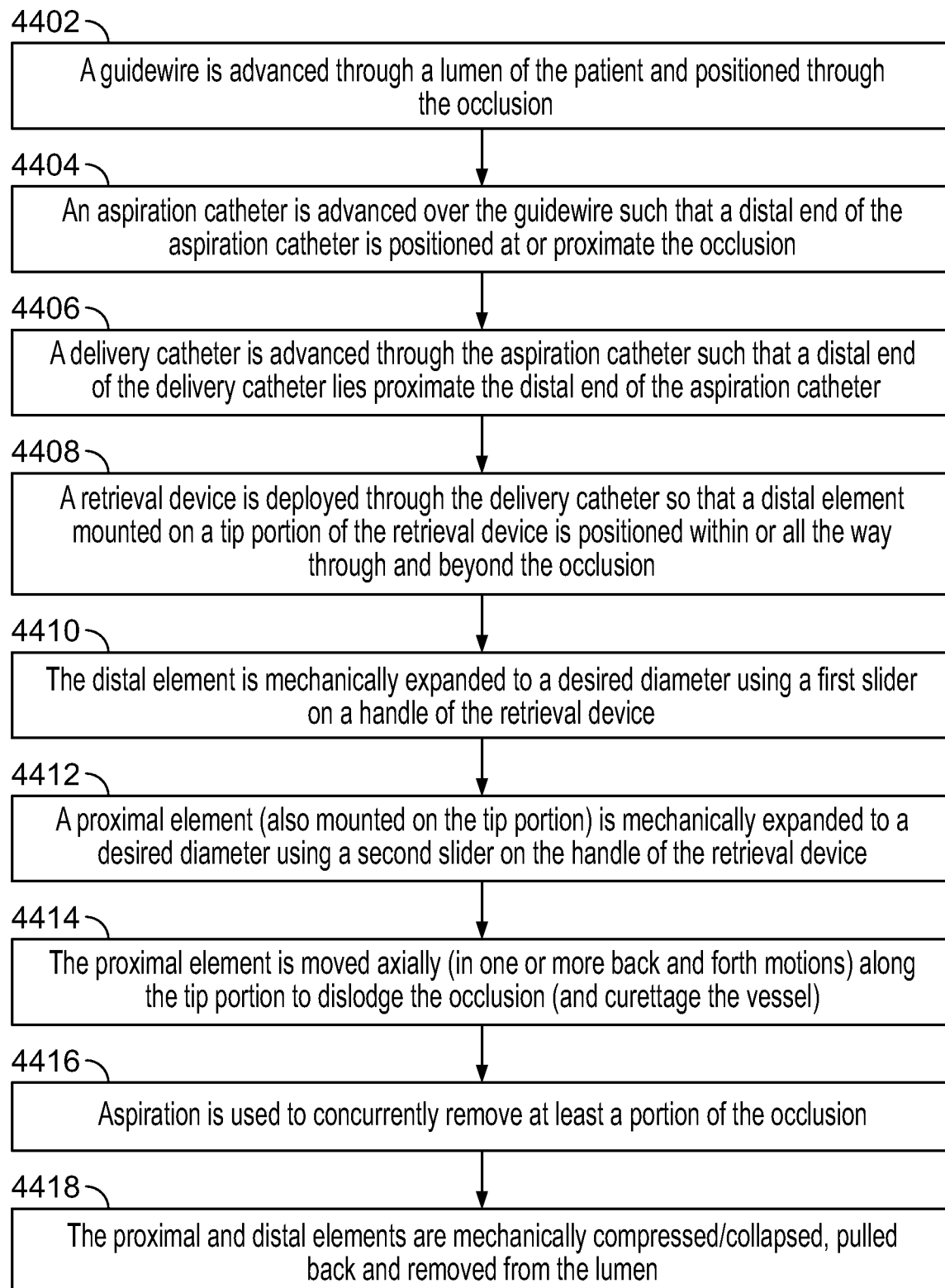
FIG. 44 is a flowchart of a plurality of exemplary steps of removing gallstones by using a retrieval device, in accordance with an embodiment of the present specification.

FIG. 44 is a flowchart of a plurality of exemplary steps of removing gallstones by using any of the retrieval devices 2800, 2900 or 3000, in accordance with an embodiment of the present specification. In some embodiments, the retrieval device is used to perform an ERCP procedure in order to remove a gallstone (hereinafter referred to as an 'occlusion').

At step 4402, a guidewire is advanced through the lumen of the patient and positioned through the occlusion. At step 4404, an aspiration catheter is advanced over the guidewire such that a distal end of the aspiration catheter is positioned at or proximate the occlusion. At step 4406, a delivery catheter is advanced through the aspiration catheter such that a distal end of the delivery catheter lies proximate the distal end of the aspiration catheter. At step 4408, a retrieval device is deployed through the delivery catheter so that a distal element mounted on a tip portion of the retrieval device is positioned within or all the way through and beyond the occlusion.

At step 4410, the distal element is mechanically expanded to a desired diameter using a first slider on a handle of the retrieval device. In some embodiments, the distal element is a mechanically expandable and rigid anchor fixedly attached proximate a distal end of the tip portion.

At step 4412, a proximal element (also mounted on the tip portion) is mechanically expanded to a desired diameter using a second slider on the handle of the retrieval device.

At step 4414, the proximal element is moved axially (in one or more back and forth motions) along the tip portion to dislodge the occlusion (and curettage the vessel). In some embodiments, the axial fore and aft movement of the proximal element results in capturing at least a portion of the occlusion between the proximal and distal elements.

In various embodiments, the anchoring of the rigid distal element proximate the distal end of the tip portion followed by a mechanical expansion of the distal element using the first slider (as opposed to a Nitinol temperature-based expansion) provides the distal element a required minimum degree of rigidity to anchor in place within the lumen and/or preferably wedged into the occlusion. Persons of ordinary skill in the art would appreciate that if the distal element is not rigid and not solidly anchored, the retrieval device may not have sufficient leverage to dislodge the occlusion.

In some embodiments, the anchoring of the distal element to the tip portion and the occlusion (in embodiment where the distal element is positioned within the occlusion) while attaining a required degree of rigidity locks the distal element in a desired location with respect to the occlusion, and allows the proximal element to move back and forth longitudinally with respect to the distal element to dislodge the occlusion.

In an embodiment, the distal element is positioned and expanded within the occlusion (like a fishing hook), and in another embodiment the distal element is positioned and expanded distal to (or beyond) the occlusion. In an embodiment the proximal element is expanded proximal to (prior to) or within the occlusion, such that the proximal element can be moved all the way into the expanded (concave or cup-shaped) distal element to generate a vice-like grip and trap the occlusion between the proximal and distal elements. In some embodiments, once the occlusion is trapped between the proximal and distal elements, the distance between the proximal element and the distal element may be reduced further such that the proximal element moves all the way into or proximate the distal element.

At step 4416, aspiration is used to concurrently remove at least a portion of the occlusion. In some embodiments, aspiration is performed by applying negative pressure at a proximal end of the aspiration catheter.

At step 4418, the proximal and distal elements are mechanically compressed/collapsed, pulled back and removed from the lumen.

In some embodiments, the portion of the occlusion captured between the proximal and distal elements is removed by pulling out the proximal element, the portion of the occlusion and the distal element together from the lumen of the patient.

In some embodiments, a first portion of the occlusion captured between the proximal and distal elements is removed by pulling out the proximal element, the first portion of the occlusion and the distal element while a remaining second portion is aspirated using an aspiration catheter. In various embodiments, the exact technique of removing the occlusion varies depending upon factors such as, but not limited to, the anatomical location of the occlusion within the patient's body, and the complexity and density of the occlusion. However, in various embodiments, removal of the occlusion involves some degree of moving the proximal element relative to the distal element to dislodge, trap and aspirate the occlusion.

Removing Renal Calculi (Kidney Stones)

In accordance with some aspects, the retrieval devices of the present specification, comprising at least one mechanically expandable element, may be used to remove kidney stones.

In some embodiments, an endoscope is advanced from urethral meatus into a patient's bladder and then into the ureter. Thereafter, a retrieval device of the present specification is advanced into the ureter so that a tip portion is positioned proximate the kidney stone. The proximal and distal elements are then mechanically expanded and maneuvered (using a handle and physically manipulable interfaces on the handle) to remove the kidney stone. It should be appreciated, that the retrieval device may also be advanced into the patient's renal pelvis to remove/extract stones.

Figure 45:
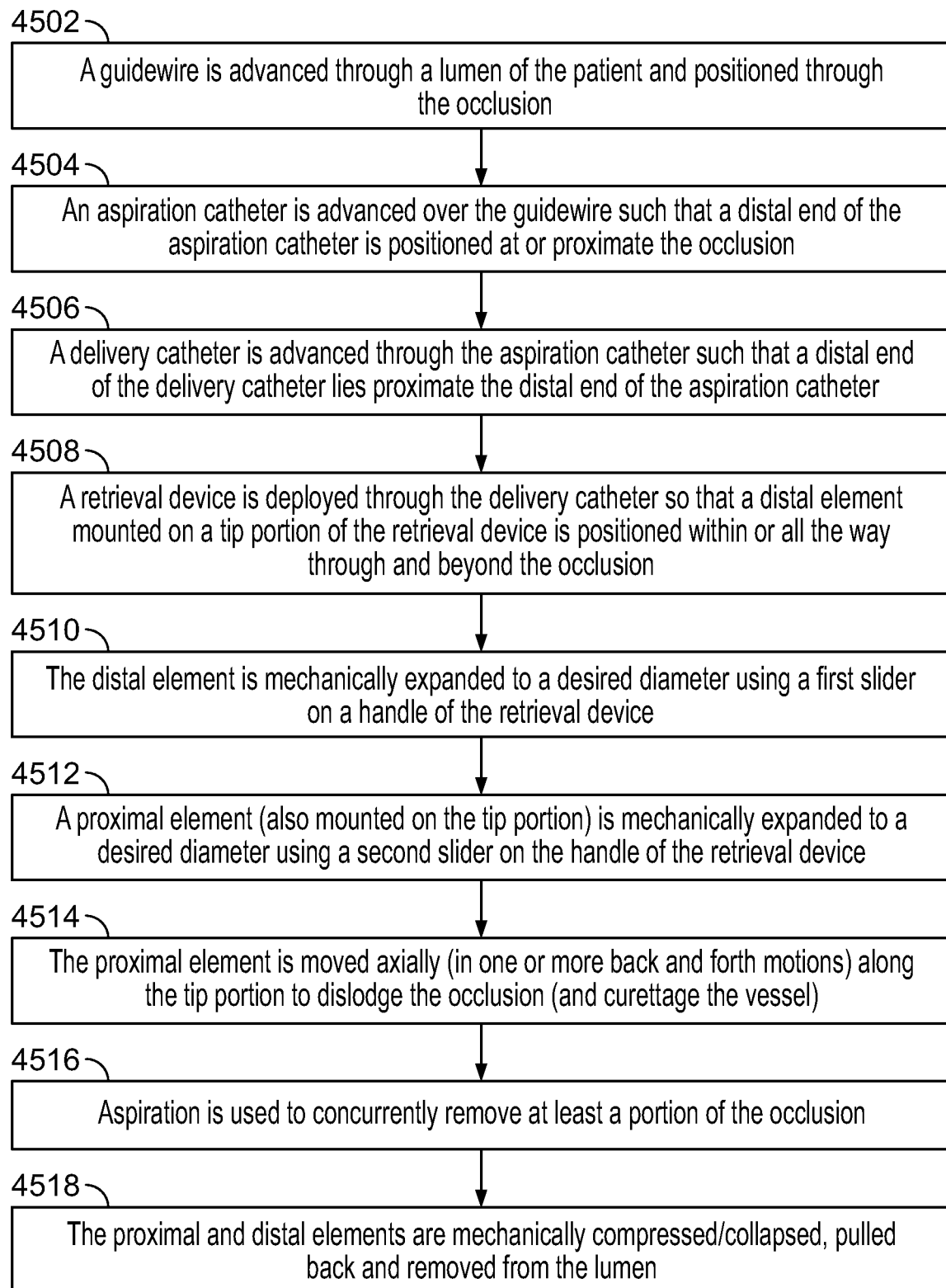
FIG. 45 is a flowchart of a plurality of exemplary steps of removing kidney stones by using a retrieval device, in accordance with an embodiment of the present specification.

FIG. 45 is a flowchart of a plurality of exemplary steps of removing kidney stones by using any of the retrieval devices 2800, 2900 or 3000, in accordance with an embodiment of the present specification. In some embodiments, the retrieval device is advanced from urethral meatus into a patient's bladder and then into the ureter. Thereafter, the retrieval device is advanced into the ureter so that a tip portion is positioned proximate the kidney stone (hereinafter referred to as an 'occlusion').

At step 4502, a guidewire is advanced through the lumen of the patient and positioned through the occlusion. At step 4504, an aspiration catheter is advanced over the guidewire such that a distal end of the aspiration catheter is positioned at or proximate the occlusion. At step 4506, a delivery catheter is advanced through the aspiration catheter such that a distal end of the delivery catheter lies proximate the distal end of the aspiration catheter. At step 4508, a retrieval device is deployed through the delivery catheter so that a distal element mounted on a tip portion of the retrieval device is positioned within or all the way through and beyond the occlusion.

At step 4510, the distal element is mechanically expanded to a desired diameter using a first slider on a handle of the retrieval device. In some embodiments, the distal element is a mechanically expandable and rigid anchor fixedly attached proximate a distal end of the tip portion.

At step 4512, a proximal element (also mounted on the tip portion) is mechanically expanded to a desired diameter using a second slider on the handle of the retrieval device.

At step 4514, the proximal element is moved axially (in one or more back and forth motions) along the tip portion to dislodge the occlusion (and curettage the vessel). In some embodiments, the axial fore and aft movement of the proximal element results in capturing at least a portion of the occlusion between the proximal and distal elements.

In various embodiments, the anchoring of the rigid distal element proximate the distal end of the tip portion followed by a mechanical expansion of the distal element using the first slider (as opposed to a Nitinol temperature-based expansion) provides the distal element a required minimum degree of rigidity to anchor in place within the lumen and/or preferably wedged into the occlusion. Persons of ordinary skill in the art would appreciate that if the distal element is not rigid and not solidly anchored, the retrieval device may not have sufficient leverage to dislodge the occlusion.

In some embodiments, the anchoring of the distal element to the tip portion and the occlusion (in embodiment where the distal element is positioned within the occlusion) while attaining a required degree of rigidity locks the distal element in a desired location with respect to the occlusion, and allows the proximal element to move back and forth longitudinally with respect to the distal element to dislodge the occlusion.

In an embodiment, the distal element is positioned and expanded within the occlusion (like a fishing hook), and in another embodiment the distal element is positioned and expanded distal to (or beyond) the occlusion. In an embodiment the proximal element is expanded proximal to (prior to) or within the occlusion, such that the proximal element can be moved all the way into the expanded (concave or cup-shaped) distal element to generate a vice-like grip and trap the occlusion between the proximal and distal elements. In some embodiments, once the occlusion is trapped between the proximal and distal elements, the distance between the proximal element and the distal element may be reduced further such that the proximal element moves all the way into or proximate the distal element.

At step 4516, aspiration is used to concurrently remove at least a portion of the occlusion. In some embodiments, aspiration is performed by applying negative pressure at a proximal end of the aspiration catheter.

At step 4518, the proximal and distal elements are mechanically compressed/collapsed, pulled back and removed from the lumen.

In some embodiments, the portion of the occlusion captured between the proximal and distal elements is removed by pulling out the proximal element, the portion of the occlusion and the distal element together from the lumen of the patient.

In some embodiments, a first portion of the occlusion captured between the proximal and distal elements is removed by pulling out the proximal element, the first portion of the occlusion and the distal element while a remaining second portion is aspirated using an aspiration catheter. In various embodiments, the exact technique of removing the occlusion varies depending upon factors such as, but not limited to, the anatomical location of the occlusion within the patient's body, and the complexity and density of the occlusion. However, in various embodiments, removal of the occlusion involves some degree of moving the proximal element relative to the distal element to dislodge, trap and aspirate the occlusion.

In accordance with some aspects, at least one pressure transducer or sensor (such as, for example, a fiber-optic pressure sensor, electro-mechanical pressure sensor and hydraulic pressure sensor) is positioned at a distal end of an aspiration catheter that is used along with a retrieval device of the present specification during various procedures related to removal of an occlusion from a vessel lumen. In some embodiments, the at least one pressure transducer or sensor is in the form of an elongated member that is co-extruded into the aspiration catheter so that the elongated member runs along a full length of the aspiration catheter. In embodiments, the pressure transducer or sensor is in electrical communication with electronic circuitry located in a handle of the retrieval device. The handle includes a pressure display. In various embodiments, the pressure transducer or sensor is configured to sense a pressure change or drop and, in particular, provide the physician with an indication that, as the occlusion is removed, there is an associated change of pressure indicative of a right side drop in right heart pressure. A right side drop in right heart pressure indicates that a problematic occlusion is being successfully removed.

The above examples are merely illustrative of the many applications of the systems and methods of the present specification. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A device adapted to remove unwanted material from a vessel of a patient comprising:
   a. an elongated member comprising a first proximal end and a first distal end;
   b. a proximal element comprising a first proximal end point and a first distal end point, said first proximal end point of said proximal element releasably engaged to a first portion of said elongated member and said first distal end point of said proximal element releasably engaged to a second portion of said elongated member, whereby, when said first proximal end point and said first distal end point of said proximal element are released from said elongated member, first translation of said proximal element along said elongated member is allowed,
   said proximal element adapted to expand from a first pre-expansion configuration to a first expanded configuration;
   c. a distal element comprising a second proximal end point and a second distal end point, said second proximal end point releasably engaged to a third portion of said elongated member, said second distal end point releasably engaged to a fourth portion of said elongated member, whereby, when said second proximal end point and said second distal end point of said distal element are released from said elongated member, second translation of said distal element along said elongated member is allowed,
   said distal element adapted to expand from a second pre-expansion configuration to a second expanded configuration,
   said first portion, second portion, third portion, and fourth portion of said elongated member representing different locations along said elongated member; and
   d. a handle in physical communication with said elongated member, said handle comprising a first physically manipulable interface and a second physically manipulable interface,
   said first physically manipulable interface adapted to mechanically induce said expansion of said proximal element from said first pre-expansion configuration to said first expanded configuration or induce said expansion of said distal element from said second pre-expansion configuration to said second expanded configuration when said first physically manipulable interface is moved,
   said second physically manipulable interface adapted to induce said first slidable translation of said proximal element along said elongated member without inducing said second slidable translation of said distal element along said elongated member or induce said second slidable translation of said distal element along said elongated member without inducing said first slidable translation of said proximal element along said elongated member when said second physically manipulable interface is moved.

2. The device of claim 1, wherein said proximal element is further adapted to contract from said first expanded configuration to a first contracted configuration and said distal element is further adapted to contract from said second expanded configuration to a second contracted configuration, and wherein said first physically manipulable interface is further adapted to mechanically induce said contraction of said proximal element from said first expanded configuration to said first contracted configuration or induce said contraction of said distal element from said second expanded configuration to said second contracted configuration when said first physically manipulable interface is moved.

3. The device of claim 2, wherein said handle further comprises a third physically manipulable interface adapted to mechanically induce said expansion of said distal element from said second pre-expansion configuration to said second expanded configuration or induce said contraction of said distal element from said second expanded configuration to said second contracted configuration when said third physically manipulable interface is moved.

4. The device of claim 1, wherein said handle further comprises a pin positioned and adapted to abate movement of said first physically manipulable interface and said second physically manipulable interface, a keyhole accessible from a first side of said handle, and a key configured to pass into said keyhole and physically communicate with said pin.

5. The device of claim 1, wherein said elongated member further comprises a first shaft, a second shaft, a third shaft, and a fourth shaft, and wherein said first shaft is concentrically positioned around said second shaft, said second shaft is concentrically positioned around said third shaft, and said third shaft is concentrically positioned around said fourth shaft.

* * * * *